United States Patent
Barouch et al.

(10) Patent No.: US 10,611,801 B2
(45) Date of Patent: Apr. 7, 2020

(54) COMPOSITIONS AND METHODS FOR PREVENTING AND TREATING ZIKA VIRUS INFECTION

(71) Applicant: Beth Israel Deaconess Medical Center, Inc., Boston, MA (US)

(72) Inventors: Dan H. Barouch, Newton, MA (US); Peter Abbink, Winthrop, MA (US); Rafael Larocca, Canton, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 16/099,254

(22) PCT Filed: Jun. 9, 2017

(86) PCT No.: PCT/US2017/036900
§ 371 (c)(1),
(2) Date: Nov. 6, 2018

(87) PCT Pub. No.: WO2017/214596
PCT Pub. Date: Dec. 14, 2017

(65) Prior Publication Data
US 2019/0144506 A1 May 16, 2019

Related U.S. Application Data

(60) Provisional application No. 62/348,087, filed on Jun. 9, 2016.

(51) Int. Cl.
| | |
|---|---|
| A61K 39/00 | (2006.01) |
| A61K 39/12 | (2006.01) |
| C07K 14/005 | (2006.01) |
| C12N 7/00 | (2006.01) |
| C12Q 1/70 | (2006.01) |
| A61P 31/14 | (2006.01) |
| C07K 16/10 | (2006.01) |

(52) U.S. Cl.
CPC ............ *C07K 14/005* (2013.01); *A61K 39/12* (2013.01); *A61P 31/14* (2018.01); *C07K 16/10* (2013.01); *A61K 39/00* (2013.01); *A61K 2039/5256* (2013.01); *A61K 2039/53* (2013.01); *A61K 2039/55* (2013.01); *C07K 2317/24* (2013.01); *C12N 2770/24122* (2013.01); *C12N 2770/24134* (2013.01); *Y02A 50/392* (2018.01)

(58) Field of Classification Search
CPC ........ A61K 39/12; Y02A 50/51; Y02A 50/53; C12N 7/00; C07K 14/005
See application file for complete search history.

(56) References Cited

U.S. PATENT DOCUMENTS

| | | | |
|---|---|---|---|
| 8,158,131 B2 * | 4/2012 | Apt ..................... | C07K 14/005 424/192.1 |
| 2011/0045024 A1 | 2/2011 | Dittmer et al. | |
| 2017/0014502 A1 | 1/2017 | Sumathy et al. | |

FOREIGN PATENT DOCUMENTS

| | | |
|---|---|---|
| WO | WO-2017/015463 A2 | 1/2017 |
| WO | WO-2017/140905 A1 | 8/2017 |

OTHER PUBLICATIONS

Abbink et al., "Protective efficacy of multiple vaccine platforms against Zika virus challenge in rhesus monkeys," available in PMC Mar. 9, 2017, published in final edited form as: Science. 353(6304):1129-32 (2016) (12 pages).
Fonseca et al., "First case of Zika virus infection in a returning Canadian traveler," Am J Trop Med Hyg. 91(5):1035-8 (2014).
GenBank Accession KF993678.1, "Zika virus strain PLCal_ZV from Canada polyprotein gene, partial cds," last modified Nov. 6, 2014 (9 pages).
International Search Report and Written Opinion for International Application No. PCT/US2017/036900, dated Sep. 6, 2017 (19 pages).
Larocca et al., "Vaccine protection against Zika virus from Brazil," available in PMC Feb. 25, 2017, published in final edited form as: Nature. 536(7617):474-8 (2016) (24 pages).
Raviprakash et al., "A tetravalent dengue vaccine based on a complex adenovirus vector provides significant protection in rhesus monkeys against all four serotypes of dengue virus," J Virol. 82(14):6927-34 (2008).
Cox et al., "Predicting Zika virus structural biology: Challenges and opportunities for intervention," Antivir Chem Chemother. 24(3-4):118-26 (2015).
Extended European Search Report for European Patent Application No. 17811141.5, dated Nov. 20, 2019 (7 pages).
GenBank Accession No. KU365780, "Zika virus strain BeH815744 gene, complete cds," last modified Jan. 26, 2016 (4 pages).
Logan, "Zika—how fast does this virus mutate?," <https://pdfs.semanticscholar.org/1c7e/1fe9ec1d799511ffed273af0dacf744e8304.pdf>, dated Feb. 19, 2016 (9 pages).

* cited by examiner

*Primary Examiner* — Barry A Chestnut
(74) *Attorney, Agent, or Firm* — Clark & Elbing LLP

(57) ABSTRACT

The invention relates to immunogenic compositions and vaccines containing a ZIKV protein or a polynucleotide encoding a Zika virus (ZIKV) protein and uses thereof. The invention also provides methods of treating and/or preventing a ZiKV infection by administering an immunogenic composition or vaccine of the invention to a subject (e.g., a human).

28 Claims, 42 Drawing Sheets
Specification includes a Sequence Listing.

FIG. 2

ZIKV Isolate
- Brazil ZKV2015 (Brazil strain; ZIKV-BR challenge stock)
- PRVABC59 (Puerto Rico strain; ZIKV-PR challenge stock)
- BeH815744 (Brazil strain; immunogen design)
- H PF 2013 (French Polynesian strain)
- MR766 (African strain)

AA identical

|  | ZIKV-BR | ZIKV-PR | BeH815744 | H PF 2013 | MR766 |
|---|---|---|---|---|---|
| ZIKV-BR |  | 3418 | 3419 | 3419 | 3294 |
| ZIKV-PR | 5 |  | 3420 | 3420 | 3295 |
| BeH815744 | 4 | 3 |  | 3421 | 3296 |
| H PF 2013 | 4 | 3 | 2 |  | 3298 |
| MR766 | 125 | 124 | 123 | 121 |  |

AA divergent

Percent identity

|  | ZIKV-BR | ZIKV-PR | BeH815744 | H PF 2013 | MR766 |
|---|---|---|---|---|---|
| ZIKV-BR |  | 99.9 | 99.9 | 99.9 | 96.5 |
| ZIKV-PR | 0.1 |  | 99.9 | 99.9 | 96.5 |
| BeH815744 | 0.1 | 0.1 |  | 99.9 | 96.5 |
| H PF 2013 | 0.1 | 0.1 | 0.1 |  | 96.6 |
| MR766 | 3.6 | 3.6 | 3.6 | 3.5 |  |

Divergence

FIG. 3C

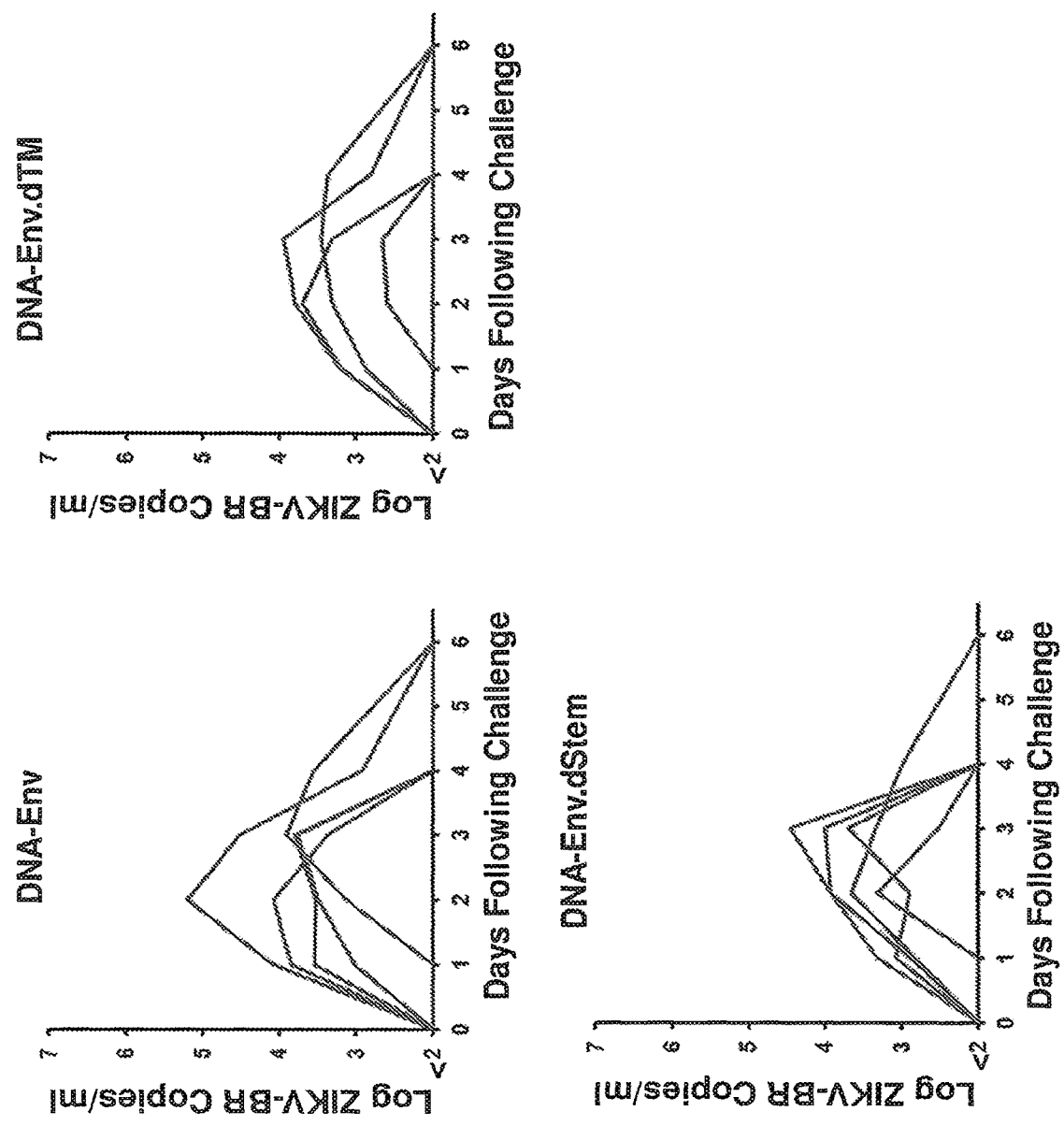

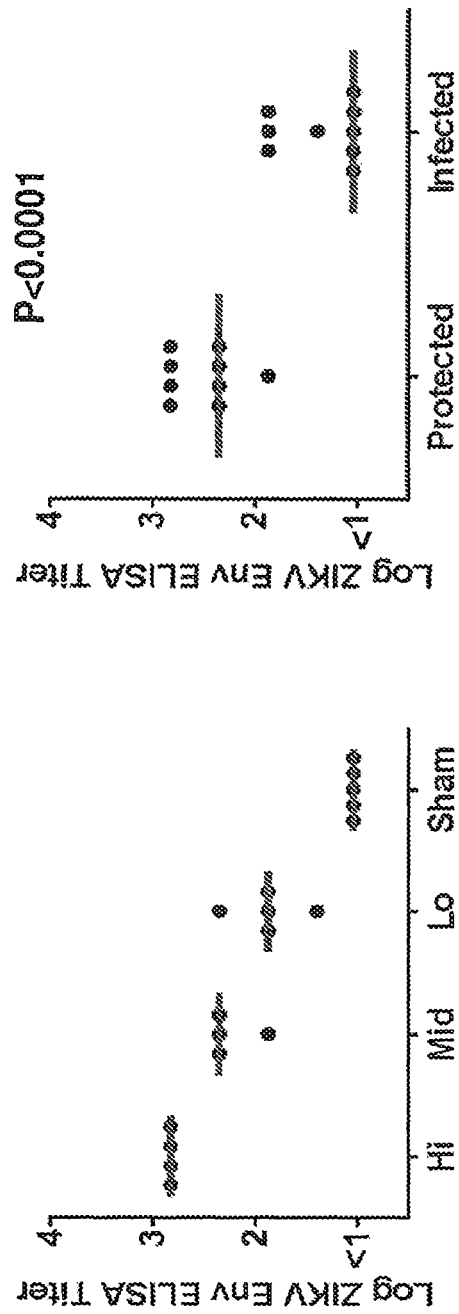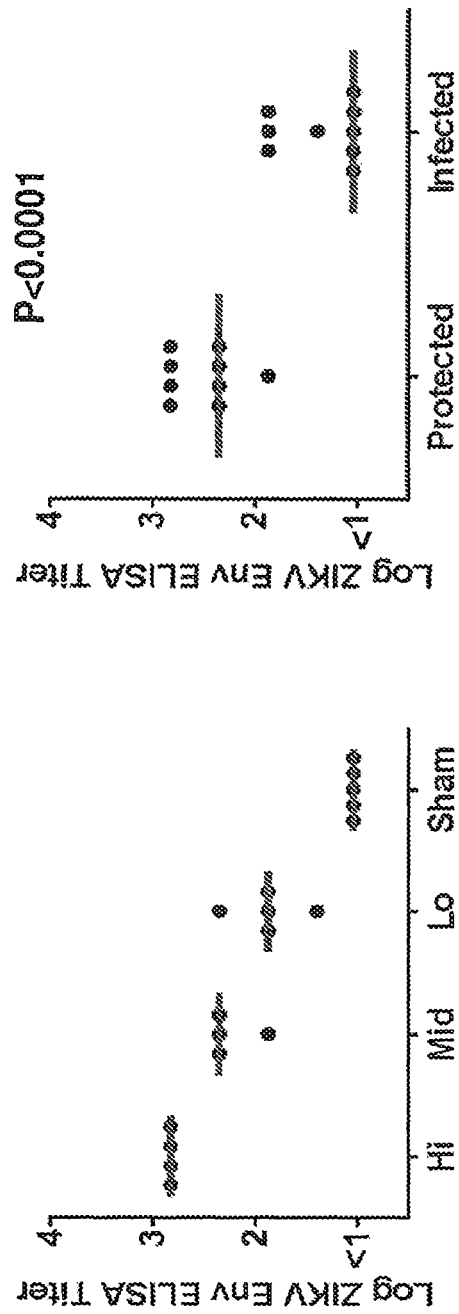
FIG. 8A
FIG. 8B

SEQUENCE LISTING

```
<160> NUMBER OF SEQ ID NOS: 27

<210> SEQ ID NO 1
<211> LENGTH: 1740
<212> TYPE: DNA
<213> ORGANISM: Artificial Sequence
<220> FEATURE:
<223> OTHER INFORMATION: Synthetic construct

<400> SEQUENCE: 1
gctgtgacac tgcctagcca cagcacccgg aagctgcaga ccagaagcca gacctggctg      60
gaaagcagag agtacaccaa gcacctgatc cgggtggaaa actggatctt ccggaacccc     120
ggcttcgccc tggccgctgc tgctattgct tggctgctgg gcagcagcac cagccagaaa     180
gtgatctacc tcgtgatgat cctgctgatc gcccctgcct acagcatccg gtgtatcggc     240
gtgtccaacc gggacttcgt ggaaggcatg agcggcggca catgggtgga cgtggtgctg     300
gaacatggcg gctgcgtgac agtgatggcc caggacaagc ccaccgtgga catcgagctc     360
gtgaccacca ccgtgtccaa tatggccgaa gtgcggagct actgctacga ggccagcatc     420
agcgacatgg ccagcgacag cagatgccct acacagggcg aggcctacct ggacaagcag     480
tccgacaccc agtacgtgtg caagcggacc ctggtggata gaggctgggg caatggctgc     540
ggcctgtttg gcaagggcag cctcgtgacc tgcgccaagt tcgcctgcag caagaagatg     600
accggcaaga gcatccagcc cgagaacctg gaataccgga tcatgctgag cgtgcacggc     660
agccagcact ccggcatgat cgtgaacgac accggccacg agacagacga gaaccgggcc     720
aaggtggaaa tcacccccaa cagccctaga gccgaggcca cactgggcgg ctttggatct     780
```

```
ctgggcctgg actgcgagcc tagaaccggc ctggatttca cgacctgta ctacctgacc      840 atgaacaaca aacactggct ggtgcacaaa gagtggttcc acgacatccc cctgccctgg     900
catgccggcg ctgatacagg cacaccccac tggaacaaca agaggcccct ggtggagttc     960
aaggacgccc acgccaagag gcagaccgtg gtggtgctgg gatctcagga aggcgccgtg    1020
catacagctc tggctggcgc cctggaagcc gaaatggatg cgctaaggg cagactgtcc     1080 agcggccacc tgaagtgccg gctgaagatg gacaagctgc ggctgaaggg cgtgtcctac    1140
agcctgtgta ccgccgcctt caccttcacc aagatccccg ccgagacact gcacggcacc    1200
gtgactgtgg aagtgcagta cgccggcacc gacggcccct gtaaagtgcc tgctcagatg    1260
gccgtggata tgcagaccct gacccctgtg ggcaggctga tcaccgccaa ccctgtgatc    1320
accgagagca ccgagaacag caagatgatg ctggaactgg acccacctt cggcgacagc     1380 tacatcgtga tcggcgtggg agagaagaag atcacccacc actggcacag aagcggcagc    1440
accatcggca aggcctttga ggctacagtg cggggagcca agagaatggc cgtgctggga    1500
gataccgcct gggactttgg ctctgtgggc ggagccctga actctctggg caagggaatc    1560
caccagatct tcggcgctgc cttcaagagc ctgttcggcg gcatgagctg gttcagccag    1620
atcctgatcg gcaccctgct gatgtggctg ggcctgaaca ccaagaacgg ctccatcagc    1680
ctgatgtgcc tggctctggg aggcgtgctg atcttcctga gcacagccgt gtccgcctga    1740
```

<210> SEQ ID NO 2
<211> LENGTH: 579
<212> TYPE: PRT
<213> ORGANISM: Artificial Sequence
<220> FEATURE:
<223> OTHER INFORMATION: Synthetic construct

<400> SEQUENCE: 2

```
Ala Val Thr Leu Pro Ser His Ser Thr Arg Lys Leu Gln Thr Arg Ser
1               5                   10                  15

Gln Thr Trp Leu Glu Ser Arg Glu Tyr Thr Lys His Leu Ile Arg Val
            20                  25                  30

Glu Asn Trp Ile Phe Arg Asn Pro Gly Phe Ala Leu Ala Ala Ala
        35                  40                  45

Ile Ala Trp Leu Leu Gly Ser Ser Thr Ser Gln Lys Val Ile Tyr Leu
    50                  55                  60

Val Met Ile Leu Leu Ile Ala Pro Ala Tyr Ser Ile Arg Cys Ile Gly
65                  70                  75                  80

Val Ser Asn Arg Asp Phe Val Glu Gly Met Ser Gly Gly Thr Trp Val
                85                  90                  95

Asp Val Val Leu Glu His Gly Gly Cys Val Thr Val Met Ala Gln Asp
            100                 105                 110

Lys Pro Thr Val Asp Ile Glu Leu Val Thr Thr Val Ser Asn Met
        115                 120                 125

Ala Glu Val Arg Ser Tyr Cys Tyr Glu Ala Ser Ile Ser Asp Met Ala
    130                 135                 140

Ser Asp Ser Arg Cys Pro Thr Gln Gly Glu Ala Tyr Leu Asp Lys Gln
145                 150                 155                 160

Ser Asp Thr Gln Tyr Val Cys Lys Arg Thr Leu Val Asp Arg Gly Trp
                165                 170                 175

Gly Asn Gly Cys Gly Leu Phe Gly Lys Gly Ser Leu Val Thr Cys Ala
            180                 185                 190

Lys Phe Ala Cys Ser Lys Lys Met Thr Gly Lys Ser Ile Gln Pro Glu
```

195                 200                 205

Asn Leu Glu Tyr Arg Ile Met Leu Ser Val His Gly Ser Gln His Ser
210                 215                 220

Gly Met Ile Val Asn Asp Thr Gly His Glu Thr Asp Glu Asn Arg Ala
225                 230                 235                 240

Lys Val Glu Ile Thr Pro Asn Ser Pro Arg Ala Glu Ala Thr Leu Gly
                245                 250                 255

Gly Phe Gly Ser Leu Gly Leu Asp Cys Glu Pro Arg Thr Gly Leu Asp
            260                 265                 270

Phe Ser Asp Leu Tyr Tyr Leu Thr Met Asn Asn Lys His Trp Leu Val
        275                 280                 285

His Lys Glu Trp Phe His Asp Ile Pro Leu Pro Trp His Ala Gly Ala
    290                 295                 300

Asp Thr Gly Thr Pro His Trp Asn Asn Lys Glu Ala Leu Val Glu Phe
305                 310                 315                 320

Lys Asp Ala His Ala Lys Arg Gln Thr Val Val Leu Gly Ser Gln
                325                 330                 335

Glu Gly Ala Val His Thr Ala Leu Ala Gly Ala Leu Glu Ala Glu Met
            340                 345                 350

Asp Gly Ala Lys Gly Arg Leu Ser Ser Gly His Leu Lys Cys Arg Leu
        355                 360                 365

Lys Met Asp Lys Leu Arg Leu Lys Gly Val Ser Tyr Ser Leu Cys Thr
    370                 375                 380

Ala Ala Phe Thr Phe Thr Lys Ile Pro Ala Glu Thr Leu His Gly Thr
385                 390                 395                 400

Val Thr Val Glu Val Gln Tyr Ala Gly Thr Asp Gly Pro Cys Lys Val
                405                 410                 415

Pro Ala Gln Met Ala Val Asp Met Gln Thr Leu Thr Pro Val Gly Arg
            420                 425                 430

Leu Ile Thr Ala Asn Pro Val Ile Thr Glu Ser Thr Glu Asn Ser Lys
        435                 440                 445

Met Met Leu Glu Leu Asp Pro Pro Phe Gly Asp Ser Tyr Ile Val Ile
    450                 455                 460

Gly Val Gly Glu Lys Lys Ile Thr His His Trp His Arg Ser Gly Ser
465                 470                 475                 480

Thr Ile Gly Lys Ala Phe Glu Ala Thr Val Arg Gly Ala Lys Arg Met
                485                 490                 495

Ala Val Leu Gly Asp Thr Ala Trp Asp Phe Gly Ser Val Gly Gly Ala
            500                 505                 510

Leu Asn Ser Leu Gly Lys Gly Ile His Gln Ile Phe Gly Ala Ala Phe
        515                 520                 525

Lys Ser Leu Phe Gly Gly Met Ser Trp Phe Ser Gln Ile Leu Ile Gly
    530                 535                 540

Thr Leu Leu Met Trp Leu Gly Leu Asn Thr Lys Asn Gly Ser Ile Ser
545                 550                 555                 560

Leu Met Cys Leu Ala Leu Gly Gly Val Leu Ile Phe Leu Ser Thr Ala
                565                 570                 575

Val Ser Ala

<210> SEQ ID NO 3
<211> LENGTH: 1559
<212> TYPE: DNA
<213> ORGANISM: Artificial Sequence
<220> FEATURE:

<223> OTHER INFORMATION: Synthetic construct

<400> SEQUENCE: 3

```
gctgtgacac tgcctagcca cagcacccgg aagctgcaga ccagaagcca gacctggctg      60
gaaagcagag agtacaccaa gcacctgatc cgggtggaaa actggatctt ccggaacccc     120
ggcttcgccc tggccgctgc tgctattgct tggctgctgg gcagcagcac cagccagaaa     180
gtgatctacc tcgtgatgat cctgctgatc gcccctgcct acagcatccg tgtatcggc      240
gtgtccaacc gggacttcgt ggaaggcatg agcggcggca catgggtgga cgtggtgctg     300
gaacatggcg gctgcgtgac agtgatggcc caggacaagc ccaccgtgga catcgagctc     360
gtgaccacca ccgtgtccaa tatggccgaa gtgcggagct actgctacga ggccagcatc     420
agcgacatgg ccagcgacag cagatgccct acacagggcg aggcctacct ggacaagcag     480
tccgacaccc agtacgtgtg caagcggacc ctggtggata gaggctgggg caatggctgc     540
ggcctgtttg caagggcag cctcgtgacc tgcgccaagt cgcctgcag caagaagatg       600
accggcaaga gcatccagcc cgagaacctg aataccgga tcatgctgag cgtgcacggc      660
agccagcact ccggcatgat cgtgaacgac accggccacg agacagacga gaaccgggcc     720
aaggtggaaa tcaccccaa cagccctaga gccgaggcca cactgggcgg ctttggatct     780
ctgggcctgg actgcgagcc tagaaccggc ctggatttca gcgacctgta ctacctgacc     840
atgaacaaca acactggct ggtgcacaaa gagtggttcc acgacatccc cctgccctgg      900
catgccggcg ctgatacagg cacaccccac tggaacaaca agaggccct ggtggagttc      960
aaggacgccc acgccaagag gcagaccgtg gtggtgctgg atctcaggaa aggcgccgtg    1020
catacagctc tggctggcgc cctggaagcc gaaatggatg gcgctaaggg cagactgtcc    1080
agcggccacc tgaagtgccg gctgaagatg gacaagctgc ggctgaaggg cgtgtcctac    1140
agcctgtgta ccgccgcctt caccttcacc aagatccccg ccgagacact gcacggcacc    1200
gtgactgtgg aagtgcagta cgccggcacc gacggcccct gtaaagtgcc tgctcagatg    1260
gccgtggata tgcagaccct gaccctgtg ggcaggctga tcaccgccaa ccctgtgatc      1320
accgagagca ccgagaacag caagatgatg ctggaactgg acccacccct cggcgacagc    1380
tacatcgtga tcggcgtggg agagaagaag atcacccac actggcacag aagcggcagc     1440
accatcggca aggcctttga ggctacagtg cggggagcca agagaatggc cgtgctggga    1500
gataccgcct gggactttgg ctctgtgggc ggagccctga actctctggg caagggtga    1559
```

<210> SEQ ID NO 4  
<211> LENGTH: 519  
<212> TYPE: PRT  
<213> ORGANISM: Artificial Sequence  
<220> FEATURE:  
<223> OTHER INFORMATION: Synthetic construct

<400> SEQUENCE: 4

```
Ala Val Thr Leu Pro Ser His Ser Thr Arg Lys Leu Gln Thr Arg Ser
1               5                   10                  15

Gln Thr Trp Leu Glu Ser Arg Glu Tyr Thr Lys His Leu Ile Arg Val
            20                  25                  30

Glu Asn Trp Ile Phe Arg Asn Pro Gly Phe Ala Leu Ala Ala Ala
        35                  40                  45

Ile Ala Trp Leu Leu Gly Ser Ser Thr Ser Gln Lys Val Ile Tyr Leu
    50                  55                  60

Val Met Ile Leu Leu Ile Ala Pro Ala Tyr Ser Ile Arg Cys Ile Gly
```

-continued

```
             65                  70                  75                  80
        Val Ser Asn Arg Asp Phe Val Glu Gly Met Ser Gly Gly Thr Trp Val
                         85                  90                  95

Asp Val Val Leu Glu His Gly Gly Cys Val Thr Val Met Ala Gln Asp
                    100                 105                 110

Lys Pro Thr Val Asp Ile Glu Leu Val Thr Thr Thr Val Ser Asn Met
                115                 120                 125

Ala Glu Val Arg Ser Tyr Cys Tyr Glu Ala Ser Ile Ser Asp Met Ala
            130                 135                 140

Ser Asp Ser Arg Cys Pro Thr Gln Gly Glu Ala Tyr Leu Asp Lys Gln
        145                 150                 155                 160

Ser Asp Thr Gln Tyr Val Cys Lys Arg Thr Leu Val Asp Arg Gly Trp
                        165                 170                 175

Gly Asn Gly Cys Gly Leu Phe Gly Lys Gly Ser Leu Val Thr Cys Ala
                    180                 185                 190

Lys Phe Ala Cys Ser Lys Lys Met Thr Gly Lys Ser Ile Gln Pro Glu
                195                 200                 205

Asn Leu Glu Tyr Arg Ile Met Leu Ser Val His Gly Ser Gln His Ser
            210                 215                 220

Gly Met Ile Val Asn Asp Thr Gly His Glu Thr Asp Glu Asn Arg Ala
        225                 230                 235                 240

Lys Val Glu Ile Thr Pro Asn Ser Pro Arg Ala Glu Ala Thr Leu Gly
                        245                 250                 255

Gly Phe Gly Ser Leu Gly Leu Asp Cys Glu Pro Arg Thr Gly Leu Asp
                    260                 265                 270

Phe Ser Asp Leu Tyr Tyr Leu Thr Met Asn Asn Lys His Trp Leu Val
                275                 280                 285

His Lys Glu Trp Phe His Asp Ile Pro Leu Pro Trp His Ala Gly Ala
            290                 295                 300

Asp Thr Gly Thr Pro His Trp Asn Asn Lys Glu Ala Leu Val Glu Phe
        305                 310                 315                 320

Lys Asp Ala His Ala Lys Arg Gln Thr Val Val Leu Gly Ser Gln
                        325                 330                 335

Glu Gly Ala Val His Thr Ala Leu Ala Gly Ala Leu Glu Ala Glu Met
                    340                 345                 350

Asp Gly Ala Lys Gly Arg Leu Ser Ser Gly His Leu Lys Cys Arg Leu
                355                 360                 365

Lys Met Asp Lys Leu Arg Leu Lys Gly Val Ser Tyr Ser Leu Cys Thr
            370                 375                 380

Ala Ala Phe Thr Phe Thr Lys Ile Pro Ala Glu Thr Leu His Gly Thr
        385                 390                 395                 400

Val Thr Val Glu Val Gln Tyr Ala Gly Thr Asp Gly Pro Cys Lys Val
                        405                 410                 415

Pro Ala Gln Met Ala Val Asp Met Gln Thr Leu Thr Pro Val Gly Arg
                    420                 425                 430

Leu Ile Thr Ala Asn Pro Val Ile Thr Glu Ser Thr Glu Asn Ser Lys
                435                 440                 445

Met Met Leu Glu Leu Asp Pro Pro Phe Gly Asp Ser Tyr Ile Val Ile
            450                 455                 460

Gly Val Gly Glu Lys Lys Ile Thr His His Trp His Arg Ser Gly Ser
        465                 470                 475                 480

Thr Ile Gly Lys Ala Phe Glu Ala Thr Val Arg Gly Ala Lys Arg Met
                        485                 490                 495
```

Ala Val Leu Gly Asp Thr Ala Trp Asp Phe Gly Ser Val Gly Gly Ala
        500                 505                 510

Leu Asn Ser Leu Gly Lys Gly
        515

<210> SEQ ID NO 5
<211> LENGTH: 1449
<212> TYPE: DNA
<213> ORGANISM: Artificial Sequence
<220> FEATURE:
<223> OTHER INFORMATION: Synthetic construct

<400> SEQUENCE: 5
gctgtgacac tgcctagcca cagcacccgg aagctgcaga ccagaagcca gacctggctg     60
gaaagcagag agtacaccaa gcacctgatc cgggtggaaa actggatctt ccggaacccc    120
ggcttcgccc tggccgctgc tgctattgct tggctgctgg gcagcagcac cagccagaaa    180
gtgatctacc tcgtgatgat cctgctgatc gcccctgcct acagcatccg gtgtatcggc    240
gtgtccaacc gggacttcgt ggaaggcatg agcggcggca catgggtgga cgtggtgctg    300
gaacatggcg gctgcgtgac agtgatggcc caggacaagc ccaccgtgga catcgagctc    360
gtgaccacca ccgtgtccaa tatggccgaa gtgcggagct actgctacga ggccagcatc    420
agcgacatgg ccagcgacag cagatgccct acacagggcg aggcctacct ggacaagcag    480
tccgacaccc agtacgtgtg caagcggacc ctggtggata gaggctgggg caatggctgc    540
ggcctgtttg gcaagggcag cctcgtgacc tgcgccaagt tcgcctgcag caagaagatg    600
accggcaaga gcatccagcc cgagaacctg aataccggat catgctgag cgtgcacggc    660 agccagcact ccggcatgat cgtgaacgac accggccacg agacagacga gaaccgggcc    720
aaggtggaaa tcaccccaa cagccctaga gccgaggcca cactgggcgg ctttggatct    780
ctgggcctgg actgcgagcc tagaaccggc ctggatttca gcgacctgta ctacctgacc    840
atgaacaaca aacactggct ggtgcacaaa gagtggttcc acgacatccc cctgccctgg    900
catgccggcg ctgatacagg cacccccac tggaacaaca agagggccct ggtggagttc    960
aaggacgccc acgccaagag gcagaccgtg gtggtgctgg atctcagga aggcgccgtg   1020 catacagctc tggctggcgc cctggaagcc gaaatggatg cgctaaggg cagactgtcc   1080 agcggccacc tgaagtgccg gctgaagatg gacaagctgc ggctgaaggg cgtgtcctac   1140
agcctgtgta ccgccgcctt caccttcacc aagatccccg ccgagacact gcacggcacc   1200
gtgactgtgg aagtgcagta cgccggcacc gacggccctt gtaaagtgcc tgctcagatg   1260
gccgtggata tgcagaccct gaccctgtg ggcaggctga tcaccgccaa ccctgtgatc   1320
accgagagca ccgagaacag caagatgatg ctggaactgg acccacccct cggcgacagc   1380
tacatcgtga tcggcgtggg agagaagaag atcacccacc actggcacag aagcggcagc   1440
accatctga                                                           1449

<210> SEQ ID NO 6
<211> LENGTH: 482
<212> TYPE: PRT
<213> ORGANISM: Artificial Sequence
<220> FEATURE:
<223> OTHER INFORMATION: Synthetic construct

<400> SEQUENCE: 6

Ala Val Thr Leu Pro Ser His Ser Thr Arg Lys Leu Gln Thr Arg Ser
1               5                   10                  15

Gln Thr Trp Leu Glu Ser Arg Glu Tyr Thr Lys His Leu Ile Arg Val
            20                  25                  30

Glu Asn Trp Ile Phe Arg Asn Pro Gly Phe Ala Leu Ala Ala Ala Ala
        35                  40                  45

Ile Ala Trp Leu Leu Gly Ser Ser Thr Ser Gln Lys Val Ile Tyr Leu
 50                  55                  60

Val Met Ile Leu Leu Ile Ala Pro Ala Tyr Ser Ile Arg Cys Ile Gly
 65                  70                  75                  80

Val Ser Asn Arg Asp Phe Val Glu Gly Met Ser Gly Gly Thr Trp Val
                85                  90                  95

Asp Val Val Leu Glu His Gly Gly Cys Val Thr Val Met Ala Gln Asp
            100                 105                 110

Lys Pro Thr Val Asp Ile Glu Leu Val Thr Thr Thr Val Ser Asn Met
        115                 120                 125

Ala Glu Val Arg Ser Tyr Cys Tyr Glu Ala Ser Ile Ser Asp Met Ala
130                 135                 140

Ser Asp Ser Arg Cys Pro Thr Gln Gly Glu Ala Tyr Leu Asp Lys Gln
145                 150                 155                 160

Ser Asp Thr Gln Tyr Val Cys Lys Arg Thr Leu Val Asp Arg Gly Trp
                165                 170                 175

Gly Asn Gly Cys Gly Leu Phe Gly Lys Gly Ser Leu Val Thr Cys Ala
            180                 185                 190

Lys Phe Ala Cys Ser Lys Lys Met Thr Gly Lys Ser Ile Gln Pro Glu
        195                 200                 205

Asn Leu Glu Tyr Arg Ile Met Leu Ser Val His Gly Ser Gln His Ser
210                 215                 220

Gly Met Ile Val Asn Asp Thr Gly His Glu Thr Asp Glu Asn Arg Ala
225                 230                 235                 240

Lys Val Glu Ile Thr Pro Asn Ser Pro Arg Ala Glu Ala Thr Leu Gly
                245                 250                 255

Gly Phe Gly Ser Leu Gly Leu Asp Cys Glu Pro Arg Thr Gly Leu Asp
            260                 265                 270

Phe Ser Asp Leu Tyr Tyr Leu Thr Met Asn Asn Lys His Trp Leu Val
        275                 280                 285

His Lys Glu Trp Phe His Asp Ile Pro Leu Pro Trp His Ala Gly Ala
290                 295                 300

Asp Thr Gly Thr Pro His Trp Asn Asn Lys Glu Ala Leu Val Glu Phe
305                 310                 315                 320

Lys Asp Ala His Ala Lys Arg Gln Thr Val Val Leu Gly Ser Gln
                325                 330                 335

Glu Gly Ala Val His Thr Ala Leu Ala Gly Ala Leu Glu Ala Glu Met
            340                 345                 350

Asp Gly Ala Lys Gly Arg Leu Ser Ser Gly His Leu Lys Cys Arg Leu
        355                 360                 365

Lys Met Asp Lys Leu Arg Leu Lys Gly Val Ser Tyr Ser Leu Cys Thr
370                 375                 380

Ala Ala Phe Thr Phe Thr Lys Ile Pro Ala Glu Thr Leu His Gly Thr
385                 390                 395                 400

Val Thr Val Glu Val Gln Tyr Ala Gly Thr Asp Gly Pro Cys Lys Val
                405                 410                 415

Pro Ala Gln Met Ala Val Asp Met Gln Thr Leu Thr Pro Val Gly Arg
            420                 425                 430

Leu Ile Thr Ala Asn Pro Val Ile Thr Glu Ser Thr Glu Asn Ser Lys
         435                 440                 445

Met Met Leu Glu Leu Asp Pro Pro Phe Gly Asp Ser Tyr Ile Val Ile
    450                 455                 460

Gly Val Gly Glu Lys Lys Ile Thr His His Trp His Arg Ser Gly Ser
465                 470                 475                 480

Thr Ile

<210> SEQ ID NO 7
<211> LENGTH: 1515
<212> TYPE: DNA
<213> ORGANISM: Artificial Sequence
<220> FEATURE:
<223> OTHER INFORMATION: Synthetic construct

<400> SEQUENCE: 7

```
atcagatgca tcggcgtgtc aaccgggac ttcgtggaag gcatgagcgg cggcacatgg       60
gtggacgtgg tgctggaaca tggcggctgc gtgacagtga tggcccagga caagcccacc      120
gtggacatcg agctcgtgac caccaccgtg tccaatatgg ccgaagtgcg gagctactgc      180
tacgaggcca gcatcagcga catggccagc gacagcagat gccctacaca gggcgaggcc      240
tacctggaca gcagagcga cacccagtac gtgtgcaagc ggaccctggt ggatagaggc       300
tggggcaatg gctgcggcct gtttggcaag ggcagcctcg tgacctgcgc caagttcgcc      360
tgcagcaaga agatgaccgg caagagcatc cagcccgaga acctggaata ccggatcatg      420
ctgagcgtgc acggcagcca gcactccggc atgatcgtga cgacaccgg ccacgagaca       480
gacgagaacc gggccaaggt ggaaatcacc cccaacagcc ctagagccga ggccacactg      540
ggcggctttg gatctctggg cctggactgc gagcctagaa ccggcctgga tttcagcgac      600
ctgtactacc tgaccatgaa caacaagcac tggctggtgc acaaagagtg gttccacgac      660
atcccccctgc cctggcatgc tggcgctgat acaggcaccc ctcactggaa caacaaagag      720
gctctggtgg agttcaagga cgcccacgcc aagaggcaga ccgtggtggt gctgggatct      780
caggaaggcg ccgtgcatac agctctggct ggcgccctgg aagccgaaat ggatggcgct      840
aagggcagac tgagcagcgg ccacctgaag tgccggctga gatggacaa gctgcggctg       900
aagggcgtgt cctacagcct gtgtaccgcc gccttcacct tcaccaagat ccccgccgag      960
acactgcacg gcaccgtgac tgtggaagtg cagtacgccg gcaccgacgg ccttgtaaa      1020
gtgcctgctc agatggccgt ggatatgcag accctgaccc ctgtgggcag gctgatcacc     1080
gccaaccctg tgatcaccga gagcaccgag aacagcaaga tgatgctgga actggaccca     1140
cccttcggcg acagctacat cgtgatcggc gtgggagaga agaagatcac ccaccactgg     1200
cacagaagcg gcagcaccat cggcaaggcc tttgaggcta cagtgcgggg agccaagaga     1260
atggccgtgc tgggagatac cgcctgggac tttggctctg tgggcggagc cctgaactct     1320
ctgggcaagg gaatccacca gatcttcggc gctgccttca gagcctgtt cggcggcatg      1380
agctggttca gccagatcct gatcggcacc ctgctgatgt ggctgggcct gaacaccaag     1440
aacggctcca tcagcctgat gtgcctggct ctgggaggcg tgctgatctt cctgagcaca     1500
gccgtgtccg cctga                                                      1515
```

<210> SEQ ID NO 8
<211> LENGTH: 504
<212> TYPE: PRT
<213> ORGANISM: Artificial Sequence
<220> FEATURE:

<223> OTHER INFORMATION: Synthetic construct

<400> SEQUENCE: 8

```
Ile Arg Cys Ile Gly Val Ser Asn Arg Asp Phe Val Glu Gly Met Ser
1               5                   10                  15
Gly Gly Thr Trp Val Asp Val Val Leu Glu His Gly Gly Cys Val Thr
            20                  25                  30
Val Met Ala Gln Asp Lys Pro Thr Val Asp Ile Glu Leu Val Thr Thr
        35                  40                  45
Thr Val Ser Asn Met Ala Glu Val Arg Ser Tyr Cys Tyr Glu Ala Ser
    50                  55                  60
Ile Ser Asp Met Ala Ser Asp Ser Arg Cys Pro Thr Gln Gly Glu Ala
65                  70                  75                  80
Tyr Leu Asp Lys Gln Ser Asp Thr Gln Tyr Val Cys Lys Arg Thr Leu
                85                  90                  95
Val Asp Arg Gly Trp Gly Asn Gly Cys Gly Leu Phe Gly Lys Gly Ser
            100                 105                 110
Leu Val Thr Cys Ala Lys Phe Ala Cys Ser Lys Lys Met Thr Gly Lys
        115                 120                 125
Ser Ile Gln Pro Glu Asn Leu Glu Tyr Arg Ile Met Leu Ser Val His
    130                 135                 140
Gly Ser Gln His Ser Gly Met Ile Val Asn Asp Thr Gly His Glu Thr
145                 150                 155                 160
Asp Glu Asn Arg Ala Lys Val Glu Ile Thr Pro Asn Ser Pro Arg Ala
                165                 170                 175
Glu Ala Thr Leu Gly Gly Phe Gly Ser Leu Gly Leu Asp Cys Glu Pro
            180                 185                 190
Arg Thr Gly Leu Asp Phe Ser Asp Leu Tyr Tyr Leu Thr Met Asn Asn
        195                 200                 205
Lys His Trp Leu Val His Lys Glu Trp Phe His Asp Ile Pro Leu Pro
    210                 215                 220
Trp His Ala Gly Ala Asp Thr Gly Thr Pro His Trp Asn Asn Lys Glu
225                 230                 235                 240
Ala Leu Val Glu Phe Lys Asp Ala His Ala Lys Arg Gln Thr Val Val
                245                 250                 255
Val Leu Gly Ser Gln Glu Gly Ala Val His Thr Ala Leu Ala Gly Ala
            260                 265                 270
Leu Glu Ala Glu Met Asp Gly Ala Lys Gly Arg Leu Ser Ser Gly His
        275                 280                 285
Leu Lys Cys Arg Leu Lys Met Asp Lys Leu Arg Leu Lys Gly Val Ser
    290                 295                 300
Tyr Ser Leu Cys Thr Ala Ala Phe Thr Phe Thr Lys Ile Pro Ala Glu
305                 310                 315                 320
Thr Leu His Gly Thr Val Thr Val Glu Val Gln Tyr Ala Gly Thr Asp
                325                 330                 335
Gly Pro Cys Lys Val Pro Ala Gln Met Ala Val Asp Met Gln Thr Leu
            340                 345                 350
Thr Pro Val Gly Arg Leu Ile Thr Ala Asn Pro Val Ile Thr Glu Ser
        355                 360                 365
Thr Glu Asn Ser Lys Met Met Leu Glu Leu Asp Pro Pro Phe Gly Asp
    370                 375                 380
Ser Tyr Ile Val Ile Gly Val Gly Glu Lys Lys Ile Thr His His Trp
385                 390                 395                 400
```

```
His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 9
<211> LENGTH: 1335
<212> TYPE: DNA
<213> ORGANISM: Artificial Sequence
<220> FEATURE:
<223> OTHER INFORMATION: Synthetic construct

<400> SEQUENCE: 9

```
atcagatgca tcggcgtgtc caaccgggac ttcgtggaag gcatgagcgg cggcacatgg      60
gtggacgtgg tgctggaaca tggcggctgc gtgacagtga tgcccagga caagcccacc     120
gtggacatcg agctcgtgac caccaccgtg tccaatatgg ccgaagtgcg gagctactgc    180
tacgaggcca gcatcagcga catggccagc gacagcagat gccctacaca gggcgaggcc    240
tacctggaca gcagagcga cacccagtac gtgtgcaagc ggaccctggt ggatagaggc    300
tggggcaatg gctgcggcct gtttggcaag gcagcctcg tgacctgcgc caagttcgcc     360
tgcagcaaga gatgaccgg caagagcatc cagcccgaga acctggaata ccggatcatg     420
ctgagcgtgc acggcagcca gcactccggc atgatcgtga cgacaccgg ccacgagaca     480
gacgagaacc gggccaaggt ggaaatcacc cccaacagcc ctagagccga ggccacactg    540
ggcggctttg gatctctggg cctggactgc gagcctagaa ccggcctgga tttcagcgac    600
ctgtactacc tgaccatgaa caacaagcac tggctggtgc acaaagagtg gttccacgac    660
atccccctgc cctggcatgc tggcgctgat acaggcaccc ctcactgaa caacaaagag    720
gctctggtgg agttcaagga cgcccacgcc aagaggcaga ccgtggtggt gctgggatct    780
caggaaggcg ccgtgcatac agctctggct ggcgccctgg aagccgaaat ggatggcgct    840
aagggcagac tgagcagcgg ccacctgaag tgccggctga agatggacaa gctgcggctg    900
aagggcgtgt cctacagcct gtgtaccgcc gccttcacct tcaccaagat ccccgccgag    960
acactgcacg gcaccgtgac tgtggaagtg cagtacgccg gcaccgacgg ccccttgtaaa   1020
gtgcctgctc agatggccgt ggatatgcag accctgaccc ctgtgggcag gctgatcacc   1080
gccaaccctg tgatcaccga gagcaccgag aacagcaaga tgatgctgga actggaccca   1140
cccttcggcg acagctacat cgtgatcggc gtgggagaga agaagatcac ccaccactgg   1200
cacagaagcg gcagcaccat cggcaaggcc tttgaggcta cagtgcgggg agccaagaga   1260
atggccgtgc tgggagatac cgcctggac tttggctctg tgggcggagc cctgaactct   1320
ctgggcaagg gatga                                                    1335
```

<210> SEQ ID NO 10

<211> LENGTH: 444
<212> TYPE: PRT
<213> ORGANISM: Artificial Sequence
<220> FEATURE:
<223> OTHER INFORMATION: Synthetic construct

<400> SEQUENCE: 10

```
Ile Arg Cys Ile Gly Val Ser Asn Arg Asp Phe Val Glu Gly Met Ser
1               5                   10                  15
Gly Gly Thr Trp Val Asp Val Val Leu Glu His Gly Gly Cys Val Thr
            20                  25                  30
Val Met Ala Gln Asp Lys Pro Thr Val Asp Ile Glu Leu Val Thr Thr
        35                  40                  45
Thr Val Ser Asn Met Ala Glu Val Arg Ser Tyr Cys Tyr Glu Ala Ser
50                  55                  60
Ile Ser Asp Met Ala Ser Asp Ser Arg Cys Pro Thr Gln Gly Glu Ala
65                  70                  75                  80
Tyr Leu Asp Lys Gln Ser Asp Thr Gln Tyr Val Cys Lys Arg Thr Leu
                85                  90                  95
Val Asp Arg Gly Trp Gly Asn Gly Cys Gly Leu Phe Gly Lys Gly Ser
            100                 105                 110
Leu Val Thr Cys Ala Lys Phe Ala Cys Ser Lys Lys Met Thr Gly Lys
        115                 120                 125
Ser Ile Gln Pro Glu Asn Leu Glu Tyr Arg Ile Met Leu Ser Val His
130                 135                 140
Gly Ser Gln His Ser Gly Met Ile Val Asn Asp Thr Gly His Glu Thr
145                 150                 155                 160
Asp Glu Asn Arg Ala Lys Val Glu Ile Thr Pro Asn Ser Pro Arg Ala
                165                 170                 175
Glu Ala Thr Leu Gly Gly Phe Gly Ser Leu Gly Leu Asp Cys Glu Pro
            180                 185                 190
Arg Thr Gly Leu Asp Phe Ser Asp Leu Tyr Tyr Leu Thr Met Asn Asn
        195                 200                 205
Lys His Trp Leu Val His Lys Glu Trp Phe His Asp Ile Pro Leu Pro
210                 215                 220
Trp His Ala Gly Ala Asp Thr Gly Thr Pro His Trp Asn Asn Lys Glu
225                 230                 235                 240
Ala Leu Val Glu Phe Lys Asp Ala His Ala Lys Arg Gln Thr Val Val
                245                 250                 255
Val Leu Gly Ser Gln Glu Gly Ala Val His Thr Ala Leu Ala Gly Ala
            260                 265                 270
Leu Glu Ala Glu Met Asp Gly Ala Lys Gly Arg Leu Ser Ser Gly His
        275                 280                 285
Leu Lys Cys Arg Leu Lys Met Asp Lys Leu Arg Leu Lys Gly Val Ser
290                 295                 300
Tyr Ser Leu Cys Thr Ala Ala Phe Thr Phe Thr Lys Ile Pro Ala Glu
305                 310                 315                 320
Thr Leu His Gly Thr Val Thr Val Glu Val Gln Tyr Ala Gly Thr Asp
                325                 330                 335
Gly Pro Cys Lys Val Pro Ala Gln Met Ala Val Asp Met Gln Thr Leu
            340                 345                 350
Thr Pro Val Gly Arg Leu Ile Thr Ala Asn Pro Val Ile Thr Glu Ser
        355                 360                 365
Thr Glu Asn Ser Lys Met Met Leu Glu Leu Asp Pro Pro Phe Gly Asp
370                 375                 380
```

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
            405                 410                 415

Gly Ala Lys Arg Met Ala Val Leu Gly Asp Thr Ala Trp Asp Phe Gly
        420                 425                 430

Ser Val Gly Gly Ala Leu Asn Ser Leu Gly Lys Gly
    435                 440

<210> SEQ ID NO 11
<211> LENGTH: 1224
<212> TYPE: DNA
<213> ORGANISM: Artificial Sequence
<220> FEATURE:
<223> OTHER INFORMATION: Synthetic construct

<400> SEQUENCE: 11
atcagatgca tcggcgtgtc aaccgggac ttcgtggaag gcatgagcgg cggcacatgg      60
gtggacgtgg tgctggaaca tggcggctgc gtgacagtga tggcccagga caagcccacc     120
gtggacatcg agctcgtgac caccaccgtg tccaatatgg ccgaagtgcg gagctactgc     180
tacgaggcca gcatcagcga catggccagc gacagcagat gccctacaca gggcgaggcc     240
tacctggaca gcagagcga cacccagtac gtgtgcaagc ggaccctggt ggatagaggc     300
tggggcaatg gctgcggcct gtttggcaag ggcagcctcg tgacctgcgc caagttcgcc     360
tgcagcaaga gatgaccgg caagagcatc cagcccgaga acctggaata ccggatcatg     420
ctgagcgtgc acggcagcca gcactccggc atgatcgtga cgacaccgg ccacgagaca     480 gacgagaacc gggccaaggt ggaaatcacc cccaacagcc ctagagccga ggccacactg     540
ggcggctttg gatctctggg cctggactgc gagcctagaa ccggcctgga tttcagcgac     600
ctgtactacc tgaccatgaa caacaagcac tggctggtgc acaaagagtg gttccacgac     660
atccccctgc cctggcatgc tggcgctgat acaggcaccc ctcactggaa caacaaagag     720
gctctggtgg agttcaagga cgcccacgcc aagaggcaga ccgtggtggt gctgggatct     780
caggaaggcg ccgtgcatac agctctggct ggcgccctgg aagccgaaat ggatggcgct     840
aagggcagac tgagcagcgg ccacctgaag tgccggctga gatggacaa gctgcggctg     900 aagggcgtgt cctacagcct gtgtaccgcc gccttcacct tcaccaagat ccccgccgag     960
acactgcacg gcaccgtgac tgtggaagtg cagtacgccg gcaccgacgg ccccttgtaaa    1020 gtgcctgctc agatggccgt ggatatgcag accctgaccc ctgtgggcag gctgatcacc    1080
gccaaccctg tgatcaccga gagcaccgag aacagcaaga tgatgctgga actggacca     1140 cccttcggcg acagctacat cgtgatcggc gtgggagaga agaagatcac ccaccactgg    1200
cacagaagcg gcagcaccat ctga                                            1224

<210> SEQ ID NO 12
<211> LENGTH: 407
<212> TYPE: PRT
<213> ORGANISM: Artificial Sequence
<220> FEATURE:
<223> OTHER INFORMATION: Synthetic construct

<400> SEQUENCE: 12

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr

```
            20                  25                  30
Val Met Ala Gln Asp Lys Pro Thr Val Asp Ile Glu Leu Val Thr Thr
            35                  40                  45

Thr Val Ser Asn Met Ala Glu Val Arg Ser Tyr Cys Tyr Glu Ala Ser
 50                  55                  60

Ile Ser Asp Met Ala Ser Asp Ser Arg Cys Pro Thr Gln Gly Glu Ala
 65                  70                  75                  80

Tyr Leu Asp Lys Gln Ser Asp Thr Gln Tyr Val Cys Lys Arg Thr Leu
                 85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
            115                 120                 125

Ser Ile Gln Pro Glu Asn Leu Glu Tyr Arg Ile Met Leu Ser Val His
            130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
                180                 185                 190

Arg Thr Gly Leu Asp Phe Ser Asp Leu Tyr Tyr Leu Thr Met Asn Asn
            195                 200                 205

Lys His Trp Leu Val His Lys Glu Trp Phe His Asp Ile Pro Leu Pro
            210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
                260                 265                 270

Leu Glu Ala Glu Met Asp Gly Ala Lys Gly Arg Leu Ser Ser Gly His
            275                 280                 285

Leu Lys Cys Arg Leu Lys Met Asp Lys Leu Arg Leu Lys Gly Val Ser
            290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
                340                 345                 350

Thr Pro Val Gly Arg Leu Ile Thr Ala Asn Pro Val Ile Thr Glu Ser
            355                 360                 365

Thr Glu Asn Ser Lys Met Met Leu Glu Leu Asp Pro Pro Phe Gly Asp
            370                 375                 380

Ser Tyr Ile Val Ile Gly Val Gly Glu Lys Lys Ile Thr His His Trp
385                 390                 395                 400

His Arg Ser Gly Ser Thr Ile
                405

<210> SEQ ID NO 13
<211> LENGTH: 72
<212> TYPE: DNA
<213> ORGANISM: Artificial Sequence
```

<220> FEATURE:
<223> OTHER INFORMATION: Synthetic construct

<400> SEQUENCE: 13

| | | | | | |
|---|---|---|---|---|---|
| atgggcaaaa | gatccgccgg | cagcatcatg | tggctggcca | gtctggctgt | cgtgatcgcc | 60 |
| tgtgctggcg | cc | | | | | 72 |

<210> SEQ ID NO 14
<211> LENGTH: 24
<212> TYPE: PRT
<213> ORGANISM: Artificial Sequence
<220> FEATURE:
<223> OTHER INFORMATION: Synthetic construct

<400> SEQUENCE: 14

Met Gly Lys Arg Ser Ala Gly Ser Ile Met Trp Leu Ala Ser Leu Ala
1               5                   10                  15

Val Val Ile Ala Cys Ala Gly Ala
            20

<210> SEQ ID NO 15
<211> LENGTH: 10662
<212> TYPE: DNA
<213> ORGANISM: Artificial Sequence
<220> FEATURE:
<223> OTHER INFORMATION: Synthetic construct

<400> SEQUENCE: 15

| | | | | | |
|---|---|---|---|---|---|
| gtgaatcaga | ctgcgacagt | tcgagtttga | agcgaaagct | agcaacagta | tcaacaggtt | 60 |
| ttattttgga | tttggaaacg | agagtttctg | gtcatgaaaa | acccaaaaaa | gaaatccgga | 120 |
| ggattccgga | ttgtcaatat | gctaaaacgc | ggagtagccc | gtgtgagccc | ctttgggggc | 180 |
| ttgaagaggc | tgccagccgg | acttctgctg | ggtcatgggc | ccatcaggat | ggtcttggcg | 240 |
| attctagcct | ttttgagatt | cacggcaatc | aagccatcac | tgggtctcat | caatagatgg | 300 |
| ggttcagtgg | ggaaaaaaga | ggctatggaa | ataataaaga | agttcaagaa | agatctggct | 360 |
| gccatgctga | gaataatcaa | tgctaggaag | gagaagaaga | gacgaggcgc | agatactagt | 420 |
| gtcggaattg | ttggcctcct | gctgaccaca | gctatggcag | cggaggtcac | tagacgtggg | 480 |
| agtgcatact | atatgtactt | ggacagaaac | gatgctgggg | aggccatatc | ttttccaacc | 540 |
| acattgggga | tgaataagtg | ttatatacag | atcatggatc | ttggacacat | gtgtgatgcc | 600 |
| accatgagct | atgaatgccc | tatgctggat | gaggggtgg | aaccagatga | cgtcgattgt | 660 |
| tggtgcaaca | cgacgtcaac | ttgggttgtg | tacggaacct | gccatcacaa | aaaaggtgaa | 720 |
| gcacggagat | ctagaagagc | tgtgacgctc | ccctcccatt | ccactaggaa | gctgcaaacg | 780 |
| cggtcgcaaa | cctggttgga | atcaagagaa | tacacaaagc | acttgattag | agtcgaaaat | 840 |
| tggatattta | ggaaccctgg | cttcgcgtta | gcagcagctg | ccatcgcttg | gcttttggga | 900 |
| agctcaacga | gccaaaaagt | catatacttg | gtcatgatac | tgctgattgc | cccggcatac | 960 |
| agcatcaggt | gcataggagt | cagcaatagg | gactttgtgg | aaggtatgtc | aggtgggacc | 1020 |
| tgggttgatg | ttgtcttgga | acatggaggt | tgtgtcaccg | taatggcaca | ggacaaaccg | 1080 |
| actgtcgaca | tagagctggt | tacaacaaca | gtcagcaaca | tggcggaggt | aagatcctac | 1140 |
| tgctatgagg | catcaatatc | agacatggct | tcggacagcc | gctgcccaac | acaaggtgaa | 1200 |
| gcctaccttg | acaagcaatc | agacactcaa | tatgtctgca | aaagaacgtt | agtggacaga | 1260 |
| ggctgggga | atggatgtgg | acttttggc | aaagggagcc | tggtgacatg | cgctaagttt | 1320 |

```
gcatgctcca agaaaatgac cgggaagagc atccagccag agaatctgga gtaccggata      1380
atgctgtcag ttcatggctc ccagcacagt gggatgattg ttaatgacac aggacatgaa      1440
actgatgaga atagagcgaa agttgagata acgcccaatt caccaagagc cgaagccacc      1500
ctggggggtt ttggaagcct aggacttgat tgtgaaccga ggacaggcct tgacttttca      1560
gatttgtatt acttgactat gaataacaag cactggttgg ttcacaagga gtggttccac      1620
gacattccat taccttggca cgctggggca gacaccggaa ctccacactg gaacaacaaa      1680
gaagcactgg tagagttcaa ggacgcacat gccaaaaggc aaactgtcgt ggttctaggg      1740
agtcaagaag gagcagttca cacggcccct gctggagctc tggaggctga gatggatggt      1800
gcaaagggaa ggctgtcctc tggccacttg aaatgtcgcc tgaaaatgga taaacttaga      1860
ttgaagggcg tgtcatactc cttgtgtact gcagcgttca cattcaccaa gatcccggct      1920
gaaacactgc acgggacagt cacagtggag gtacagtacg cagggacaga tggaccttgc      1980
aaggttccag ctcagatggc ggtgacacat gcaaactctga ccccagttgg gaggttgata      2040
accgctaacc ccgtaatcac tgaaagcact gagaactcta agatgatgct ggaacttgat      2100
ccaccatttg gggactctta cattgtcata ggagtcgggg agaagaagat cacccaccac      2160
tggcacagga gtgcagcac cattggaaaa gcatttgaag ccactgtgag aggtgccaag      2220
agaatggcag tcttgggaga cacagcctgg gactttggat cagttggagg cgctctcaac      2280
tcattgggca agggcatcca tcaaatttttt ggagcagctt tcaaatcatt gtttggagga      2340
atgtcctggt tctcacaaat tctcattgga acgttgctga tgtggttggg tctgaacaca      2400
aagaatggat ctatttccct tatgtgcttg gccttagggg gagtgttgat cttcttatcc      2460
acagccgtct ctgctgatgt ggggtgctcg gtggacttct caagaaggga gacgagatgc      2520
ggtacagggg tgttcgtcta taacgacgtt gaagcctgga gggacaggta caagtaccat      2580
cctgactccc cccgtagatt ggcagcagca gtcaagcaag cctgggaaga tggtatctgc      2640
gggatctcct ctgttttcaag aatggaaaac atcatgtgga gatcagtaga agggagctc      2700
aacgcaatcc tggaagagaa tggagttcaa ctgacggtcg ttgtgggatc tgtaaaaaac      2760
cccatgtgga gaggtccaca gagattgccc gtgcctgtga acgagctgcc ccacggctgg      2820
aaggcttggg ggaaatcgta cttcgtcaga gcagcaaaga caaataacag ctttgtcgtg      2880
gatggtgaca cactgaagga atgcccactc aaacatagag catggaacag ctttcttgtg      2940
gaggatcatg ggttcggggt atttcacact agtgtctggc tcaaggttag agaagattat      3000
tcattagagt gtgatccagc cgttattgga acagctgtta agggaaagga ggctgtacac      3060
agtgatctag ctactggat tgagagtgag aagaatgaca catggaggct gaagagggcc      3120
catctgatcg agatgaaaac atgtgaatgg ccaaagtccc acacattgtg gacagatgga      3180
atagaagaga gtgatctgat catacccaag tctttagctg ggccactcag ccatcacaat      3240
accagagagg gctacaggac ccaaatgaaa gggccatggc acagtgaaga gcttgaaatt      3300
cggtttgagg aatgcccagg cactaaggtc cacgtggagg aaacatgtgg aacaagagga      3360
ccatctctga gatcaaccac tgcaagcgga agggtgatcg aggaatggtg ctgcagggag      3420
tgcacaatgc ccccactgtc gttccgggct aaagatggct gttggtatgg aatggagata      3480
aggcccagga agaaccagaa agcaacttta gtaaggtcaa tggtgactgc aggatcaact      3540
gatcacatgg accacttctc ccttggagtg cttgtgattc tgctcatggt gcaggaaggg      3600
ctgaagaaga gaatgaccac aaaagatcatc ataagcacat caatggcagt gctggtagct      3660
atgatcctgg gaggattttc aatgagtgac ctggctaagc ttgcaatttt gatgggtgcc      3720
```

```
accttcgcgg aaatgaacac tggaggagat gtagctcatc tggcgctgat agcggcattc    3780
aaagtcagac cagcgttgct ggtatctttc atcttcagag ctaattggac accccgtgaa    3840
agcatgctgc tggccttggc ctcgtgtctt ttgcaaactg cgatctccgc cttggaaggc    3900
gacctgatgg ttctcatcaa tggttttgct ttggcctggt tggcaatacg agcgatggtt    3960
gttccacgca ctgataacat caccttggca atcctggctg ctctgacacc actggcccgg    4020
ggcacactgc ttgtggcgtg gagagcaggc cttgctactt gcgggggggtt tatgctcctc    4080 tctctgaagg gaaaaggcag tgtgaagaag aacttaccat tgtcatggc cctgggacta    4140 accgctgtga ggctggtcga ccccatcaac gtggtgggac tgctgttgct cacaaggagt    4200
gggaagcgga gctggccccc tagcgaagta ctcacagctg ttggcctgat atgcgcattg    4260
gctggagggt tcgccaaggc agatatagag atggctgggc ccatggccgc ggtcggtctg    4320
ctaattgtca gttacgtggt ctcaggaaag agtgtggaca tgtacattga aagagcaggt    4380
gacatcacat gggaaaaaga tgcggaagtc actggaaaca gtccccggct cgatgtggcg    4440
ctagatgaga gtggtgattt ctccctggtg gaggatgacg gtccccccat gagagagatc    4500
atactcaagg tggtcctgat gaccatctgt ggcatgaacc caatagccat accctttgca    4560
gctggagcgt ggtacgtata cgtgaagact ggaaaaagga gtggtgctct atgggatgtg    4620
cctgctccca aggaagtaaa aaaggggggag accacagatg gagtgtacag agtaatgact    4680
cgtagactgc taggttcaac acaagttgga gtgggagtta tgcaagaggg ggtcttttcac    4740 actatgtggc acgtcacaaa aggatccgcg ctgagaagcg gtgaagggag acttgatcca    4800
tactggggag atgtcaagca ggatctggtg tcatactgtg gtccatggaa gctagatgcc    4860
gcctgggacg gcacagcgga ggtgcagctc ttggccgtgc cccccggaga gagagcgagg    4920
aacatccaga ctctgcccgg aatatttaag acaaaggatg gggacattgg agcggttgcg    4980
ctggattacc cagcaggaac ttcaggatct ccaatcctag acaagtgtgg gagagtgata    5040
ggactttatg gcaatggggt cgtgatcaaa aatgggagtt atgttagtgc catcacccaa    5100
gggaggaggg aggaagagac tcctgttgag tgcttcgagc cttcgatgct gaagaagaag    5160
cagctaactg tcttagactt gcatcctgga gctgggaaaa ccaggagagt tcttcctgaa    5220
atagtccgtg aagccataaa acaagactc cgcaccgtga tcttagctcc aaccagggtt    5280
gtcgctgctg aaatggagga ggcccttaga gggcttccag tgcgttatat gacaacagca    5340
gtcaatgtca cccactctgg aacagaaatc gtcgacttaa tgtgccatgc caccttcact    5400
tcacgtctac tacagccaat cagagtcccc aactataatc tgtatattat ggatgaggcc    5460
cacttcacag atccctcaag tatagcagca agaggataca tttcaacaag ggttgagatg    5520
ggcgaggcgg ctgccatctt catgaccgcc acgccaccag gaacccgtga cgcatttccg    5580
gactccaact caccaattat ggacaccgaa gtggaagtcc cagagagagc ctggagctca    5640
ggctttgatt gggtgacgga tcattctgga aaaacagttt ggtttgttcc aagcgtgagg    5700
aacggcaatg agatcgcagc ttgtctgaca aaggctggaa aacgggtcat acagctcagc    5760
agaaagactt ttgagacaga gttccagaaa acaaaacatc aagagtggga ctttgtcgtg    5820
acaactgaca tttcagagat gggcgccaac tttaaagctg accgtgtcat agattccagg    5880
agatgcctaa agccggtcat acttgatggc gagagagtca ttctggctgg acccatgcct    5940
gtcacacatg ccagcgctgc ccagaggagg gggcgcatag gcaggaatcc caacaaacct    6000
ggagatgagt atctgtatgg aggtgggtgc gcagagactg acgaagacca tgcacactgg    6060
```

```
cttgaagcaa gaatgctcct tgacaatatt tacctccaag atggcctcat agcctcgctc    6120
tatcgacctg aggccgacaa agtagcagcc attgagggag agttcaagct taggacggag    6180
caaaggaaga cctttgtgga actcatgaaa agaggagatc ttcctgtttg gctggcctat    6240
caggttgcat ctgccggaat aacctacaca gatagaagat ggtgctttga tggcacgacc    6300
aacaacacca taatggaaga cagtgtgccg gcagaggtgt ggaccagaca cggagagaaa    6360
agagtgctca aaccgaggtg gatggacgcc agagtttgtt cagatcatgc ggccctgaag    6420
tcattcaagg agtttgccgc tgggaaaaga ggagcggctt ttggagtgat ggaagccctg    6480
ggaacactgc caggacacat gacagagaga ttccaggaag ccattgacaa cctcgctgtg    6540
ctcatgcggg cagagactgg aagcaggcct acaaagccg cggcggccca attgccggag    6600
accctagaga ccattatgct tttgggggttg ctgggaacag tctcgctggg aatcttcttc    6660
gtcttgatga ggaacaaggg cataggggaag atgggctttg gaatggtgac tcttggggcc    6720
agcgcatggc tcatgtggct ctcggaaatt gagccagcca gaattgcatg tgtcctcatt    6780
gttgtgtttc tattgctggt ggtgctcata cctgagccaa aaagcaaag atctccccag    6840 gacaaccaaa tggcaatcat catcatggta gcagtaggtc ttctgggctt gattaccgcc    6900
aatgaactcg gatggttgga gagaacaaag agtgacctaa gccatctaat gggaaggaga    6960
gaggaggggg caaccatagg attctcaatg acattgacc tgcggccagc ctcagcttgg    7020
gccatctatg ctgccttgac aactttcatt accccagccg tccaacatgc agtgaccact    7080
tcatacaaca actactcctt aatggcgatg ccacgcaag ctggagtgtt gtttggtatg    7140
ggcaaaggga tgccattcta cgcatgggac tttggagtcc cgctgctaat gataggttgc    7200
tactcacaat taacaccct gaccctaata gtggccatca ttttgctcgt ggcgcactac    7260
atgtacttga tcccagggct gcaggcagca gctgcgcgtg ctgcccagaa gagaacggca    7320
gctggcatca tgaagaaccc tgttgtggat ggaatagtgg tgactgacat tgacacaatg    7380
acaattgacc cccaagtgga gaaaagatg ggacaggtgc tactcatagc agtagccgtc    7440
tccagcgcca tactgtcgcg gaccgcctgg gggtgggggg aggctgggggc cctgatcaca    7500 gccgcaactt ccactttgtg gaaggctct ccgaacaagt actggaactc ctctacagcc    7560
acttcactgt gtaacatttt taggggaagt tacttggctg gagcttctct aatctacaca    7620
gtaacaagaa acgctggctt ggtcaagaga cgtggggggtg gaacaggaga gaccctggga    7680
gagaaatgga aggcccgctt gaaccagatg tcggccctgg agttctactc ctacaaaaag    7740
tcaggcatca ccgaggtgtg cagagaagag gcccgccgcg cccctcaagga cggtgtggca    7800 acgggaggcc atgctgtgtc ccgaggaagt gcaaagctga gatggttggt ggagcgggga    7860
tacctgcagc cctatggaaa ggtcattgat cttggatgtg gcagaggggg ctggagttac    7920
tacgccgcca ccatccgcaa agttcaagaa gtgaaaggat acacaaaagg aggccctggt    7980
catgaagaac ccgtgttggt gcaaagctat gggtggaaca tagtccgtct taagagtggg    8040
gtggacgtct ttcatatggc ggctgagccg tgtgacacgt tgctgtgtga cataggtgag    8100
tcatcatcta gtcctgaagt ggaagaagca cggacgctca gagtcctctc catggtgggg    8160
gattggcttg aaaaaagacc aggagccttt tgtataaagg tgttgtgccc atacaccagc    8220
actatgatgg aaaccctgga cgcgactgcag cgtaggtatg ggggaggact ggtcagagtg    8280
ccactctccc gcaactctac acatgagatg tattgggtct ctggagcgaa aagcaacacc    8340
ataaaaagtg tgtccaccac gagccagctc ctcttgggc gcatggacgg gcctaggagg    8400
ccagtgaaat atgaggagga tgtggatctc ggctctggca cgcgggctgt ggtaagctgc    8460
```

```
gctgaagctc caacatgaa gatcattggt aaccgcattg aaaggatccg cagtgagcac    8520
gcggaaacgt ggttctttga cgagaaccac ccatataggga catgggctta ccatggaagc    8580
tatgaggccc ccacacaagg gtcagcgtcc tctctaataa acggggttgt caggctcctg    8640
tcaaaaccct gggatgtggt gactggagtc acaggaatag ccatgaccga caccacaccg    8700
tatggtcagc aaagagtttt caaggaaaaa gtggacacta gggtgccaga cccccaagaa    8760
ggcactcgtc aggttatgag catggtctct tcctggttgt ggaaagagct aggcaaacac    8820
aaacggccac gagtctgtac caagaagag ttcatcaaca aggttcgtag caatgcagca    8880
ttaggggcaa tatttgaaga ggaaaaagag tggaagactg cagtgaaagc tgtgaacgat    8940
ccaaggttct gggctctagt ggataaggaa agagagcacc acctgagagg agagtgccag    9000
agttgtgtgt acaacatgat gggaaaaaga gaaaagaaac aaggggaatt tggaaaggcc    9060
aagggcagcc gcgccatctg gtatatgtgg ctaggggcta gatttctaga gttcgaagcc    9120
cttggattct tgaacgagga tcactggatg gggagagaga actcaggagg tggtgttgaa    9180
gggctgggat tacaaagact cggatatgtc ctagaagaga tgagtcgtat accaggagga    9240
aggatgtatg cagatgacac tgctggctgg gacacccgca tcagcaggtt tgatctggag    9300
aatgaagctc taatcaccaa ccaaatggaa aaagggcaca gggccttggc attggccata    9360
atcaagtaca cataccaaaa caagtggta aaggtcctta ccagctga aaagggaaa    9420
acagttatgg acattatttc gagacaagac caaaggggga gcggacaagt tgtcacttac    9480
gctcttaaca catttaccaa cctagtggtg caactcattc ggaatatgga ggctgaggaa    9540
gttctagaga tgcaagactt gtggctgctg cggaggtcag agaaagtgac caactggttg    9600
cagagcaacg gatgggatag gctcaaacga atggcagtca gtggagatga ttgcgttgtg    9660
aagccaattg atgataggtt tgcacatgcc ctcaggttct tgaatgatat gggaaaagtt    9720
aggaaggaca cacaagagtg gaaaccctca actggatggg acaactggga agaagttccg    9780
ttttgctccc accacttcaa caagctccat ctcaaggacg ggaggtccat tgtggttccc    9840
tgccgccacc aagatgaact gattggccgg gcccgcgtct ctccagggc gggatggagc    9900
atccgggaga ctgcttgcct agcaaaatca tatgcgcaaa tgtggcagct cctttatttc    9960
cacagaaggg acctccgact gatggccaat gccatttgtt catctgtgcc agttgactgg   10020
gttccaactg gagaactac ctggtcaatc catggaaagg gagaatggat gaccactgaa   10080
gacatgcttg tggtgtggaa cagagtgtgg attgaggaga acgaccacat ggaagacaag   10140
acccagtta cgaaatggac agacattccc tatttgggaa aaagggaaga cttgtggtgt   10200
ggatctctca tagggcacag accgcgcacc acctgggctg agaacattaa aaacacagtc   10260
aacatggtgc gcaggatcat aggtgatgaa gaaaagtaca tggactacct atccacccaa   10320
gttcgctact gggtgaaga agggtctaca cctggagtgc tgtaagcacc aatcttaatg   10380
ttgtcaggcc tgctagtcag ccacagcttg gggaaagctg tgcagcctgt gacccccag   10440
gagaagctgg gaaaccaagc ctatagtcag gccgagaacg ccatggcacg gaagaagcca   10500
tgctgcctgt gagcccctca ggggacactg agtcaaaaaa cccccacgcgc ttggaggcgc   10560
aggatgggaa aagaaggtgg cgaccttccc caccttcaa tctggggcct gaactggaga   10620
tcagctgtgg atctccagaa gagggactag tggttagagg ag                      10662
```

<210> SEQ ID NO 16
<211> LENGTH: 3423
<212> TYPE: PRT

<213> ORGANISM: Artificial Sequence
<220> FEATURE:
<223> OTHER INFORMATION: Synthetic construct

<400> SEQUENCE: 16

```
Met Lys Asn Pro Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
            35                  40                  45

Ala Ile Leu Ala Phe Leu Arg Phe Thr Ala Ile Lys Pro Ser Leu Gly
50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala Ala Glu Val Thr Arg Arg
        115                 120                 125

Gly Ser Ala Tyr Tyr Met Tyr Leu Asp Arg Asn Asp Ala Gly Glu Ala
        130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
        210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
        290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
        370                 375                 380

Thr Leu Val Asp Arg Gly Trp Gly Asn Gly Cys Gly Leu Phe Gly Lys
```

-continued

```
            385                 390                 395                 400
        Gly Ser Leu Val Thr Cys Ala Lys Phe Ala Cys Ser Lys Lys Met Thr
                            405                 410                 415
        Gly Lys Ser Ile Gln Pro Glu Asn Leu Glu Tyr Arg Ile Met Leu Ser
                            420                 425                 430
        Val His Gly Ser Gln His Ser Gly Met Ile Val Asn Asp Thr Gly His
                            435                 440                 445
        Glu Thr Asp Glu Asn Arg Ala Lys Val Glu Ile Thr Pro Asn Ser Pro
        450                 455                 460
        Arg Ala Glu Ala Thr Leu Gly Gly Phe Gly Ser Leu Gly Leu Asp Cys
        465                 470                 475                 480
        Glu Pro Arg Thr Gly Leu Asp Phe Ser Asp Leu Tyr Tyr Leu Thr Met
                            485                 490                 495
        Asn Asn Lys His Trp Leu Val His Lys Glu Trp Phe His Asp Ile Pro
                            500                 505                 510
        Leu Pro Trp His Ala Gly Ala Asp Thr Gly Thr Pro His Trp Asn Asn
                            515                 520                 525
        Lys Glu Ala Leu Val Glu Phe Lys Asp Ala His Ala Lys Arg Gln Thr
                            530                 535                 540
        Val Val Val Leu Gly Ser Gln Glu Gly Ala Val His Thr Ala Leu Ala
        545                 550                 555                 560
        Gly Ala Leu Glu Ala Glu Met Asp Gly Ala Lys Gly Arg Leu Ser Ser
                            565                 570                 575
        Gly His Leu Lys Cys Arg Leu Lys Met Asp Lys Leu Arg Leu Lys Gly
                            580                 585                 590
        Val Ser Tyr Ser Leu Cys Thr Ala Ala Phe Thr Phe Thr Lys Ile Pro
                            595                 600                 605
        Ala Glu Thr Leu His Gly Thr Val Thr Val Glu Val Gln Tyr Ala Gly
                            610                 615                 620
        Thr Asp Gly Pro Cys Lys Val Pro Ala Gln Met Ala Val Asp Met Gln
        625                 630                 635                 640
        Thr Leu Thr Pro Val Gly Arg Leu Ile Thr Ala Asn Pro Val Ile Thr
                            645                 650                 655
        Glu Ser Thr Glu Asn Ser Lys Met Met Leu Glu Leu Asp Pro Pro Phe
                            660                 665                 670
        Gly Asp Ser Tyr Ile Val Ile Gly Val Gly Glu Lys Lys Ile Thr His
                            675                 680                 685
        His Trp His Arg Ser Gly Ser Thr Ile Gly Lys Ala Phe Glu Ala Thr
                            690                 695                 700
        Val Arg Gly Ala Lys Arg Met Ala Val Leu Gly Asp Thr Ala Trp Asp
        705                 710                 715                 720
        Phe Gly Ser Val Gly Gly Ala Leu Asn Ser Leu Gly Lys Gly Ile His
                            725                 730                 735
        Gln Ile Phe Gly Ala Ala Phe Lys Ser Leu Phe Gly Gly Met Ser Trp
                            740                 745                 750
        Phe Ser Gln Ile Leu Ile Gly Thr Leu Leu Met Trp Leu Gly Leu Asn
                            755                 760                 765
        Thr Lys Asn Gly Ser Ile Ser Leu Met Cys Leu Ala Leu Gly Gly Val
                            770                 775                 780
        Leu Ile Phe Leu Ser Thr Ala Val Ser Ala Asp Val Gly Cys Ser Val
        785                 790                 795                 800
        Asp Phe Ser Lys Lys Glu Thr Arg Cys Gly Thr Gly Val Phe Val Tyr
                            805                 810                 815
```

```
Asn Asp Val Glu Ala Trp Arg Asp Arg Tyr Lys Tyr His Pro Asp Ser
            820                 825                 830

Pro Arg Arg Leu Ala Ala Ala Val Lys Gln Ala Trp Glu Asp Gly Ile
            835                 840                 845

Cys Gly Ile Ser Ser Val Ser Arg Met Glu Asn Ile Met Trp Arg Ser
    850                 855                 860

Val Glu Gly Glu Leu Asn Ala Ile Leu Glu Glu Asn Gly Val Gln Leu
865                 870                 875                 880

Thr Val Val Val Gly Ser Val Lys Asn Pro Met Trp Arg Gly Pro Gln
                885                 890                 895

Arg Leu Pro Val Pro Val Asn Glu Leu Pro His Gly Trp Lys Ala Trp
        900                 905                 910

Gly Lys Ser Tyr Phe Val Arg Ala Ala Lys Thr Asn Asn Ser Phe Val
            915                 920                 925

Val Asp Gly Asp Thr Leu Lys Glu Cys Pro Leu Lys His Arg Ala Trp
930                 935                 940

Asn Ser Phe Leu Val Glu Asp His Gly Phe Gly Val Phe His Thr Ser
945                 950                 955                 960

Val Trp Leu Lys Val Arg Glu Asp Tyr Ser Leu Glu Cys Asp Pro Ala
                965                 970                 975

Val Ile Gly Thr Ala Val Lys Gly Lys Glu Ala Val His Ser Asp Leu
            980                 985                 990

Gly Tyr Trp Ile Glu Ser Glu Lys Asn Asp Thr Trp Arg Leu Lys Arg
        995                 1000                1005

Ala His Leu Ile Glu Met Lys Thr Cys Glu Trp Pro Lys Ser His
    1010                1015                1020

Thr Leu Trp Thr Asp Gly Ile Glu Glu Ser Asp Leu Ile Ile Pro
    1025                1030                1035

Lys Ser Leu Ala Gly Pro Leu Ser His His Asn Thr Arg Glu Gly
    1040                1045                1050

Tyr Arg Thr Gln Met Lys Gly Pro Trp His Ser Glu Glu Leu Glu
    1055                1060                1065

Ile Arg Phe Glu Glu Cys Pro Gly Thr Lys Val His Val Glu Glu
    1070                1075                1080

Thr Cys Gly Thr Arg Gly Pro Ser Leu Arg Ser Thr Thr Ala Ser
    1085                1090                1095

Gly Arg Val Ile Glu Glu Trp Cys Cys Arg Glu Cys Thr Met Pro
    1100                1105                1110

Pro Leu Ser Phe Arg Ala Lys Asp Gly Cys Trp Tyr Gly Met Glu
    1115                1120                1125

Ile Arg Pro Arg Lys Glu Pro Glu Ser Asn Leu Val Arg Ser Met
    1130                1135                1140

Val Thr Ala Gly Ser Thr Asp His Met Asp His Phe Ser Leu Gly
    1145                1150                1155

Val Leu Val Ile Leu Leu Met Val Gln Glu Gly Leu Lys Lys Arg
    1160                1165                1170

Met Thr Thr Lys Ile Ile Ile Ser Thr Ser Met Ala Val Leu Val
    1175                1180                1185

Ala Met Ile Leu Gly Gly Phe Ser Met Ser Asp Leu Ala Lys Leu
    1190                1195                1200

Ala Ile Leu Met Gly Ala Thr Phe Ala Glu Met Asn Thr Gly Gly
    1205                1210                1215
```

```
Asp Val Ala His Leu Ala Leu Ile Ala Ala Phe Lys Val Arg Pro
1220                1225                1230

Ala Leu Leu Val Ser Phe Ile Phe Arg Ala Asn Trp Thr Pro Arg
1235                1240                1245

Glu Ser Met Leu Leu Ala Leu Ala Ser Cys Leu Leu Gln Thr Ala
1250                1255                1260

Ile Ser Ala Leu Glu Gly Asp Leu Met Val Leu Ile Asn Gly Phe
1265                1270                1275

Ala Leu Ala Trp Leu Ala Ile Arg Ala Met Val Val Pro Arg Thr
1280                1285                1290

Asp Asn Ile Thr Leu Ala Ile Leu Ala Ala Leu Thr Pro Leu Ala
1295                1300                1305

Arg Gly Thr Leu Leu Val Ala Trp Arg Ala Gly Leu Ala Thr Cys
1310                1315                1320

Gly Gly Phe Met Leu Leu Ser Leu Lys Gly Lys Gly Ser Val Lys
1325                1330                1335

Lys Asn Leu Pro Phe Val Met Ala Leu Gly Leu Thr Ala Val Arg
1340                1345                1350

Leu Val Asp Pro Ile Asn Val Val Gly Leu Leu Leu Leu Thr Arg
1355                1360                1365

Ser Gly Lys Arg Ser Trp Pro Pro Ser Glu Val Leu Thr Ala Val
1370                1375                1380

Gly Leu Ile Cys Ala Leu Ala Gly Gly Phe Ala Lys Ala Asp Ile
1385                1390                1395

Glu Met Ala Gly Pro Met Ala Ala Val Gly Leu Leu Ile Val Ser
1400                1405                1410

Tyr Val Val Ser Gly Lys Ser Val Asp Met Tyr Ile Glu Arg Ala
1415                1420                1425

Gly Asp Ile Thr Trp Glu Lys Asp Ala Glu Val Thr Gly Asn Ser
1430                1435                1440

Pro Arg Leu Asp Val Ala Leu Asp Glu Ser Gly Asp Phe Ser Leu
1445                1450                1455

Val Glu Asp Asp Gly Pro Pro Met Arg Glu Ile Ile Leu Lys Val
1460                1465                1470

Val Leu Met Thr Ile Cys Gly Met Asn Pro Ile Ala Ile Pro Phe
1475                1480                1485

Ala Ala Gly Ala Trp Tyr Val Tyr Val Lys Thr Gly Lys Arg Ser
1490                1495                1500

Gly Ala Leu Trp Asp Val Pro Ala Pro Lys Glu Val Lys Lys Gly
1505                1510                1515

Glu Thr Thr Asp Gly Val Tyr Arg Val Met Thr Arg Arg Leu Leu
1520                1525                1530

Gly Ser Thr Gln Val Gly Val Gly Val Met Gln Glu Gly Val Phe
1535                1540                1545

His Thr Met Trp His Val Thr Lys Gly Ser Ala Leu Arg Ser Gly
1550                1555                1560

Glu Gly Arg Leu Asp Pro Tyr Trp Gly Asp Val Lys Gln Asp Leu
1565                1570                1575

Val Ser Tyr Cys Gly Pro Trp Lys Leu Asp Ala Ala Trp Asp Gly
1580                1585                1590

His Ser Glu Val Gln Leu Leu Ala Val Pro Pro Gly Glu Arg Ala
1595                1600                1605

Arg Asn Ile Gln Thr Leu Pro Gly Ile Phe Lys Thr Lys Asp Gly
```

```
              1610                1615                1620
Asp  Ile  Gly  Ala  Val  Ala  Leu  Asp  Tyr  Pro  Ala  Gly  Thr  Ser  Gly
              1625                1630                1635

Ser  Pro  Ile  Leu  Asp  Lys  Cys  Gly  Arg  Val  Ile  Gly  Leu  Tyr  Gly
              1640                1645                1650

Asn  Gly  Val  Val  Ile  Lys  Asn  Gly  Ser  Tyr  Val  Ser  Ala  Ile  Thr
              1655                1660                1665

Gln  Gly  Arg  Arg  Glu  Glu  Glu  Thr  Pro  Val  Glu  Cys  Phe  Glu  Pro
              1670                1675                1680

Ser  Met  Leu  Lys  Lys  Lys  Gln  Leu  Thr  Val  Leu  Asp  Leu  His  Pro
              1685                1690                1695

Gly  Ala  Gly  Lys  Thr  Arg  Arg  Val  Leu  Pro  Glu  Ile  Val  Arg  Glu
              1700                1705                1710

Ala  Ile  Lys  Thr  Arg  Leu  Arg  Thr  Val  Ile  Leu  Ala  Pro  Thr  Arg
              1715                1720                1725

Val  Val  Ala  Ala  Glu  Met  Glu  Glu  Ala  Leu  Arg  Gly  Leu  Pro  Val
              1730                1735                1740

Arg  Tyr  Met  Thr  Thr  Ala  Val  Asn  Val  Thr  His  Ser  Gly  Thr  Glu
              1745                1750                1755

Ile  Val  Asp  Leu  Met  Cys  His  Ala  Thr  Phe  Thr  Ser  Arg  Leu  Leu
              1760                1765                1770

Gln  Pro  Ile  Arg  Val  Pro  Asn  Tyr  Asn  Leu  Tyr  Ile  Met  Asp  Glu
              1775                1780                1785

Ala  His  Phe  Thr  Asp  Pro  Ser  Ser  Ile  Ala  Ala  Arg  Gly  Tyr  Ile
              1790                1795                1800

Ser  Thr  Arg  Val  Glu  Met  Gly  Glu  Ala  Ala  Ile  Phe  Met  Thr
              1805                1810                1815

Ala  Thr  Pro  Pro  Gly  Thr  Arg  Asp  Ala  Phe  Pro  Asp  Ser  Asn  Ser
              1820                1825                1830

Pro  Ile  Met  Asp  Thr  Glu  Val  Glu  Val  Pro  Glu  Arg  Ala  Trp  Ser
              1835                1840                1845

Ser  Gly  Phe  Asp  Trp  Val  Thr  Asp  His  Ser  Gly  Lys  Thr  Val  Trp
              1850                1855                1860

Phe  Val  Pro  Ser  Val  Arg  Asn  Gly  Asn  Glu  Ile  Ala  Ala  Cys  Leu
              1865                1870                1875

Thr  Lys  Ala  Gly  Lys  Arg  Val  Ile  Gln  Leu  Ser  Arg  Lys  Thr  Phe
              1880                1885                1890

Glu  Thr  Glu  Phe  Gln  Lys  Thr  Lys  His  Gln  Glu  Trp  Asp  Phe  Val
              1895                1900                1905

Val  Thr  Thr  Asp  Ile  Ser  Glu  Met  Gly  Ala  Asn  Phe  Lys  Ala  Asp
              1910                1915                1920

Arg  Val  Ile  Asp  Ser  Arg  Arg  Cys  Leu  Lys  Pro  Val  Ile  Leu  Asp
              1925                1930                1935

Gly  Glu  Arg  Val  Ile  Leu  Ala  Gly  Pro  Met  Pro  Val  Thr  His  Ala
              1940                1945                1950

Ser  Ala  Ala  Gln  Arg  Arg  Gly  Arg  Ile  Gly  Arg  Asn  Pro  Asn  Lys
              1955                1960                1965

Pro  Gly  Asp  Glu  Tyr  Leu  Tyr  Gly  Gly  Gly  Cys  Ala  Glu  Thr  Asp
              1970                1975                1980

Glu  Asp  His  Ala  His  Trp  Leu  Glu  Ala  Arg  Met  Leu  Leu  Asp  Asn
              1985                1990                1995

Ile  Tyr  Leu  Gln  Asp  Gly  Leu  Ile  Ala  Ser  Leu  Tyr  Arg  Pro  Glu
              2000                2005                2010
```

-continued

Ala Asp Lys Val Ala Ala Ile Glu Gly Glu Phe Lys Leu Arg Thr
2015                2020                2025

Glu Gln Arg Lys Thr Phe Val Glu Leu Met Lys Arg Gly Asp Leu
2030                2035                2040

Pro Val Trp Leu Ala Tyr Gln Val Ala Ser Ala Gly Ile Thr Tyr
2045                2050                2055

Thr Asp Arg Arg Trp Cys Phe Asp Gly Thr Thr Asn Asn Thr Ile
2060                2065                2070

Met Glu Asp Ser Val Pro Ala Glu Val Trp Thr Arg His Gly Glu
2075                2080                2085

Lys Arg Val Leu Lys Pro Arg Trp Met Asp Ala Arg Val Cys Ser
2090                2095                2100

Asp His Ala Ala Leu Lys Ser Phe Lys Glu Phe Ala Ala Gly Lys
2105                2110                2115

Arg Gly Ala Ala Phe Gly Val Met Glu Ala Leu Gly Thr Leu Pro
2120                2125                2130

Gly His Met Thr Glu Arg Phe Gln Glu Ala Ile Asp Asn Leu Ala
2135                2140                2145

Val Leu Met Arg Ala Glu Thr Gly Ser Arg Pro Tyr Lys Ala Ala
2150                2155                2160

Ala Ala Gln Leu Pro Glu Thr Leu Glu Thr Ile Met Leu Leu Gly
2165                2170                2175

Leu Leu Gly Thr Val Ser Leu Gly Ile Phe Phe Val Leu Met Arg
2180                2185                2190

Asn Lys Gly Ile Gly Lys Met Gly Phe Gly Met Val Thr Leu Gly
2195                2200                2205

Ala Ser Ala Trp Leu Met Trp Leu Ser Glu Ile Glu Pro Ala Arg
2210                2215                2220

Ile Ala Cys Val Leu Ile Val Val Phe Leu Leu Leu Val Val Leu
2225                2230                2235

Ile Pro Glu Pro Glu Lys Gln Arg Ser Pro Gln Asp Asn Gln Met
2240                2245                2250

Ala Ile Ile Ile Met Val Ala Val Gly Leu Leu Gly Leu Ile Thr
2255                2260                2265

Ala Asn Glu Leu Gly Trp Leu Glu Arg Thr Lys Ser Asp Leu Ser
2270                2275                2280

His Leu Met Gly Arg Arg Glu Glu Gly Ala Thr Ile Gly Phe Ser
2285                2290                2295

Met Asp Ile Asp Leu Arg Pro Ala Ser Ala Trp Ala Ile Tyr Ala
2300                2305                2310

Ala Leu Thr Thr Phe Ile Thr Pro Ala Val Gln His Ala Val Thr
2315                2320                2325

Thr Ser Tyr Asn Asn Tyr Ser Leu Met Ala Met Ala Thr Gln Ala
2330                2335                2340

Gly Val Leu Phe Gly Met Gly Lys Gly Met Pro Phe Tyr Ala Trp
2345                2350                2355

Asp Phe Gly Val Pro Leu Leu Met Ile Gly Cys Tyr Ser Gln Leu
2360                2365                2370

Thr Pro Leu Thr Leu Ile Val Ala Ile Ile Leu Leu Val Ala His
2375                2380                2385

Tyr Met Tyr Leu Ile Pro Gly Leu Gln Ala Ala Ala Arg Ala
2390                2395                2400

```
Ala Gln Lys Arg Thr Ala Ala Gly Ile Met Lys Asn Pro Val Val
2405                2410                2415

Asp Gly Ile Val Val Thr Asp Ile Asp Thr Met Thr Ile Asp Pro
2420                2425                2430

Gln Val Glu Lys Lys Met Gly Gln Val Leu Leu Ile Ala Val Ala
2435                2440                2445

Val Ser Ser Ala Ile Leu Ser Arg Thr Ala Trp Gly Trp Gly Glu
2450                2455                2460

Ala Gly Ala Leu Ile Thr Ala Ala Thr Ser Thr Leu Trp Glu Gly
2465                2470                2475

Ser Pro Asn Lys Tyr Trp Asn Ser Ser Thr Ala Thr Ser Leu Cys
2480                2485                2490

Asn Ile Phe Arg Gly Ser Tyr Leu Ala Gly Ala Ser Leu Ile Tyr
2495                2500                2505

Thr Val Thr Arg Asn Ala Gly Leu Val Lys Arg Arg Gly Gly Gly
2510                2515                2520

Thr Gly Glu Thr Leu Gly Glu Lys Trp Lys Ala Arg Leu Asn Gln
2525                2530                2535

Met Ser Ala Leu Glu Phe Tyr Ser Tyr Lys Lys Ser Gly Ile Thr
2540                2545                2550

Glu Val Cys Arg Glu Glu Ala Arg Arg Ala Leu Lys Asp Gly Val
2555                2560                2565

Ala Thr Gly Gly His Ala Val Ser Arg Gly Ser Ala Lys Leu Arg
2570                2575                2580

Trp Leu Val Glu Arg Gly Tyr Leu Gln Pro Tyr Gly Lys Val Ile
2585                2590                2595

Asp Leu Gly Cys Gly Arg Gly Gly Trp Ser Tyr Tyr Ala Ala Thr
2600                2605                2610

Ile Arg Lys Val Gln Glu Val Lys Gly Tyr Thr Lys Gly Gly Pro
2615                2620                2625

Gly His Glu Glu Pro Val Leu Val Gln Ser Tyr Gly Trp Asn Ile
2630                2635                2640

Val Arg Leu Lys Ser Gly Val Asp Val Phe His Met Ala Ala Glu
2645                2650                2655

Pro Cys Asp Thr Leu Leu Cys Asp Ile Gly Glu Ser Ser Ser Ser
2660                2665                2670

Pro Glu Val Glu Glu Ala Arg Thr Leu Arg Val Leu Ser Met Val
2675                2680                2685

Gly Asp Trp Leu Glu Lys Arg Pro Gly Ala Phe Cys Ile Lys Val
2690                2695                2700

Leu Cys Pro Tyr Thr Ser Thr Met Met Glu Thr Leu Glu Arg Leu
2705                2710                2715

Gln Arg Arg Tyr Gly Gly Gly Leu Val Arg Val Pro Leu Ser Arg
2720                2725                2730

Asn Ser Thr His Glu Met Tyr Trp Val Ser Gly Ala Lys Ser Asn
2735                2740                2745

Thr Ile Lys Ser Val Ser Thr Thr Ser Gln Leu Leu Leu Gly Arg
2750                2755                2760

Met Asp Gly Pro Arg Arg Pro Val Lys Tyr Glu Glu Asp Val Asp
2765                2770                2775

Leu Gly Ser Gly Thr Arg Ala Val Val Ser Cys Ala Glu Ala Pro
2780                2785                2790

Asn Met Lys Ile Ile Gly Asn Arg Ile Glu Arg Ile Arg Ser Glu
```

```
                2795                2800                2805
His Ala Glu Thr Trp Phe Phe Asp Glu Asn His Pro Tyr Arg Thr
    2810                2815                2820

Trp Ala Tyr His Gly Ser Tyr Glu Ala Pro Thr Gln Gly Ser Ala
    2825                2830                2835

Ser Ser Leu Ile Asn Gly Val Val Arg Leu Leu Ser Lys Pro Trp
    2840                2845                2850

Asp Val Val Thr Gly Val Thr Gly Ile Ala Met Thr Asp Thr Thr
    2855                2860                2865

Pro Tyr Gly Gln Gln Arg Val Phe Lys Glu Lys Val Asp Thr Arg
    2870                2875                2880

Val Pro Asp Pro Gln Glu Gly Thr Arg Gln Val Met Ser Met Val
    2885                2890                2895

Ser Ser Trp Leu Trp Lys Glu Leu Gly Lys His Lys Arg Pro Arg
    2900                2905                2910

Val Cys Thr Lys Glu Glu Phe Ile Asn Lys Val Arg Ser Asn Ala
    2915                2920                2925

Ala Leu Gly Ala Ile Phe Glu Glu Lys Glu Trp Lys Thr Ala
    2930                2935                2940

Val Glu Ala Val Asn Asp Pro Arg Phe Trp Ala Leu Val Asp Lys
    2945                2950                2955

Glu Arg Glu His His Leu Arg Gly Glu Cys Gln Ser Cys Val Tyr
    2960                2965                2970

Asn Met Met Gly Lys Arg Glu Lys Lys Gln Gly Glu Phe Gly Lys
    2975                2980                2985

Ala Lys Gly Ser Arg Ala Ile Trp Tyr Met Trp Leu Gly Ala Arg
    2990                2995                3000

Phe Leu Glu Phe Glu Ala Leu Gly Phe Leu Asn Glu Asp His Trp
    3005                3010                3015

Met Gly Arg Glu Asn Ser Gly Gly Gly Val Glu Gly Leu Gly Leu
    3020                3025                3030

Gln Arg Leu Gly Tyr Val Leu Glu Glu Met Ser Arg Ile Pro Gly
    3035                3040                3045

Gly Arg Met Tyr Ala Asp Asp Thr Ala Gly Trp Asp Thr Arg Ile
    3050                3055                3060

Ser Arg Phe Asp Leu Glu Asn Glu Ala Leu Ile Thr Asn Gln Met
    3065                3070                3075

Glu Lys Gly His Arg Ala Leu Ala Leu Ala Ile Ile Lys Tyr Thr
    3080                3085                3090

Tyr Gln Asn Lys Val Val Lys Val Leu Arg Pro Ala Glu Lys Gly
    3095                3100                3105

Lys Thr Val Met Asp Ile Ile Ser Arg Gln Asp Gln Arg Gly Ser
    3110                3115                3120

Gly Gln Val Val Thr Tyr Ala Leu Asn Thr Phe Thr Asn Leu Val
    3125                3130                3135

Val Gln Leu Ile Arg Asn Met Glu Ala Glu Glu Val Leu Glu Met
    3140                3145                3150

Gln Asp Leu Trp Leu Leu Arg Arg Ser Glu Lys Val Thr Asn Trp
    3155                3160                3165

Leu Gln Ser Asn Gly Trp Asp Arg Leu Lys Arg Met Ala Val Ser
    3170                3175                3180

Gly Asp Asp Cys Val Val Lys Pro Ile Asp Asp Arg Phe Ala His
    3185                3190                3195
```

```
Ala Leu Arg Phe Leu Asn Asp Met Gly Lys Val Arg Lys Asp Thr
    3200                3205                3210

Gln Glu Trp Lys Pro Ser Thr Gly Trp Asp Asn Trp Glu Glu Val
    3215                3220                3225

Pro Phe Cys Ser His His Phe Asn Lys Leu His Leu Lys Asp Gly
    3230                3235                3240

Arg Ser Ile Val Val Pro Cys Arg His Gln Asp Glu Leu Ile Gly
    3245                3250                3255

Arg Ala Arg Val Ser Pro Gly Ala Gly Trp Ser Ile Arg Glu Thr
    3260                3265                3270

Ala Cys Leu Ala Lys Ser Tyr Ala Gln Met Trp Gln Leu Leu Tyr
    3275                3280                3285

Phe His Arg Arg Asp Leu Arg Leu Met Ala Asn Ala Ile Cys Ser
    3290                3295                3300

Ser Val Pro Val Asp Trp Val Pro Thr Gly Arg Thr Thr Trp Ser
    3305                3310                3315

Ile His Gly Lys Gly Glu Trp Met Thr Thr Glu Asp Met Leu Val
    3320                3325                3330

Val Trp Asn Arg Val Trp Ile Glu Glu Asn Asp His Met Glu Asp
    3335                3340                3345

Lys Thr Pro Val Thr Lys Trp Thr Asp Ile Pro Tyr Leu Gly Lys
    3350                3355                3360

Arg Glu Asp Leu Trp Cys Gly Ser Leu Ile Gly His Arg Pro Arg
    3365                3370                3375

Thr Thr Trp Ala Glu Asn Ile Lys Asn Thr Val Asn Met Val Arg
    3380                3385                3390

Arg Ile Ile Gly Asp Glu Glu Lys Tyr Met Asp Tyr Leu Ser Thr
    3395                3400                3405

Gln Val Arg Tyr Leu Gly Glu Glu Gly Ser Thr Pro Gly Val Leu
    3410                3415                3420

<210> SEQ ID NO 17
<211> LENGTH: 10793
<212> TYPE: DNA
<213> ORGANISM: Artificial Sequence
<220> FEATURE:
<223> OTHER INFORMATION: Synthetic construct

<400> SEQUENCE: 17
ccaatctgtg aatcagactg cgacagttcg agtttgaagc gaaagctagc aacagtatca    60
acaggtttta ttttggattt ggaaacgaga gtttctggtc atgaaaaacc caaaaaagaa   120
atccggagga ttccggattg tcaatatgct aaaacgcgga gtagcccgtg tgagcccctt   180
tgggggcttg aagaggctgc cagccggact tctgctgggt catgggccca tcaggatggt   240
cttggcgatt ctagcctttt tgagattcac ggcaatcaag ccatcactgg gtctcatcaa   300
tagatggggt tcagtgggga aaaagaggc tatggaaata ataagaagt tcaagaaaga   360 tctggctgcc atgctgagaa taatcaatgc caggaaggag aagaagagac gaggcgcaga   420
tactagtgtc ggaatcgttg gcctcctgct gaccacagct atggcagcgg aggtcactag   480
acgtgggagt gcatactata tgtacttgga cagaaacgat gctggggagg ccatatcttt   540
tccaaccaca ttggggatga ataagtgtta tatacagatc atggatcttg acacatgtg    600 tgatgccacc atgagctatg aatgcccctat gctggatgag ggggtggaac cagatgacgt   660
cgattgttgg tgcaacacga cgtcaacttg ggttgtgtac ggaacctgcc atcacaaaaa   720
```

```
aggtgaagca cggagatcta aagagctgt gacgctcccc tcccattcca ctaggaagct    780
gcaaacgcgg tcgcaaacct ggttggaatc aagagaatac acaaagcact tgattagagt    840
cgaaaattgg atattcagga accctggctt cgcgttagca gcagctgcca tcgcttggct    900
tttgggaagc tcaacgagcc aaaaagtcat atacttggtc atgatactgc tgattgcccc    960
ggcatacagc atcaggtgca taggagtcag caatagggac tttgtggaag gtatgtcagg   1020
tgggacttgg gttgatgttg tcttggaaca tgggggttgt gtcaccgtaa tggcacagga   1080
caaaccgact gtcgacatag agctggttac aacaacagtc agcaacatgg cggaggtaag   1140
atcctactgc tatgaggcat caatatcaga catggcttcg gacagccgct gcccaacaca   1200
aggtgaagcc taccttgaca agcaatcaga cactcaatat gtctgcaaaa gaacgttagt   1260
ggacagaggc tggggaaatg gatgtggact ttttggcaaa gggagcctgg tgacatgcgc   1320
taagtttgca tgctccaaga aaatgaccgg gaagagcatc cagccagaga tctggagta   1380
ccggataatg ctgtcagttc atggctccca gcacagtggg atgatcgtta atgacacagg   1440
acatgaaact gatgagaata gagcgaaggt tgagataacg cccaattcac caagagccga   1500
agccaccctg gggggttttg gaagcttagg acttgattgt gaaccgagga caggccttga   1560
cttttcagat ttgtattact tgactatgaa taacaagcac tggttggttc acaaggagtg   1620
gttccacgac attccattac cttggcacgc tggggcagac accggaactc cacactggaa   1680
caacaaagaa gcactggtag agttcaagga cgcacatgcc aaaaggcaaa ctgtcgtggt   1740
tctagggact caagaaggag cagttcacac ggcccttgct ggagctctgg aggctgagat   1800
ggatggtgca aagggaaggc tgtcctctgg ccacttgaaa tgtcgcctga aaatggataa   1860
acttagattg aagggcgtgt catactcctt gtgtaccgca gcgttcacat tcaccaagat   1920
cccggctgaa acactgcacg ggacagtcac agtggaggta cagtacgcag ggacagatgg   1980
accttgcaag gttccagctc agatggcggt ggacatgcaa actctgaccc cagttgggag   2040
gttgataacc gctaaccccg taatcactga aagcactgag aactctaaga tgatgctgga   2100
acttgatcca ccatttgggg actcttacat tgtcatagga gtcggggaga agaagatcac   2160
ccaccactgg cacaggagtg gcagcaccat tggaaaagca tttgaagcca ctgtgagagg   2220
tgccaagaga atggcagtct tgggagacac agcctgggac tttggatcag ttggaggcgc   2280
tctcaactca ttgggcaagg gcatccatca aattttttgga gcagctttca atcattgtt   2340
tggaggaatg tcctggttct cacaaattct cattggaacg ttgctgatgt ggttgggtct   2400
gaacacaaag aatggatcta tttcccttat gtgcttggcc ttaggggag tgttgatctt   2460
cttatccaca gccgtctctg ctgatgtggg gtgctcggtg gacttctcaa agaaggagac   2520
gagatgtggt acagggtgt tcgtctataa cgacgttgaa gcctggagg acaggtacaa   2580
gtaccatcct gactctcccc gtagattggc agcagcagtc aagcaagcct gggaagatgg   2640
tatctgcggg atctcctctg tttcaagaat ggaaaacatc atgtgagat cagtagaagg   2700
ggagcttaac gcaatcctgg aagagaatgg agttcaactg acggtcgttg tgggatctgt   2760
aaaaaacccc atgtgagag gtccacagag attgcccgtg cctgtgaacg agctgcccca   2820
cggctggaag gcttgggga atcgtactt cgtcagagca gcaaagacaa ataacagctt   2880
tgtcgtggat ggtgacacac tgaaggaatg cccactcaaa catagagcat ggaacagctt   2940
tcttgtggag gatcatgggt tcggggtatt tcacactagt gtctggctca aggttagaga   3000
agattattca ttagagtgtg atccagccgt tattggaaca gctgttaagg gaaggaggc   3060
```

```
tgtacacagt gatctaggct actggattga gagtgagaag aatgacacat ggaggctgaa    3120
gagggcccat ctgatcgaga tgaaaacatg tgaatggcca aagtcccaca cattgtggac    3180
agatggaata gaagagagtg atctgatcat acccaagtct ttagctgggc cactcagcca    3240
tcacaatacc agagagggct acaggaccca aatgaaaggg ccatggcaca gtgaagagct    3300
tgaaattcgg tttgaggaat gcccaggcac taaggtccac gtggaggaaa catgtggaac    3360
aagaggacca tctctgagat caaccactgc aagcggaagg gtgatcgagg aatggtgctg    3420
cagggagtgc acaatgcccc cactgtcgtt ccgggctaaa gatggctgtt ggtatggaat    3480
ggagataagg cccaggaaag aaccagaaag caacttagta aggtcaatgg tgactgcagg    3540
atcaactgat cacatggatc acttctccct tggagtgctt gtgattctgc tcatggtgca    3600
ggaagggctg aagaagagaa tgaccacaaa gatcatcata agcacatcaa tggcagtgct    3660
ggtagctatg atcctgggag attttcaat gagtgacctg gctaagcttg caattttgat     3720
gggtgccacc ttcgcggaaa tgaacactgg aggagatgta gctcatctgg cgctgatagc    3780
ggcattcaaa gtcagaccag cgttgctggt atctttcatc ttcagagcta attggacacc    3840
ccgtgaaagc atgctgctgg ccttggcctc gtgttttttg caaactgcga tctccgcctt    3900
ggaaggcgac ctgatggttc tcatcaatgg ttttgctttg gctggttgg caatacgagc      3960
gatggttgtt ccacgcactg acaacatcac cttggcaatc ctggctgctc tgacaccact    4020
ggcccggggc acactgcttg tggcgtggag agcaggcctt gctacttgcg gggggtttat    4080
gctcctctct ctgaagggaa aaggcagtgt gaagaagaac ttaccatttg tcatggccct    4140
gggactaacc gctgtgaggc tggtcgaccc catcaacgtg gtgggactgc tgttgctcac    4200
aaggagtggg aagcggagct ggccccctag cgaagtactc acagctgttg gcctgatatg    4260
cgcattggct ggagggttcg ccaaggcaga tatagagatg gctgggccca tggccgcggt    4320
cggtctgcta attgtcagtt acgtggtctc aggaaagagt gtggacatgt acattgaaag    4380
agcaggtgac atcacatggg aaaaagatgc ggaagtcact ggaaacagtc cccggctcga    4440
tgtggcgcta gatgagagtg gtgacttctc cctggtggag gatgacggtc ccccatgag      4500
agagatcata ctcaaggtgg tcctgatgac catctgtggc atgaacccaa tagccatacc    4560
ctttgcagct ggagcgtggt acgtatacgt gaagactgga aaaaggagtg gtgctctatg    4620
ggatgtgcct gctcccaagg aagtaaaaaa ggggagacc acagatggag tgtacagagt      4680
aatgactcgt agactgctag gttcaacaca agttggagtg ggagttatgc aagaggggt      4740
cttcacact atgtggcacg tcacaaaagg atccgcgctg agaagcggtg aagggagact      4800
tgatccatac tggggagatg tcaagcagga tctggtgtca tactgtggtc catggaagct    4860
agatgccgcc tgggacgggc acagcgaggt gcagctcttg gccgtgcccc ccggagagag    4920
agcgaggaac atccagactc tgcccggaat atttaagaca aaggatgggg acattggagc    4980
ggttgcgctg gattacccag caggaacttc aggatctcca atcctagaca gtgtgggag      5040
agtgatagga ctttatggca atgggtcgt gataaaaaat gggagttatg ttagtgccat     5100
cacccaaggg aggagggagg aagagactcc tgttgagtgc ttcgagcctt cgatgctgaa    5160
gaagaagcag ctaactgtct tagacttgca tcctggagct gggaaaacca ggagagttct    5220
tcctgaaata gtccgtgaag ccataaaaac aagactccgt actgtgatct agctccaac      5280
cagggttgtc gctgctgaaa tggaggaagc ccttagaggg cttccagtgc gttatatgac    5340
aacagcagtc aatgtcaccc actctggaac agaaatcgtc gacttaatgt gccatgccac    5400
cttcacttca cgtctactac agccaatcag agtccccaac tataatctgt atattatgga    5460
```

```
tgaggcccac ttcacagatc cctcaagcat agcagcaaga ggatacattt caacaagggt   5520
tgagatgggc gaggcggctg ccatcttcat gaccgccacg ccaccaggaa cccgtgacgc   5580
atttccggac tccaactcac caattatgga caccgaagtg gaagtcccag agagagcctg   5640
gagctcaggc tttgattggg tgacggatca ttctggaaaa acagtttggt ttgttccaag   5700
cgtgaggaac ggcaatgaga tcgcagcttg tctgacaaag gctggaaaac gggtcataca   5760
gctcagcaga aagactttg agacagagtt ccagaaaaca aaacatcaag agtgggactt    5820
tgtcgtgaca actgacattt cagagatggg cgccaacttt aaagctgacc gtgtcataga   5880
ttccaggaga tgcctaaagc cggtcatact tgatggcgag agagtcattc tggctggacc   5940
catgcctgtc acacatgcca gcgctgccca gaggagggg cgcataggca ggaatcccaa    6000
caaacctgga gatgagtacc tgtatggagg tgggtgcgca gagactgacg aagaccatgc   6060
acactggctt gaagcaagaa tgctccttga caatatttac ctccaagatg gcctcatagc   6120
ctcgctctat cgacctgagg ccgacaaagt agcagccatt gagggagagt tcaagcttag   6180
gacggagcaa aggaagacct tgtggaact catgaaaaga ggagatcttc ctgtttggct    6240
ggcctatcag gttgcatctg ccggaataac ctacacagat agaagatggt gctttgatgg   6300
cacgaccaac aacaccataa tggaagacag tgtgccggca gaggtgtgga ccagacacgg   6360
agagaaaaga gtgctcaaac cgaggtggat ggacgccaga gtttgttcag atcatgcggc   6420
cctgaagtca ttcaaggagt tgccgctgg gaaaagagga gcggcttttg gagtgatgga    6480
agccctggga acactgccag acacatgac agagagattc caggaagcca ttgacaacct    6540
cgctgtgctc atgcgggcag agactggaag caggccttac aaagccgcgg cggcccaatt   6600
gccggagacc ctagagacca ttatgctttt ggggttgctg gaacagtct cgctgggaat    6660
cttttttcgtc ttgatgagga acaagggcat agggaagatg gcttggaa tggtgactct    6720
tgggccagc gcatggctca tgtggctctc ggaaattgag ccagccagaa ttgcatgtgt    6780
cctcattgtt gtgttcctat tgctggtggt gctcatacct gagccagaaa agcaaagatc   6840
tcccaggac aaccaaatgg caatcatcat catggtagca gtaggtcttc tgggcttgat    6900
taccgccaat gaactcggat ggttggagag aacaaagagt gacctaagcc atctaatggg   6960
aaggagagag gagggggcaa ccataggatt ctcaatggac attgacctgc ggccagcctc   7020
agcttgggcc atctatgctg ccttgacaac tttcattacc ccagccgtcc aacatgcagt   7080
gaccacttca tacaacaact actccttaat ggcgatggcc acgcaagctg gagtgttgtt   7140
tggtatgggc aaagggatgc cattctacgc atgggactt ggagtcccgc tgctaatgat    7200
aggttgctac tcacaattaa cacccctgac cctaatagtg gccatcattt gctcgtggc    7260
gcactacatg tacttgatcc cagggctgca ggcagcagct gcgcgtgctg cccagaagag   7320
aacggcagct ggcatcatga agaaccctgt tgtggatgga atagtggtga ctgacattga   7380
cacaatgaca attgaccccc aagtggagaa aaagatggga caggtgctac tcatagcagt   7440
agccgtctcc agcgccatac tgtcgcggac cgcctggggg tgggggagg ctgggccct    7500
gatcacagcc gcaacttcca ctttgtggga aggctctccg aacaagtact ggaactcctc   7560
tacagccact tcactgtgta acattttag ggaagttac ttggctggag cttctctaat    7620
ctacacagta acaagaaacg ctggcttggt caagagacgt gggggtggaa caggagagac   7680
cctgggagag aaatgaagg cccgcttgaa ccagatgtcg gcctggagt tctactccta    7740
caaaaagtca ggcatcaccg aggtgtgcag agaagaggcc cgccgcgccc tcaaggacgg   7800
```

```
tgtggcaacg ggaggccatg ctgtgtcccg aggaagtgca aagctgagat ggttggtgga    7860
gcggggatac ctgcagccct atggaaaggt cattgatctt ggatgtggca gaggggggctg   7920
gagttactac gccgccacca tccgcaaagt tcaagaagtg aaaggataca caaaaggagg    7980
ccctggtcat gaagaacccg tgttggtgca aagctatggg tggaacatag tccgtcttaa    8040
gagtgggggtg gacgtctttc atatggcggc tgagccgtgt gacacgttgc tgtgtgacat   8100
aggtgagtca tcatctagtc ctgaagtgga agaagcacgg acgctcagag tcctctccat    8160
ggtgggggat tggcttgaaa aaagaccagg agccttttgc ataaaagtgt tgtgcccata    8220
caccagcact atgatggaaa ccctggagcg actgcagcgt aggtatgggg gaggactggt    8280
cagagtgcca ctctcccgca actctacaca tgagatgtac tgggtctctg gagcgaaaag    8340
caacaccata aaaagtgtgt ccaccacgag ccagctcctc ttggggcgca tggacgggcc    8400
taggaggcca gtgaaatatg aggaggatgt gaatctcggc tctggcacgc gggctgtggt    8460
aagctgcgct gaagctccca acatgaagat cattggtaac cgcattgaaa ggatccgcag    8520
tgagcacgcg gaaacgtggt tctttgacga aaaccaccca tataggacat gggcttacca    8580
tggaagctat gtggccccca cacaagggtc agcgtcctct ctaataaacg gggttgtcag    8640
gctcctgtca aaaccctggg atgtggtgac tggagtcaca ggaatagcca tgaccgacac    8700
cacaccgtat ggtcagcaaa gagttttcaa ggaaaaagtg gacactaggg tgccagaccc    8760
ccaagaaggc actcgtcagg ttatgagcat ggtctcttcc tggttgtgga agagctagg    8820
caaacacaaa cgaccacgag tctgtaccaa agaagagttc atcaacaagg ttcgtagcaa    8880
tgcagcatta ggggcaatat ttgaagagga aaaagagtgg aagactgcag tggaagctgt    8940
gaacgatcca aggttctggg ctctagtgga caaggaaaga gagcaccacc tgagaggaga    9000
gtgccagagt tgtgtgtaca acatgatggg aaaaagagaa aagaaacaag gggaatttgg    9060
aaaggccaag ggcagccgcg ccatctggta tatgtggcta ggggctagat ttctagagtt    9120
cgaagccctt ggattcttga cgaggatca ctggatgggg agagagaact caggaggtgg    9180
tgttgaaggg ctgggattac aaagactcgg atatgtccta aagagatga gtcgcatacc    9240
aggaggaagg atgtatgcag atgacactgc tggctgggac acccgcatca gcaggtttga    9300
tctggagaat gaagctctaa tcaccaacca aatggagaaa gggcacaggg ccttggcatt    9360
ggccataatc aagtacacat accaaaacaa agtggtaaag gtccttagac cagctgaaaa    9420
agggaaaaca gttatggaca ttatttcgag acaagaccaa aggggagcg acaagttgt     9480
cacttacgct cttaacacat ttaccaacct agtggtgcaa ctcattcgga atatggaggc    9540
tgaggaagtt ctagagatgc aagacttgtg gctgctgcgg aggtcagaga aagtgaccaa    9600
ctggttgcag agcaacggat gggataggct caaacgaatg gcagtcagtg gagatgattg    9660
cgttgtgaag ccaattgatg ataggtttgc acatgccctc aggttcttga atgatatggg    9720
aaaagttagg aaggacacac aagagtgaaa accctcaact ggatgggaca actgggaaga    9780
agttccgttt tgctcccacc acttcaacaa gctccatctc aaggacggga ggtccattgt    9840
ggttccctgc cgccaccaag atgaactgat ggccgggcc cgcgtctctc caggggcggg    9900
atggagcatc cggagactg cttgcctagc aaaatcatat gcgcaaatgt ggcagctcct    9960
ttatttccac agaagggacc tccgactgat ggccaatgcc atttgttcat ctgtgccagt   10020
tgactgggtt ccaactggga gaactacctg gtcaatccat ggaaagggag aatggatgac   10080
cactgaagac atgcttgtgg tgtggaacag agtgtggatt gaggagaacg accacatgga   10140
agacaagacc ccagttacga aatggacaga cattccctat ttgggaaaaa gggaagactt   10200
```

```
gtggtgtgga tctctcatag ggcacagacc gcgcaccacc tgggctgaga acattaaaaa    10260
tacagtcaac atggtgcgca ggatcatagg tgatgaagaa aagtacatgg actacctatc    10320
cacccaagtt cgctacttgg gtgaagaagg gtctacacct ggagtgctgt gagcaccaat    10380
cttaatgttg tcaggcctgc tagtcagcca cagcttgggg aaagctgtgc agcctgtgac    10440
ccctccagga gaagctgggt aaccaagcct atagtcaggc cgagaacgcc atggcacgga    10500
agaagccatg ctgcctgtga gcccctcaga ggacactgag tcaaaaaacc ccacgcgctt    10560
ggaggcgcag gatgggaaaa gaaggtggcg accttcccca cccttcaatc tggggcctga    10620
actggagatc agctgtggat ctccagaaga gggactagtg gttagaggag accccccgga    10680
aaacgcaaaa cagcatattg acgctgggaa agaccagaga ctccatgagt ttccaccacg    10740
ctggccgcca ggcacagatc gccgaatagc ggcggccggt gtggggaaat cca           10793
```

<210> SEQ ID NO 18
<211> LENGTH: 3423
<212> TYPE: PRT
<213> ORGANISM: Artificial Sequence
<220> FEATURE:
<223> OTHER INFORMATION: Synthetic construct

<400> SEQUENCE: 18

```
Met Lys Asn Pro Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala Ala Glu Val Thr Arg Arg
        115                 120                 125

Gly Ser Ala Tyr Tyr Met Tyr Leu Asp Arg Asn Asp Ala Gly Glu Ala
    130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255
```

-continued

```
Phe Ala Leu Ala Ala Ala Ile Ala Trp Leu Leu Gly Ser Ser Thr
                260                 265                 270

Ser Gln Lys Val Ile Tyr Leu Val Met Ile Leu Leu Ile Ala Pro Ala
    275                 280                 285

Tyr Ser Ile Arg Cys Ile Gly Val Ser Asn Arg Asp Phe Val Glu Gly
290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
                340                 345                 350

Ala Ser Ile Ser Asp Met Ala Ser Asp Ser Arg Cys Pro Thr Gln Gly
            355                 360                 365

Glu Ala Tyr Leu Asp Lys Gln Ser Asp Thr Gln Tyr Val Cys Lys Arg
        370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
                420                 425                 430

Val His Gly Ser Gln His Ser Gly Met Ile Val Asn Asp Thr Gly His
            435                 440                 445

Glu Thr Asp Glu Asn Arg Ala Lys Val Glu Ile Thr Pro Asn Ser Pro
        450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
                500                 505                 510

Leu Pro Trp His Ala Gly Ala Asp Thr Gly Thr Pro His Trp Asn Asn
            515                 520                 525

Lys Glu Ala Leu Val Glu Phe Lys Asp Ala His Ala Lys Arg Gln Thr
        530                 535                 540

Val Val Val Leu Gly Thr Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
                580                 585                 590

Val Ser Tyr Ser Leu Cys Thr Ala Ala Phe Thr Phe Thr Lys Ile Pro
            595                 600                 605

Ala Glu Thr Leu His Gly Thr Val Thr Val Glu Val Gln Tyr Ala Gly
        610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
                660                 665                 670

Gly Asp Ser Tyr Ile Val Ile Gly Val Gly Glu Lys Lys Ile Thr His
```

-continued

```
            675                 680                 685
His Trp His Arg Ser Gly Ser Thr Ile Gly Lys Ala Phe Glu Ala Thr
690                 695                 700

Val Arg Gly Ala Lys Arg Met Ala Val Leu Gly Asp Thr Ala Trp Asp
705                 710                 715                 720

Phe Gly Ser Val Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
            755                 760                 765

Thr Lys Asn Gly Ser Ile Ser Leu Met Cys Leu Ala Leu Gly Gly Val
770                 775                 780

Leu Ile Phe Leu Ser Thr Ala Val Ser Ala Asp Val Gly Cys Ser Val
785                 790                 795                 800

Asp Phe Ser Lys Lys Glu Thr Arg Cys Gly Thr Gly Val Phe Val Tyr
            805                 810                 815

Asn Asp Val Glu Ala Trp Arg Asp Arg Tyr Lys Tyr His Pro Asp Ser
            820                 825                 830

Pro Arg Leu Ala Ala Ala Val Lys Gln Ala Trp Glu Asp Gly Ile
            835                 840                 845

Cys Gly Ile Ser Ser Val Ser Arg Met Glu Asn Ile Met Trp Arg Ser
850                 855                 860

Val Glu Gly Glu Leu Asn Ala Ile Leu Glu Glu Asn Gly Val Gln Leu
865                 870                 875                 880

Thr Val Val Val Gly Ser Val Lys Asn Pro Met Trp Arg Gly Pro Gln
                885                 890                 895

Arg Leu Pro Val Pro Val Asn Glu Leu Pro His Gly Trp Lys Ala Trp
            900                 905                 910

Gly Lys Ser Tyr Phe Val Arg Ala Ala Lys Thr Asn Asn Ser Phe Val
            915                 920                 925

Val Asp Gly Asp Thr Leu Lys Glu Cys Pro Leu Lys His Arg Ala Trp
930                 935                 940

Asn Ser Phe Leu Val Glu Asp His Gly Phe Gly Val Phe His Thr Ser
945                 950                 955                 960

Val Trp Leu Lys Val Arg Glu Asp Tyr Ser Leu Glu Cys Asp Pro Ala
                965                 970                 975

Val Ile Gly Thr Ala Val Lys Gly Lys Glu Ala Val His Ser Asp Leu
            980                 985                 990

Gly Tyr Trp Ile Glu Ser Glu Lys Asn Asp Thr Trp Arg Leu Lys Arg
            995                 1000                1005

Ala His Leu Ile Glu Met Lys Thr Cys Glu Trp Pro Lys Ser His
            1010                1015                1020

Thr Leu Trp Thr Asp Gly Ile Glu Glu Ser Asp Leu Ile Ile Pro
            1025                1030                1035

Lys Ser Leu Ala Gly Pro Leu Ser His His Asn Thr Arg Glu Gly
            1040                1045                1050

Tyr Arg Thr Gln Met Lys Gly Pro Trp His Ser Glu Glu Leu Glu
            1055                1060                1065

Ile Arg Phe Glu Glu Cys Pro Gly Thr Lys Val His Val Glu Glu
            1070                1075                1080

Thr Cys Gly Thr Arg Gly Pro Ser Leu Arg Ser Thr Thr Ala Ser
            1085                1090                1095
```

```
Gly Arg Val Ile Glu Glu Trp Cys Cys Arg Glu Cys Thr Met Pro
    1100            1105            1110

Pro Leu Ser Phe Arg Ala Lys Asp Gly Cys Trp Tyr Gly Met Glu
    1115            1120            1125

Ile Arg Pro Arg Lys Glu Pro Glu Ser Asn Leu Val Arg Ser Met
    1130            1135            1140

Val Thr Ala Gly Ser Thr Asp His Met Asp His Phe Ser Leu Gly
    1145            1150            1155

Val Leu Val Ile Leu Leu Met Val Gln Glu Gly Leu Lys Lys Arg
    1160            1165            1170

Met Thr Thr Lys Ile Ile Ile Ser Thr Ser Met Ala Val Leu Val
    1175            1180            1185

Ala Met Ile Leu Gly Gly Phe Ser Met Ser Asp Leu Ala Lys Leu
    1190            1195            1200

Ala Ile Leu Met Gly Ala Thr Phe Ala Glu Met Asn Thr Gly Gly
    1205            1210            1215

Asp Val Ala His Leu Ala Leu Ile Ala Ala Phe Lys Val Arg Pro
    1220            1225            1230

Ala Leu Leu Val Ser Phe Ile Phe Arg Ala Asn Trp Thr Pro Arg
    1235            1240            1245

Glu Ser Met Leu Leu Ala Leu Ala Ser Cys Phe Leu Gln Thr Ala
    1250            1255            1260

Ile Ser Ala Leu Glu Gly Asp Leu Met Val Leu Ile Asn Gly Phe
    1265            1270            1275

Ala Leu Ala Trp Leu Ala Ile Arg Ala Met Val Val Pro Arg Thr
    1280            1285            1290

Asp Asn Ile Thr Leu Ala Ile Leu Ala Ala Leu Thr Pro Leu Ala
    1295            1300            1305

Arg Gly Thr Leu Leu Val Ala Trp Arg Ala Gly Leu Ala Thr Cys
    1310            1315            1320

Gly Gly Phe Met Leu Leu Ser Leu Lys Gly Lys Gly Ser Val Lys
    1325            1330            1335

Lys Asn Leu Pro Phe Val Met Ala Leu Gly Leu Thr Ala Val Arg
    1340            1345            1350

Leu Val Asp Pro Ile Asn Val Val Gly Leu Leu Leu Leu Thr Arg
    1355            1360            1365

Ser Gly Lys Arg Ser Trp Pro Pro Ser Glu Val Leu Thr Ala Val
    1370            1375            1380

Gly Leu Ile Cys Ala Leu Ala Gly Gly Phe Ala Lys Ala Asp Ile
    1385            1390            1395

Glu Met Ala Gly Pro Met Ala Ala Val Gly Leu Leu Ile Val Ser
    1400            1405            1410

Tyr Val Val Ser Gly Lys Ser Val Asp Met Tyr Ile Glu Arg Ala
    1415            1420            1425

Gly Asp Ile Thr Trp Glu Lys Asp Ala Glu Val Thr Gly Asn Ser
    1430            1435            1440

Pro Arg Leu Asp Val Ala Leu Asp Glu Ser Gly Asp Phe Ser Leu
    1445            1450            1455

Val Glu Asp Asp Gly Pro Pro Met Arg Glu Ile Ile Leu Lys Val
    1460            1465            1470

Val Leu Met Thr Ile Cys Gly Met Asn Pro Ile Ala Ile Pro Phe
    1475            1480            1485
```

```
Ala Ala Gly Ala Trp Tyr Val Tyr Val Lys Thr Gly Lys Arg Ser
    1490                1495                1500

Gly Ala Leu Trp Asp Val Pro Ala Pro Lys Glu Val Lys Lys Gly
    1505                1510                1515

Glu Thr Thr Asp Gly Val Tyr Arg Val Met Thr Arg Arg Leu Leu
    1520                1525                1530

Gly Ser Thr Gln Val Gly Val Gly Val Met Gln Glu Gly Val Phe
    1535                1540                1545

His Thr Met Trp His Val Thr Lys Gly Ser Ala Leu Arg Ser Gly
    1550                1555                1560

Glu Gly Arg Leu Asp Pro Tyr Trp Gly Asp Val Lys Gln Asp Leu
    1565                1570                1575

Val Ser Tyr Cys Gly Pro Trp Lys Leu Asp Ala Ala Trp Asp Gly
    1580                1585                1590

His Ser Glu Val Gln Leu Leu Ala Val Pro Pro Gly Glu Arg Ala
    1595                1600                1605

Arg Asn Ile Gln Thr Leu Pro Gly Ile Phe Lys Thr Lys Asp Gly
    1610                1615                1620

Asp Ile Gly Ala Val Ala Leu Asp Tyr Pro Ala Gly Thr Ser Gly
    1625                1630                1635

Ser Pro Ile Leu Asp Lys Cys Gly Arg Val Ile Gly Leu Tyr Gly
    1640                1645                1650

Asn Gly Val Val Ile Lys Asn Gly Ser Tyr Val Ser Ala Ile Thr
    1655                1660                1665

Gln Gly Arg Arg Glu Glu Glu Thr Pro Val Glu Cys Phe Glu Pro
    1670                1675                1680

Ser Met Leu Lys Lys Lys Gln Leu Thr Val Leu Asp Leu His Pro
    1685                1690                1695

Gly Ala Gly Lys Thr Arg Arg Val Leu Pro Glu Ile Val Arg Glu
    1700                1705                1710

Ala Ile Lys Thr Arg Leu Arg Thr Val Ile Leu Ala Pro Thr Arg
    1715                1720                1725

Val Val Ala Ala Glu Met Glu Glu Ala Leu Arg Gly Leu Pro Val
    1730                1735                1740

Arg Tyr Met Thr Thr Ala Val Asn Val Thr His Ser Gly Thr Glu
    1745                1750                1755

Ile Val Asp Leu Met Cys His Ala Thr Phe Thr Ser Arg Leu Leu
    1760                1765                1770

Gln Pro Ile Arg Val Pro Asn Tyr Asn Leu Tyr Ile Met Asp Glu
    1775                1780                1785

Ala His Phe Thr Asp Pro Ser Ser Ile Ala Ala Arg Gly Tyr Ile
    1790                1795                1800

Ser Thr Arg Val Glu Met Gly Glu Ala Ala Ile Phe Met Thr
    1805                1810                1815

Ala Thr Pro Pro Gly Thr Arg Asp Ala Phe Pro Asp Ser Asn Ser
    1820                1825                1830

Pro Ile Met Asp Thr Glu Val Glu Val Pro Glu Arg Ala Trp Ser
    1835                1840                1845

Ser Gly Phe Asp Trp Val Thr Asp His Ser Gly Lys Thr Val Trp
    1850                1855                1860

Phe Val Pro Ser Val Arg Asn Gly Asn Glu Ile Ala Ala Cys Leu
    1865                1870                1875

Thr Lys Ala Gly Lys Arg Val Ile Gln Leu Ser Arg Lys Thr Phe
```

-continued

```
                1880                1885                1890
Glu Thr Glu Phe Gln Lys Thr Lys His Gln Glu Trp Asp Phe Val
        1895                1900                1905
Val Thr Thr Asp Ile Ser Glu Met Gly Ala Asn Phe Lys Ala Asp
        1910                1915                1920
Arg Val Ile Asp Ser Arg Arg Cys Leu Lys Pro Val Ile Leu Asp
        1925                1930                1935
Gly Glu Arg Val Ile Leu Ala Gly Pro Met Pro Val Thr His Ala
        1940                1945                1950
Ser Ala Ala Gln Arg Arg Gly Arg Ile Gly Arg Asn Pro Asn Lys
        1955                1960                1965
Pro Gly Asp Glu Tyr Leu Tyr Gly Gly Gly Cys Ala Glu Thr Asp
        1970                1975                1980
Glu Asp His Ala His Trp Leu Glu Ala Arg Met Leu Leu Asp Asn
        1985                1990                1995
Ile Tyr Leu Gln Asp Gly Leu Ile Ala Ser Leu Tyr Arg Pro Glu
        2000                2005                2010
Ala Asp Lys Val Ala Ala Ile Glu Gly Glu Phe Lys Leu Arg Thr
        2015                2020                2025
Glu Gln Arg Lys Thr Phe Val Glu Leu Met Lys Arg Gly Asp Leu
        2030                2035                2040
Pro Val Trp Leu Ala Tyr Gln Val Ala Ser Ala Gly Ile Thr Tyr
        2045                2050                2055
Thr Asp Arg Arg Trp Cys Phe Asp Gly Thr Thr Asn Asn Thr Ile
        2060                2065                2070
Met Glu Asp Ser Val Pro Ala Glu Val Trp Thr Arg His Gly Glu
        2075                2080                2085
Lys Arg Val Leu Lys Pro Arg Trp Met Asp Ala Arg Val Cys Ser
        2090                2095                2100
Asp His Ala Ala Leu Lys Ser Phe Lys Glu Phe Ala Ala Gly Lys
        2105                2110                2115
Arg Gly Ala Ala Phe Gly Val Met Glu Ala Leu Gly Thr Leu Pro
        2120                2125                2130
Gly His Met Thr Glu Arg Phe Gln Glu Ala Ile Asp Asn Leu Ala
        2135                2140                2145
Val Leu Met Arg Ala Glu Thr Gly Ser Arg Pro Tyr Lys Ala Ala
        2150                2155                2160
Ala Ala Gln Leu Pro Glu Thr Leu Glu Thr Ile Met Leu Leu Gly
        2165                2170                2175
Leu Leu Gly Thr Val Ser Leu Gly Ile Phe Phe Val Leu Met Arg
        2180                2185                2190
Asn Lys Gly Ile Gly Lys Met Gly Phe Gly Met Val Thr Leu Gly
        2195                2200                2205
Ala Ser Ala Trp Leu Met Trp Leu Ser Glu Ile Glu Pro Ala Arg
        2210                2215                2220
Ile Ala Cys Val Leu Ile Val Val Phe Leu Leu Leu Val Val Leu
        2225                2230                2235
Ile Pro Glu Pro Glu Lys Gln Arg Ser Pro Gln Asp Asn Gln Met
        2240                2245                2250
Ala Ile Ile Ile Met Val Ala Val Gly Leu Leu Gly Leu Ile Thr
        2255                2260                2265
Ala Asn Glu Leu Gly Trp Leu Glu Arg Thr Lys Ser Asp Leu Ser
        2270                2275                2280
```

-continued

His Leu Met Gly Arg Arg Glu Glu Gly Ala Thr Ile Gly Phe Ser
2285                 2290                2295

Met Asp Ile Asp Leu Arg Pro Ala Ser Ala Trp Ala Ile Tyr Ala
2300                 2305                2310

Ala Leu Thr Thr Phe Ile Thr Pro Ala Val Gln His Ala Val Thr
2315                 2320                2325

Thr Ser Tyr Asn Asn Tyr Ser Leu Met Ala Met Ala Thr Gln Ala
2330                 2335                2340

Gly Val Leu Phe Gly Met Gly Lys Gly Met Pro Phe Tyr Ala Trp
2345                 2350                2355

Asp Phe Gly Val Pro Leu Leu Met Ile Gly Cys Tyr Ser Gln Leu
2360                 2365                2370

Thr Pro Leu Thr Leu Ile Val Ala Ile Ile Leu Leu Val Ala His
2375                 2380                2385

Tyr Met Tyr Leu Ile Pro Gly Leu Gln Ala Ala Ala Arg Ala
2390                 2395                2400

Ala Gln Lys Arg Thr Ala Ala Gly Ile Met Lys Asn Pro Val Val
2405                 2410                2415

Asp Gly Ile Val Val Thr Asp Ile Asp Thr Met Thr Ile Asp Pro
2420                 2425                2430

Gln Val Glu Lys Lys Met Gly Gln Val Leu Leu Ile Ala Val Ala
2435                 2440                2445

Val Ser Ser Ala Ile Leu Ser Arg Thr Ala Trp Gly Trp Gly Glu
2450                 2455                2460

Ala Gly Ala Leu Ile Thr Ala Ala Thr Ser Thr Leu Trp Glu Gly
2465                 2470                2475

Ser Pro Asn Lys Tyr Trp Asn Ser Ser Thr Ala Thr Ser Leu Cys
2480                 2485                2490

Asn Ile Phe Arg Gly Ser Tyr Leu Ala Gly Ala Ser Leu Ile Tyr
2495                 2500                2505

Thr Val Thr Arg Asn Ala Gly Leu Val Lys Arg Arg Gly Gly Gly
2510                 2515                2520

Thr Gly Glu Thr Leu Gly Glu Lys Trp Lys Ala Arg Leu Asn Gln
2525                 2530                2535

Met Ser Ala Leu Glu Phe Tyr Ser Tyr Lys Lys Ser Gly Ile Thr
2540                 2545                2550

Glu Val Cys Arg Glu Glu Ala Arg Arg Ala Leu Lys Asp Gly Val
2555                 2560                2565

Ala Thr Gly Gly His Ala Val Ser Arg Gly Ser Ala Lys Leu Arg
2570                 2575                2580

Trp Leu Val Glu Arg Gly Tyr Leu Gln Pro Tyr Gly Lys Val Ile
2585                 2590                2595

Asp Leu Gly Cys Gly Arg Gly Gly Trp Ser Tyr Tyr Ala Ala Thr
2600                 2605                2610

Ile Arg Lys Val Gln Glu Val Lys Gly Tyr Thr Lys Gly Gly Pro
2615                 2620                2625

Gly His Glu Glu Pro Val Leu Val Gln Ser Tyr Gly Trp Asn Ile
2630                 2635                2640

Val Arg Leu Lys Ser Gly Val Asp Val Phe His Met Ala Ala Glu
2645                 2650                2655

Pro Cys Asp Thr Leu Leu Cys Asp Ile Gly Glu Ser Ser Ser Ser
2660                 2665                2670

```
Pro Glu Val Glu Glu Ala Arg Thr Leu Arg Val Leu Ser Met Val
2675                2680                2685

Gly Asp Trp Leu Glu Lys Arg Pro Gly Ala Phe Cys Ile Lys Val
2690                2695                2700

Leu Cys Pro Tyr Thr Ser Thr Met Met Glu Thr Leu Glu Arg Leu
2705                2710                2715

Gln Arg Arg Tyr Gly Gly Gly Leu Val Arg Val Pro Leu Ser Arg
2720                2725                2730

Asn Ser Thr His Glu Met Tyr Trp Val Ser Gly Ala Lys Ser Asn
2735                2740                2745

Thr Ile Lys Ser Val Ser Thr Thr Ser Gln Leu Leu Leu Gly Arg
2750                2755                2760

Met Asp Gly Pro Arg Arg Pro Val Lys Tyr Glu Glu Asp Val Asn
2765                2770                2775

Leu Gly Ser Gly Thr Arg Ala Val Val Ser Cys Ala Glu Ala Pro
2780                2785                2790

Asn Met Lys Ile Ile Gly Asn Arg Ile Glu Arg Ile Arg Ser Glu
2795                2800                2805

His Ala Glu Thr Trp Phe Phe Asp Glu Asn His Pro Tyr Arg Thr
2810                2815                2820

Trp Ala Tyr His Gly Ser Tyr Val Ala Pro Thr Gln Gly Ser Ala
2825                2830                2835

Ser Ser Leu Ile Asn Gly Val Val Arg Leu Leu Ser Lys Pro Trp
2840                2845                2850

Asp Val Val Thr Gly Val Thr Gly Ile Ala Met Thr Asp Thr Thr
2855                2860                2865

Pro Tyr Gly Gln Gln Arg Val Phe Lys Glu Lys Val Asp Thr Arg
2870                2875                2880

Val Pro Asp Pro Gln Glu Gly Thr Arg Gln Val Met Ser Met Val
2885                2890                2895

Ser Ser Trp Leu Trp Lys Glu Leu Gly Lys His Lys Arg Pro Arg
2900                2905                2910

Val Cys Thr Lys Glu Glu Phe Ile Asn Lys Val Arg Ser Asn Ala
2915                2920                2925

Ala Leu Gly Ala Ile Phe Glu Glu Glu Lys Glu Trp Lys Thr Ala
2930                2935                2940

Val Glu Ala Val Asn Asp Pro Arg Phe Trp Ala Leu Val Asp Lys
2945                2950                2955

Glu Arg Glu His His Leu Arg Gly Glu Cys Gln Ser Cys Val Tyr
2960                2965                2970

Asn Met Met Gly Lys Arg Glu Lys Lys Gln Gly Glu Phe Gly Lys
2975                2980                2985

Ala Lys Gly Ser Arg Ala Ile Trp Tyr Met Trp Leu Gly Ala Arg
2990                2995                3000

Phe Leu Glu Phe Glu Ala Leu Gly Phe Leu Asn Glu Asp His Trp
3005                3010                3015

Met Gly Arg Glu Asn Ser Gly Gly Gly Val Glu Gly Leu Gly Leu
3020                3025                3030

Gln Arg Leu Gly Tyr Val Leu Glu Glu Met Ser Arg Ile Pro Gly
3035                3040                3045

Gly Arg Met Tyr Ala Asp Asp Thr Ala Gly Trp Asp Thr Arg Ile
3050                3055                3060

Ser Arg Phe Asp Leu Glu Asn Glu Ala Leu Ile Thr Asn Gln Met
```

```
              3065                3070                3075

Glu Lys Gly His Arg Ala Leu Ala Leu Ala Ile Ile Lys Tyr Thr
    3080                3085                3090

Tyr Gln Asn Lys Val Val Lys Val Leu Arg Pro Ala Glu Lys Gly
    3095                3100                3105

Lys Thr Val Met Asp Ile Ile Ser Arg Gln Asp Gln Arg Gly Ser
    3110                3115                3120

Gly Gln Val Val Thr Tyr Ala Leu Asn Thr Phe Thr Asn Leu Val
    3125                3130                3135

Val Gln Leu Ile Arg Asn Met Glu Ala Glu Val Leu Glu Met
    3140                3145                3150

Gln Asp Leu Trp Leu Leu Arg Arg Ser Glu Lys Val Thr Asn Trp
    3155                3160                3165

Leu Gln Ser Asn Gly Trp Asp Arg Leu Lys Arg Met Ala Val Ser
    3170                3175                3180

Gly Asp Asp Cys Val Val Lys Pro Ile Asp Asp Arg Phe Ala His
    3185                3190                3195

Ala Leu Arg Phe Leu Asn Asp Met Gly Lys Val Arg Lys Asp Thr
    3200                3205                3210

Gln Glu Trp Lys Pro Ser Thr Gly Trp Asp Asn Trp Glu Glu Val
    3215                3220                3225

Pro Phe Cys Ser His His Phe Asn Lys Leu His Leu Lys Asp Gly
    3230                3235                3240

Arg Ser Ile Val Val Pro Cys Arg His Gln Asp Glu Leu Ile Gly
    3245                3250                3255

Arg Ala Arg Val Ser Pro Gly Ala Gly Trp Ser Ile Arg Glu Thr
    3260                3265                3270

Ala Cys Leu Ala Lys Ser Tyr Ala Gln Met Trp Gln Leu Leu Tyr
    3275                3280                3285

Phe His Arg Arg Asp Leu Arg Leu Met Ala Asn Ala Ile Cys Ser
    3290                3295                3300

Ser Val Pro Val Asp Trp Val Pro Thr Gly Arg Thr Thr Trp Ser
    3305                3310                3315

Ile His Gly Lys Gly Glu Trp Met Thr Thr Glu Asp Met Leu Val
    3320                3325                3330

Val Trp Asn Arg Val Trp Ile Glu Glu Asn Asp His Met Glu Asp
    3335                3340                3345

Lys Thr Pro Val Thr Lys Trp Thr Asp Ile Pro Tyr Leu Gly Lys
    3350                3355                3360

Arg Glu Asp Leu Trp Cys Gly Ser Leu Ile Gly His Arg Pro Arg
    3365                3370                3375

Thr Thr Trp Ala Glu Asn Ile Lys Asn Thr Val Asn Met Val Arg
    3380                3385                3390

Arg Ile Ile Gly Asp Glu Glu Lys Tyr Met Asp Tyr Leu Ser Thr
    3395                3400                3405

Gln Val Arg Tyr Leu Gly Glu Glu Gly Ser Thr Pro Gly Val Leu
    3410                3415                3420

<210> SEQ ID NO 19
<211> LENGTH: 10675
<212> TYPE: DNA
<213> ORGANISM: Artificial Sequence
<220> FEATURE:
<223> OTHER INFORMATION: Synthetic construct
```

```
<400> SEQUENCE: 19
gttgttgatc tgtgtgaatc agactgcgac agttcgagtt tgaagcgaaa gctagcaaca      60
gtatcaacag gttttatttt ggatttggaa acgagagttt ctggtcatga aaacccaaa     120 aaagaaatcc ggaggattcc ggattgtcaa tatgctaaaa cgcggagtag cccgtgtgag     180
ccccttgggg ggcttgaaga ggctgccagc cggacttctg ctgggtcatg ggcccatcag     240
gatggtcttg gcgattctag cctttttgag attcacggca atcaagccat cactgggtct     300
catcaataga tggggttcag tggggaaaaa agaggctatg gaaacaataa agaagttcaa     360
gaaagatctg gctgccatgc tgagaataat caatgctagg aaggagaaga agagacgagg     420
cgcagatact agtgtcggaa ttgttggcct cctgctgacc acagctatgg cagcggaggt     480
cactagacgt gggagtgcat actatatgta cttggacaga aacgatgctg ggaggccat     540 atcttttcca accacattgg ggatgaataa gtgttatata cagatcatgg atcttggaca     600
catgtgtgat gccaccatga gctatgaatg ccctatgctg gatgaggggg tggaaccaga     660
tgacgtcgat tgttggtgca acacgacgtc aacttgggtt gtgtacggaa cctgccatca     720
caaaaaaggt gaagcacgga gatctagaag agctgtgacg ctccctccc attccaccag     780 gaagctgcaa acgcggtcgc aaacctggtt ggaatcaaga gaatacacaa agcacttgat     840
tagagtcgaa aattggatat tcaggaaccc tggcttcgcg ttagcagcag ctgccatcgc     900
ttggcttttg ggaagctcaa cgagccaaaa agtcatatac ttggtcatga tactgctgat     960
tgccccggca tacagcatca ggtgcatagg agtcagcaat agggactttg tggaaggtat    1020
gtcaggtggg acttggggttg atgttgtctt ggaacatgga ggttgtgtca ccgtaatggc    1080
acaggacaaa ccgactgtcg acatagagct ggttacaaca acagtcagca acatggcgga    1140
ggtaagatcc tactgctatg aggcatcaat atcagacatg gcttctgaca gccgctgccc    1200
aacacaaggt gaagcctacc ttgacaagca atcagacact caatatgtct gcaaaagaac    1260
gttagtggac agaggctggg gaaatggatg tggactttt ggcaaaggga gcctggtgac    1320
atgcgctaag tttgcatgct ccaagaaaat gaccgggaag agcatccagc cagagaatct    1380
ggagtaccgg ataatgctgt cagttcatgg ctcccagcac agtgggatga tcgttaatga    1440
cacaggacat gaaactgatg agaatagagc gaaagttgag ataacgccca attcaccgag    1500
agccgaagcc accctggggg gttttggaag cctaggactt gattgtgaac cgaggacagg    1560
ccttgacttt tcagatttgt attacttgac tatgaataac aagcactggt tggttcacaa    1620
ggagtggttc cacgacattc cattaccttg gcacgctggg gcagacaccg gaactccaca    1680
ctggaacaac aaagaagcac tggtagagtt caaggacgca catgccaaaa ggcaaactgt    1740
cgtggttcta gggagtcaag aaggagcagt tcacacggcc cttgctggag ctctggaggc    1800
tgagatggat ggtgcaaagg gaaggctgtc ctctggccac ttgaaatgtc gcctgaaaat    1860
ggataaactt agattgaagg gcgtgtcata ctccttgtgt actgcagcgt tcacattcac    1920
caagatcccg gctgaaacac tgcacgggac agtcacagtg gaggtacagt acgcagggac    1980
agatggacct tgcaaggttc agctcagat ggcggtggac atgcaaactc tgaccccagt    2040
tgggaggttg ataaccgcta accccgtaat cactgaaagc actgagaact ctaagatgat    2100
gctggaactt gatccaccat ttggggactc ttacattgtc ataggagtcg gggagaagaa    2160
gatcacccac cactggcaca ggagtggcag caccattgga aaagcatttg aagccactgt    2220
gagaggtgcc aagagaatgg cagtcttggg agacacagcc tggacttttg atcagttgg    2280 aggcgctctc aactcattgg gcaagggcat ccatcaaatt tttggagcag ctttcaaatc    2340
```

```
attgtttgga ggaatgtcct ggttctcaca aattctcatt ggaacgttgc tgatgtggtt    2400
gggtctgaac acaaagaatg gatctatttc ccttatgtgc ttggccttag ggggagtgtt    2460
gatcttctta tccacagccg tctctgctga tgtggggtgc tcggtggact tctcaaagaa    2520
ggagacgaga tgcggtacag gggtgttcgt ctataacgac gttgaagcct ggagggacag    2580
gtacaagtac catcctgact ccccccgtag attggcagca gcagtcaagc aagcctggga    2640
agatggtatc tgcgggatct cctctgtttc aagaatggaa aacatcatgt ggagatcagt    2700
agaaggggag ctcaacgcaa tcctggaaga gaatggagtt caactgacgg tcgttgtggg    2760
atctgtaaaa aaccccatgt ggagaggtcc acagagattg cccgtgcctg tgaacgagct    2820
gccccacggc tggaaggctt gggggaaatc gtatttcgtc agagcagcaa agacaaataa    2880
cagctttgtc gtggatggtg acacactgaa ggaatgccca ctcaaacata gagcatggaa    2940
cagctttctt gtggaggatc atgggttcgg ggtatttcac actagtgtct ggctcaaggt    3000
tagagaagat tattcattag agtgtgatcc agccgttatt ggaacagctg ttaagggaaa    3060
ggaggctgta cacagtgatc taggctactg gattgagagt gagaagaatg acacatggag    3120
gctgaagagg gccatctga tcgagatgaa aacatgtgaa tggccaaagt cccacacatt    3180
gtggacagat ggaatagaag agagtgatct gatcataccc aagtctttag ctgggccact    3240
cagccatcac aataccagag agggctacag gacccaaatg aaagggccat ggcacagtga    3300
agagcttgaa attcggtttg aggaatgccc aggcactaag gtccacgtgg aggaaacatg    3360
tggaacaaga ggaccatctc tgagatcaac cactgcaagc ggaagggtga tcgaggaatg    3420
gtgctgcagg gagtgcacaa tgcccccact gtcgttccgg gctaaagatg gctgttggta    3480
tggaatggag ataaggccca ggaaagaacc agaaagcaac ttagtaaggt caatggtgac    3540
tgcaggatca actgatcaca tggaccactt ctcccttgga gtgcttgtga tcctgctcat    3600
ggtgcaggaa gggctgaaga agagaatgac cacaaagatc atcataagca catcaatggc    3660
agtgctggta gctatgatcc tgggaggatt ttcaatgagt gacctggcta agcttgcaat    3720
tttgatgggt gccaccttcg cggaaatgaa cactggagga gatgtagctc atctggcgct    3780
gatagcggca ttcaaagtca gaccagcgtt gctggtatct ttcatcttca gagctaattg    3840
gacaccccgt gaaagcatgc tgctggcctt ggcctcgtgt cttttgcaaa ctgcgatctc    3900
cgccttggaa ggcgacctga tggttctcat caatggtttt gctttggcct ggttggcaat    3960
acgagcgatg gttgttccac gcactgataa catcaccttg gcaatcctgg ctgctctgac    4020
accactggcc cggggcacac tgcttgtggc gtggagagca ggccttgcta cttgcggggg    4080
gtttatgctc ctctctctga agggaaaagg cagtgtgaag aagaacttac catttgtcat    4140
ggccctggga ctaaccgctg tgaggctggt cgaccccatc aacgtggtgg gactgctgtt    4200
gctcacaagg agtgggaagc ggagctggcc ccctagcgaa gtactcacag ctgttggcct    4260
gatatgcgca ttggctggag ggttcgccaa ggcagatata gagatggctg gcccatggc    4320 cgcggtcggt ctgctaattg tcagttacgt ggtctcagga aagagtgtgg acatgtacat    4380
tgaaagagca ggtgacatca catgggaaaa agatgcggaa gtcactggaa acagtccccg    4440
gctcgatgtg gcgctagatg agagtggtga tttctccctg gtggaggatg acggtccccg    4500
catgagagag atcatactca aggtggtcct gatgaccatc tgtggcatga acccaatagc    4560
catacccttt gcagctggag cgtggtacgt atacgtgaag actggaaaaa ggagtggtgc    4620
tctatgggat gtgcctgctc ccaaggaagt aaaaaagggg gagaccacag atggagtgta    4680
```

```
cagagtaatg actcgtagac tgctaggttc aacacaagtt ggagtgggag ttatgcaaga    4740
gggggtcttt cacactatgt ggcacgtcac aaaaggatcc gcgctgagaa gcggtgaagg    4800
gagacttgat ccatactggg gagatgtcaa gcaggatctg gtgtcatact gtggtccatg    4860
gaagctagat gccgcctggg atgggcacag cgaggtgcag ctcttggccg tgccccccgg    4920
agagagagcg aggaacatcc agactctgcc cggaatattt aagacaaagg atggggacat    4980
tggagcggtt gcgctggatt acccagcagg aacttcagga tctccaatcc tagacaagtg    5040
tgggagagtg ataggacttt atggcaatgg ggtcgtgatc aaaaacggga gttatgttag    5100
tgccatcacc caaggaggga gggaggaaga gactcctgtt gagtgcttcg agccctcgat    5160
gctgaagaag aagcagctaa ctgtcttaga cttgcatcct ggagctggga aaaccaggag    5220
agttcttcct gaaatagtcc gtgaagccat aaaaacaaga ctccgtactg tgatcttagc    5280
tccaaccagg gttgtcgctg ctgaaatgga ggaggccctt agagggcttc cagtgcgtta    5340
tatgacaaca gcagtcaatg tcacccactc tggaacagaa atcgtcgact taatgtgcca    5400
tgccaccttc acttcacgtc tactacagcc aatcagagtc cccaactata atctgtatat    5460
tatggatgag gcccacttca cagatcccct aagtatagca gcaagaggat acatttcaac    5520
aagggttgag atgggcgagg cggctgccat cttcatgacc gccacgccac caggaaccocg    5580 tgacgcattt ccggactcca actcaccaat tatggacacc gaagtggaag tcccagagag    5640
agcctggagc tcaggctttg attgggtgac ggatcattct ggaaaaacag tttggtttgt    5700
tccaagcgtg aggaacggca atgagatcgc agcttgtctg acaaaggctg gaaaacgggt    5760
catacagctc agcagaaaga cttttgagac agagttccag aaaacaaaac atcaagagtg    5820
ggactttgtc gtgacaactg acatttcaga gatgggcgcc aactttaaag ctgaccgtgt    5880
catagattcc aggagatgcc taaagccggt catacttgat ggcgagagag tcattctggc    5940
tggacccatg cctgtcacac atgccagcgc tgcccagagg agggggcgca taggcaggaa    6000
tcccaacaaa cctggagatg agtatctgta tggaggtggg tgcgcagaga ctgacgaaga    6060
ccatgcacac tggcttgaag caagaatgct ccttgacaat atttacctcc aagatggcct    6120
catagcctcg ctctatcgac ctgaggccga caaagtagca gccattgagg gagagttcaa    6180
gcttaggacg gagcaaagga aagacctttgt ggaactcatg aaaagaggag atcttcctgt    6240
ttggctggcc tatcaggttg catctgccgg aataacctac acagatagaa gatggtgctt    6300
tgatggcacg accaacaaca ccataatgga agacagtgtg ccggcagagg tgtggaccag    6360
acacggagag aaaagagtgc tcaaaccgag gtggatggac gccagagttt gttcagatca    6420
tgcggccctg aagtcattca aggagtttgc cgctgggaaa agaggagcgg cttttggagt    6480
gatggaagcc ctgggaacac tgccaggaca catgacagag agattccagg aagccattga    6540
caacctcgct gtgctcatgc gggcagagac tggaagcagg ccttacaaag ccgcggcggc    6600
ccaattgccg gagaccctag agaccataat gctttggggg ttgctgggaa cagtctcgct    6660
gggaatcttc ttcgtcttga tgaggaacaa gggcataggg aagatgggct ttggaatggt    6720
gactcttggg gccagcgcat ggctcatgtg gctctcggaa attgagccag ccagaattgc    6780
atgtgtcctc attgttgtgt tcctattgct ggtggtgctc atacctgagc cagaaaagca    6840
aagatctccc caggacaacc aaatggcaat catcatcatg gtagcagtag tcttctgggg    6900
cttgattacc gccaatgaac tcggatggtt ggagagaaca aagagtgacc taagccatct    6960
aatgggaagg agagaggagg gggcaaccat aggattctca atggacattg acctgcggcc    7020
agcctcagct tgggccatct atgctgcctt gacaactttc attaccccag ccgtccaaca    7080
```

```
tgcagtgacc acctcataca acaactactc cttaatggcg atggccacgc aagctggagt    7140
gttgtttggc atgggcaaag ggatgccatt ctacgcatgg gactttggag tcccgctgct    7200
aatgataggt tgctactcac aattaacacc cctgacccta atagtggcca tcattttgct    7260
cgtggcgcac tacatgtact tgatcccagg gctgcaggca gcagctgcgc gtgctgccca    7320
gaagagaacg gcagctggca tcatgaagaa ccctgttgtg gatggaatag tggtgactga    7380
cattgacaca atgacaattg accccccaagt ggagaaaaag atgggacagg tgctactcat    7440
agcagtagcc gtctccagcg ccatactgtc gcggaccgcc tggggtggg gggaggctgg    7500
ggctctgatc acagccgcaa cttccacttt gtgggaaggc tctccgaaca agtactggaa    7560
ctcctctaca gccacttcac tgtgtaacat ttttagggga agttacttgg ctggagcttc    7620
tctaatctac acagtaacaa gaaacgctgg cttggtcaag agacgtgggg gtggaacagg    7680
agagaccctg ggagagaaat ggaaggcccg cttgaaccag atgtcggccc tggagttcta    7740
ctcctacaaa aagtcaggca tcaccgaggt gtgcagagaa gaggcccgcc gcgccctcaa    7800
ggacggtgtg gcaacgggag gccatgctgt gtcccgagga agtgcaaagc tgagatggtt    7860
ggtgagcgg ggatacctgc agccctatgg aaaggtcatt gatcttggat gtggcagagg    7920
gggctggagt tactacgtcg ccaccatccg caaagttcaa gaagtgaaag gatacacaaa    7980
aggaggccct ggtcatgaag aacccgtgtt ggtgcaaagc tatgggtgga acatagtccg    8040
tcttaagagt ggggtggacg tctttcatat ggcggctgag ccgtgtgaca cgttgctgtg    8100
tgacataggt gagtcatcat ctagtcctga agtggaagaa gcacggacgc tcagagtcct    8160
ctccatggtg ggggattggc ttgaaaaaag accaggagcc ttttgtataa aagtgttgtg    8220
cccatacacc agcactatga tggaaaccct ggagcgactg cagcgtaggt atggggagg    8280
actggtcaga gtgccactct cccgcaactc tacacatgag atgtactggg tctctggagc    8340
gaaaagcaac accataaaaa gtgtgtccac cacgagccag ctcctcttgg ggcgcatgga    8400
cgggcctagg aggccagtga aatatgagga ggatgtgaat ctcggctctg gcacgcgggc    8460
tgtggtaagc tgcgctgaag ctcccaacat gaagatcatt ggtaaccgca ttgaaaggat    8520
ccgcagtgag cacgcggaaa cgtggttctt tgacgagaac cacccatata ggacatgggc    8580
ttaccatgga agctatgagg cccccacaca agggtcagcg tcctctctaa taaacggggt    8640
tgtcaggctc ctgtcaaaac cctgggatgt ggtgactgga gtcacaggaa tagccatgac    8700
cgacaccaca ccgtatggtc agcaaagagt tttcaaggaa aaagtggaca ctagggtgcc    8760
agaccccaa gaaggcactc gtcaggttat gagcatggtc tcttcctggt tgtggaaga    8820
gctaggcaaa cacaaacggc cacgagtctg caccaaagaa gagttcatca acaaggttcg    8880
tagcaatgca gcattagggg caatatttga agaggaaaaa gagtggaaga ctgcagtgga    8940
agctgtgaac gatccaaggt tctgggctct agtggacaag gaaagagagc accacctgag    9000
aggagagtgc cagagctgtg tgtacaacat gatgggaaaa agagaaaaga aacaagggga    9060
atttggaaag gccaagggca ccgcgccat ctggtatatg tggctagggg ctagatttct    9120
agagttcgaa gcccttggat tcttgaacga ggatcactgg atggggagag agaactcagg    9180
aggtggtgtt gaagggctgg gattacaaag actcggatat gtcctagaag agatgagtcg    9240
tataccagga ggaaggatgt atgcagatga cactgctggc tgggacaccc gcattagcag    9300
gtttgatctg gagaatgaag ctctaatcac caaccaaatg gagaaagggc acagggcctt    9360
ggcattggcc ataatcaagt acacatacca aaacaaagtg gtaaaggtcc ttagaccagc    9420
```

```
tgaaaaaggg aaaacagtta tggacattat ttcgagacaa gaccaaaggg ggagcggaca    9480
agttgtcact tacgctctta acacatttac caacctagtg gtgcaactca ttcggaatat    9540
ggaggctgag gaagttctag agatgcaaga cttgtggctg ctgcggaggt cagagaaagt    9600
gaccaactgg ttgcagagca acggatggga taggctcaaa cgaatggcag tcagtggaga    9660
tgattgcgtt gtgaagccaa ttgatgatag gtttgcacat gccctcaggt tcttgaatga    9720
tatgggaaaa gttaggaagg acacacaaga gtggaaaccc tcaactggat gggacaactg    9780
ggaagaagtt ccgttttgct cccaccactt caacaagctc catctcaagg acgggaggtc    9840
cattgtggtt ccctgccgcc accaagatga actgattggc cgggcccgcg tctctccagg    9900
ggcgggatgg agcatccggg agactgcttg cctagcaaaa tcatatgcgc aaatgtggca    9960
gctcctttat ttccacagaa gggacctccg actgatggcc aatgccattt gttcatctgt   10020
gccagttgac tgggttccaa ctgggagaac tacctggtca atccatggaa agggagaatg   10080
gatgaccact gaagacatgc ttgtggtgtg gaacagagtg tggattgagg agaacgacca   10140 catgaagac aagaccccag ttacgaaatg gacagacatt ccctatttgg gaaaaaggga   10200
agacttgtgg tgtggatctc tcatagggca cagaccgcgc accacctggg ctgagaacat   10260
taaaaacaca gtcaacatgg tgcgcaggat cataggtgat gaagaaaagt acatggacta   10320
cctatccacc caagttcgct acttgggtga agaagggtct acacctggag tgctgtaagc   10380
accaatctta atgttgtcag gcctgctagt cagccacagc ttggggaaag ctgtgcagcc   10440
tgtgaccccc ccaggagaag ctgggaaacc aagcctatag tcaggccgag aacgccatgg   10500
cacggaagaa gccatgctgc ctgtgagccc ctcagaggac actgagtcaa aaaccccac   10560 gcgcttggag gcgcaggatg ggaaaagaag gtggcgacct tccccaccct tcaatctggg   10620
gcctgaactg gagatcagct gtggatctcc agaagaggga ctagtggtta gagga         10675
```

<210> SEQ ID NO 20
<211> LENGTH: 3423
<212> TYPE: PRT
<213> ORGANISM: Artificial Sequence
<220> FEATURE:
<223> OTHER INFORMATION: Synthetic construct

<400> SEQUENCE: 20

```
Met Lys Asn Pro Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Thr
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala Ala Glu Val Thr Arg Arg
        115                 120                 125

Gly Ser Ala Tyr Tyr Met Tyr Leu Asp Arg Asn Asp Ala Gly Glu Ala
    130                 135                 140
```

```
Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
            165                 170                 175

Met Leu Asp Glu Gly Val Glu Pro Asp Asp Val Asp Cys Trp Cys Asn
        180                 185                 190

Thr Thr Ser Thr Trp Val Val Tyr Gly Thr Cys His His Lys Lys Gly
    195                 200                 205

Glu Ala Arg Arg Ser Arg Arg Ala Val Thr Leu Pro Ser His Ser Thr
210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
            245                 250                 255

Phe Ala Leu Ala Ala Ala Ala Ile Ala Trp Leu Leu Gly Ser Ser Thr
        260                 265                 270

Ser Gln Lys Val Ile Tyr Leu Val Met Ile Leu Leu Ile Ala Pro Ala
    275                 280                 285

Tyr Ser Ile Arg Cys Ile Gly Val Ser Asn Arg Asp Phe Val Glu Gly
290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
            325                 330                 335

Thr Thr Thr Val Ser Asn Met Ala Glu Val Arg Ser Tyr Cys Tyr Glu
        340                 345                 350

Ala Ser Ile Ser Asp Met Ala Ser Asp Ser Arg Cys Pro Thr Gln Gly
    355                 360                 365

Glu Ala Tyr Leu Asp Lys Gln Ser Asp Thr Gln Tyr Val Cys Lys Arg
370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
            405                 410                 415

Gly Lys Ser Ile Gln Pro Glu Asn Leu Glu Tyr Arg Ile Met Leu Ser
        420                 425                 430

Val His Gly Ser Gln His Ser Gly Met Ile Val Asn Asp Thr Gly His
    435                 440                 445

Glu Thr Asp Glu Asn Arg Ala Lys Val Glu Ile Thr Pro Asn Ser Pro
450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
            485                 490                 495

Asn Asn Lys His Trp Leu Val His Lys Glu Trp Phe His Asp Ile Pro
        500                 505                 510

Leu Pro Trp His Ala Gly Ala Asp Thr Gly Thr Pro His Trp Asn Asn
    515                 520                 525

Lys Glu Ala Leu Val Glu Phe Lys Asp Ala His Ala Lys Arg Gln Thr
530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
```

-continued

```
                565                 570                 575
Gly His Leu Lys Cys Arg Leu Lys Met Asp Lys Leu Arg Leu Lys Gly
                580                 585                 590

Val Ser Tyr Ser Leu Cys Thr Ala Ala Phe Thr Phe Thr Lys Ile Pro
                595                 600                 605

Ala Glu Thr Leu His Gly Thr Val Thr Val Glu Val Gln Tyr Ala Gly
                610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
                660                 665                 670

Gly Asp Ser Tyr Ile Val Ile Gly Val Gly Glu Lys Lys Ile Thr His
                675                 680                 685

His Trp His Arg Ser Gly Ser Thr Ile Gly Lys Ala Phe Glu Ala Thr
                690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
                740                 745                 750

Phe Ser Gln Ile Leu Ile Gly Thr Leu Leu Met Trp Leu Gly Leu Asn
                755                 760                 765

Thr Lys Asn Gly Ser Ile Ser Leu Met Cys Leu Ala Leu Gly Gly Val
                770                 775                 780

Leu Ile Phe Leu Ser Thr Ala Val Ser Ala Asp Val Gly Cys Ser Val
785                 790                 795                 800

Asp Phe Ser Lys Lys Glu Thr Arg Cys Gly Thr Gly Val Phe Val Tyr
                805                 810                 815

Asn Asp Val Glu Ala Trp Arg Asp Arg Tyr Lys Tyr His Pro Asp Ser
                820                 825                 830

Pro Arg Arg Leu Ala Ala Ala Val Lys Gln Ala Trp Glu Asp Gly Ile
                835                 840                 845

Cys Gly Ile Ser Ser Val Ser Arg Met Glu Asn Ile Met Trp Arg Ser
850                 855                 860

Val Glu Gly Glu Leu Asn Ala Ile Leu Glu Glu Asn Gly Val Gln Leu
865                 870                 875                 880

Thr Val Val Val Gly Ser Val Lys Asn Pro Met Trp Arg Gly Pro Gln
                885                 890                 895

Arg Leu Pro Val Pro Val Asn Glu Leu Pro His Gly Trp Lys Ala Trp
                900                 905                 910

Gly Lys Ser Tyr Phe Val Arg Ala Ala Lys Thr Asn Asn Ser Phe Val
                915                 920                 925

Val Asp Gly Asp Thr Leu Lys Glu Cys Pro Leu Lys His Arg Ala Trp
                930                 935                 940

Asn Ser Phe Leu Val Glu Asp His Gly Phe Gly Val Phe His Thr Ser
945                 950                 955                 960

Val Trp Leu Lys Val Arg Glu Asp Tyr Ser Leu Glu Cys Asp Pro Ala
                965                 970                 975

Val Ile Gly Thr Ala Val Lys Gly Lys Glu Ala Val His Ser Asp Leu
                980                 985                 990
```

```
Gly Tyr Trp Ile Glu Ser Glu Lys Asn Asp Thr Trp Arg Leu Lys Arg
        995                 1000                1005

Ala His Leu Ile Glu Met Lys Thr Cys Glu Trp Pro Lys Ser His
    1010                1015                1020

Thr Leu Trp Thr Asp Gly Ile Glu Glu Ser Asp Leu Ile Ile Pro
    1025                1030                1035

Lys Ser Leu Ala Gly Pro Leu Ser His His Asn Thr Arg Glu Gly
    1040                1045                1050

Tyr Arg Thr Gln Met Lys Gly Pro Trp His Ser Glu Glu Leu Glu
    1055                1060                1065

Ile Arg Phe Glu Glu Cys Pro Gly Thr Lys Val His Val Glu Glu
    1070                1075                1080

Thr Cys Gly Thr Arg Gly Pro Ser Leu Arg Ser Thr Thr Ala Ser
    1085                1090                1095

Gly Arg Val Ile Glu Glu Trp Cys Cys Arg Glu Cys Thr Met Pro
    1100                1105                1110

Pro Leu Ser Phe Arg Ala Lys Asp Gly Cys Trp Tyr Gly Met Glu
    1115                1120                1125

Ile Arg Pro Arg Lys Glu Pro Glu Ser Asn Leu Val Arg Ser Met
    1130                1135                1140

Val Thr Ala Gly Ser Thr Asp His Met Asp His Phe Ser Leu Gly
    1145                1150                1155

Val Leu Val Ile Leu Leu Met Val Gln Glu Gly Leu Lys Lys Arg
    1160                1165                1170

Met Thr Thr Lys Ile Ile Ile Ser Thr Ser Met Ala Val Leu Val
    1175                1180                1185

Ala Met Ile Leu Gly Gly Phe Ser Met Ser Asp Leu Ala Lys Leu
    1190                1195                1200

Ala Ile Leu Met Gly Ala Thr Phe Ala Glu Met Asn Thr Gly Gly
    1205                1210                1215

Asp Val Ala His Leu Ala Leu Ile Ala Ala Phe Lys Val Arg Pro
    1220                1225                1230

Ala Leu Leu Val Ser Phe Ile Phe Arg Ala Asn Trp Thr Pro Arg
    1235                1240                1245

Glu Ser Met Leu Leu Ala Leu Ala Ser Cys Leu Leu Gln Thr Ala
    1250                1255                1260

Ile Ser Ala Leu Glu Gly Asp Leu Met Val Leu Ile Asn Gly Phe
    1265                1270                1275

Ala Leu Ala Trp Leu Ala Ile Arg Ala Met Val Val Pro Arg Thr
    1280                1285                1290

Asp Asn Ile Thr Leu Ala Ile Leu Ala Ala Leu Thr Pro Leu Ala
    1295                1300                1305

Arg Gly Thr Leu Leu Val Ala Trp Arg Ala Gly Leu Ala Thr Cys
    1310                1315                1320

Gly Gly Phe Met Leu Leu Ser Leu Lys Gly Lys Gly Ser Val Lys
    1325                1330                1335

Lys Asn Leu Pro Phe Val Met Ala Leu Gly Leu Thr Ala Val Arg
    1340                1345                1350

Leu Val Asp Pro Ile Asn Val Val Gly Leu Leu Leu Leu Thr Arg
    1355                1360                1365

Ser Gly Lys Arg Ser Trp Pro Pro Ser Glu Val Leu Thr Ala Val
    1370                1375                1380
```

-continued

```
Gly Leu Ile Cys Ala Leu Ala Gly Gly Phe Ala Lys Ala Asp Ile
    1385                1390                1395
Glu Met Ala Gly Pro Met Ala Ala Val Gly Leu Leu Ile Val Ser
    1400                1405                1410
Tyr Val Val Ser Gly Lys Ser Val Asp Met Tyr Ile Glu Arg Ala
    1415                1420                1425
Gly Asp Ile Thr Trp Glu Lys Asp Ala Glu Val Thr Gly Asn Ser
    1430                1435                1440
Pro Arg Leu Asp Val Ala Leu Asp Glu Ser Gly Asp Phe Ser Leu
    1445                1450                1455
Val Glu Asp Asp Gly Pro Pro Met Arg Glu Ile Ile Leu Lys Val
    1460                1465                1470
Val Leu Met Thr Ile Cys Gly Met Asn Pro Ile Ala Ile Pro Phe
    1475                1480                1485
Ala Ala Gly Ala Trp Tyr Val Tyr Val Lys Thr Gly Lys Arg Ser
    1490                1495                1500
Gly Ala Leu Trp Asp Val Pro Ala Pro Lys Glu Val Lys Lys Gly
    1505                1510                1515
Glu Thr Thr Asp Gly Val Tyr Arg Val Met Thr Arg Arg Leu Leu
    1520                1525                1530
Gly Ser Thr Gln Val Gly Val Gly Val Met Gln Glu Gly Val Phe
    1535                1540                1545
His Thr Met Trp His Val Thr Lys Gly Ser Ala Leu Arg Ser Gly
    1550                1555                1560
Glu Gly Arg Leu Asp Pro Tyr Trp Gly Asp Val Lys Gln Asp Leu
    1565                1570                1575
Val Ser Tyr Cys Gly Pro Trp Lys Leu Asp Ala Ala Trp Asp Gly
    1580                1585                1590
His Ser Glu Val Gln Leu Leu Ala Val Pro Pro Gly Glu Arg Ala
    1595                1600                1605
Arg Asn Ile Gln Thr Leu Pro Gly Ile Phe Lys Thr Lys Asp Gly
    1610                1615                1620
Asp Ile Gly Ala Val Ala Leu Asp Tyr Pro Ala Gly Thr Ser Gly
    1625                1630                1635
Ser Pro Ile Leu Asp Lys Cys Gly Arg Val Ile Gly Leu Tyr Gly
    1640                1645                1650
Asn Gly Val Val Ile Lys Asn Gly Ser Tyr Val Ser Ala Ile Thr
    1655                1660                1665
Gln Gly Arg Arg Glu Glu Glu Thr Pro Val Glu Cys Phe Glu Pro
    1670                1675                1680
Ser Met Leu Lys Lys Lys Gln Leu Thr Val Leu Asp Leu His Pro
    1685                1690                1695
Gly Ala Gly Lys Thr Arg Arg Val Leu Pro Glu Ile Val Arg Glu
    1700                1705                1710
Ala Ile Lys Thr Arg Leu Arg Thr Val Ile Leu Ala Pro Thr Arg
    1715                1720                1725
Val Val Ala Ala Glu Met Glu Glu Ala Leu Arg Gly Leu Pro Val
    1730                1735                1740
Arg Tyr Met Thr Thr Ala Val Asn Val Thr His Ser Gly Thr Glu
    1745                1750                1755
Ile Val Asp Leu Met Cys His Ala Thr Phe Thr Ser Arg Leu Leu
    1760                1765                1770
Gln Pro Ile Arg Val Pro Asn Tyr Asn Leu Tyr Ile Met Asp Glu
```

```
                1775                1780                1785

Ala His Phe Thr Asp Pro Ser Ser Ile Ala Ala Arg Gly Tyr Ile
    1790                1795                1800

Ser Thr Arg Val Glu Met Gly Glu Ala Ala Ile Phe Met Thr
    1805                1810                1815

Ala Thr Pro Pro Gly Thr Arg Asp Ala Phe Pro Asp Ser Asn Ser
    1820                1825                1830

Pro Ile Met Asp Thr Glu Val Glu Val Pro Glu Arg Ala Trp Ser
    1835                1840                1845

Ser Gly Phe Asp Trp Val Thr Asp His Ser Gly Lys Thr Val Trp
    1850                1855                1860

Phe Val Pro Ser Val Arg Asn Gly Asn Glu Ile Ala Ala Cys Leu
    1865                1870                1875

Thr Lys Ala Gly Lys Arg Val Ile Gln Leu Ser Arg Lys Thr Phe
    1880                1885                1890

Glu Thr Glu Phe Gln Lys Thr Lys His Gln Glu Trp Asp Phe Val
    1895                1900                1905

Val Thr Thr Asp Ile Ser Glu Met Gly Ala Asn Phe Lys Ala Asp
    1910                1915                1920

Arg Val Ile Asp Ser Arg Arg Cys Leu Lys Pro Val Ile Leu Asp
    1925                1930                1935

Gly Glu Arg Val Ile Leu Ala Gly Pro Met Pro Val Thr His Ala
    1940                1945                1950

Ser Ala Ala Gln Arg Arg Gly Arg Ile Gly Arg Asn Pro Asn Lys
    1955                1960                1965

Pro Gly Asp Glu Tyr Leu Tyr Gly Gly Gly Cys Ala Glu Thr Asp
    1970                1975                1980

Glu Asp His Ala His Trp Leu Glu Ala Arg Met Leu Leu Asp Asn
    1985                1990                1995

Ile Tyr Leu Gln Asp Gly Leu Ile Ala Ser Leu Tyr Arg Pro Glu
    2000                2005                2010

Ala Asp Lys Val Ala Ala Ile Glu Gly Glu Phe Lys Leu Arg Thr
    2015                2020                2025

Glu Gln Arg Lys Thr Phe Val Glu Leu Met Lys Arg Gly Asp Leu
    2030                2035                2040

Pro Val Trp Leu Ala Tyr Gln Val Ala Ser Ala Gly Ile Thr Tyr
    2045                2050                2055

Thr Asp Arg Arg Trp Cys Phe Asp Gly Thr Thr Asn Asn Thr Ile
    2060                2065                2070

Met Glu Asp Ser Val Pro Ala Glu Val Trp Thr Arg His Gly Glu
    2075                2080                2085

Lys Arg Val Leu Lys Pro Arg Trp Met Asp Ala Arg Val Cys Ser
    2090                2095                2100

Asp His Ala Ala Leu Lys Ser Phe Lys Glu Phe Ala Ala Gly Lys
    2105                2110                2115

Arg Gly Ala Ala Phe Gly Val Met Glu Ala Leu Gly Thr Leu Pro
    2120                2125                2130

Gly His Met Thr Glu Arg Phe Gln Glu Ala Ile Asp Asn Leu Ala
    2135                2140                2145

Val Leu Met Arg Ala Glu Thr Gly Ser Arg Pro Tyr Lys Ala Ala
    2150                2155                2160

Ala Ala Gln Leu Pro Glu Thr Leu Glu Thr Ile Met Leu Leu Gly
    2165                2170                2175
```

```
Leu Leu Gly Thr Val Ser Leu Gly Ile Phe Phe Val Leu Met Arg
    2180            2185                2190

Asn Lys Gly Ile Gly Lys Met Gly Phe Gly Met Val Thr Leu Gly
    2195            2200                2205

Ala Ser Ala Trp Leu Met Trp Leu Ser Glu Ile Glu Pro Ala Arg
    2210            2215                2220

Ile Ala Cys Val Leu Ile Val Val Phe Leu Leu Leu Val Val Leu
    2225            2230                2235

Ile Pro Glu Pro Glu Lys Gln Arg Ser Pro Gln Asp Asn Gln Met
    2240            2245                2250

Ala Ile Ile Ile Met Val Ala Val Gly Leu Leu Gly Leu Ile Thr
    2255            2260                2265

Ala Asn Glu Leu Gly Trp Leu Glu Arg Thr Lys Ser Asp Leu Ser
    2270            2275                2280

His Leu Met Gly Arg Arg Glu Glu Gly Ala Thr Ile Gly Phe Ser
    2285            2290                2295

Met Asp Ile Asp Leu Arg Pro Ala Ser Ala Trp Ala Ile Tyr Ala
    2300            2305                2310

Ala Leu Thr Thr Phe Ile Thr Pro Ala Val Gln His Ala Val Thr
    2315            2320                2325

Thr Ser Tyr Asn Asn Tyr Ser Leu Met Ala Met Ala Thr Gln Ala
    2330            2335                2340

Gly Val Leu Phe Gly Met Gly Lys Gly Met Pro Phe Tyr Ala Trp
    2345            2350                2355

Asp Phe Gly Val Pro Leu Leu Met Ile Gly Cys Tyr Ser Gln Leu
    2360            2365                2370

Thr Pro Leu Thr Leu Ile Val Ala Ile Ile Leu Leu Val Ala His
    2375            2380                2385

Tyr Met Tyr Leu Ile Pro Gly Leu Gln Ala Ala Ala Ala Arg Ala
    2390            2395                2400

Ala Gln Lys Arg Thr Ala Ala Gly Ile Met Lys Asn Pro Val Val
    2405            2410                2415

Asp Gly Ile Val Val Thr Asp Ile Asp Thr Met Thr Ile Asp Pro
    2420            2425                2430

Gln Val Glu Lys Lys Met Gly Gln Val Leu Leu Ile Ala Val Ala
    2435            2440                2445

Val Ser Ser Ala Ile Leu Ser Arg Thr Ala Trp Gly Trp Gly Glu
    2450            2455                2460

Ala Gly Ala Leu Ile Thr Ala Ala Thr Ser Thr Leu Trp Glu Gly
    2465            2470                2475

Ser Pro Asn Lys Tyr Trp Asn Ser Ser Thr Ala Thr Ser Leu Cys
    2480            2485                2490

Asn Ile Phe Arg Gly Ser Tyr Leu Ala Gly Ala Ser Leu Ile Tyr
    2495            2500                2505

Thr Val Thr Arg Asn Ala Gly Leu Val Lys Arg Gly Gly Gly
    2510            2515                2520

Thr Gly Glu Thr Leu Gly Glu Lys Trp Lys Ala Arg Leu Asn Gln
    2525            2530                2535

Met Ser Ala Leu Glu Phe Tyr Ser Tyr Lys Lys Ser Gly Ile Thr
    2540            2545                2550

Glu Val Cys Arg Glu Glu Ala Arg Arg Ala Leu Lys Asp Gly Val
    2555            2560                2565
```

```
Ala  Thr  Gly  Gly  His  Ala  Val  Ser  Arg  Gly  Ser  Ala  Lys  Leu  Arg
2570                2575                     2580

Trp  Leu  Val  Glu  Arg  Gly  Tyr  Leu  Gln  Pro  Tyr  Gly  Lys  Val  Ile
2585                2590                     2595

Asp  Leu  Gly  Cys  Gly  Arg  Gly  Gly  Trp  Ser  Tyr  Tyr  Val  Ala  Thr
2600                2605                     2610

Ile  Arg  Lys  Val  Gln  Glu  Val  Lys  Gly  Tyr  Thr  Lys  Gly  Gly  Pro
2615                2620                     2625

Gly  His  Glu  Glu  Pro  Val  Leu  Val  Gln  Ser  Tyr  Gly  Trp  Asn  Ile
2630                2635                     2640

Val  Arg  Leu  Lys  Ser  Gly  Val  Asp  Val  Phe  His  Met  Ala  Ala  Glu
2645                2650                     2655

Pro  Cys  Asp  Thr  Leu  Leu  Cys  Asp  Ile  Gly  Glu  Ser  Ser  Ser  Ser
2660                2665                     2670

Pro  Glu  Val  Glu  Glu  Ala  Arg  Thr  Leu  Arg  Val  Leu  Ser  Met  Val
2675                2680                     2685

Gly  Asp  Trp  Leu  Glu  Lys  Arg  Pro  Gly  Ala  Phe  Cys  Ile  Lys  Val
2690                2695                     2700

Leu  Cys  Pro  Tyr  Thr  Ser  Thr  Met  Met  Glu  Thr  Leu  Glu  Arg  Leu
2705                2710                     2715

Gln  Arg  Arg  Tyr  Gly  Gly  Gly  Leu  Val  Arg  Val  Pro  Leu  Ser  Arg
2720                2725                     2730

Asn  Ser  Thr  His  Glu  Met  Tyr  Trp  Val  Ser  Gly  Ala  Lys  Ser  Asn
2735                2740                     2745

Thr  Ile  Lys  Ser  Val  Ser  Thr  Thr  Ser  Gln  Leu  Leu  Leu  Gly  Arg
2750                2755                     2760

Met  Asp  Gly  Pro  Arg  Arg  Pro  Val  Lys  Tyr  Glu  Glu  Asp  Val  Asn
2765                2770                     2775

Leu  Gly  Ser  Gly  Thr  Arg  Ala  Val  Val  Ser  Cys  Ala  Glu  Ala  Pro
2780                2785                     2790

Asn  Met  Lys  Ile  Ile  Gly  Asn  Arg  Ile  Glu  Arg  Ile  Arg  Ser  Glu
2795                2800                     2805

His  Ala  Glu  Thr  Trp  Phe  Phe  Asp  Glu  Asn  His  Pro  Tyr  Arg  Thr
2810                2815                     2820

Trp  Ala  Tyr  His  Gly  Ser  Tyr  Glu  Ala  Pro  Thr  Gln  Gly  Ser  Ala
2825                2830                     2835

Ser  Ser  Leu  Ile  Asn  Gly  Val  Val  Arg  Leu  Leu  Ser  Lys  Pro  Trp
2840                2845                     2850

Asp  Val  Val  Thr  Gly  Val  Thr  Gly  Ile  Ala  Met  Thr  Asp  Thr  Thr
2855                2860                     2865

Pro  Tyr  Gly  Gln  Gln  Arg  Val  Phe  Lys  Glu  Lys  Val  Asp  Thr  Arg
2870                2875                     2880

Val  Pro  Asp  Pro  Gln  Glu  Gly  Thr  Arg  Gln  Val  Met  Ser  Met  Val
2885                2890                     2895

Ser  Ser  Trp  Leu  Trp  Lys  Glu  Leu  Gly  Lys  His  Lys  Arg  Pro  Arg
2900                2905                     2910

Val  Cys  Thr  Lys  Glu  Glu  Phe  Ile  Asn  Lys  Val  Arg  Ser  Asn  Ala
2915                2920                     2925

Ala  Leu  Gly  Ala  Ile  Phe  Glu  Glu  Lys  Glu  Trp  Lys  Thr  Ala
2930                2935                     2940

Val  Glu  Ala  Val  Asn  Asp  Pro  Arg  Phe  Trp  Ala  Leu  Val  Asp  Lys
2945                2950                     2955

Glu  Arg  Glu  His  His  Leu  Arg  Gly  Glu  Cys  Gln  Ser  Cys  Val  Tyr
```

-continued

```
              2960              2965              2970
Asn Met Met Gly Lys Arg Glu Lys Lys Gln Gly Glu Phe Gly Lys
    2975              2980              2985
Ala Lys Gly Ser Arg Ala Ile Trp Tyr Met Trp Leu Gly Ala Arg
    2990              2995              3000
Phe Leu Glu Phe Glu Ala Leu Gly Phe Leu Asn Glu Asp His Trp
    3005              3010              3015
Met Gly Arg Glu Asn Ser Gly Gly Val Glu Gly Leu Gly Leu
    3020              3025              3030
Gln Arg Leu Gly Tyr Val Leu Glu Glu Met Ser Arg Ile Pro Gly
    3035              3040              3045
Gly Arg Met Tyr Ala Asp Asp Thr Ala Gly Trp Asp Thr Arg Ile
    3050              3055              3060
Ser Arg Phe Asp Leu Glu Asn Glu Ala Leu Ile Thr Asn Gln Met
    3065              3070              3075
Glu Lys Gly His Arg Ala Leu Ala Leu Ala Ile Ile Lys Tyr Thr
    3080              3085              3090
Tyr Gln Asn Lys Val Val Lys Val Leu Arg Pro Ala Glu Lys Gly
    3095              3100              3105
Lys Thr Val Met Asp Ile Ile Ser Arg Gln Asp Gln Arg Gly Ser
    3110              3115              3120
Gly Gln Val Val Thr Tyr Ala Leu Asn Thr Phe Thr Asn Leu Val
    3125              3130              3135
Val Gln Leu Ile Arg Asn Met Glu Ala Glu Glu Val Leu Glu Met
    3140              3145              3150
Gln Asp Leu Trp Leu Leu Arg Arg Ser Glu Lys Val Thr Asn Trp
    3155              3160              3165
Leu Gln Ser Asn Gly Trp Asp Arg Leu Lys Arg Met Ala Val Ser
    3170              3175              3180
Gly Asp Asp Cys Val Val Lys Pro Ile Asp Asp Arg Phe Ala His
    3185              3190              3195
Ala Leu Arg Phe Leu Asn Asp Met Gly Lys Val Arg Lys Asp Thr
    3200              3205              3210
Gln Glu Trp Lys Pro Ser Thr Gly Trp Asp Asn Trp Glu Glu Val
    3215              3220              3225
Pro Phe Cys Ser His His Phe Asn Lys Leu His Leu Lys Asp Gly
    3230              3235              3240
Arg Ser Ile Val Val Pro Cys Arg His Gln Asp Glu Leu Ile Gly
    3245              3250              3255
Arg Ala Arg Val Ser Pro Gly Ala Gly Trp Ser Ile Arg Glu Thr
    3260              3265              3270
Ala Cys Leu Ala Lys Ser Tyr Ala Gln Met Trp Gln Leu Leu Tyr
    3275              3280              3285
Phe His Arg Arg Asp Leu Arg Leu Met Ala Asn Ala Ile Cys Ser
    3290              3295              3300
Ser Val Pro Val Asp Trp Val Pro Thr Gly Arg Thr Thr Trp Ser
    3305              3310              3315
Ile His Gly Lys Gly Glu Trp Met Thr Thr Glu Asp Met Leu Val
    3320              3325              3330
Val Trp Asn Arg Val Trp Ile Glu Glu Asn Asp His Met Glu Asp
    3335              3340              3345
Lys Thr Pro Val Thr Lys Trp Thr Asp Ile Pro Tyr Leu Gly Lys
    3350              3355              3360
```

Arg Glu Asp Leu Trp Cys Gly Ser Leu Ile Gly His Arg Pro Arg
    3365            3370                3375

Thr Thr Trp Ala Glu Asn Ile Lys Asn Thr Val Asn Met Val Arg
    3380            3385                3390

Arg Ile Ile Gly Asp Glu Glu Lys Tyr Met Asp Tyr Leu Ser Thr
    3395            3400                3405

Gln Val Arg Tyr Leu Gly Glu Gly Ser Thr Pro Gly Val Leu
    3410            3415                3420

<210> SEQ ID NO 21
<211> LENGTH: 12
<212> TYPE: DNA
<213> ORGANISM: Artificial Sequence
<220> FEATURE:
<223> OTHER INFORMATION: Synthetic construct

<400> SEQUENCE: 21
ggatccggta cc                                                           12

<210> SEQ ID NO 22
<211> LENGTH: 12
<212> TYPE: DNA
<213> ORGANISM: Artificial Sequence
<220> FEATURE:
<223> OTHER INFORMATION: Synthetic construct

<400> SEQUENCE: 22
gctagcgaat tc                                                           12

<210> SEQ ID NO 23
<211> LENGTH: 6
<212> TYPE: DNA
<213> ORGANISM: Artificial Sequence
<220> FEATURE:
<223> OTHER INFORMATION: Synthetic construct]

<400> SEQUENCE: 23 gccacc                                                                   6

<210> SEQ ID NO 24
<211> LENGTH: 2121
<212> TYPE: DNA
<213> ORGANISM: Artificial Sequence
<220> FEATURE:
<223> OTHER INFORMATION: Synthetic Construct

<400> SEQUENCE: 24
ggatccggta ccgccaccat gggcaaaaga tccgccggca gcatcatgtg gctggccagt      60
ctggctgtcg tgatcgcctg tgctggcgcc gccgaagtga ccagaagagg cagcgcctac     120
tacatgtacc tggaccggaa cgatgccggc gaggccatca gctttccaac caccctgggc     180
atgaacaagt gctacatcca gatcatggac ctgggccaca tgtgcgacgc caccatgagc     240
tacgagtgcc ccatgctgga cgagggcgtg aacccgacg atgtggactg ctggtgcaac     300
accaccagca cctgggtggt gtacggcacc tgtcaccaca gaagggcga agccagaaga     360 agccggcggg ctgtgacact gcctagccac agcacccgga gctgcagac cagaagccag     420 acctggctgg aaagcagaga gtacaccaag cacctgatcc gggtggaaaa ctggatcttc     480
cggaaccccg gcttcgccct ggccgctgct gctattgctt ggctgctggg cagcagcacc     540
agccagaaag tgatcctacct cgtgatgatc ctgctgatcg ccctgccta cagcatccgg     600

-continued

```
tgtatcggcg tgtccaaccg ggacttcgtg gaaggcatga gcggcggcac atgggtggac    660
gtggtgctgg aacatggcgg ctgcgtgaca gtgatggccc aggacaagcc caccgtggac    720
atcgagctcg tgaccaccac cgtgtccaat atggccgaag tgcggagcta ctgctacgag    780
gccagcatca gcgacatggc cagcgacagc agatgcccta cagggcgcga ggcctacctg    840
gacaagcagt ccgacaccca gtacgtgtgc aagcggaccc tggtggatag aggctgggc     900
aatggctgcg gcctgtttgg caagggcagc ctcgtgacct cgccaagtt cgcctgcagc     960
aagaagatga ccggcaagag catccagccc gagaacctgg aataccggat catgctgagc    1020
gtgcacggca ccagcactc cggcatgatc gtgaacgaca ccggccacga cagacgcgag    1080
aaccgggcca aggtggaaat cacccccaac agccctagag ccgaggccac actgggcggc    1140
tttggatctc tgggcctgga ctgcgagcct agaaccggcc tggatttcag cgacctgtac    1200
tacctgacca tgaacaacaa acactggctg gtgcacaaag agtggttcca cgacatcccc    1260
ctgccctggc atgccggcgc tgatacaggc acccccact ggaacaacaa agaggccctg    1320
gtggagttca aggacgccca cgccaagagg cagaccgtgg tggtgctggg atctcaggaa    1380
ggcgccgtgc atacagctct ggctggcgcc ctggaagccg aaatggatgg cgctaagggc    1440
agactgtcca gcgccacct gaagtgccgg ctgaagatgg acaagctgcg gctgaagggc    1500
gtgtcctaca gcctgtgtac cgccgccttc accttcacca agatcccgc cgagacactg    1560
cacggcaccg tgactgtgga agtgcagtac gccggcaccg acggcccttg taaagtgcct    1620
gctcagatgg ccgtggatat gcagaccctg accctgtgg gcaggctgat caccgccaac    1680
cctgtgatca ccgagagcac cgagaacagc aagatgatgc tggaactgga cccaccttc     1740
ggcgacagct acatcgtgat cggcgtggga gagaagaaga tcacccacca ctggcacaga    1800
agcggcagca ccatcggcaa ggcctttgag gctacagtgc ggggagccaa gagaatggcc    1860
gtgctgggag ataccgcctg ggactttggc tctgtgggcg agccctgaa ctctctgggc    1920
aagggaatcc accagatctt cggcgctgcc ttcaagagcc tgttcggcgg catgagctgg    1980
ttcagccaga tcctgatcgg caccctgctg atgtggctgg gcctgaacac caagaacggc    2040
tccatcagcc tgatgtgcct ggctctggga ggcgtgctga tcttcctgag cacagccgtg    2100
tccgcctgag ctagcgaatt c                                              2121
```

<210> SEQ ID NO 25
<211> LENGTH: 696
<212> TYPE: PRT
<213> ORGANISM: Artificial Sequence
<220> FEATURE:
<223> OTHER INFORMATION: Synthetic Construct

<400> SEQUENCE: 25

```
Met Gly Lys Arg Ser Ala Gly Ser Ile Met Trp Leu Ala Ser Leu Ala
1               5                   10                  15

Val Val Ile Ala Cys Ala Gly Ala Ala Glu Val Thr Arg Arg Gly Ser
            20                  25                  30

Ala Tyr Tyr Met Tyr Leu Asp Arg Asn Asp Ala Gly Glu Ala Ile Ser
        35                  40                  45

Phe Pro Thr Thr Leu Gly Met Asn Lys Cys Tyr Ile Gln Ile Met Asp
    50                  55                  60

Leu Gly His Met Cys Asp Ala Thr Met Ser Tyr Glu Cys Pro Met Leu
65                  70                  75                  80

Asp Glu Gly Val Glu Pro Asp Asp Val Asp Cys Trp Cys Asn Thr Thr
                85                  90                  95
```

```
Ser Thr Trp Val Val Tyr Gly Thr Cys His His Lys Lys Gly Glu Ala
            100                 105                 110

Arg Arg Ser Arg Arg Ala Val Thr Leu Pro Ser His Ser Thr Arg Lys
            115                 120                 125

Leu Gln Thr Arg Ser Gln Thr Trp Leu Glu Ser Arg Glu Tyr Thr Lys
            130                 135                 140

His Leu Ile Arg Val Glu Asn Trp Ile Phe Arg Asn Pro Gly Phe Ala
145                 150                 155                 160

Leu Ala Ala Ala Ile Ala Trp Leu Leu Gly Ser Ser Thr Ser Gln
                165                 170                 175

Lys Val Ile Tyr Leu Val Met Ile Leu Leu Ile Ala Pro Ala Tyr Ser
            180                 185                 190

Ile Arg Cys Ile Gly Val Ser Asn Arg Asp Phe Val Glu Gly Met Ser
            195                 200                 205

Gly Gly Thr Trp Val Asp Val Val Leu Glu His Gly Gly Cys Val Thr
            210                 215                 220

Val Met Ala Gln Asp Lys Pro Thr Val Asp Ile Glu Leu Val Thr Thr
225                 230                 235                 240

Thr Val Ser Asn Met Ala Glu Val Arg Ser Tyr Cys Tyr Glu Ala Ser
            245                 250                 255

Ile Ser Asp Met Ala Ser Asp Ser Arg Cys Pro Thr Gln Gly Glu Ala
            260                 265                 270

Tyr Leu Asp Lys Gln Ser Asp Thr Gln Tyr Val Cys Lys Arg Thr Leu
            275                 280                 285

Val Asp Arg Gly Trp Gly Asn Gly Cys Gly Leu Phe Gly Lys Gly Ser
            290                 295                 300

Leu Val Thr Cys Ala Lys Phe Ala Cys Ser Lys Lys Met Thr Gly Lys
305                 310                 315                 320

Ser Ile Gln Pro Glu Asn Leu Glu Tyr Arg Ile Met Leu Ser Val His
            325                 330                 335

Gly Ser Gln His Ser Gly Met Ile Val Asn Asp Thr Gly His Glu Thr
            340                 345                 350

Asp Glu Asn Arg Ala Lys Val Glu Ile Thr Pro Asn Ser Pro Arg Ala
            355                 360                 365

Glu Ala Thr Leu Gly Gly Phe Gly Ser Leu Gly Leu Asp Cys Glu Pro
            370                 375                 380

Arg Thr Gly Leu Asp Phe Ser Asp Leu Tyr Tyr Leu Thr Met Asn Asn
385                 390                 395                 400

Lys His Trp Leu Val His Lys Glu Trp Phe His Asp Ile Pro Leu Pro
            405                 410                 415

Trp His Ala Gly Ala Asp Thr Gly Thr Pro His Trp Asn Asn Lys Glu
            420                 425                 430

Ala Leu Val Glu Phe Lys Asp Ala His Ala Lys Arg Gln Thr Val Val
            435                 440                 445

Val Leu Gly Ser Gln Glu Gly Ala Val His Thr Ala Leu Ala Gly Ala
            450                 455                 460

Leu Glu Ala Glu Met Asp Gly Ala Lys Gly Arg Leu Ser Ser Gly His
465                 470                 475                 480

Leu Lys Cys Arg Leu Lys Met Asp Lys Leu Arg Leu Lys Gly Val Ser
            485                 490                 495

Tyr Ser Leu Cys Thr Ala Ala Phe Thr Phe Thr Lys Ile Pro Ala Glu
            500                 505                 510
```

| | | | | | | | | | | | |
|---|---|---|---|---|---|---|---|---|---|---|---|
|Thr|Leu|His|Gly|Thr|Val|Thr|Val|Glu|Val|Gln|Tyr|Ala|Gly|Thr|Asp|
| |515| | | |520| | | |525| | | | | | |

Gly Pro Cys Lys Val Pro Ala Gln Met Ala Val Asp Met Gln Thr Leu
        530                 535                 540

Thr Pro Val Gly Arg Leu Ile Thr Ala Asn Pro Val Ile Thr Glu Ser
545                 550                 555                 560

Thr Glu Asn Ser Lys Met Met Leu Glu Leu Asp Pro Pro Phe Gly Asp
                565                 570                 575

Ser Tyr Ile Val Ile Gly Val Gly Glu Lys Lys Ile Thr His His Trp
            580                 585                 590

His Arg Ser Gly Ser Thr Ile Gly Lys Ala Phe Glu Ala Thr Val Arg
    595                 600                 605

Gly Ala Lys Arg Met Ala Val Leu Gly Asp Thr Ala Trp Asp Phe Gly
610                 615                 620

Ser Val Gly Gly Ala Leu Asn Ser Leu Gly Lys Gly Ile His Gln Ile
625                 630                 635                 640

Phe Gly Ala Ala Phe Lys Ser Leu Phe Gly Gly Met Ser Trp Phe Ser
                645                 650                 655

Gln Ile Leu Ile Gly Thr Leu Leu Met Trp Leu Gly Leu Asn Thr Lys
            660                 665                 670

Asn Gly Ser Ile Ser Leu Met Cys Leu Ala Leu Gly Gly Val Leu Ile
        675                 680                 685

Phe Leu Ser Thr Ala Val Ser Ala
    690                 695

<210> SEQ ID NO 26
<211> LENGTH: 2121
<212> TYPE: DNA
<213> ORGANISM: Artificial Sequence
<220> FEATURE:
<223> OTHER INFORMATION: Synthetic Construct

<400> SEQUENCE: 26

```
ggatccggta ccgccaccat gggcaaaaga tccgccggca gcatcatgtg gctggccagt     60
ctggctgtcg tgatcgcctg tgctggcgcc gccgaagtga ccagaagagg cagcgcctac    120
tacatgtacc tggaccggaa cgatgccggc gaggccatca gctttccaac caccctgggc    180
atgaacaagt gctacatcca gatcatggac ctgggccaca tgtgcgacgc caccatgagc    240
tacgagtgcc ccatgctgga cgagggcgtg gaacccgacg atgtggactg ctggtgcaac    300
accaccagca cctgggtggt gtacggcacc tgtcaccaca gaagggcga agccagaaga    360
agccggcggg ctgtgacact gcctagccac agcacccgga gctgcagac cagaagccag    420
acctggctgg aaagcagaga gtacaccaag cacctgatcc gggtggaaaa ctggatcttc    480
cggaaccccg gcttcgccct ggccgctgct gctattgctt ggctgctggg cagcagcacc    540
agccagaaag tgatctacct cgtgatgatc ctgctgatcg cccctgccta cagcatccgg    600
tgtatcggcg tgtccaaccg ggacttcgtg gaaggcatga gcggcggcac atgggtggac    660
gtggtgctgg aacatggcgg ctgcgtgaca gtgatggccc aggacaagcc caccgtggac    720
atcgagctcg tgaccaccac cgtgtccaat atggccgaag tgcggagcta ctgctacgag    780
gccagcatca gcgacatggc cagcgacagc agatgcccta cacagggcga ggcctacctg    840
gacaagcagt ccgacaccca gtacgtgtgc aagcggaccc tggtggatag aggctggggc    900
aatggctgcg gcctgtttgg caagggcagc ctcgtgacct cgccaagtt cgcctgcagc    960
aagaagatga ccggcaagag catccagccc gagaacctgg aataccggat catgctgagc   1020
```

-continued

```
gtgcacggca gccagcactc cggcatgatc gtgaacgaca ccggccacga gacagacgag   1080
aaccgggcca aggtggaaat caccccaac agccctagag ccgaggccac actgggcggc    1140
tttggatctc tgggcctgga ctgcgagcct agaaccggcc tggatttcag cgacctgtac   1200
tacctgacca tgaacaacaa acactggctg gtgcacaaag agtggttcca cgacatcccc   1260
ctgccctggc atgccggcgc tgatacaggc acccccact ggaacaacaa agaggccctg    1320
gtggagttca aggacgccca cgccaagagg cagaccgtgg tggtgctggg atctcaggaa   1380
ggcgccgtgc atacagctct ggctggcgcc ctggaagccg aaatggatgg cgctaagggc   1440
agactgtcca gcgccacct gaagtgccgg ctgaagatgg acaagctgcg gctgaagggc    1500
gtgtcctaca gcctgtgtac cgccgccttc accttcacca agatcccgc cgagacactg    1560 cacggcaccg tgactgtgga agtgcagtac gccggcaccg acggcccttg taaagtgcct   1620
gctcagatgg ccgtggatat gcagaccctg acccctgtgg gcaggctgat caccgccaac   1680
cctgtgatca ccgagagcac cgagaacagc aagatgatgc tggaactgga cccacccttc   1740
ggcgacagct acatcgtgat cggcgtggga gagaagaaga tcacccacca ctggcacaga   1800
agcggcagca ccctgggcaa ggcctttagc accacactga agggcgccca gagactggcc   1860
gccctgggag atacagcctg ggactttggc tctatcggcg gcgtgttcaa cagcatcggc   1920
aaggccgtgc accaggtgtt cggcggagcc ttcagaaccc tgtttggcgg catgagctgg   1980
atcacccagg gcctgatggg agccctgctg ctgtggatgg gagtgaacgc ccgggacaga   2040
tctatcgccc tggcctttct ggccaccggc ggagtgctgg tgttcctggc cacaaatgtg   2100
cacgcctgag ctagcgaatt c                                             2121
```

<210> SEQ ID NO 27
<211> LENGTH: 696
<212> TYPE: PRT
<213> ORGANISM: Artificial Sequence
<220> FEATURE:
<223> OTHER INFORMATION: Synthetic Construct

<400> SEQUENCE: 27

```
Met Gly Lys Arg Ser Ala Gly Ser Ile Met Trp Leu Ala Ser Leu Ala
1               5                   10                  15

Val Val Ile Ala Cys Ala Gly Ala Ala Glu Val Thr Arg Arg Gly Ser
            20                  25                  30

Ala Tyr Tyr Met Tyr Leu Asp Arg Asn Asp Ala Gly Glu Ala Ile Ser
        35                  40                  45

Phe Pro Thr Thr Leu Gly Met Asn Lys Cys Tyr Ile Gln Ile Met Asp
    50                  55                  60

Leu Gly His Met Cys Asp Ala Thr Met Ser Tyr Glu Cys Pro Met Leu
65                  70                  75                  80

Asp Glu Gly Val Glu Pro Asp Asp Val Asp Cys Trp Cys Asn Thr Thr
                85                  90                  95

Ser Thr Trp Val Val Tyr Gly Thr Cys His His Lys Lys Gly Glu Ala
            100                 105                 110

Arg Arg Ser Arg Arg Ala Val Thr Leu Pro Ser His Ser Thr Arg Lys
        115                 120                 125

Leu Gln Thr Arg Ser Gln Thr Trp Leu Glu Ser Arg Glu Tyr Thr Lys
    130                 135                 140

His Leu Ile Arg Val Glu Asn Trp Ile Phe Arg Asn Pro Gly Phe Ala
145                 150                 155                 160
```

```
Leu Ala Ala Ala Ala Ile Ala Trp Leu Leu Gly Ser Ser Thr Ser Gln
                    165                 170                 175
Lys Val Ile Tyr Leu Val Met Ile Leu Leu Ile Ala Pro Ala Tyr Ser
            180                 185                 190
Ile Arg Cys Ile Gly Val Ser Asn Arg Asp Phe Val Glu Gly Met Ser
        195                 200                 205
Gly Gly Thr Trp Val Asp Val Leu Glu His Gly Gly Cys Val Thr
    210                 215                 220
Val Met Ala Gln Asp Lys Pro Thr Val Asp Ile Glu Leu Val Thr Thr
225                 230                 235                 240
Thr Val Ser Asn Met Ala Glu Val Arg Ser Tyr Cys Tyr Glu Ala Ser
            245                 250                 255
Ile Ser Asp Met Ala Ser Asp Ser Arg Cys Pro Thr Gln Gly Glu Ala
        260                 265                 270
Tyr Leu Asp Lys Gln Ser Asp Thr Gln Tyr Val Cys Lys Arg Thr Leu
    275                 280                 285
Val Asp Arg Gly Trp Gly Asn Gly Cys Gly Leu Phe Gly Lys Gly Ser
    290                 295                 300
Leu Val Thr Cys Ala Lys Phe Ala Cys Ser Lys Lys Met Thr Gly Lys
305                 310                 315                 320
Ser Ile Gln Pro Glu Asn Leu Glu Tyr Arg Ile Met Leu Ser Val His
            325                 330                 335
Gly Ser Gln His Ser Gly Met Ile Val Asn Asp Thr Gly His Glu Thr
        340                 345                 350
Asp Glu Asn Arg Ala Lys Val Glu Ile Thr Pro Asn Ser Pro Arg Ala
    355                 360                 365
Glu Ala Thr Leu Gly Gly Phe Gly Ser Leu Gly Leu Asp Cys Glu Pro
    370                 375                 380
Arg Thr Gly Leu Asp Phe Ser Asp Leu Tyr Tyr Leu Thr Met Asn Asn
385                 390                 395                 400
Lys His Trp Leu Val His Lys Glu Trp Phe His Asp Ile Pro Leu Pro
            405                 410                 415
Trp His Ala Gly Ala Asp Thr Gly Thr Pro His Trp Asn Asn Lys Glu
        420                 425                 430
Ala Leu Val Glu Phe Lys Asp Ala His Ala Lys Arg Gln Thr Val Val
    435                 440                 445
Val Leu Gly Ser Gln Glu Gly Ala Val His Thr Ala Leu Ala Gly Ala
    450                 455                 460
Leu Glu Ala Glu Met Asp Gly Ala Lys Gly Arg Leu Ser Ser Gly His
465                 470                 475                 480
Leu Lys Cys Arg Leu Lys Met Asp Lys Leu Arg Leu Lys Gly Val Ser
            485                 490                 495
Tyr Ser Leu Cys Thr Ala Ala Phe Thr Phe Thr Lys Ile Pro Ala Glu
        500                 505                 510
Thr Leu His Gly Thr Val Thr Val Glu Val Gln Tyr Ala Gly Thr Asp
    515                 520                 525
Gly Pro Cys Lys Val Pro Ala Gln Met Ala Val Asp Met Gln Thr Leu
    530                 535                 540
Thr Pro Val Gly Arg Leu Ile Thr Ala Asn Pro Val Ile Thr Glu Ser
545                 550                 555                 560
Thr Glu Asn Ser Lys Met Met Leu Glu Leu Asp Pro Pro Phe Gly Asp
            565                 570                 575
Ser Tyr Ile Val Ile Gly Val Gly Glu Lys Lys Ile Thr His His Trp
```

```
                580                 585                 590
His Arg Ser Gly Ser Thr Leu Gly Lys Ala Phe Ser Thr Thr Leu Lys
            595                 600                 605

Gly Ala Gln Arg Leu Ala Ala Leu Gly Asp Thr Ala Trp Asp Phe Gly
        610                 615                 620

Ser Ile Gly Gly Val Phe Asn Ser Ile Gly Lys Ala Val His Gln Val
625                 630                 635                 640

Phe Gly Gly Ala Phe Arg Thr Leu Phe Gly Gly Met Ser Trp Ile Thr
                645                 650                 655

Gln Gly Leu Met Gly Ala Leu Leu Leu Trp Met Gly Val Asn Ala Arg
            660                 665                 670

Asp Arg Ser Ile Ala Leu Ala Phe Leu Ala Thr Gly Gly Val Leu Val
        675                 680                 685

Phe Leu Ala Thr Asn Val His Ala
690                 695
```

COMPOSITIONS AND METHODS FOR PREVENTING AND TREATING ZIKA VIRUS INFECTION

STATEMENT AS TO FEDERALLY FUNDED RESEARCH

This invention was made with government support under Grant No. AI096040, awarded by the National Institutes of Health (NIH) and National Institute of Allergy and Infectious Diseases (NIAID). The government has certain rights in the invention.

BACKGROUND OF THE INVENTION

Zika virus (ZIKV) is a flavivirus that is responsible for an unprecedented current epidemic in Brazil and the Americas. ZIKV has been causally associated with microcephaly, intrauterine growth restriction, and other birth defects in humans and in murine models. ZIKV is believed to cause neuropathology in developing fetuses by crossing the placenta and targeting cortical neural progenitor cells, leading to impaired neurogenesis and resulting in microcephaly and other congenital malformations.

The World Health Organization declared the clusters of microcephaly and neurological disorders and their association with ZIKV infection to be a global public health emergency on Feb. 1, 2016. ZIKV also has been associated with neurologic conditions such as Guillain-Barré syndrome. While the rapid development of a safe and effective ZIKV vaccine is a global health priority, very little is currently known about ZIKV immunology and mechanisms of immune protection.

Accordingly, there is an unmet need in the field for ZIKV therapies.

SUMMARY OF THE INVENTION

The present invention features optimized, non-naturally occurring Zika virus (ZIKV) nucleic acid molecules and polypeptides for the generation of DNA vaccines, immunogenic compositions, and anti-ZIKV antibodies for use in methods of preventing and treating ZIKV infection in a subject (e.g, a mammalian subject (e.g., a human)).

A first aspect of the invention features an isolated nucleic acid molecule including a nucleotide sequence having at least 85% sequence identity to all or a portion of any one of SEQ ID NOs: 1, 3, 5, 7, 9, and 11, or a complementary sequence thereof.

A second aspect of the invention features an isolated nucleic acid molecule including a nucleotide sequence that encodes all or a portion of a polypeptide having at least 85% sequence identity to an amino acid sequence of any one of SEQ ID NOs: 2, 4, 6, 8, 10, and 12.

In some embodiments of the first and second aspects, the isolated nucleic acid molecules of the first and second aspect have at least 86, 87, 88, 89, 90, 91, 92, 93, 94, 95, 96, 97, 98, or 99% sequence identity to, or the nucleotide sequence of, any one of SEQ ID NOs: 1, 3, 5, 7, 9, and 11, or a complementary sequence thereof. In some embodiments, the nucleic acid molecules, or a portion thereof, are capable of eliciting an immune response in a subject.

In some embodiments of the first and second aspects, a portion of a nucleic acid molecule may include about 10, 20, 30, 40, 50, 60, 70, 80, 90, 100, 200, 300, 400, 500, 800, 900, 1000, 1500 or fewer nucleotides, where a reduction in length of the nucleic acid can occur either from the 5' or 3' end.

A third aspect of the invention features an isolated polypeptide including an amino acid sequence having at least 85% sequence identity to all or a portion of any one of SEQ ID NOs: 2, 4, 6, 8, 10, or 12. In some embodiments, the isolated polypeptide has at least 86, 87, 88, 89, 90, 91, 92, 93, 94, 95, 96, 97, 98, or 99% sequence identity to, or the amino acid sequence of, any one of SEQ ID NOs: 2, 4, 6, 8, 10, and 12. In some embodiments, the isolated polypeptide, or a portion thereof, is capable of eliciting an immune response in a subject.

In some embodiments of the third aspect, a portion of a polypeptide may include about 10, 20, 30, 40, 50, 60, 70, 80, 90, 100, 200, 300, 400, or 500, or fewer amino acids, where the reduction can occur either from the amino-terminus or the carboxyl-terminus.

A fourth aspect of the invention features a vector including one or more of the nucleic acid molecules of any one of the first and second aspects. In some embodiments, the vector is a mammalian, bacterial, or viral derived expression vector. In some embodiments, the vector is a viral vector derived from a virus selected from the group consisting of a retrovirus, adenovirus, adeno-associated virus, parvovirus, coronavirus, negative strand RNA viruses, orthomyxovirus, rhabdovirus, paramyxovirus, positive strand RNA viruses, picornavirus, alphavirus, double stranded DNA viruses, herpesvirus, Epstein-Barr virus, cytomegalovirus, fowlpox, and canarypox. In some embodiments, the vector is an adenovirus. In some embodiments, the adenovirus is a human, chimpanzee, or rhesus adenovirus vector. In other embodiments, the adenovirus vector is selected from the group consisting of Ad2, Ad5, Ad11, Ad12, Ad24, Ad26, Ad34, Ad35. Ad40. Ad48. Ad49, Ad50, Ad52 (e.g., RhAd52), and Pan9, such as an Ad5 vector; these vectors can be, for example, human, chimpanzee, or rhesus adenovirus vectors.

A fifth aspect of the invention features a composition including the nucleic acid molecule of the first or second aspects, the polypeptide of the third aspect, or the vector of the fourth aspect. In some embodiments, the composition further includes a pharmaceutically acceptable carrier, excipient, or diluent. In some embodiments, the composition further includes an adjuvant or an immunostimulatory agent.

A sixth aspect of the invention features a vaccine including the composition of the fourth aspect. In some embodiments, the vaccine is capable of treating or reducing the risk of a ZIKV infection in a subject in need thereof. In some embodiments, the vaccine elicits production of neutralizing anti-ZIKV antisera after administration to said subject. In some embodiments, the subject is a mammal. In some embodiments, the subject is human. In some embodiments, the subject is a pregnant female.

A seventh aspect of the invention features an isolated antibody that specifically binds to the polypeptide of the third aspect. In some embodiments, the antibody is generated by immunizing a mammal with the nucleic acid of the first and second aspects, the polypeptide of the third aspect, the vector of the fourth aspect, the composition of the fifth aspect, or the vaccine of the sixth aspect. In some embodiments, the mammal is a human. In some embodiments, the antibody is humanized. In some embodiments, the antibody is an IgG. In some embodiments, the antibody is a bis-Fab, Fv, Fab, Fab'-SH, F(ab')$_2$, a diabody, a linear antibody, or a scFV.

An eight aspect of the invention features a method of treating or reducing the risk of a ZIKV infection in a subject in need thereof, including administering a therapeutically effective amount of at least one of the nucleic acid molecule of the first or second aspects, the polypeptide of the third aspect, the vector of the fourth aspect, the composition of the fifth aspect, the vaccine of sixth aspect, and the antibody of the seventh aspect to said subject.

A ninth aspect of the invention features a method of reducing a ZIKV-mediated activity in a subject infected with a ZIKV, including administering a therapeutically effective amount of at least one of the nucleic acid molecule of the first or second aspects, the polypeptide of the third aspect, the vector of the fourth aspect, the composition of the fifth aspect, the vaccine of sixth aspect, and the antibody of the seventh aspect to said subject (e.g., an amount between about 10 μg to about 10 mg).

In some embodiments of the eighth and ninth aspects, the therapeutically effective amount is sufficient to produce a log serum anti-Env antibody titer greater than 2 in a subject, as measured by an ELISA assay. In some embodiments, the therapeutically effective amount is about 10 μg to about 10 mg (e.g., about 15 μg to about 300 μg) of at least one of the nucleic acid molecule of the first or second aspects, the polypeptide of the third aspect, the vector of the fourth aspect, the composition of the fifth aspect, the vaccine of sixth aspect, and the antibody of the seventh aspect. In some embodiments, the ZIKV-mediated activity is viral titer, viral spread, infection, or cell fusion. In some embodiments, the ZIKV titer is decreased after administration of at least one of the nucleic acid molecule of the first or second aspects, the polypeptide of the third aspect, the vector of the fourth aspect, the composition of the fifth aspect, the vaccine of sixth aspect, and the antibody of the seventh aspect to said subject. In some embodiments, the ZIKV titer is decreased by 25% or more. In some embodiments, the ZIKV titer is decreased by 50% or more. In some embodiments, the ZIKV titer is decreased by 75% or more. In some embodiments, the ZIKV is undetectable after said administration. In some embodiments, the ZIKV is a ZIKV strain from the Asian or African lineages. In some embodiments, the ZIKV is a ZIKV strain from Brazil or Puerto Rico. In some embodiments, the ZIKV is Brazil-ZKV2015 or PRVABC59.

A tenth aspect of the invention features a method of producing anti-ZIKV antibodies, including administering an amount of at least one of the nucleic acid molecule of the first or second aspects, the polypeptide of the third aspect, the vector of the fourth aspect, the composition of the fifth aspect, the vaccine of sixth aspect to a subject that is sufficient to elicit the production of neutralizing anti-ZIKV antisera after administration to said subject (e.g., about 10 μg to about 10 mg (e.g., about 15 μg to about 300 μg)).

An eleventh aspect of the invention features an isolated anti-ZIKV antibody produced by the method of the tenth aspect. In some embodiments, an isolated anti-ZIKV antibody binds to an epitope within any one of SEQ ID NOs: 2, 4, 6, 8, 10, or 12.

A twelfth aspect of the invention features a method of treating or reducing the risk of a ZIKV infection in a subject in need thereof, including administering a therapeutically effective amount of the ZIKV antibody of the seventh and eleventh aspects.

A thirteenth aspect of the invention features a method of reducing a ZIKV-mediated activity in a subject infected with a ZIKV, including administering a therapeutically effective amount of the ZIKV antibody of the seventh and eleventh aspects.

In some embodiments of the eighth, ninth, twelfth and thirteenth aspects, the administering occurs prior to exposure to a ZIKV. In some embodiments, the administering occurs at least 1 hour prior to exposure to said ZIKV. In some embodiments, the administering occurs at least 1 week, 1 month, or a year prior to exposure to said ZIKV. In some embodiments, the administering occurs post-exposure to the ZIKV. In some embodiments, the administering occurs at least 15 minutes post-exposure to said ZIKV. In some embodiments, the administering occurs at least 1 hour, 1 day, or 1 week post-exposure to said ZIKV. In some embodiments, the subject is administered at least one dose of the nucleic acid molecule, polypeptide, vector, composition, vaccine, or antibody. In some embodiments, the subject is administered at least two doses. In some embodiments, the nucleic acid molecule of the first or second aspects, the polypeptide of the third aspect, the vector of the fourth aspect, the composition of the fifth aspect, or the vaccine of sixth aspect is administered to said subject as a prime, a boost, or as a prime-boost. In some embodiments, the nucleic acid molecule, polypeptide, vector, composition, vaccine, or antibody is administered intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivelly, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, by gavage, in creams, or in lipid compositions. In some embodiments, the subject is a mammal. In some embodiments, the subject is human. In some embodiments, the subject is a pregnant female. In some embodiments, the method promotes an immune response in said subject. In some embodiments, the immune response is a humoral immune response. In some embodiments, the humoral response is an IgG response.

A fourteenth aspect of the invention features a composition for use in treating or reducing the risk of a ZIKV infection in a subject in need thereof, including a therapeutically effective amount of at least one of the nucleic acid molecule of the first and second aspects, the polypeptide of the third aspect, the vector of the fourth aspect, the composition of the fifth aspect, the vaccine of the sixth aspect, and the antibody of the seventh and eleventh aspects.

A fifteenth aspect of the invention features a composition for use in reducing a ZIKV-mediated activity in a subject infected with a ZIKV, including a therapeutically effective amount of at least one of the nucleic acid molecule of the first and second aspects, the polypeptide of the third aspect, the vector of the fourth aspect, the composition of the fifth aspect, the vaccine of the sixth aspect, and the antibody of the seventh and eleventh aspects.

A sixteenth aspect of the invention features a method of manufacturing a vaccine for treating or reducing the risk of a ZIKV infection in a subject in need thereof, in which the method includes the steps of: administering at least one of the nucleic acid molecule of the first and second aspects, the polypeptide of the third aspect, the vector of the fourth aspect, the composition of the fifth aspect, and the antibody of the seventh and eleventh aspects with a pharmaceutically acceptable carrier, excipient, or diluent to form the vaccine; and placing the vaccine in a container.

A seventeenth aspect of the invention features a kit including: a first container including at least one of the nucleic acid molecule of the first and second aspects, the polypeptide of the third aspect, the vector of the fourth aspect, the composition of the fifth aspect, the vaccine of the sixth aspect, and the antibody of the seventh and eleventh aspects; instructions for use thereof; and optionally a second container including a pharmaceutically acceptable carrier, excipient, or diluent. In some embodiments, the first container further comprises a pharmaceutically acceptable carrier, excipient, or diluent. In some embodiments, the kit optionally includes an adjuvant and/or an immunostimulatory agent.

DEFINITIONS

As used herein, the term "about" means+/−10% of the recited value.

The terms "adenovirus vector" and "adenoviral vector" are used interchangeably and refer to a genetically-engineered adenovirus that is designed to insert a polynucleotide of interest (e.g., a polynucleotide encoding a ZIKV immunogen of the invention) into a eukaryotic cell, such that the polynucleotide is subsequently expressed. Examples of adenoviruses that can be used as a viral vector of the invention include those having, or derived from, the serotypes Ad2, Ad5, Ad11, Ad12, Ad24, Ad26, Ad34, Ad35, Ad40, Ad48, Ad49, Ad50, Ad52 (e.g., RhAd52), and Pan9 (also known as AdC68); these vectors can be derived from, for example, human, chimpanzee, or rhesus adenoviruses.

The term "adjuvant" refers to a pharmacological or immunological agent that modifies the effect of other agents (e.g., vaccines) while having few if any direct effects when given by itself. They are often included in vaccines to enhance the recipient's immune response to a supplied antigen while keeping the injected foreign material at a minimum.

As used herein, by "administering" is meant a method of giving a dosage of a pharmaceutical composition (e.g., an immunogenic composition (e.g., a vaccine (e.g., a Zika virus (ZIKV) vaccine))) to a subject. The compositions utilized in the methods described herein can be administered, for example, intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, by gavage, in cremes, or in lipid compositions. The preferred method of administration can vary depending on various factors (e.g., the components of the composition being administered and the severity of the condition being treated).

The terms "antibody" and "immunoglobulin (Ig)" are used interchangeably in the broadest sense and include monoclonal antibodies (e.g., full-length or intact monoclonal antibodies), polyclonal antibodies, multivalent antibodies, multispecific antibodies (e.g., bispecific antibodies so long as they exhibit the desired biological activity) and may also include certain antibody fragments. An antibody typically comprises both "light chains" and "heavy chains." The light chains of antibodies (immunoglobulins) from any vertebrate species can be assigned to one of two clearly distinct types, called kappa (κ) and lambda (λ), based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (Isotypes), e.g., IgG1, IgG2, IgG3, IgG4, IgA1, and IgA2. The heavy chain constant domains that correspond to the different classes of immunoglobulins are called α, δ, ε, γ, and μ, respectively. The subunit structures and three-dimensional configurations of different classes of immunoglobulins are well known.

The term "codon" as used herein refers to any group of three consecutive nucleotide bases in a given messenger RNA molecule, or coding strand of DNA, that specifies a particular amino acid or a starting or stopping signal for translation. The term codon also refers to base triplets in a DNA strand.

Throughout this specification and claims, the word "comprise," or variations such as "comprises" or "comprising," will be understood to imply the inclusion of a stated integer or group of integers but not the exclusion of any other integer or group of integers.

A "gene delivery vehicle" is defined as any molecule that can carry inserted polynucleotides into a host cell. Examples of gene delivery vehicles are liposomes, biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art that have been described for expression in a variety of eukaryotic and prokaryotic hosts, and may be used for gene therapy as well as for simple protein expression.

"Gene delivery," "gene transfer," and the like as used herein, are terms referring to the introduction of an exogenous polynucleotide (sometimes referred to as a "transgene") into a host cell, irrespective of the method used for the introduction. Such methods include a variety of techniques such as, for example, vector-mediated gene transfer (e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides).

The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are capable of mediating transfer of genes to mammalian cells.

By "gene product" is meant to include mRNAs or other nucleic acids (e.g., microRNAs) transcribed from a gene, as well as polypeptides translated from those mRNAs. In some embodiments, the gene product is from a virus (e.g., a ZIKV) and may include, for example, any one or more of the viral proteins, or fragments thereof, described herein.

By "heterologous nucleic acid molecule" is meant a nucleotide sequence that may encode proteins derived or obtained from pathogenic organisms, such as viruses, which may be incorporated into a polynucleotide or vector of the invention. Heterologous nucleic acids may also encode synthetic or artificial proteins, such as immunogenic epitopes, constructed to induce immunity. An example of a heterologous nucleic acid molecule is one that encodes one or more immunogenic peptides or polypeptides derived from a Zika virus (ZIKV). The heterologous nucleic acid molecule is one that is not normally associated with the other nucleic acid molecules found in the polynucleotide or vector into which the heterologous nucleic acid molecule is incorporated.

The term "host cell," refers to cells into which an exogenous nucleic acid has been introduced, including the progeny of such cells. Host cells include "transformants" and "transformed cells," which include the primary transformed cell and progeny derived therefrom without regard to the number of passages. Host cells include cells within the body of a subject (e.g., a mammalian subject (e.g., a human)) into which an exogenous nucleic acid has been introduced.

By "immunogen" is meant any polypeptide that can induce an immune response in a subject upon administration. In some embodiments, the immunogen is encoded by a nucleic acid molecule that may be incorporated into, for example, a polynucleotide or vector of the invention, for subsequent expression of the immunogen (e.g., a gene product of interest, or fragment thereof (e.g., a polypeptide)). In some embodiments, the immunogen is derived from a ZIKV (e.g., a ZIKV from the Asian and/or African lineage (e.g., ZIKV strain BeH815744 (accession number KU365780 (SEQ ID NOs: 15-16))). In some embodiments, the immunogen is administered in the context of a nucleic acid molecule expressing a polypeptide that is derived from a ZIKV (e.g., a ZIKV from the Asian and/or African lineage (e.g., ZIKV strain BeH815744 (accession number KU365780 (SEQ ID NOs: 15-16))).

The term "immunogenic composition" as used herein, is defined as material used to provoke an immune response and may confer immunity after administration of the immunogenic composition to a subject.

The term "immunostimulatory agent" refers to substances (e.g., drugs and nutrients) that stimulate the immune system by inducing activation or increasing activity of any of its components. An immunostimulatory agent includes a cytokine (e.g., the granulocyte macrophage colony-stimulating factor) and interferon (e.g., IFN-$\alpha$ and/or IFN-$\gamma$).

By "isolated" is meant separated, recovered, or purified from a component of its natural environment. For example, a nucleic acid molecule or polypeptide of the invention may be isolated from a component of its natural environment by 1% (2%, 3%, 4%, 5%, 6%, 7%, 8% 9% 10%, 20%, 30%, 40%, 50%, 60% 70%, 80%, or 90%) or more.

By "pharmaceutical composition" is meant any composition that contains a therapeutically or biologically active agent, such as an immunogenic composition or vaccine of the invention (e.g., a ZIKV nucleic acid molecule, vector, and/or polypeptide of the invention), preferably including a nucleotide sequence encoding an antigenic gene product of interest, or fragment thereof, that is suitable for administration to a subject and that treats or prevents a disease (e.g., ZIKV infection) or reduces or ameliorates one or more symptoms of the disease (e.g., ZIKV viral titer, viral spread, infection, and/or cell fusion)). For the purposes of this invention, pharmaceutical compositions include vaccines, and pharmaceutical compositions suitable for delivering a therapeutic or biologically active agent can include, for example, tablets, gelcaps, capsules, pills, powders, granulates, suspensions, emulsions, solutions, gels, hydrogels, oral gels, pastes, eye drops, ointments, creams, plasters, drenches, delivery devices, suppositories, enemas, injectables, implants, sprays, or aerosols. Any of these formulations can be prepared by well-known and accepted methods of art. See, for example, *Remington: The Science and Practice of Pharmacy* ($21^{st}$ ed.), ed. A. R. Gennaro, Lippincott Williams & Wilkins, 2005, and *Encyclopedia of Pharmaceutical Technology*, ed. J. Swarbrick, Informa Healthcare, 2006, each of which is hereby incorporated by reference.

The terms "linked" or "links" or "link" as used herein are meant to refer to the covalent joining of two amino acid sequences or two nucleic acid sequences together through peptide or phosphodiester bonds, respectively, such joining can include any number of additional amino acid or nucleic acid sequences between the two amino acid sequences or nucleic acid sequences that are being joined.

"Nucleic acid molecule" or "polynucleotide," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label.

A "nucleic acid vaccine" or "DNA vaccine" refers to a vaccine that includes a heterologous nucleic acid molecule under the control of a promoter for expression in a subject. The heterologous nucleic acid molecule can be incorporated into an expression vector, such as a plasmid.

A nucleic acid is "operably linked" when it is placed into a structural or functional relationship with another nucleic acid sequence. For example, one segment of DNA may be operably linked to another segment of DNA if they are positioned relative to one another on the same contiguous DNA molecule and have a structural or functional relationship, such as a promoter or enhancer that is positioned relative to a coding sequence so as to facilitate transcription of the coding sequence; a ribosome binding site that is positioned relative to a coding sequence so as to facilitate translation; or a pre-sequence or secretory leader that is positioned relative to a coding sequence so as to facilitate expression of a pre-protein (e.g., a pre-protein that participates in the secretion of the encoded polypeptide). In other examples, the operably linked nucleic acid sequences are not contiguous, but are positioned in such a way that they have a functional relationship with each other as nucleic acids or as proteins that are expressed by them. Enhancers, for example, do not have to be contiguous. Linking may be accomplished by ligation at convenient restriction sites or by using synthetic oligonucleotide adaptors or linkers.

The terms "optimized codon" and "codon optimized" as used herein refer to a codon sequence that has been modified to match codon frequencies in a target (e.g., a subject) or host organism, but that does not alter the amino acid sequence of the original translated protein.

By "pharmaceutically acceptable diluent, excipient, carrier, or adjuvant" is meant a diluent, excipient, carrier, or adjuvant that is physiologically acceptable to the subject while retaining the therapeutic properties of the pharmaceutical composition with which it is administered. One exemplary pharmaceutically acceptable carrier is physiological saline. Other physiologically acceptable diluents, excipients, carriers, or adjuvants and their formulations are known to one skilled in the art (see, e.g., U.S. Pub. No. 2012/0076812).

By "portion" or "fragment" is meant a part of a whole. A portion may comprise at least 10%, 20%, 30%, 40%, 50%, 60%, 70%, 80%, 90%, or 95% of the entire length of a polynucleotide or polypeptide sequence region. For polynucleotides, for example, a portion may include at least 5, 6, 7, 8, 9, 10, 20, 30, 40, 50, 60, 70, 80, 90, 100, 200, 300, 400, 500, 600, 700, 800, 900, 1000, 1100, 1200, 1300, 1400, 1500, 1600, 1700, 1800 or more contiguous nucleotides of a reference polynucleotide molecule. For polypeptides, for example, a portion may include at least 5, 6, 7, 8, 9, 10, 11, 12, 13, 14, 15, 16, 17, 18, 19, 20, 25, 50, 75, 90, 100, 125, 150, 175, 200, 225, 250, 275, 300, 325, 350, 375, 400, 425, 450, 475, 500, 525, 550, 575, or 600 or more continuous amino acids of a reference polypeptide molecule.

In some instances, a fragment of a nucleic acid molecule of the invention may include at least 20, 30, 40, 50, 60, 70, 80, 90, 100, 200, 300, 400, 500, 600, 700, 800, 900, 1000, 1100, 1200, 1300, 1400, 1500, 1600, 1700 or more consecutive nucleotides of the polynucleotide prM-Env (SEQ ID NO: 1). In some instances, a fragment of a nucleic acid molecule of the invention may include at least 20, 30, 40, 50, 60, 70, 80, 90, 100, 200, 300, 400, 500, 600, 700, 800, 900, 1000, 1100, 1200, 1300, 1400, 1500, or more consecutive nucleotides of the polynucleotide prM-Env.dTM (SEQ ID NO: 3). In some instances, a fragment of a nucleic acid molecule of the invention may include at least 20, 30, 40, 50, 60, 70, 80, 90, 100, 200, 300, 400, 500, 600, 700, 800, 900, 1000, 1100, 1200, 1300, 1400, or more consecutive nucleotides of the polynucleotide prM-Env.dStem (SEQ ID NO: 5). In some instances, a fragment of a nucleic acid molecule of the invention may include at least 20, 30, 40, 50, 60, 70, 80, 90, 100, 200, 300, 400, 500, 600, 700, 800, 900, 1000, 1100, 1200, 1300, 1400, 1500, or more consecutive nucleotides of the polynucleotide Env (SEQ ID NO: 7). In some instances, a fragment of a nucleic acid molecule of the invention may include at least 20, 30, 40, 50, 60, 70, 80, 90, 100, 200, 300, 400, 500, 600, 700, 800, 900, 1000, 1100, 1200, 1300, or more consecutive nucleotides of the polynucleotide Env.dTM (SEQ ID NO: 9). In some instances, a fragment of a nucleic acid molecule of the invention may include at least 20, 30, 40, 50, 60, 70, 80, 90, 100, 200, 300, 400, 500, 600, 700, 800, 900, 1000, 1100, 1200, or more consecutive nucleotides of the polynucleotide Env.dStem (SEQ ID NO: 11). In some instances, a fragment of a nucleic acid molecule of the invention may include at least 5, 6, 7, 8, 9, 10, 20, 30, 40, 50, 60, 70, 80, 90, 100, 200, 300, 400, 500, 600, 700, 800, 900, 1000, 1100, 1200, 1300, 1400, 1500, 1600, 1700, 1800, 1900, 2000, or more consecutive nucleotides of the polynucleotide prM-Env (full length) (SEQ ID NO: 24). In some instances, a fragment of a nucleic acid molecule of the invention may include at least 20, 30, 40, 50, 60, 70, 80, 90, 100, 200, 300, 400, 500, 600, 700, 800, 900, 1000, 1100, 1200, 1300, 1400, 1500, 1600, 1700, 1800, 1900, 2000, or more consecutive nucleotides of the polynucleotide prM-Env with JEV Stem/TM (SEQ ID NO: 26).

In some instances, a fragment of a polypeptide of the invention may include at least 20, 25, 50, 75, 90, 100, 125, 150, 175, 200, 225, 250, 275, 300, 325, 350, 375, 400, 425, 450, 475, 500, 525, 550, or more consecutive amino acids of polypeptide prM-Env (SEQ ID NO: 2). In some instances, a fragment of a polypeptide of the invention may include at least 20, 25, 50, 75, 90, 100, 125, 150, 175, 200, 225, 250, 275, 300, 325, 350, 375, 400, 425, 450, 475, 500, or more consecutive amino acids of polypeptide prM-Env.dTM (SEQ ID NO: 4). In some instances, a fragment of a polypeptide of the invention may include at least 20, 25, 50, 75, 90, 100, 125, 150, 175, 200, 225, 250, 275, 300, 325, 350, 375, 400, 425, 450, 475, or more consecutive amino acids of polypeptide prM-Env.dStem (SEQ ID NO: 6). In some instances, a fragment of a polypeptide of the invention may include at least 20, 25, 50, 75, 90, 100, 125, 150, 175, 200, 225, 250, 275, 300, 325, 350, 375, 400, 425, 450, 475, 500, or more consecutive amino acids of polypeptide Env (SEQ ID NO: 8). In some instances, a fragment of a polypeptide of the invention may include at least 20, 25, 50, 75, 90, 100, 125, 150, 175, 200, 225, 250, 275, 300, 325, 350, 375, 400, 425, or more consecutive amino acids of polypeptide Env.dTM (SEQ ID NO: 10). In some instances, a fragment of a polypeptide of the invention may include at least 20, 25, 50, 75, 90, 100, 125, 150, 175, 200, 225, 250, 275, 300, 325, 350, 375, 400, or more consecutive amino acids of polypeptide Env.dStem (SEQ ID NO: 12). In some instances, a fragment of a polypeptide of the invention may include at least 20, 25, 50, 75, 90, 100, 125, 150, 175, 200, 225, 250, 275, 300, 325, 350, 375, 400, 425, 450, 475, 500, 525, 550, 575, 600, 625, 650, 675, or more consecutive amino acids of polypeptide prM-Env (full length) (SEQ ID NO: 25). In some instances, a fragment of a polypeptide of the invention may include at least 20, 25, 50, 75, 90, 100, 125, 150, 175, 200, 225, 250, 275, 300, 325, 350, 375, 400, 425, 450, 475, 500, 525, 550, 575, 600, 625, 650, 675, or more consecutive amino acids of polypeptide prM-Env with JEV Stem/TM (SEQ ID NO: 27).

In some instances, administration of a fragment of a polynucleotide (e.g., SEQ ID NOs: 1, 3, 5, 7, 9, 11, 24, and/or 26) and/or a polypeptide (e.g., SEQ ID NOs: 2, 4, 6, 8, 10, 12, 25, and/or 27) of the invention to a subject may illicit an immune response in the subject.

A "promoter" is a nucleic acid sequence enabling the initiation of the transcription of a gene sequence in a messenger RNA, such transcription being initiated with the binding of an RNA polymerase on or nearby the promoter.

By "promotes an immune response" is meant eliciting a humoral response (e.g., the production of antibodies) or a cellular response (e.g., the activation of T cells, macrophages, neutrophils, and/or natural killer cells) directed against, for example, one or more infective agents (e.g., a virus (e.g., a ZIKV)) or protein targets in a subject to which the pharmaceutical composition (e.g., an immunogenic composition or vaccine) has been administered.

By "sequence identity" or "sequence similarity" is meant that the identity or similarity, respectively, between two or more amino acid sequences, or two or more nucleotide sequences, is expressed in terms of the identity or similarity between the sequences. Sequence identity can be measured in terms of "percentage (%) identity," in which a higher percentage indicates greater identity shared between the sequences. Sequence similarity can be measured in terms of percentage similarity (which takes into account conservative amino acid substitutions); the higher the percentage, the more similarity shared between the sequences. Homologs or orthologs of nucleic acid or amino acid sequences possess a relatively high degree of sequence identity/similarity when aligned using standard methods. Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications. Sequence identity/similarity can be determined across all or a defined portion of the two or more sequences compared.

As used herein, the phrase "specifically binds" refers to a binding reaction which is determinative of the presence of an antigen in a heterogeneous population of proteins and other biological molecules that is recognized, e.g., by an antibody or antigen-binding fragment thereof, with particularity. An antibody or antigen-binding fragment thereof that specifically binds to an antigen will bind to the antigen with a $K_D$ of less than 100 nM. For example, an antibody or antigen-binding fragment thereof that specifically binds to an antigen will bind to the antigen with a $K_D$ of up to 100 nM (e.g., between 1 pM and 100 nM). An antibody or antigen-binding fragment thereof that does not exhibit specific binding to a particular antigen or epitope thereof will exhibit a $K_D$ of greater than 100 nM (e.g., greater than 500 nm, 1 µM, 100 µM, 500 µM, or 1 mM) for that particular antigen or epitope thereof. A variety of immunoassay formats may be used to select antibodies specifically immunoreactive with a particular protein or carbohydrate. For example, solid-phase ELISA immunoassays are routinely used to select antibodies specifically immunoreactive with a protein or carbohydrate. See, Harlow & Lane, Antibodies, A Laboratory Manual, Cold Spring Harbor Press, New York (1988) and Harlow & Lane, Using Antibodies, A Laboratory Manual, Cold Spring Harbor Press, New York (1999), for a description of immunoassay formats and conditions that can be used to determine specific immunoreactivity.

A "subject" is a vertebrate, such as a mammal (e.g., a primate and a human, such as a female, in particular a pregnant women or a women of childbearing age). Mammals also include, but are not limited to, farm animals (such as cows), sport animals (e.g., horses), pets (such as cats, and dogs), mice, and rats. A subject to be treated according to the methods described herein (e.g., a subject in need of protection from a ZIKV infection or having a ZIKV infection may be one who has been diagnosed by a medical practitioner as having such a need or infection. Diagnosis may be performed by any suitable means. A subject in whom the development of an infection is being prevented may or may not have received such a diagnosis. One skilled in the art will understand that a subject to be treated according to the present invention may have been subjected to standard tests or may have been identified, without examination, as one with a suspected infection or at high risk of infection due to the presence of one or more risk factors (e.g., exposure to a ZIKV, for example, due to travel to an area where ZIKV infection is prevalent). Additionally, as ZIKV is believed to cause neuropathology in developing fetuses by crossing the placenta and targeting cortical neural progenitor cells, leading to impaired neurogenesis and resulting in microcephaly and other congenital malformations, pregnant women are identified as subjects with a high risk for ZIKV infection. The methods of treating a human subject with a composition of the invention are, therefore, particularly useful in treating and/or preventing a ZIKV infection in pregnant women.

As used herein, the term "transfection" refers to any of a wide variety of techniques commonly used for the introduction of an exogenous nucleic acid molecule (e.g., DNA, such as an expression vector) into a prokaryotic or eukaryotic host cell, e.g., electroporation, lipofection, calcium-phosphate precipitation, DEAE-dextran transfection, and the like.

As used herein, and as well understood in the art, "treatment" is an approach for obtaining beneficial or desired results, such as clinical results. Beneficial or desired results can include, but are not limited to, alleviation or amelioration of one or more symptoms (e.g., fever, joint pain, rash, conjunctivitis, muscle pain, headache, retro-orbital pain, edema, lymphadenopathy, malaise, asthenia, sore throat, cough, nausea, vomiting, diarrhea, and hematospermia) or conditions (Zammarchi et al., *J. Clin. Virol.* 63:32-5, 2015; Waddell et al., *PLoS One* 11(5): e0156376, 2016); diminishment of the extent of disease, disorder, or condition; stabilization (e.g., not worsening) of a state of disease, disorder, or condition; prevention of spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or the time course of the progression is slowed or lengthened, as compared to the extent or time course in the absence of treatment.

The term "vaccine" as used herein, is defined as material used to provoke an immune response and that confers immunity for a period of time after administration of the vaccine to a subject.

By "vector" is meant a DNA construct that includes one or more polynucleotides, or fragments thereof, such as from a viral species, such as a ZIKV species. The vector can be used to infect cells of a subject, which results in the translation of the polynucleotides of the vector into a protein product. One type of vector is a "plasmid," which refers to a circular double stranded DNA loop into which additional DNA segments may be ligated. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may, at times, be used interchangeably as the plasmid is the most commonly used form of vector. Other vectors include, e.g., viral vectors, such as adenoviral vectors, in particular, those described herein.

The term "virus," as used herein, is defined as an infectious agent that is unable to grow or reproduce outside a host cell and that infects mammals (e.g., humans).

A "viral vector" is defined as a recombinantly produced virus or viral; particle that comprises a polynucleotide to be delivered into a host cell. Examples of viral vectors include retroviral vectors, adenovirus vectors, adeno-associated virus vectors (e.g., see PCT publication no. WO 2006/002203), alphavirus vectors and the like.

In aspects where gene transfer is mediated by a DNA viral vector, such as an adenovirus (Ad) or adeno-associated virus (AAV), a vector construct refers to the polynucleotide comprising the viral genome or part thereof, and a transgene. Ads are a relatively well characterized, homogenous group of viruses, including over 50 serotypes (WO 95/27071). Ads are easy to grow and do not require integration into the host cell genome. Recombinant Ad derived vectors, particularly those that reduce the potential for recombination and generation of wild-type virus, have also been constructed (WO 95/00655 and WO 95/11984). Vectors that contain both a promoter and a cloning site into which a polynucleotide can be operatively linked are known in the art. Such vectors are capable of transcribing RNA in vitro or in vivo. To optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation.

Other features and advantages of the invention will be apparent from the following Detailed Description, the drawings, and the claims.

BRIEF DESCRIPTION OF THE DRAWINGS

FIG. 2 are charts showing both the number and percentage of amino acid differences between ZIKV polyprotein sequences from the following ZIKV isolates: ZIKV-BR, ZIKV-PR, BeH815744 (Brazil strain), H/PF/2013 (French Polynesian strain), and MR766 (African strain). The BeH815744 nucleotide sequence is used as the basis for the design of optimized immunogens (e.g., immunogenic ZIKV polypeptides) of the invention (FIG. 3A).

FIG. 3C are graphs comparing the ability of the DNA vaccines prM-Env, prM-Env.dTM, prM-Env.dStem, Env, Env.dTM, and Env.dStem to induce a humoral response in Balb/c mice. Balb/c mice (N=5/group) received a single immunization with 50 μg of these DNA vaccines by the intramuscular (i.m.) route and were assessed at week three following vaccination by Env-specific ELISA. Bars reflect the median values.

FIG. 4C are graphs comparing serum viral loads from Balb/c mice that were immunized with either DNA-Env, DNA-Env.dTM, or DNA-Env.dStem and subsequently challenged by ZIKV-BR infection. Balb/c mice (N=5/group) received a single immunization of 50 μg vaccine by the i.m. route. Mice were then challenged four weeks after immunization by intravenous administration of $10^5$ VP ($10^2$ PFU) of ZIKV-BR.

FIG. 8A is a graph comparing Env-specific serum antibody titers in recipient Balb/c mice (N=4-5/group) following adoptive transfer of varying amounts (high, mid, or low) of IgG purified from the serum of mice immunized with a sham vaccine or DNA-prM-Env. Passive infusion of 100 μL purified IgG (titers between 25-2025) resulted in median Env-specific log serum antibody titers of 2.82 (high), 2.35 (mid), and 1.87 (low) in recipient mice following adoptive transfer.

FIG. 8B is a graph examining the correlation between Env-specific antibody titers and protective efficacy. Bars reflect median values. P-values reflect t-tests and Spearman rank-correlation tests.

FIG. 10B is a Western blot of transgene expression from the prM-Env (216-794) or "M-Env" (SEQ ID NO: 1), prM-Env (full length) (SEQ ID NO: 24), and prM-Env with JEV Stem/TM (SEQ ID NO: 26) DNA vaccines transfected into 293T cells. The DNA vaccines were generated by incorporating the nucleic acid molecules encoding the ZIKV immunogens of FIG. 10A into a mammalian expression vector pcDNA3.1+(Invitrogen, CA, USA). The following DNA vaccines were generated: prM-Env (216-794) or "M-Env," comprising SEQ ID NO: 1 ("DNA-prM-Env (M-Env)", prM-Env (full length) ("DNA-prM-Env (full length)"), comprising SEQ ID NO: 24, and prM-Env with JEV Stem/TM ("DNA-prM-Env (JEV Stem), comprising SEQ ID NO: 26. Polypeptides were successfully expressed from each construct, respectively, in 293T cells.

FIG. 10C are graphs comparing the ability of the DNA vaccines DNA-prM-Env (M-Env), DNA-prM-Env (full length), and DNA-prM-Env (JEV Stem) to induce a humoral response in Balb/c mice. Balb/c mice received a single immunization with 50 μg of these DNA vaccines by the intramuscular (i.m.) route and were assessed at week three following vaccination by Env-specific ELISA. Bars reflect the median values.

FIG. 14 are graphs comparing the durability of the protective effect of immunization with the DNA vaccine DNA-prM-Env (M-Env) (left panel) or adenovirus vector-based vaccine RhAd52-prM-Env (right panel) in rhesus monkeys (N=4/group) challenged by ZIKV-BR infection one year post immunization. Bars reflect the median values. Arrows indicated time of immunization.

FIG. 18 are graphs comparing serum viral loads from Balb/c mice that were immunized with the indicated adenovirus vector-based vaccine of DNA vaccine or naive control and subsequently challenged with ZIKV-BR infection. Balb/c mice were challenged at week 20 post immunization by the intramuscular (i.m.) route with $10^2$ plaque-forming units (PFU) of ZIKV-BR. Env-specific antibody responses were evaluated at week two, week four, week eight, week ten, week twelve, week fourteen, and week twenty post immunization by ELISA.

FIG. 28 are graphs comparing serum viral loads from Balb/c mice having no baseline Flavivirus immunity (N=5) and with Flavivirus immunity (N=35) that were immunized with DNA vaccine DNA-prM-ENV (containing SEQ ID NO: 1), and RhAd52-prM-ENV, (containing SEQ ID NO: 1), or sham control, and subsequently challenged by ZIKV-BR.

DETAILED DESCRIPTION OF THE INVENTION

Figure 1:
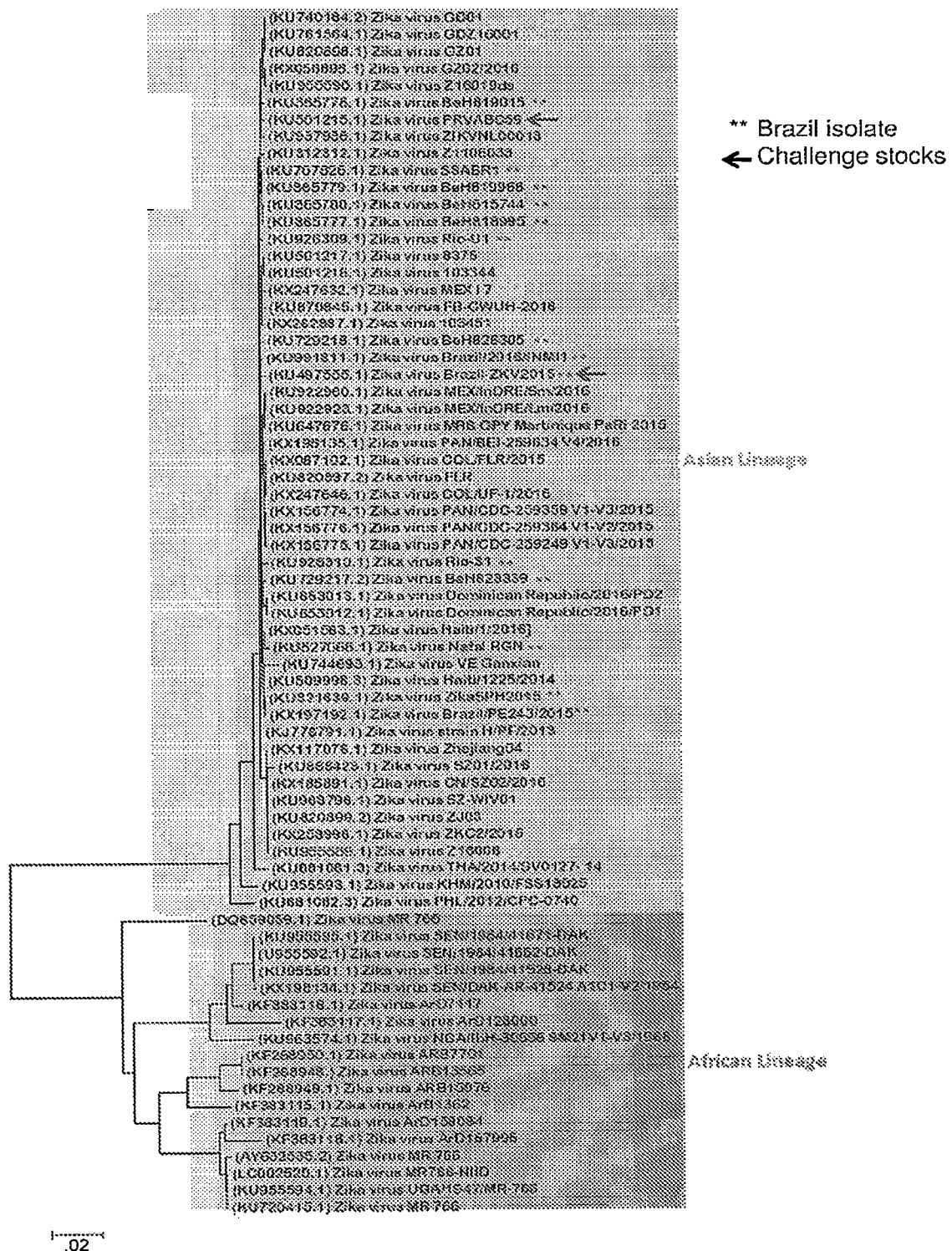
FIG. 1 is a phylogenetic tree showing a maximum likelihood analysis of Zika viruses (ZIKV) from Asian and African lineages. The Brazil/ZKV2015 (accession number KU497555.1 (SEQ ID NOs: 17-18); "ZIKV-BR") and PRV-ABC59 (accession number KU501215.1 (SEQ ID NOs: 19-20); "ZIKV-PR") strains were obtained as low passage isolates, and are indicated by arrows. Brazil isolates are indicated with double asterisks (**). The ZIKV-BR and ZIKV-PR isolates were used herein as challenge isolates.

We have discovered that Zika virus (ZIKV) polypeptides can be used to elicit protective and therapeutic immune responses against a ZIKV infection when administered to a subject (e.g., a human subject) infected with or likely to be exposed to a ZIKV. The compositions that can be prepared for administration to a subject include a ZIKV protein (e.g., a prM-Env, prM-Env.dTM, prM-Env.dStem, Env, Env.dTM, and/or Env.dStem or a portion thereof) or a vector containing a nucleic acid sequence that encodes the ZIKV protein (e.g., an expression vector, such as a plasmid, or a viral vector, such as an adenovirus, poxvirus, adeno-associated virus, retroviral, or other viral vector, or naked or encapsulated DNA.

In particular, we describe the generation of DNA vaccines expressing a truncated ZIKV pre-membrane and envelope (prM-Env) region, the envelope region alone (Env), and deletion mutants that remove either the transmembrane (TM) or stem (Stem) polyproteins (Table 1) that provide protection from ZIKV infection. The ZIKV DNA vaccines of the invention were generated by incorporating a polynucleotide of Table 1 into the mammalian expression vector pcDNA3.1+ (Invitrogen, CA, USA) to generate the prM-Env vaccine ("DNA-prM-Env"), prM-Env.dTM DNA vaccine ("DNA-prM-Env.dTM"), the prM-Env.dStem DNA vaccine ("DNA-prM-Env.dStem"), the Env vaccine ("DNA-Env"), the Env.dTM vaccine ("DNA-Env.dTM"), and the Env.dStem vaccine ("DNA-Env.dStem").

We demonstrate that the DNA vaccines of the invention provide protection against ZIKV challenge, and that protective efficacy is correlated with Env-specific antibody titers. Additionally, we show that adoptive transfer of purified IgG from a vaccinated subject confers passive protection from ZIKV infection.

The nucleic acid molecules, polypeptides, vectors, vaccines, compositions, antibodies, and methods treating and preventing a ZIKV infection of the invention are described herein.

TABLE 1

ZIKV derived polynucleotide and polypeptide molecules

| | SEQ ID NO. | |
|---|---|---|
| Region of ZIKV | polynucleotide | polypeptide |
| prM-Env ("prM-Env (216-794)" or "M-Env" or prM-Env (pr deleted)) | 1 | 2 |
| prM-Env.dTM | 3 | 4 |
| prM-Env.dStem | 5 | 6 |
| Env | 7 | 8 |
| Env.dTM | 9 | 10 |
| Env.dStem | 11 | 12 |
| prM-Env (full length) | 24 | 25 |
| prM-Env with JEV Stem/TM | 26 | 27 |

I. COMPOSITIONS AND METHODS

Nucleic Acid Molecules of the Invention

The nucleic acid molecules of the invention (Table 1) were designed based on the Zika virus (ZIKV) strain BeH815744 (accession number KU365780 (SEQ ID NOs: 15-16)). The nucleic acid molecules of the invention encode regions of the Zika virus (ZIKV) polyprotein, for example, the pre-membrane and envelope (prM-Env) region, the Env region alone, or deletion mutants of the prM-Env or Env regions in which the transmembrane (TM) or Stem region have been removed. The nucleic acid molecules of the invention prM-Env (SEQ ID NO: 1), prM-Env.dTM (SEQ ID NO: 3), prM-Env.dStem (SEQ ID NO: 5), Env (SEQ ID NO: 7), Env.dTM (SEQ ID NO: 9), and Env.dStem (SEQ ID NO: 11) have been optimized relative to the wild-type BeH815744 nucleotide sequences for improved expression in host cells (e.g., mammalian (e.g., human) host cells) and particle formation, and encode the polypeptides set forth in SEQ ID NOs: 2, 4, 6, 8, 10, or 12, respectively (Table 1). Optimization can included the addition of a leader sequence, such as a Japanese encephalitis virus (JEV) leader sequence (e.g., SEQ ID NO: 13), restriction site (e.g., SEQ ID NOs: 21-22), and/or a Kozak sequence (e.g., SEQ ID NO: 23).

The prM-Env (full length) (e.g., SEQ ID NOs: 24-25) contains the full-length sequence of the prM-Env region, while prM-Env with JEV Stem/TM (e.g., SEQ ID NOs: 26-27) includes the ZIKV prM signal region of Japanese encephalitis virus (JEV) with the final 98 amino acids comprising the stem and transmembrane regions exchanged with corresponding JEV sequences.

The nucleic acid molecules have a nucleotide sequence with at least 85% (e.g., at least 86%, 87%, 88%, 89%, 90%, 91%, 92%, 93%, 94%, 95%, 96%, 97%, 98%, 99% or 100%) sequence identity to, all or a portion of any one of SEQ ID NOs: 1, 3, 5, 7, 9, or 11, or a complementary sequence thereof. Alternatively, an isolated nucleic acid molecule has a nucleotide sequence that encodes a ZIKV polypeptide with at least 85% (e.g., at least 86%, 87%, 88%, 89%, 90%, 91%, 92%, 93%, 94%, 95%, 96%, 97%, 98%, 99% or 100%) sequence identity to an amino acid sequence of any one of SEQ ID NOs: 2, 4, 6, 8, 10, or 12.

The nucleic acid molecules of the invention may be further optimized, such as by codon optimization, for expression in a targeted mammalian subject (e.g., human).

The nucleic acid molecules may also be inserted into expression vectors, such as a plasmid, or a viral vector, such as an adenovirus, poxvirus, adeno-associated virus, retroviral, or other viral vector, or prepared as naked or encapsulated DNA and incorporated into compositions of the invention.

Polypeptides of the Invention

The polypeptides of the invention are ZIKV polypeptides corresponding to, for example, the pre-membrane and envelope (prM-Env) region, the Env region alone, or deletion mutants of the prM-Env or Env regions in which the transmembrane (TM) or Stem region has been removed. Polypeptides of the invention include prM-Env (SEQ ID NO: 2), prM-Env.dTM (SEQ ID NO: 4), prM-Env.dStem (SEQ ID NO: 6), Env (SEQ ID NO: 8), Env.dTM (SEQ ID NO: 10), and Env.dStem (SEQ ID NO: 12) and variants having at least 85% (e.g., at least 86%, 87%, 88%, 89%, 90%, 91%, 92%, 93%, 94%, 95%, 96%, 97%, 98%, 99% or 100%) sequence identity to, all or a portion of any one of SEQ ID NOs: 2, 4, 6, 8, 10, or 12. The polypeptides of the invention may include at least 5, 6, 7, 8, 9, 10, 20, 30, 40, 50, 60, 70, 80, 90, 100, 200, 300, 400, 500, 600, 700, 800, 900, 1000, 1100, 1200, 1300, 1400, 1500, 1600, 1700, or 1800 or more continuous or non-continuous amino acids of any one of SEQ ID NOs: 2, 4, 6, 8, 10, or 12. Polypeptides of the invention may also include a leader sequence, such as a Japanese encephalitis virus (JEV) leader sequence (SEQ ID NO: 14). The polypeptides may also be isolated from other components (e.g., components with which the polypeptides are natively associated) and incorporated into compositions of the invention.

Vectors of the Invention

The invention also features recombinant vectors including any one or more of the polynucleotides described above. The vectors of the invention can be used to deliver an nucleic acid expressing an immunogen of the invention (e.g., one of more of SEQ ID NOs: 2, 4, 6, 8, 10, or 12 or variants thereof, having at least 85-99% sequence identity thereto, for example at least greater than 90% sequence identity thereto), and in include mammalian, viral, and bacterial expression vectors. The mammalian, viral, and bacterial vectors of the invention can be genetically modified to contain one or more nucleic acid sequences set forth in SEQ ID NOs: 1, 3, 5, 7, 9, or 11 or variants thereof, having at least 85-99% sequence identity thereto, for example at least greater than 90% sequence identity thereto, and complements thereof.

The vectors may be, for example, plasmids, artificial chromosomes (e.g. BAG, PAC, YAC), and virus or phage vectors, and may optionally include a promoter, enhancer, or regulator for the expression of the polynucleotide. The vectors may also contain one or more selectable marker genes, for example an ampicillin, neomycin, and/or kanamycin resistance gene in the case of a bacterial plasmid or a resistance gene for a fungal vector. Vectors may be used in vitro, for example, for the production of DNA or RNA or used to transfect or transform a host cell, for example, a mammalian host cell, e.g., for the production of protein encoded by the vector. The vectors may also be adapted to be used in vivo, for example in a method of DNA vaccination or of gene therapy.

Promoters and other expression regulation signals may be selected to be compatible with the host cell for which expression is designed. For example, mammalian promoters include the metallothionein promoter, which can be induced in response to heavy metals, such as cadmium, and the β-actin promoter. A viral promoter, which can be obtained from the genome of a virus, such as, for example, polyoma virus, fowlpox virus, adenovirus (A), bovine papilloma virus, avian sarcoma virus, cytomegalovirus (CMV), a retrovirus, hepatitis-B virus, and Simian Virus 40 (SV40), and human papillomavirus (HPV), may also be used. These promoters are well known and readily available in the art.

A preferred promoter element is the CMV immediate early promoter. In some embodiments, the expression plasmid is pcDNA3.1+ (Invitrogen, CA, USA). In some embodiments, the expression vector is a viral vector, such as a vector derived from adenovirus or poxvirus.

Viral genomes provide a rich source of vectors that can be used for the efficient delivery of exogenous genes into the genome of a cell (e.g., a eukaryotic or prokaryotic cell). Viral genomes are particularly useful vectors for gene delivery because the polynucleotides contained within such genomes are typically incorporated into the genome of a target cell by generalized or specialized transduction. These processes occur as part of the natural viral replication cycle, and do not require added proteins or reagents in order to induce gene integration. Examples of viral vectors that can be used to deliver a nucleic acid expressing an immunogen of the invention (e.g., one of more of SEQ ID NOs: 2, 4, 6, 8, 10, or 12 or variants thereof having at least 85-99% sequence identity thereto, for example at least greater than 90% sequence identity thereto) include a retrovirus, adenovirus (e.g., Ad2, Ad5, Ad11, Ad12, Ad24, Ad26, Ad34, Ad35, Ad40, Ad48, Ad49, Ad50, Ad52 (e.g., RhAd52), and Pan9 (also known as AdC68)), parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses, such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, modified vaccinia Ankara (MVA), fowlpox and canarypox). Other viruses useful for delivering polynucleotides encoding immunogens (e.g., polypeptides) of the invention include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D-type viruses, HTLV-BLV group, lentivirus, spumavirus (Coffin. J. M., Retroviridae: The viruses and their replication, In Fundamental Virology, Third Edition, B. N. Fields, et al., Eds., Lippincott-Raven Publishers, Philadelphia, 1996). These adenovirus vectors can be derived from, for example, human, chimpanzee, or rhesus adenoviruses. Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, in McVey et al., (U.S. Pat. No. 5,801,030); incorporated herein in its entirety by reference. The nucleic acid material (e.g., including a nucleic acid molecule of the invention) of the viral vector may be encapsulated, e.g., in a lipid membrane or by structural proteins (e.g., capsid proteins), that may include one or more viral polypeptides (e.g., a glycoprotein). The viral vector can be used to infect cells of a subject, which, in turn, promotes the translation of the heterologous gene(s) of the viral vector into the immunogens of the invention. For example, a viral vector of the invention can be genetically modified to contain one or more nucleic acid sequences set forth in SEQ ID NOs: 1, 3, 5, 7, 9, or 11 or variants thereof having at least 85-99% sequence identity thereto, for example at least greater than 90% sequence identity thereto, and complements thereof.

Adenoviral vectors disclosed in International Patent Application Publications WO 2006/040330 and WO 2007/104792, each incorporated by reference herein, are particularly useful as vectors of the invention. These adenoviral vectors can encode and/or deliver one or more of the immunogens of the invention (e.g., ZIKV polypeptides) to treat a subject having a pathological condition associated with a viral infection (e.g., a ZIKV infection). In some embodiments, one or more recombinant adenovirus vectors can be administered to the subject in order to express more than one type of immunogen (e.g., ZIKV polypeptide) of the invention. Besides adenoviral vectors, other viral vectors and techniques are known in the art that can be used to facilitate delivery and/or expression of one or more of the immunogens of the invention in a subject (e.g., a human). These viruses include poxviruses (e.g., vaccinia virus and modified vaccinia virus Ankara (MVA); see, e.g., U.S. Pat. Nos. 4,603,112 and 5,762,938, each incorporated by reference herein), herpesviruses, togaviruses (e.g., Venezuelan Equine Encephalitis virus; see, e.g., U.S. Pat. No. 5,643,576, incorporated by reference herein), picornaviruses (e.g., poliovirus; see, e.g., U.S. Pat. No. 5,639,649, incorporated by reference herein), baculoviruses, and others described by Wattanapitayakul and Bauer (Biomed. Pharmacother. 54:487 (2000), incorporated by reference herein).

Gene transfer techniques using these viruses are known to those skilled in the art. Retrovirus vectors for example may be used to stably integrate the polynucleotide of the invention into the host genome, although such recombination is not preferred. Replication-defective adenovirus vectors by contrast remain episomal and therefore allow transient expression.

Vectors capable of driving expression in insect cells (for example baculovirus vectors), in human cells, in yeast or in bacteria may be employed in order to produce quantities of the ZIKV protein encoded by the polynucleotides of the present invention, for example, for use as subunit vaccines or in immunoassays.

Antibodies of the Invention

Anti-ZIKV antibodies of the invention are capable of specifically binding to a ZIKV polypeptide and are capable of inhibiting a ZIKV-mediated activity (e.g., viral spread, infection, and or cell fusion) in a subject (e.g., a human). The result of such binding may be, for example, a reduction in viral titer (e.g., viral load), by about 1% (e.g., 2%, 3%, 4%, 5%, 6%, 7%, 8%, 9%, 10%, 20%, 30%, 40%, 50%, 60%, 70%, 80%, or 90%) or more, after administration of an antibody of the invention to a subject infected with ZIKV. The anti-ZIKV antibodies of the invention may selectively bind to an epitope comprising all, or a portion of, the Env region of the ZIKV polyprotein. In particular, the anti-ZIKV antibodies of the invention may selectively bind to an epitope comprising all, or a portion of, any one of SEQ ID NOs: 2, 4, 6, 8, 10, or 12. The antibodies of the invention can therefore be used to prevent or treat an ZIKV infection.

The specific binding of an antibody or antibody fragment of the invention to a ZIKV polyprotein can be determined by any of a variety of established methods. The affinity can be represented quantitatively by various measurements, including the concentration of antibody needed to achieve half-maximal inhibition of viral spread (e.g., viral titer) in vitro ($IC_{50}$) and the equilibrium constant ($K_D$) of the antibody-ZIKV polyprotein complex dissociation. The equilibrium constant, $K_D$, that describes the interaction of ZIKV polyprotein with an antibody of the invention is the chemical equilibrium constant for the dissociation reaction of a ZIKV polyprotein-antibody complex into solvent-separated ZIKV polyprotein and antibody molecules that do not interact with one another.

Antibodies of the invention are those that specifically bind to a ZIKV polyprotein (e.g., the Env region of ZIKV) with a $K_D$ value of less than 1 µM (e.g., 900 nM, 800 nM, 700 nM, 600 nM, 500 nM, 400 nM, 300 nM, 200 nM, 100 nM, 95 nM, 90 nM, 85 nM, 80 nM, 75 nM, 70 nM, 65 nM, 60 nM, 55 nM, 50 nM, 45 nM, 40 nM, 35 nM, 30 nM, 25 nM, 20 nM, 15 nM, 10 nM, 5 nM, 4 nM, 3 nM, 2 nM, or 1 nM). In certain cases, antibodies of the invention are those that specifically bind to a ZIKV polyprotein with a $K_D$ value of less than 1 nM (e.g., 990 pM, 980 pM, 970 pM, 960 pM, 950 pM, 940 pM, 930 pM, 920 pM, 910 pM, 900 pM, 890 pM, 880 pM, 870 pM, 860 pM, 850 pM, 840 pM, 830 pM, 820 pM, 810 pM, 800 pM, 790 pM, 780 pM, 770 pM, 760 pM, 750 pM, 740 pM, 730 pM, 720 pM, 710 pM, 700 pM, 690 pM, 680 pM, 670 pM, 660 pM, 650 pM, 640 pM, 630 pM, 620 pM, 610 pM, 600 pM, 590 pM, 580 pM, 570 pM, 560 pM, 550 pM, 540 pM, 530 pM, 520 pM, 510 pM, 500 pM, 490 pM, 480 pM, 470 pM, 460 pM, 450 pM, 440 pM, 430 pM, 420 pM, 410 pM, 400 pM, 390 pM, 380 pM, 370 pM, 360 pM, 350 pM, 340 pM, 330 pM, 320 pM, 310 pM, 300 pM, 290 pM, 280 pM, 270 pM, 260 pM, 250 pM, 240 pM, 230 pM, 220 pM, 210 pM, 200 pM, 190 pM, 180 pM, 170 pM, 160 pM, 150 pM, 140 pM, 130 pM, 120 pM, 110 pM, 100 pM, 90 pM, 80 pM, 70 pM, 80 pM, 50 pM, 40 pM, 30 pM, 20 pM, 10 pM, 5 pM, or 1 pM).

Antibodies of the invention can also be characterized by a variety of in vitro binding assays. Examples of experiments that can be used to determine the $K_D$ or $IC_{50}$ of a ZIKV antibody include, e.g., surface plasmon resonance, isothermal titration calorimetry, fluorescence anisotropy, and ELISA-based assays, among others. ELISA represents a particularly useful method for analyzing antibody activity, as such assays typically require minimal concentrations of antibodies. A common signal that is analyzed in a typical ELISA assay is luminescence, which is typically the result of the activity of a peroxidase conjugated to a secondary antibody that specifically binds a primary antibody (e.g., a ZIKV antibody of the invention). Antibodies of the invention are capable of binding ZIKV and epitopes derived thereof, such as epitopes containing one or more of residues of any one of SEQ ID NOs: 2, 4, 6, 8, 10, or 12, as well as isolated peptides derived from ZIKV that structurally pre-organize various residues in a manner that may simulate the conformation of these amino acids in the native protein. For instance, antibodies of the invention may bind peptides containing the amino acid sequence of any one of SEQ ID NOs: 2, 4, 6, 8, 10, or 12, or a peptide containing between about 10 and about 30 continuous or discontinuous amino acids of any one of SEQ ID NOs: 2, 4, 6, 8, 10, or 12. In a direct ELISA experiment, this binding can be quantified, e.g., by analyzing the luminescence that occurs upon incubation of an HRP substrate (e.g., 2,2'-azino-di-3-ethylbenz-thiazoline sulfonate) with an antigen-antibody complex bound to a HRP-conjugated secondary antibody.

Antibodies of the invention include those that are generated by immunizing a host (e.g., a mammalian host, such as a human) with the polypeptides of SEQ ID NOs: SEQ ID NOs: 2, 4, 6, 8, 10, or 12. The antibodies can be prepared recombinantly and, if necessary, humanized, for subsequent administration to a human recipient if the host in which the anti-ZIKV antibodies are generated is not a human.

Compositions of the Invention

Compositions of the invention include DNA vectors containing a heterologous nucleic acid molecule encoding an antigenic or therapeutic gene product, or fragment thereof, from a ZIKV (e.g., all or a portion of the nucleic acid molecule of SEQ ID NO: 1, 3, 5, 7, 9, or 11, or a variant thereof having at least 85% (e.g., 86%, 87%, 88%, 89%, 90%, 91%, 92%, 93%, 94%, 95%, 96%, 97%, 98%, 99% or 100%) sequence identity to SEQ ID NO: 1, 3, 5, 7, 9, or 11, and complements thereof). Additional compositions of the invention include an immunogenic polypeptide, or fragment thereof, from a ZIKV polyprotein (e.g., all or a portion of the polypeptide of SEQ ID NO: 2, 4, 6, 8, 10, or 12, or a variant thereof having at least 85% (e.g., 86%, 87%, 88%, 89%, 90%, 91%, 92%, 93%, 94%, 95%, 96%, 97%, 98%, 99% or 100%) sequence identity to SEQ ID NOs: 2, 4, 6, 8, 10, or 12). The compositions of the invention may also include a ZIKV antibody (e.g., an anti-Env antibody) capable of binding ZIKV and epitopes derived thereof, such as epitopes containing one or more of residues of any one of SEQ ID NOs: 2, 4, 6, 8, 10, or 12. The antibody may be generated by immunization of a host with a polypeptide of any one of SEQ ID NOs: 2, 4, 6, 8, 10, or 12.

Optionally, the compositions can be formulated, for example, for administration via a viral vector (e.g., an adenovirus vector or a poxvirus vector). Recombinant adenoviruses offer several significant advantages for use as vectors for the expression of, for example, one or more of the immunogens of the invention (e.g., ZIKV polypeptides). The viruses can be prepared to high titer, can infect non-replicating cells, and can confer high-efficiency transduction of target cells ex vivo following contact with a target cell population. Furthermore, adenoviruses do not integrate their DNA into the host genome. Thus, their use as expression vectors has a reduced risk of inducing spontaneous proliferative disorders. In animal models, adenoviral vectors have generally been found to mediate high-level expression for approximately one week. The duration of transgene expression (expression of a nucleic acid molecule of the invention) can be prolonged by using cell or tissue-specific promoters. Other improvements in the molecular engineering of the adenovirus vector itself have produced more sustained transgene expression and less inflammation. This is seen with so-called "second generation" vectors harboring specific mutations in additional early adenoviral genes and "gutless" vectors in which virtually all the viral genes are deleted utilizing a Cre-Lox strategy (Engelhardt et al., *Proc. Natl. Aced. Sci. USA* 91:6196 (1994) and Kochanek et al., *Proc. Natl. Acad. Sci. USA* 93:5731 (1996), each herein incorporated by reference).

Therapeutic formulations of the compositions of the invention are prepared for administration to a subject (e.g., a human) using standard methods known in the art by mixing the active ingredient having the desired degree of purity with optional physiologically acceptable carriers, excipients or stabilizers (Remington's Pharmaceutical Sciences ($20^{th}$ edition), ed. A. Gennaro, 2000. Lippincott, Williams & Wilkins, Philadelphia, Pa.). Therapeutic formulations of the compositions of the invention are prepared using standard methods known in the art by mixing the active ingredient having the desired degree of purity with optional physiologically acceptable carriers, excipients or stabilizers (Remington's Pharmaceutical Sciences ($20^{th}$ edition), ed. A. Gennaro, 2000, Lippincott, Williams & Wilkins, Philadelphia, Pa.). Acceptable carriers, include saline, or buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagines, arginine or lysine; mono-saccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, but preferably, the formulation contains a pharmaceutically acceptable salt, preferably sodium chloride, and preferably at about physiological concentrations. Optionally, the formulations of the invention can contain a pharmaceutically acceptable preservative. The preservative concentration may range from about 0.1 to about 2.0%, typically v/v. Suitable preservatives include those known in the pharmaceutical arts, such as benzyl alcohol, phenol, m-cresol, methylparaben, and propylparaben. Optionally, the formulations of the invention can include a pharmaceutically acceptable surfactant at a concentration of about 0.005 to about 0.02%.

Optionally, the compositions of the invention may be formulated to include for co-administration, or sequential administration with, an adjuvant and/or an immunostimulatory agent, (e.g., a protein), such as receptor molecules, nucleic acids, immunogenic proteins, pharmaceuticals, chemotherapy agents, and accessory cytokines. For example, interleukin-3 (IL-3), interleukin-4 (IL-4), interleukin-5 (IL-5), interleukin-7 (IL-7), interleukin-8 (IL-8), interleukin-10 (IL-10), interleukin-11 (IL-11), interleukin-12 (IL-12), interleukin-13 (IL-13), lipid A, phospholipase A2, endotoxins, staphylococcal enterotoxin B, Type I interferon, Type II interferon, transforming growth factor-β (TGF-β), lymphotoxin migration inhibition factor, granulocyte-macrophage colony-stimulating factor (CSF), monocyte-macrophage CSF, granulocyte CSF, vascular epithelial growth factor (VEGF), angiogenin, transforming growth factor (TGF-α), heat shock proteins (HSPs), carbohydrate moieties of blood groups, Rh factors, fibroblast growth factors, nucleotides, DNA, RNA, mRNA, MART, MAGE, BAGE, mutant p53, tyrosinase, AZT, angiostatin, endostatin, or a combination thereof, may be included in formulations of, or for co-administration with, the compositions of the invention.

The pharmaceutical compositions of the invention can be administered in a therapeutically effective amount that provides an immunogenic and/or protective effect against an infective agent (e.g., a ZIKV. In some embodiments, a composition comprising a nucleic acid molecule, polypeptide, vector, and/or antibodies of the invention may be formulated for administration at a dose of at least 1-1,000 µg (e.g., at least 15, 16, 17, 18, 19, 20, 30, 40, 50, 60, 70, 80, 90, 100, 125, 150, 175, 200, 225, 250, 275, or 300 µg or more). In some embodiments, a composition comprising a nucleic acid molecule, vector, and/or vaccine of the invention of the invention is administered at a dose of 50 µg.

The compositions utilized in the methods described herein can be formulated, for example, for administration intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, by gavage, in cremes, or in lipid compositions.

Pharmaceutical compositions according to the invention described herein may be formulated to release the composition immediately upon administration (e.g., targeted delivery) or at any predetermined time period after administration using controlled or extended release formulations. Administration of the pharmaceutical composition in controlled or extended release formulations is useful where the composition, either alone or in combination, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window at the site of release (e.g., the gastro-intestinal tract); or (iii) a short biological half-life, so that frequent dosing during a day is required in order to sustain a therapeutic level.

Many strategies can be pursued to obtain controlled or extended release in which the rate of release outweighs the rate of metabolism of the pharmaceutical composition. For example, controlled release can be obtained by the appropriate selection of formulation parameters and ingredients, including, e.g., appropriate controlled release compositions and coatings. Suitable formulations are known to those of skill in the art. Examples include single or multiple unit tablet or capsule compositions, oil solutions, suspensions, emulsions, microcapsules, microspheres, nanoparticles, patches, and liposomes.

The compositions may be sterilized by conventional sterilization techniques, or may be sterile filtered. The resulting aqueous solutions may be packaged for use as is, or lyophilized, the lyophilized preparation may be administered in powder form or combined with a sterile aqueous carrier prior to administration. The pH of the preparations typically will be between 3 and 11, more preferably between 5 and 9 or between 8 and 8, and most preferably between 7 and 8, such as 7 to 7.5. The resulting compositions in solid form may be packaged in multiple single dose units, each containing a fixed amount of an immunogenic composition (e.g., a vaccine or an anti-ZIKV antibody) of the invention and, if desired, one or more immunomodulatory agents, such as in a sealed package of tablets or capsules, or in a suitable dry powder inhaler (DPI) capable of administering one or more doses.

Methods of Treatment Using Compositions of the Invention

The pharmaceutical compositions (e.g., immunogenic compositions and anti-ZIKV antibodies) of the invention can be used to treat a subject (e.g., a human) at risk of exposure (e.g., due to travel to a region were Zika virus (ZIKV) infection is prevalent) to a ZIKV or to treat a subject having a ZIKV infection. In particular, the compositions of the invention can be used to treat (pre- or post-exposure) infection by a ZIKV. In some embodiments, treatment with a composition of the invention may reduce a ZIKV-mediated activity in a subject, such as viral titer, viral spread, infection, and or cell fusion. In some embodiments, ZIKV titer in a treated subject infected with ZIKV is decreased by about 1% (e.g., 2%, 3%, 4%, 5%, 6%, 7%, 8%, 9%, 10%, 20%, 30%, 40%, 50%, 60%, 70%, 80%, or 90%) or more after administration of a composition (e.g., vaccine) of the invention to the subject. The ZIKV infection and/or exposure may be to a strain of the Asian Lineage (FIG. 1), such as a strain of ZIKV from Brazil (e.g., Brazil/ZKV2015) or Puerto Rico (e.g, PRVABC59).

The vectors (e.g., mammalian, bacterial, or viral derived expression vectors) of the invention can be used to deliver a nucleic acid expressing an immunogen of the invention (e.g., one of more of SEQ ID NOs: 2, 4, 6, 8, 10, or 12 or variants thereof, having at least 85-99% sequence identity thereto, for example at least greater than 90% sequence identity thereto) to a subject in a method of preventing and/or treating a ZIKV infection. The vectors (e.g., mammalian, bacterial, or viral derived expression vectors) of the invention can be genetically modified to contain one or more nucleic acid sequences set forth in SEQ ID NOs: 1, 3, 5, 7, 9, or 11 or variants thereof having at least 85-99% sequence identity thereto, for example at least greater than 90% sequence identity thereto, and complements thereof. In particular, adenoviral vectors (e.g., vectors derived from Ad2, Ad5, Ad11, Ad12, Ad24, Ad26, Ad34, Ad35, Ad40, Ad48, Ad49, Ad50, Ad52, and Pan9 (also known as AdC68)) disclosed in International Patent Application Publications WO 2006/040330 and WO 2007/104792, each incorporated by reference herein, are particularly useful as vectors of the invention in methods of delivering an immunogen of the invention to a subject. Other examples of vectors are described, for example, in McVey et al., (U.S. Pat. No. 5,801,030); incorporated herein, in its entirety, by reference.

Useful gene therapy methods for the delivery of immunogens of the invention to a subject in need thereof include those described in PCT publication no. WO 2006/060641, U.S. Pat. No. 7,179,903, and PCT publication no. WO 2001/036620, which described the use of, for example, an adenovirus vector (e.g., vectors derived from Ad2, Ad5, Ad11, Ad12, Ad24, Ad26, Ad34, Ad35, Ad40, Ad48, Ad49, Ad50, Ad52, and Pan9 (also known as AdC68)) for therapeutic protein delivery.

Administration

The pharmaceutical compositions of the invention can be administered to a subject (e.g., a human) pre- or post-exposure to an infective agent (e.g., a ZIKV) to treat, prevent, ameliorate, inhibit the progression of, or reduce the severity of one or more symptoms of virus infection (e.g., ZIKV infection). For example, the compositions of the invention can be administered to a subject having a ZIKV infection. Examples of symptoms of diseases caused by a viral infection, such as ZIKV, that can be treated using the compositions of the invention include, for example, fever, joint pain, rash, conjunctivitis, muscle pain, headache, retro-orbital pain, edema, lymphadenopathy, malaise, asthenia, sore throat, cough, nausea, vomiting, diarrhea, and hematospermia. These symptoms, and their resolution during treatment, may be measured by, for example, a physician during a physical examination or by other tests and methods known in the art.

The preferred method of administration can vary depending on various factors (e.g., the components of the composition being administered and the severity of the condition being treated). Formulations suitable for oral or nasal administration may consist of liquid solutions, such as an effective amount of the composition dissolved in a diluent (e.g., water, saline, or PEG-400), capsules, sachets, tablets, or gels, each containing a predetermined amount of the chimeric Ad5 vector composition of the invention. The pharmaceutical composition may also be an aerosol formulation for inhalation, for example, to the bronchial passageways. Aerosol formulations may be mixed with pressurized, pharmaceutically acceptable propellants (e.g., dichlorodifluoromethane, propane, or nitrogen). In particular, administration by inhalation can be accomplished by using, for example, an aerosol containing sorbitan trioleate or oleic acid, for example, together with trichlorofluoromethane, dichlorofluoromethane, dichlorotetrafluoroethane, or any other biologically compatible propellant gas.

Immunogenicity of the composition of the invention may be significantly improved if it is co-administered with an immunostimulatory agent and/or adjuvant. Suitable adjuvants well-known to those skilled in the art include, for example, aluminum phosphate, aluminum hydroxide, QS21, Quil A (and derivatives and components thereof), calcium phosphate, calcium hydroxide, zinc hydroxide, glycolipid analogs, octadecyl esters of an amino acid, muramyl dipeptides, polyphosphazene, lipoproteins, ISCOM matrix, DC-Chol, DDA, cytokines, and other adjuvants and derivatives thereof.

The compositions of the invention may be administered to provide pre-exposure prophylaxis or after a subject has been diagnosed as having a viral infection (e.g., ZIKV infection) or a subject exposed to an infective agent, such as a virus (e.g., a ZIKV). The composition may be administered, for example, 1, 2, 3, 4, 5, 6, 7, 8, 9, 10, 15, 20, 30, 35, 40, 45, 50, 55, or 60 minutes, 2, 4, 6, 10, 15, or 24 hours, 2, 3, 5, or 7 days, 2, 4, 6 or 8 weeks, or even 3, 4, or 6 months pre-exposure to a ZIKV, or may be administered to the subject 15-30 minutes or 1, 2, 3, 4, 5, 6, 7, 8, 9, 10, 12, 20, 24, 48, or 72 hours, 2, 3, 5, or 7 days, 2, 4, 6 or 8 weeks, 3, 4, 6, or 9 months, 1, 2, 3, 4, 5, 6, 7, 8, 9, 10, 15, or 20 years or post-exposure to a ZIKV.

When treating viral infection (e.g., a ZIKV infection), the compositions of the invention may be administered to the subject either before the occurrence of symptoms or a definitive diagnosis or after diagnosis or symptoms become evident. For example, the composition may be administered, for example, immediately after diagnosis or the clinical recognition of symptoms or 2, 4, 6, 10, 15, or 24 hours, 2, 3, 5, or 7 days after diagnosis or detection of symptoms.

One or more doses (e.g., 1, 2, 3, 4, 5, 6, 7, 8, 9, or 10 doses) of an immunogenic composition or anti-ZIKV antibody-containing composition of the invention may be administered to a subject in need thereof. In some embodiments, a subject is administered at least one dose. In some embodiments, a subject is administered at least two doses. In some embodiments, an immunogenic composition of the invention is administered to a subject in need thereof as a prime, a boost, or as a prime-boost.

Dosages

The dose of the compositions of the invention or the number of treatments using the compositions of the invention may be increased or decreased based on the severity of, occurrence of, or progression of, the disease in the subject (e.g., based on the severity of one or more symptoms of, e.g., viral infection).

The pharmaceutical compositions of the invention can be administered in a therapeutically effective amount that provides an immunogenic and/or protective effect against an infective agent (e.g., a ZIKV). In some embodiments, a composition comprising a nucleic acid molecule, polypeptide, vector, and/or antibodies of the invention may be administered in a dose of at least 1 µg to 10 mg (e.g., at least 10 µg, 20 µg, 30 µg, 40 µg, 50 µg, 60 µg, 70 µg, 80 µg, 90 µg, 100 µg, 125 µg, 150 µg, 175 µg, 200 µg, 225 µg, 250 µg, 275 µg, 300 µg, 325 µg, 350 µg, 375 µg, 400 µg, 425 µg, 450 µg, 475 µg, 500 µg, 525 µg, 550 µg, 575 µg, 600 µg, 625 µg, 650 µg, 875 µg, 700 µg, 725 µg, 750 µg, 775 µg, 800 µg, 825 µg, 850 µg, 875 µg, 900 µg, 925 µg, 950 µg, 975 µg, 1 mg, 2 mg, 3 mg, 4 mg, 5 mg, 6 mg, 7 mg, 8 mg, or 9 mg or more). In some embodiments, a composition comprising a nucleic acid molecule, vector, and/or antibody of the invention of the invention is administered at a dose of about 50 µg (e.g., a dose between about 25 µg and about 75 µg). In some embodiments, a composition comprising a nucleic acid molecule, vector, and/or antibody of the invention of the invention is administered at a dose of about 5 mg (e.g., a dose of about 1 mg to about 10 mg).

In some instances, administration of an effective amount of a composition of the invention (e.g., an immunogen of the invention, such as SEQ ID NO: 1) reduces ZIKV serum viral loads determined from a subject having a ZIKV infection by at least about 5%, 10%, 20%, 30%, 40%, 50%, 60%, 70%, 80%, 90%, or more compared to viral loads determined from the patient prior to administration of an effective amount of a composition of the invention. In some instances, administration of an effective amount of a composition of the invention reduces serum viral loads to an undetectable level compared to viral loads determined from the patient prior to administration of an effective amount of a composition of the invention. In some instances, administration of an effective amount of a composition of the invention results in a reduced and/or undetectable serum viral load that may be maintained for at least about 1, 2, 3, 4, 5, 6, 7 days; 1, 2, 3, 4, weeks; 1, 2, 3, 4, 5, 6, 7, 8, 9, 10, 11, or 12 months; or 1 year or more.

The dosage administered depends on the subject to be treated (e.g., the age, body weight, capacity of the immune system, and general health of the subject being treated), the form of administration (e.g., as a solid or liquid), the manner of administration (e.g., by injection, inhalation, or dry powder propellant), and the cells targeted (e.g., epithelial cells, such as blood vessel epithelial cells, nasal epithelial cells, or pulmonary epithelial cells). The composition is preferably administered in an amount that provides a sufficient level of the antigenic or therapeutic gene product, or fragment thereof (e.g., a level of an antigenic gene product that elicits an immune response without undue adverse physiological effects in the host caused by the antigenic gene product).

The method of delivery, for example of a DNA vaccine, may also determine the dose amount. In some cases, dosage administered by injections by intravenous (i.v.) or intramuscular (i.m.) route may require variable amounts of a DNA vaccine, for example from 10 µg-1 mg. However, administration using a gene gun may require a dose of a DNA vaccine between 0.2 µg and 20 µg (e.g., 0.2, 0.1, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, or 20 µg). In some instances, the use of a gene gun to deliver a dose of a DNA vaccine may require only ng quantities of DNA, for example between 10 ng and 200 ng (e.g., 10, 12, 13, 14, 15, 16, 17, 18, 19, 20.30, 40, 50, 60, 70, 80, 90, 100, 125, 150, 175, or 200 ng).

In other embodiments wherein the delivery vector is a virus, the subject can be administered at least about $1 \times 10^3$ viral particles (VP)/dose or between $1 \times 10^1$ and $1 \times 10^{20}$ VP/dose (e.g., $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, $1 \times 10^{16}$, $1 \times 10^{17}$, $1 \times 10^{18}$, $1 \times 10^{19}$, and $1 \times 10^{20}$ VP/dose).

In addition, single or multiple administrations of the compositions of the present invention may be given (pre- or post-exposure and/or pre- or post-diagnosis) to a subject (e.g., one administration or administration two or more times). For example, subjects who are particularly susceptible to, for example, viral infection (e.g., a ZIKV infection) may require multiple treatments to establish and/or maintain protection against the virus. Levels of induced immunity provided by the pharmaceutical compositions described herein can be monitored by, for example, measuring amounts of neutralizing secretory and serum antibodies. The dosages may then be adjusted or repeated as necessary to trigger the desired level of immune response. For example, the immune response triggered by a single administration (prime) of a composition of the invention may not sufficiently potent and/or persistent to provide effective protection. Accordingly, in some embodiments, repeated administration (boost), such that a prime boost regimen is established, can significantly enhance humoral and cellular responses to the antigen of the composition.

Alternatively, the efficacy of treatment can be determined by monitoring the level of the antigenic or therapeutic gene product, or fragment thereof, expressed in a subject (e.g., a human) following administration of the compositions of the invention. For example, the blood or lymph of a subject can be tested for antigenic or therapeutic gene product, or fragment thereof, using, for example, standard assays known in the art.

In some instances, efficacy of treatment can be determined by monitoring a change in the serum viral load from a sample from the subject obtained prior to and after administration of an effective amount of a composition of the invention (e.g., an immunogen of the invention, such as SEQ ID NO: 1). A reduction in serum viral load of at least about 5%, 10%, 20%, 30%, 40%, 50%, 60%, 70%, 80%, 90%, or more compared to viral load determined from the subject prior to administration of an effective amount of a composition of the invention may indicate that the subject is receiving benefit from the treatment. If a viral load does not decrease by at least about 10%, 20%, 30%, or more after administration of a composition of the invention, the dosage of the composition to be administered may be increased. For example, by increasing the µg or mg amount of a DNA vaccine (e.g., a DNA vaccine containing SEQ ID No: 1) administered to the subject or by increasing the number of viral particles (VP) of an adenovirus vector-based vaccine (e.g., an adenovirus vector-based vaccine containing SEQ ID NO: 1).

A single dose of a composition of the invention may achieve protection, pre-exposure or pre-diagnosis. In addition, a single dose administered post-exposure or post-diagnosis can function as a treatment according to the present invention.

A single dose of a composition of the invention can also be used to achieve therapy in subjects being treated for an infection (e.g., a ZIKV infection). Multiple doses (e.g., 2, 3, 4, 5, or more doses) can also be administered, in necessary, to these subjects.

II. EXAMPLES

The following examples are to illustrate the invention. They are not meant to limit the invention in any way.

Example 1. Development and Characterization of ZIKV DNA Vaccines

Introduction

Zika virus (ZIKV) is believed to cause neuropathology in developing fetuses by crossing the placenta and targeting cortical neural progenitor cells, leading to impaired neurogenesis and resulting in microcephaly and other congenital malformations. ZIKV also has been associated with neurologic conditions such as Guillain-Barre syndrome. Vaccines have been developed for other flaviviruses, including yellow fever virus, Japanese encephalitis virus, tick-borne encephalitis virus, and dengue viruses, but no vaccine currently exists for ZIKV.

Generation of Zika Virus Challenge Stocks

Zika virus (ZIKV) stocks were provided by the University of São Paulo, Brazil (Brazil ZKV2015, accession number KU497555.1 (SEQ ID NOs: 17-18); ZIKV-BR) (Cugola et al., Nature 2016) and the U.S. Centers for Disease Control and Prevention, USA (Puerto Rico PRVABC59, accession number KU501215.1 (SEQ ID NOs: 19-20); ZIKV-PR) (FIG. 1). The ZIKV-BR and ZIKV-PR strains are part of the Asian ZIKV lineage (Larocca et al., *Science.* 353(6304): 1129-1132, 2016) and differ from each other by five amino acids in the polyprotein (FIG. 2). ZIKV-BR has also recently been reported to recapitulate key clinical manifestations, including fetal microcephaly and intrauterine growth restriction, in wildtype SJL mice (Cugola et al., Nature 2016). Similarly, the related French Polynesian H/PF/2013 strain has been shown to induce placental damage and fetal demise in Ifnar$^{-/-}$ C57BL/6 mice as well as in wildtype C57BL/6 mice following IFN-α receptor blockade (Miner et al., Cell 165(5):1081-91, 2016).

Both the ZIKV-BR and ZIKV-PR strains were passage number three. To generate challenge stocks low passage number Vero E6 cells were infected at a multiplicity of infection (MOI) of 0.01 plaque-forming units (PFU)/cell. Supernatants were screened daily for viral titers and harvested at peak growth. Culture supernatants were clarified by centrifugation, and fetal bovine serum was added to 20% final concentration (v/v) and stored at −80° C.

The concentration and infectivity of the stocks were determined by RT-PCR and PFU assays. The PFU assay was conducted as follows. Vero WHO cells were seeded in a MVV6 plate to reach confluency at day three. Cells were infected with log dilutions of ZIKV for one hour and overlaid with agar. Cells were stained after six days of infection by neutral red staining. Plaques were counted, and titers were calculated by multiplying the number of plaques by the dilution and divided by the infection volume.

The RT-PCR assay was conducted as follows. Cap genes of available ZIKV genomes were aligned using Megalign (DNAstar, WI, USA), and primers and probes to a highly conserved region were designed using primer express v3.0 (Applied Biosystems, CA, USA). Primers were synthesized by Integrated DNA Technologies (Coralville, Iowa, USA) and probes by Biosearch Technologies (Petaluma, Calif., USA). To assess viral loads, RNA was extracted from serum with a QIAcube HT (Qiagen, Germany). Reverse transcription and RT-PCR were performed as previously described (Larocca et al., *Science.* 353(6304):1129-1132, 2016). The wildtype ZIKV BeH815744 Cap gene was utilized as a standard and was cloned into pcDNA3.1+, and the AmpliCap-Max T7 High Yield Message Maker Kit was used to transcribe RNA (Cellscript, WI, USA). RNA was purified using the RNA clean and concentrator kit (Zymo Research, CA, USA), and RNA quality and concentration was assessed by the BIDMC Molecular Core Facility. Log dilutions of the RNA standard were reverse transcribed and included with each RT-PCR assay.

Viral loads were calculated as virus particles (VP) per ml. The viral particle (VP) to plaque-forming unit (PFU) ratio of both stocks was approximately 1,000.

Design of ZIKV Immunogens and ZIKV DNA Vaccines

Figure 3A:
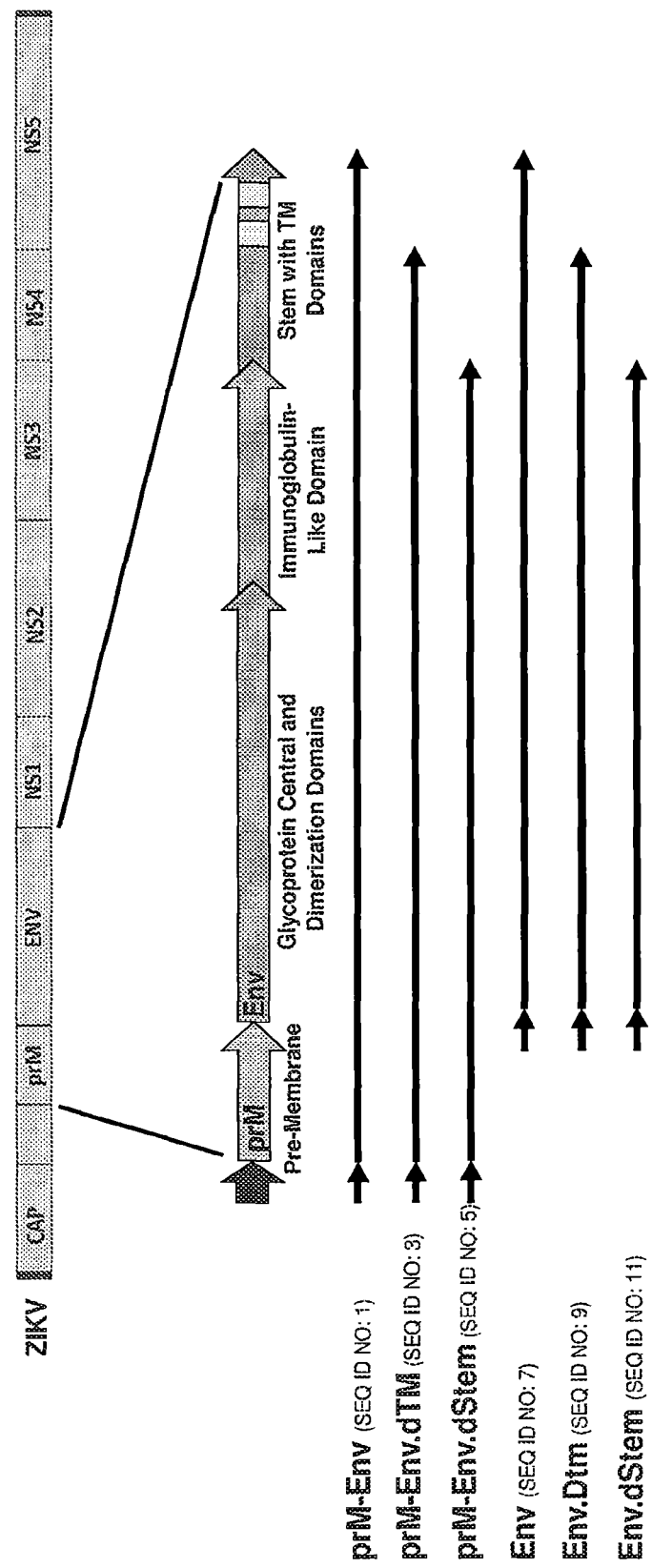
FIG. 3A is a schematic diagram showing the design of ZIKV DNA immunogens. The DNA immunogens encode the pre-membrane and envelope (prM-Env), the envelope region alone (Env), and deletions mutants that remove either the transmembrane (TM) or stem (Stem) regions of the ZIKV polyprotein. The six immunogens presented are prM-Env (SEQ ID NO: 1; also referred to herein as "M-Env"), the deletion mutant prM-Env.dTM (SEQ ID NO: 3), the deletion mutant prM-Env.dStem (SEQ ID NO: 5), Env (SEQ ID NO: 7), the deletion mutant Env.dTM (SEQ ID NO: 9), and the deletion mutant Env.dStem (SEQ ID NO: 11).

Zika virus (ZIKV) strain BeH815744 (accession number KU365780 (SEQ ID NOs: 15-16)) (FIG. 2) was used to design nucleic acid molecules (FIG. 3A), which were produced synthetically and optimized for enhanced transgene expression. DNA vaccines were generated by incorporating a nucleic acid molecule of FIG. 3A into the mammalian expression vector pcDNA3.1+ (Invitrogen, CA, USA). Specifically, the nucleic acid molecules prM-Env (SEQ ID NO: 1), prM-Env.dTM (SEQ ID NO: 3), prM-Env.dStem (SEQ ID NO: 5), Env (SEQ ID NO: 7), Env.dTM (SEQ ID NO: 9), and Env.dStem (SEQ ID NO: 11), were incorporated into the mammalian expression vector pcDNA3.1+ (Invitrogen, CA, USA) to generate the prM-Env vaccine ("DNA-prM-Env"), prM-Env.dTM DNA vaccine ("DNA-prM-Env.dTM"), the prM-Env.dStem DNA vaccine ("DNA-prM-Env.dStem"), the Env vaccine ("DNA-Env"), the Env.dTM vaccine ("DNA-Env.dTM"), and the Env.dStem vaccine ("DNA-Env.dStem"), respectively. Deletion mutants lacked the transmembrane (dTM) or stem (dStem) regions of Env (FIG. 3A). A Kozak sequence and the Japanese encephalitis virus leader sequence were included (Martin et al., J. Infect. Dis. 196(12):1732-40, 2007). Plasmids were produced with Machery-Nagel endotoxin-free gigaprep kits. Sequences were confirmed by double stranded sequencing.

Figure 3B:
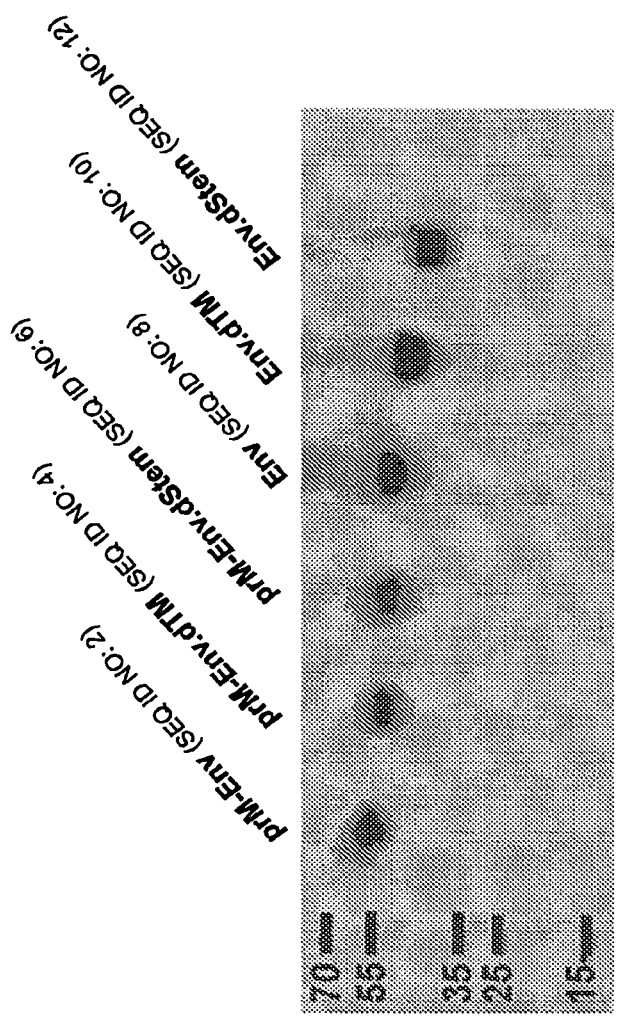
FIG. 3B is a Western blot of transgene expression from the prM-Env, prM-Env.dTM, prM-Env.dStem, Env, Env.dTM, and Env.dStem DNA vaccines transfected into 293T cells. The DNA vaccines were generated by incorporating the nucleic acid molecules encoding the ZIKV immunogens of FIG. 3A into a mammalian expression vector pcDNA3.1+ (Invitrogen, CA, USA). The following the DNA vaccines were generated: prM-Env ("DNA-prM-Env," comprising SEQ ID NO: 1), prM-Env.dTM ("DNA-prM-Env.dTM," comprising SEQ ID NO: 3), prM-Env.dStem ("DNA-prM-Env.dStem," comprising SEQ ID NO: 5), Env ("DNA-Env," comprising SEQ ID NO: 7), Env.dTM ("DNA-Env.dTM," comprising SEQ ID NO: 9), and Env.dStem ("DNA-Env.dStem," comprising SEQ ID NO: 11). The prM-Env (SEQ ID NO: 2), prM-Env.dTM (SEQ ID NO: 4), prM-Env.dStem (SEQ ID NO: 6), Env (SEQ ID NO: 8), Env.dTM (SEQ ID NO: 10), and Env.dStem (SEQ ID NO: 12) polypeptides were successfully expressed from each construct, respectively, in 293T cells.
Figure 3C:
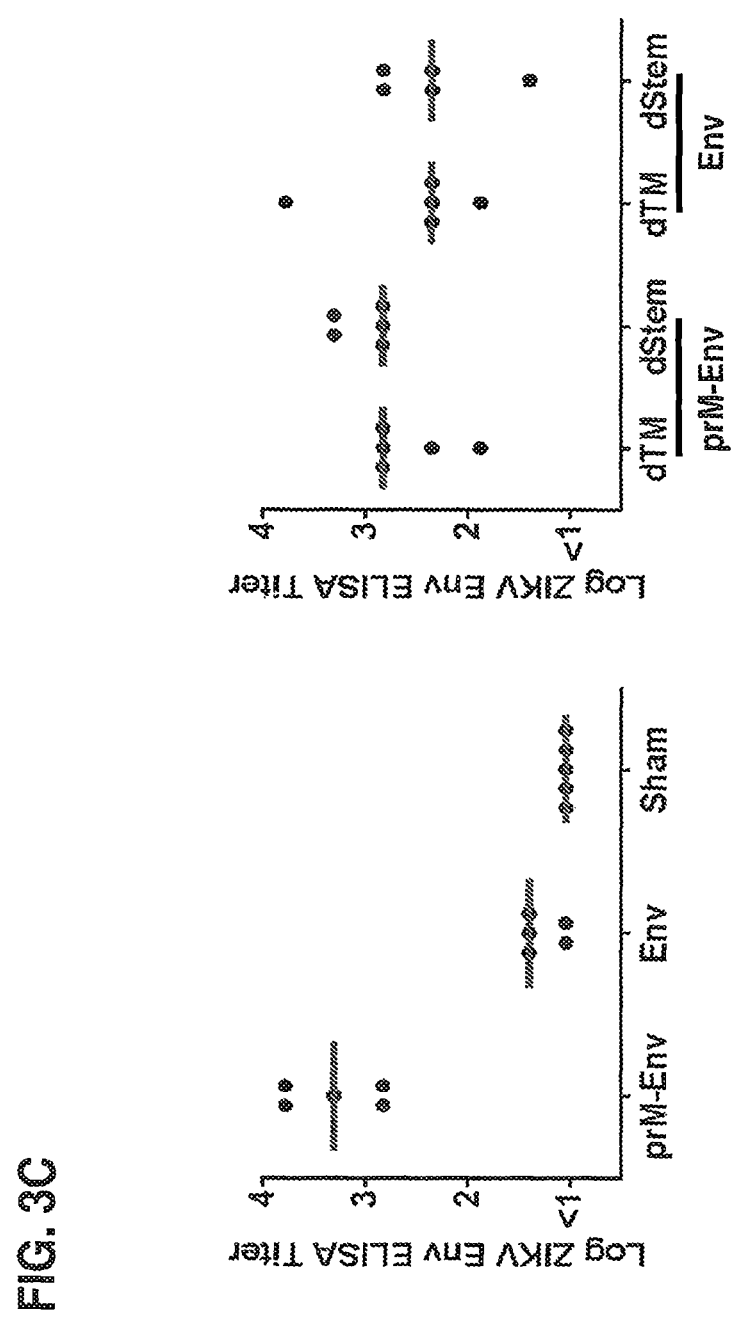
Figure 3D:
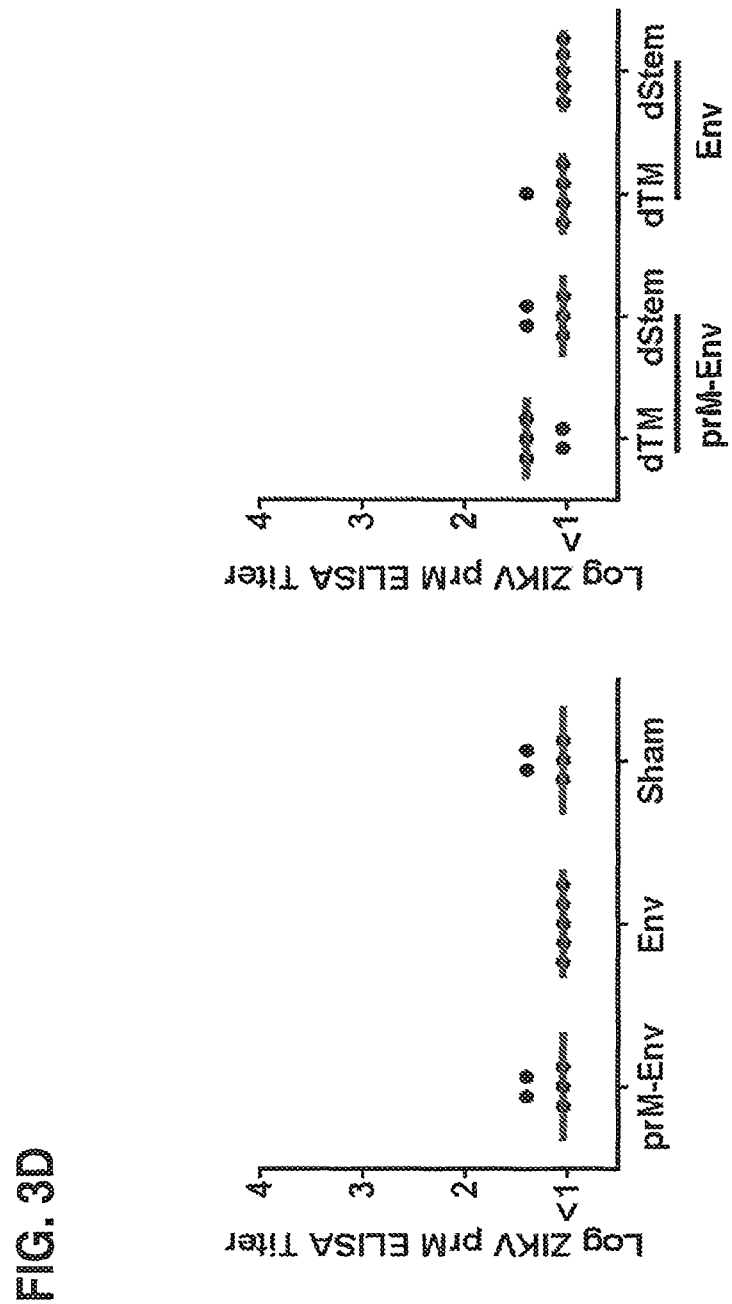
FIG. 3D are graphs comparing the ability of the DNA vaccines prM-Env, prM-Env.dTM, prM-Env.dStem, Env, Env.dTM, and Env.dStem to induce a humoral response in Balb/c mice (FIG. 3C) assessed at week three following vaccination by prM-specific ELISA. Bars reflect the median values.

To assess transgene expression (e.g., polypeptide expression (e.g., immunogen expression)) from DNA vaccines, cell lysates obtained 48 hour following lipofectamine 2000 (Invitrogen, CA, USA) transient transfection of 293T cells were mixed with reducing sample buffer, heated for five min at 100° C., cooled on ice, and run on a precast 4-15% SDS-PAGE gel (Biorad, CA, USA). Protein was transferred to PVDF membranes using the iBlot dry blotting system (Invitrogen, CA, USA), and the membranes were blocked overnight at 4° C. in PBS-T (Dulbeco's Phosphate Buffered Saline+0.2% V/V Tween 20+5% W/V non-fat milk powder). Following overnight blocking, the membranes were incubated for one hour with PBS-T containing a 1:5000 dilution of mouse anti-ZIKV Env mAb (BioFront Technologies, FL, USA). Membranes were then washed three times with PBS-T and incubated for one hour with PBS-T containing a 1:1000 dilution of rabbit anti-mouse HRP (Jackson ImmunoResearch, PA, USA). Membranes were then washed three times with PBS-T and developed using the Amersham ECL plus Western blotting detection system (GE Healthcare, Chicago, USA). Transgene expression was verified by Western blot (FIG. 3B).

In Vivo Assessment of Immunologic Response to ZIKV Immunogens

To assess the immunogenicity of the DNA vaccines prM-Env ("DNA-prM-Env," comprising SEQ ID NO: 1), prM-Env.dTM ("DNA-prM-Env.dTM," comprising SEQ ID NO: 3), prM-Env.dStem ("DNA-prM-Env.dStem," comprising SEQ ID NO: 5), Env ("DNA-Env," comprising SEQ ID NO: 7), Env.dTM ("DNA-Env.dTM," comprising SEQ ID NO: 9), and Env.dStem ("DNA-Env.dStem," comprising SEQ ID NO: 11), groups of Balb/c mice (N=5-10/group) received a single immunization of 50 μg of DNA vaccine by the intramuscular (i.m.) route at week zero. Env-specific antibody responses were evaluated at week three by ELISA. Mouse ZIKV Env ELISA kits (Alpha Diagnostic International, TX, USA) were used to determine endpoint antibody titers using a modified protocol. 96-well plates were first equilibrated at room temperature with 300 μl of kit working wash buffer for five min. 6 μl of mouse serum was added to the top row, and 3-fold serial dilutions were tested in the remaining rows. Samples were incubated at room temperature for one hour, and plates were washed four times. 100 μl of anti-mouse IgG HRP-conjugate working solution was then added to each well and incubated for 30 min at room temperature. Plates were then washed five times, developed for 15 min at room temperature with 100 μl of TMB substrate, and stopped by the addition of 100 μl of stop solution. Plates were analyzed at 450 nm/550 nm on a VersaMax microplate reader using Softmax Pro 6.0 software (Molecular Devices, CA, USA). ELISA endpoint titers were defined as the highest reciprocal serum dilution that yielded an absorbance >2-fold over background values. The full-length prM-Env DNA vaccine elicited higher Env-specific antibody titers than did the Env DNA vaccine and all the dTM and dStem deletion mutants (FIG. 3C), indicating that inclusion of the prM sequence generates a greater immune response than that observed with the Env, Env.dTM, and Env.dStem sequences. No prM-specific antibody responses were detected (FIG. 3D).

ZIKV-specific cellular immune responses were assessed by interferon-γ (IFN-γ) ELISPOT assays using a pool of overlapping 15-amino-acid peptides covering the prM or Env proteins (JPT, Berlin, Germany). The assay was performed as follows. 96-well multiscreen plates (Millipore, MA, USA) were coated overnight with 100 μl/well of 10 μg/ml anti-mouse IFN-γ (BD Biosciences, CA, USA) in endotoxin-free Dulbecco's PBS (D-PBS). The plates were then washed three times with D-PBS containing 0.25%

Tween 20 (D-PBS-Tween), blocked for two hour with D-PBS containing 5% FBS at 37° C., washed three times with D-PBS-Tween, rinsed with RPMI 1640 containing 10% FBS to remove the Tween 20, and incubated with 2 µg/ml of each peptide and 5×10 murine splenocytes in triplicate in 100 µl reaction mixture volumes. Following an 18 hour incubation at 37° C., the plates were washed nine times with PBS-Tween and once with distilled water. The plates were then incubated with 2 µg/ml biotinylated anti-mouse IFN-γ (BD Biosciences, CA, USA) for two hour at room temperature, washed six times with PBS-Tween, and incubated for two hour with a 1:500 dilution of streptavidin-alkaline phosphatase (Southern Biotechnology Associates, AL, USA). Following five washes with PBS-Tween and one with PBS, the plates were developed with nitroblue tetrazolium-5-bromo-4-chloro-3-indolyl-phosphate chromogen (Pierce, Ill., USA), stopped by washing with tap water, air dried, and read using an ELISPOT reader (Cellular Technology Ltd., OH, USA). The numbers of spot-forming cells (SFC) per $10^6$ cells were calculated. The medium background levels were typically <15 SFC per $10^6$ cells.

Figure 3F:
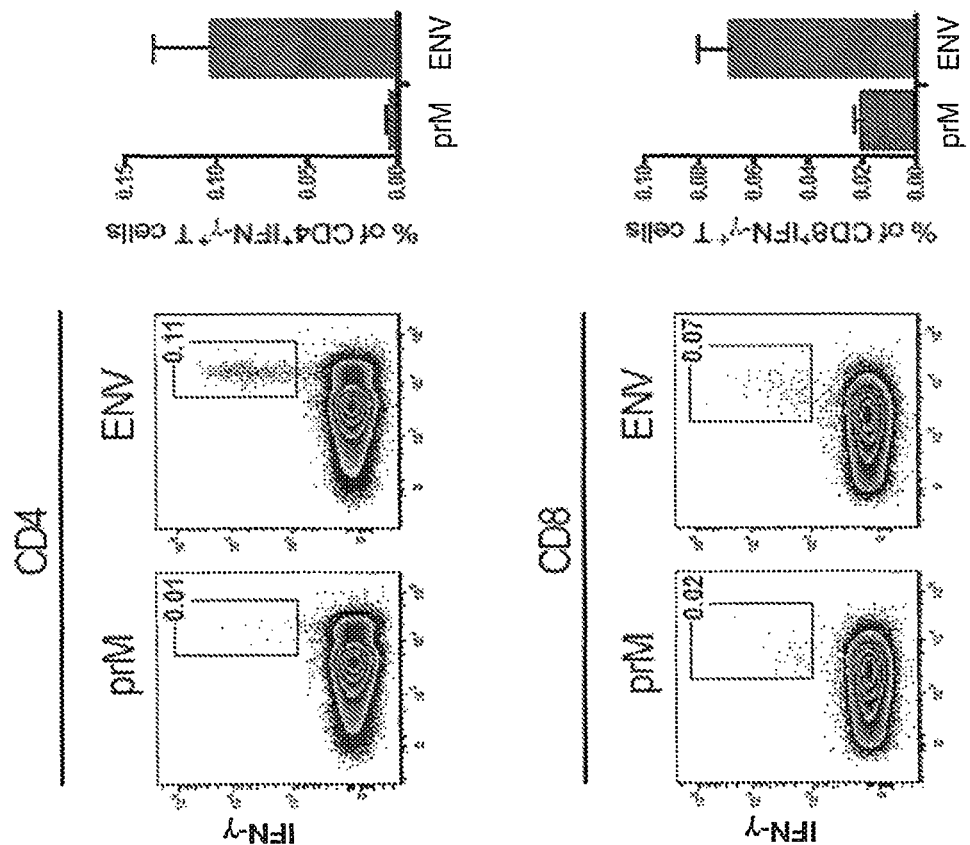
FIG. 3F are graphs comparing the cellular immune response in murine splenocytes to either prM or ENV proteins as assessed by cytokine staining and flow cytometry. Error bars reflect standard error of the mean (SEM).
Figure 3E:
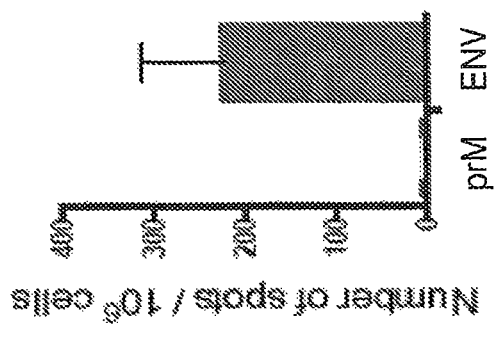
FIG. 3E is a graph comparing the cellular immune response in murine splenocytes to either prM or ENV proteins as assessed by interferon-γ (IFN-γ) ELISPOT assays.

ZIKV-specific $CD4^+$ and $CD8^+$ T lymphocyte responses were assessed using splenocytes and analyzed by flow cytometry (FIG. 3F). Cells were stimulated for one hour at 37° C. with 2 µg/ml of overlapping 15-amino-acid peptides covering the prM or Env proteins (JPT, Berlin, Germany). Following incubation, brefeldin-A and monensin (BioLegend, CA, USA) were added, and samples were incubated for six hour at 37° C. Cells were then washed, stained, permeabilized with Cytofix/Cytoperm (BD Biosciences, CA, USA). Data was acquired using an LSR II flow cytometer (BD Biosciences, CA, USA) and analyzed using FlowJo v.9.8.3 (Treestar, OR, USA). Monoclonal antibodies included: CD4 (RM4-5), CD8α (53-6.7), CD44 (IM7), and IFN-γ (XMG1.2). Antibodies were purchased from BD Biosciences, eBioscience, or BioLegend, CA, USA. Vital dye exclusion (LIVE/DEAD) was purchased from Life Technologies, CA, USA.

Figure 4A:
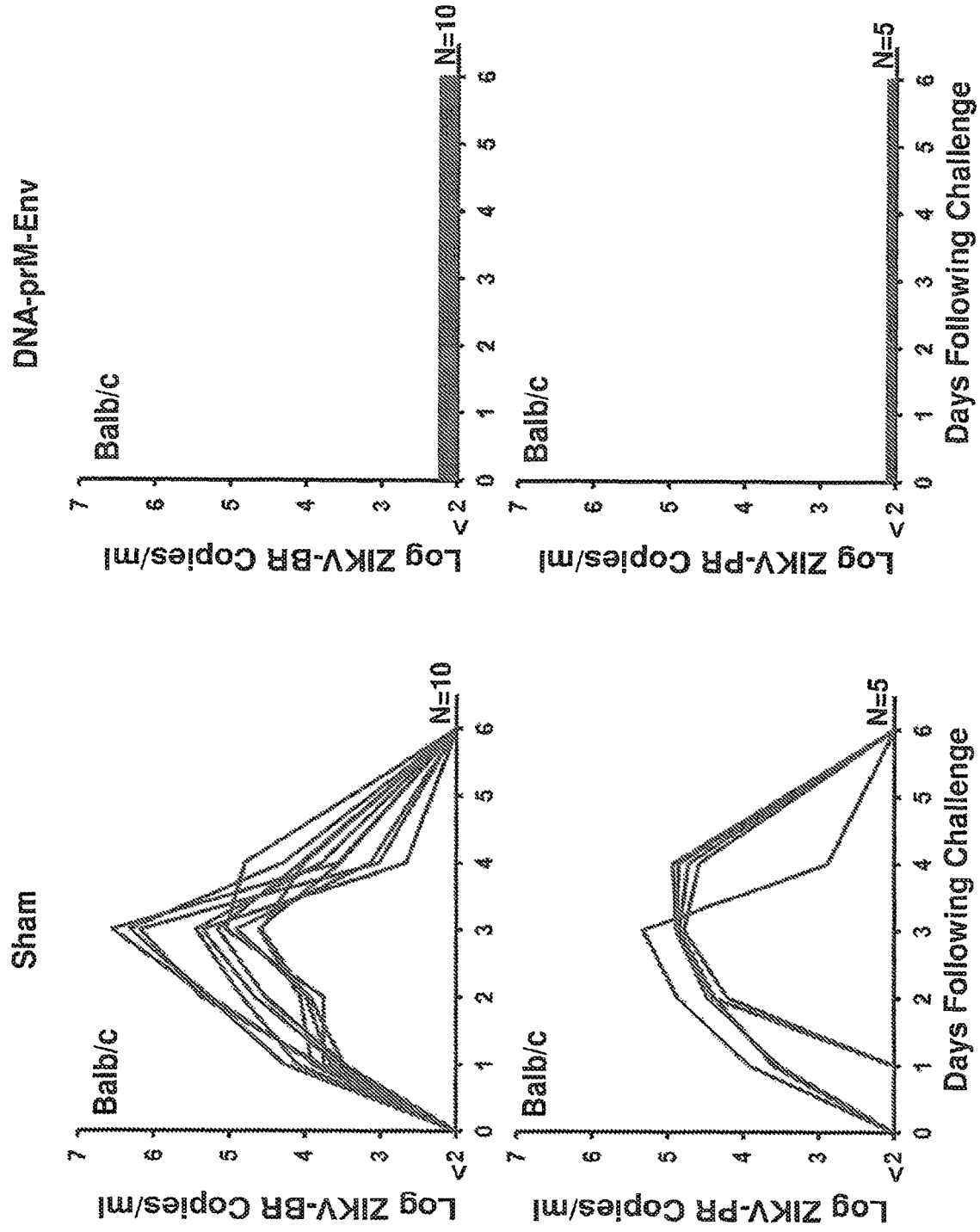
FIG. 4A are graphs comparing serum viral loads from Balb/c mice that were immunized with the DNA-prM-Env and subsequently challenged by ZIKV infection. Balb/c mice (N=5-10/group) received a single immunization of 50 μg DNA-prM-Env or a sham vaccine by the i.m. route. Mice were then challenged four weeks after immunization by intravenous administration of $10^5$ virus particles (VP) ($10^2$ plaque-forming units (PFU)) of either ZIKV-BR or ZIKV-PR.
Figure 4B:
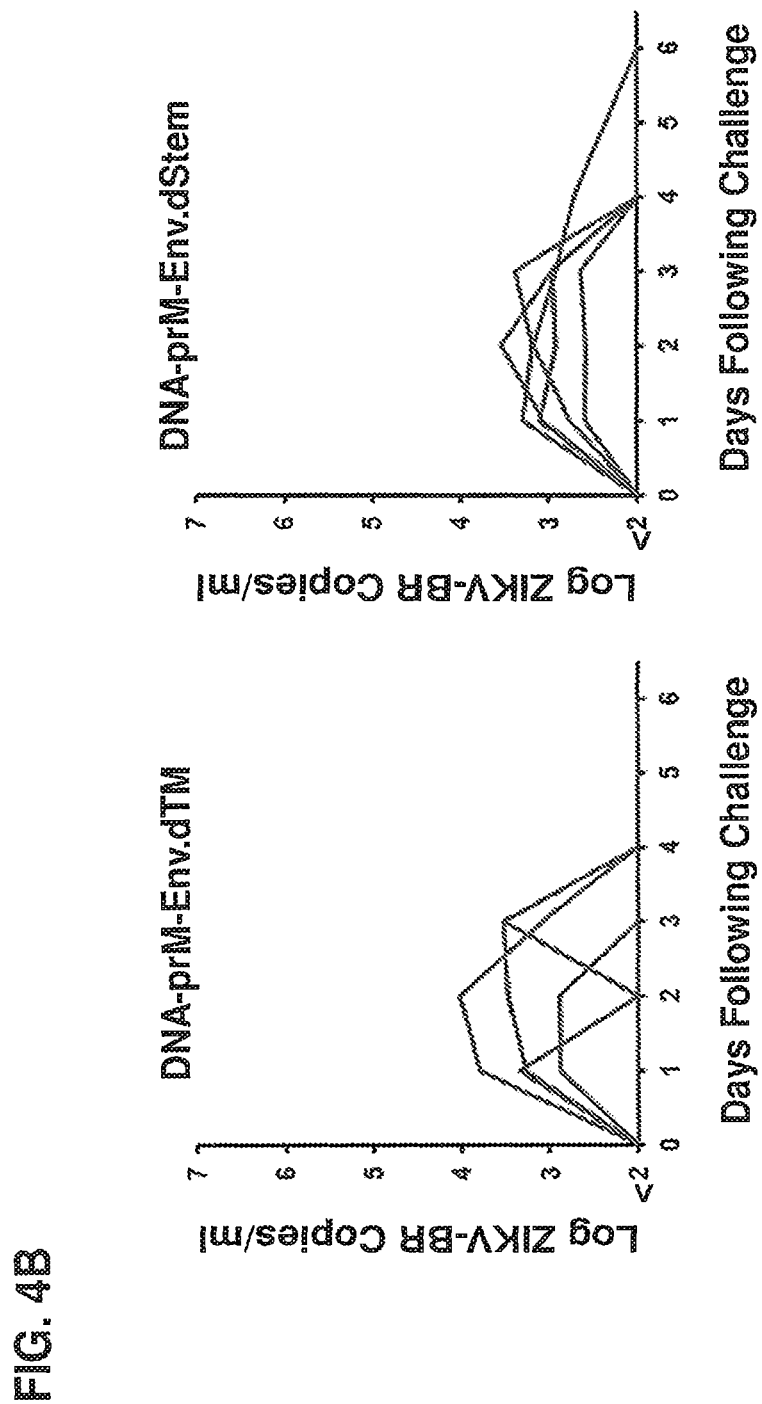
FIG. 4B are graphs comparing serum viral loads from Balb/c mice that were immunized with either DNA-prM-Env.dTM or DNA-prM-Env.dStem and subsequently challenged by ZIKV-BR infection. Balb/c mice (N=5/group) received a single immunization of 50 μg vaccine by the i.m. route. Mice were then challenged four weeks after immunization by intravenous administration of $10^5$ VP ($10^2$ PFU) of ZIKV-BR.

In Vivo Assessment of the Protective Efficacy of ZIKV DNA Vaccines Against ZIKV Challenge To assess the protective efficacy of these DNA vaccines against ZIKV challenge, vaccinated or sham control Balb/c mice were challenged at week four post immunization by the intravenous (i.v.) route with $10^5$ viral particles (VP) [$10^2$ plaque-forming units (PFU)] of ZIKV-BR or ZIKV-PR. Viral loads following ZIKV challenge were determined by RT-PCR (Larocca et al., Science. 353(6304):1129-1132, 2016), as generally described herein. Sham vaccinated mice inoculated with ZIKV-BR developed approximately 6 days of detectable viremia with a mean peak viral load of 5.42 log copies/ml (range 4.55-6.57 log copies/ml; N=10) on day three following challenge (FIG. 4A). In contrast, a single immunization to the prM-Env DNA vaccine provided complete protection against ZIKV-BR challenge with no detectable viremia at any timepoint (N=10). The prM-Env DNA vaccine also afforded complete protection against ZIKV-PR challenge (N=5) (FIG. 4A). ZIKV-PR replicated to slightly lower levels (mean peak viral load 4.96 log copies/ml; range 4.80-5.33 log copies/ml; N=5) than did ZIKV-BR in sham controls. In contrast with the full-length prM-Env DNA vaccine, the DNA vaccines lacking prM, as well as the dTM and dStem deletion mutants, afforded reduced protection against ZIKV-BR challenge (FIGS. 4B-4C); viral loads were reduced in these animals as compared with sham controls (FIG. 4A).

Figure 5A:
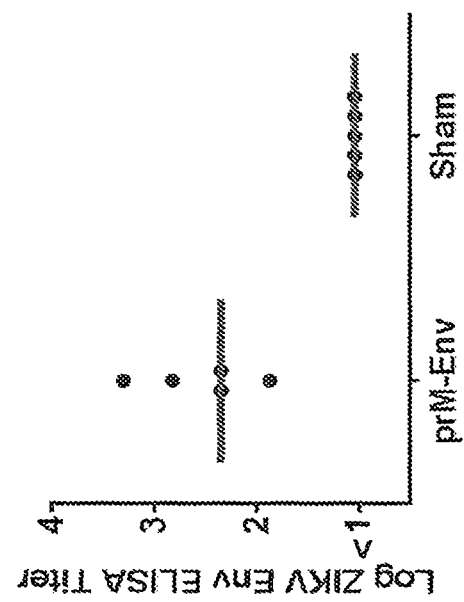
FIG. 5A is a graph comparing the ability of the DNA vaccines prM-Env or a sham vaccine to induce a humoral response in SJL mice assessed at week three following vaccination by Env-specific ELISA. Bars reflect the median values.
Figure 5B:
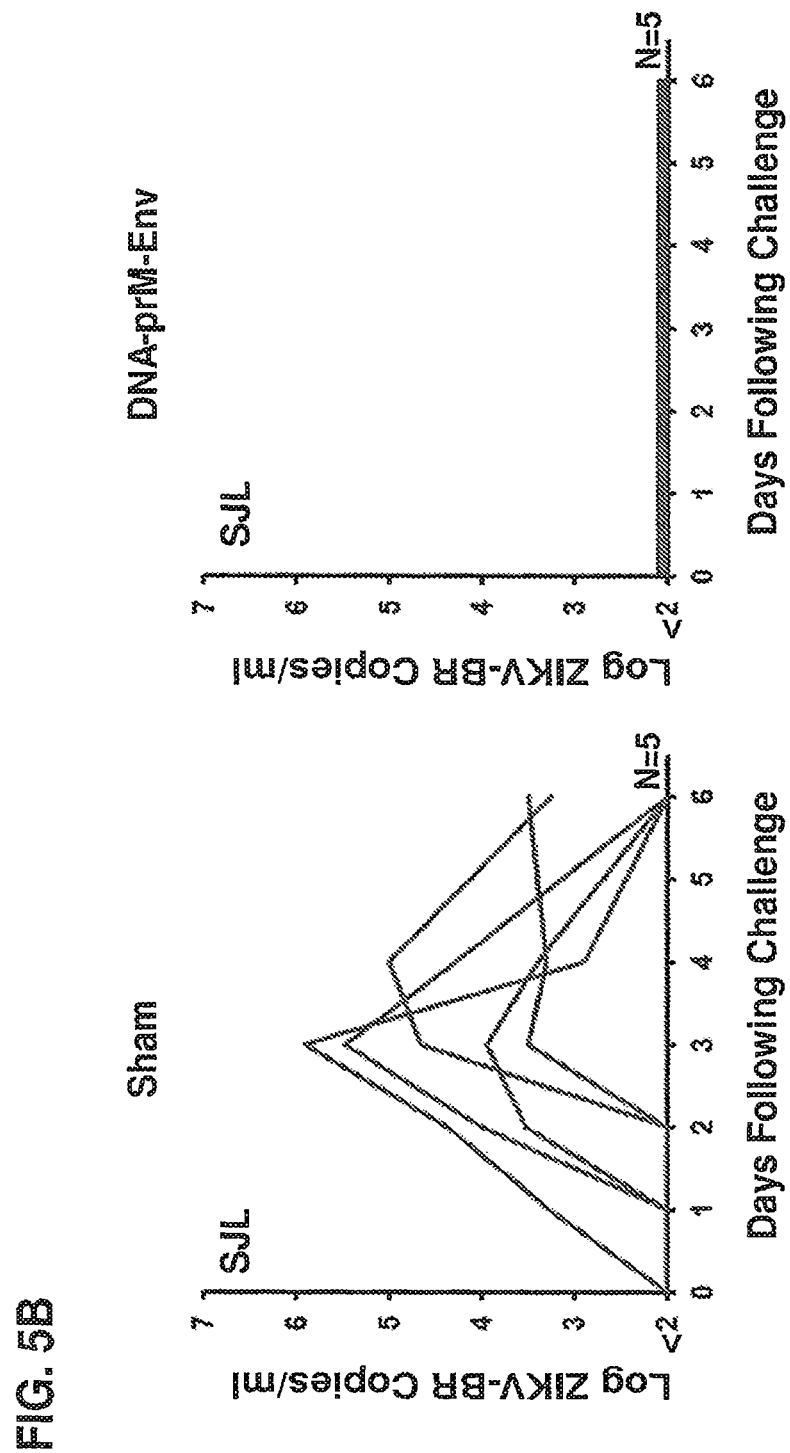
FIG. 5B are graphs comparing serum viral loads from SJL mice that were immunized with either a sham vaccine or DNA-prM-Env and subsequently challenged by ZIKV-BR infection. SJL mice (N=5/group) received a single immunization of 50 μg vaccine by the i.m. route. Mice were then challenged four weeks after immunization by intravenous administration of $10^5$ VP ($10^2$ PFU) of ZIKV-BR.
Figure 6:
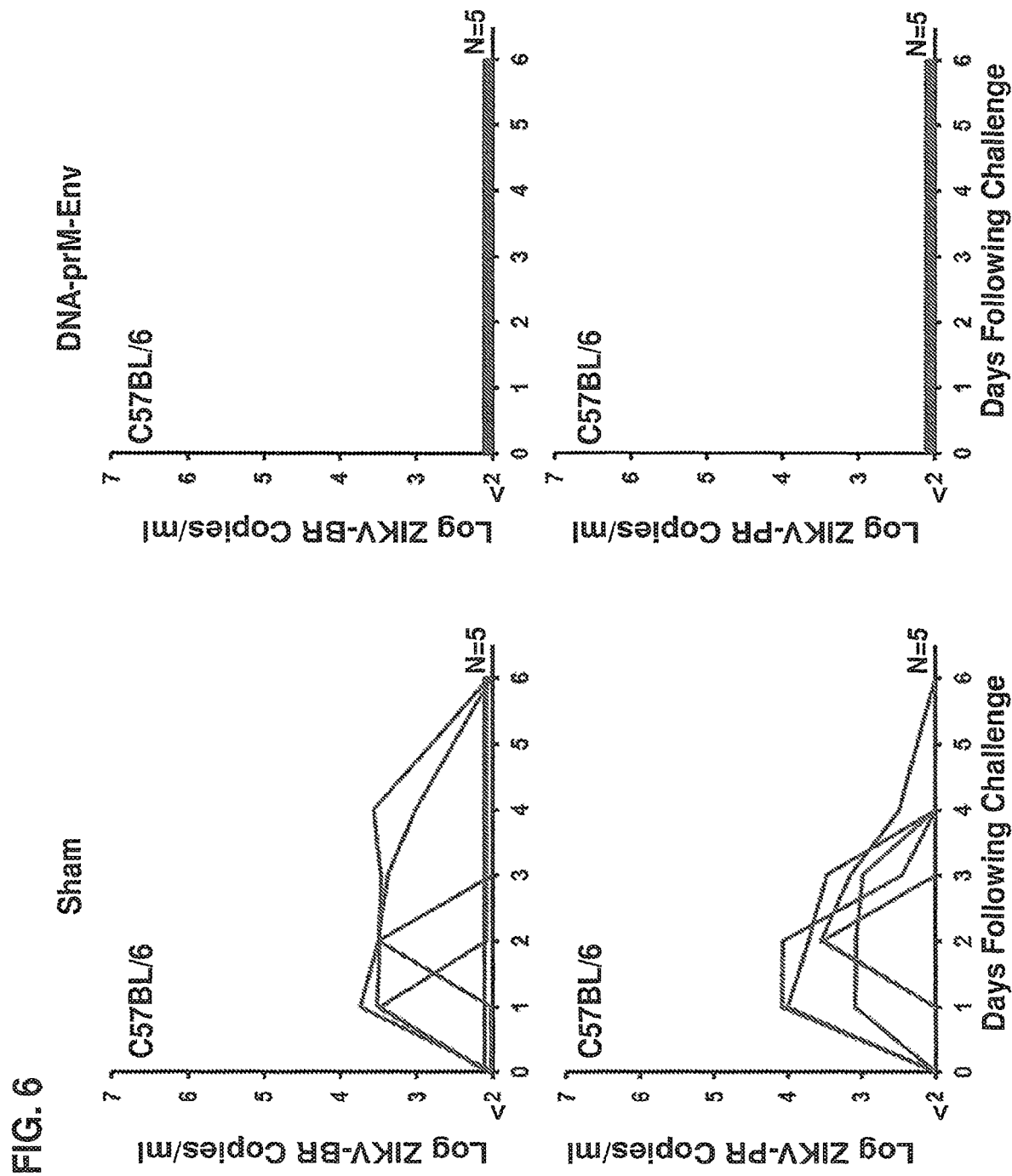
FIG. 6 are graphs comparing serum viral loads from C57BL/6 mice that were immunized with a sham vaccine or DNA-prM-Env and subsequently challenged by ZIKV infection. C57BL/6 mice (N=5/group) received a single immunization of 50 μg DNA-prM-Env or a sham vaccine by the i.m. route. Mice were then challenged four weeks after immunization by intravenous administration of $10^5$ VP ($10^2$ PFU) of either ZIKV-BR or ZIKV-PR.
Figure 7A:
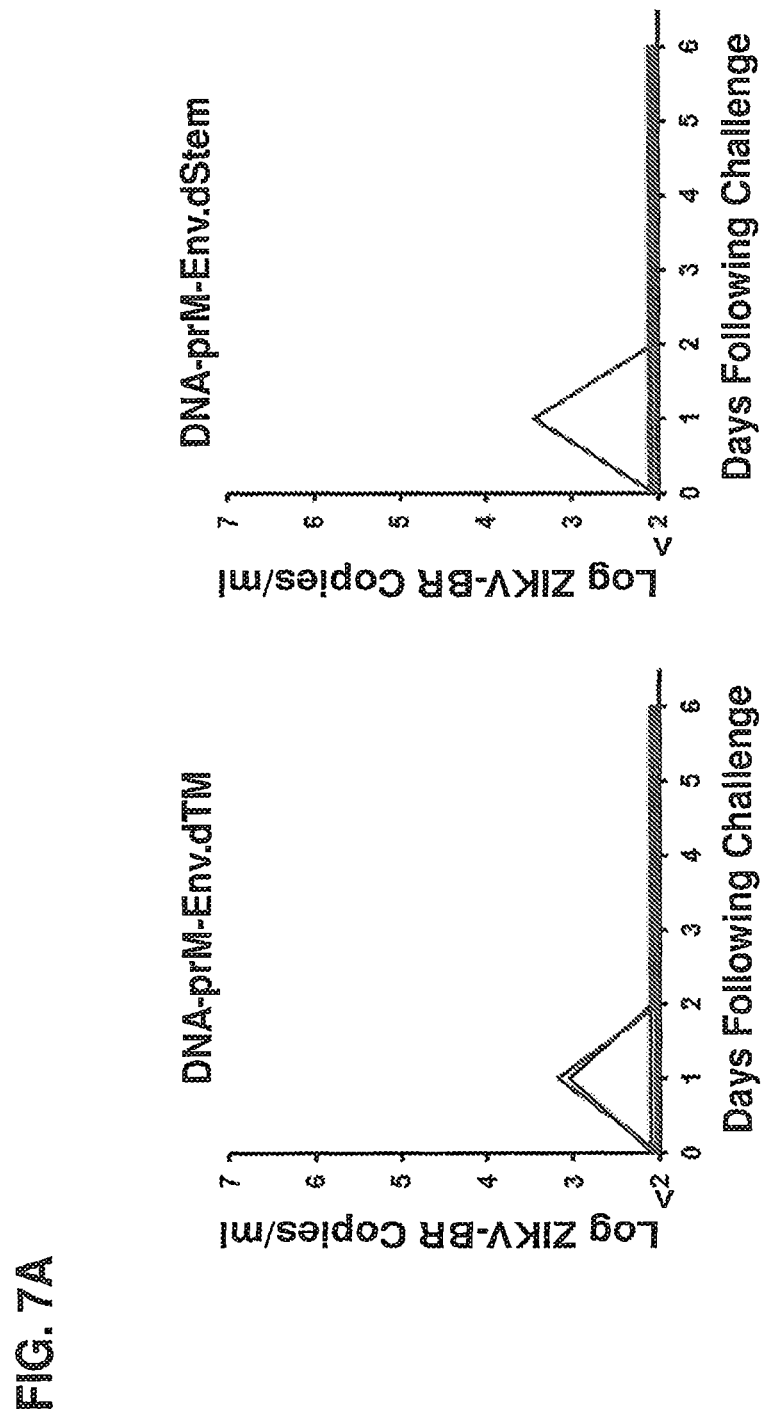
FIG. 7A are graphs comparing serum viral loads from C57BL/6 mice that were immunized with DNA-prM-Env.dTM or DNA-prM-Env.dStem and subsequently challenged by ZIKV infection. C57BL/6 mice (N=5/group) received a single immunization of 50 μg vaccine by the i.m. route. Mice were then challenged four weeks after immunization by intravenous administration of $10^5$ VP ($10^2$ PFU) of ZIKV-BR.
Figure 7B:
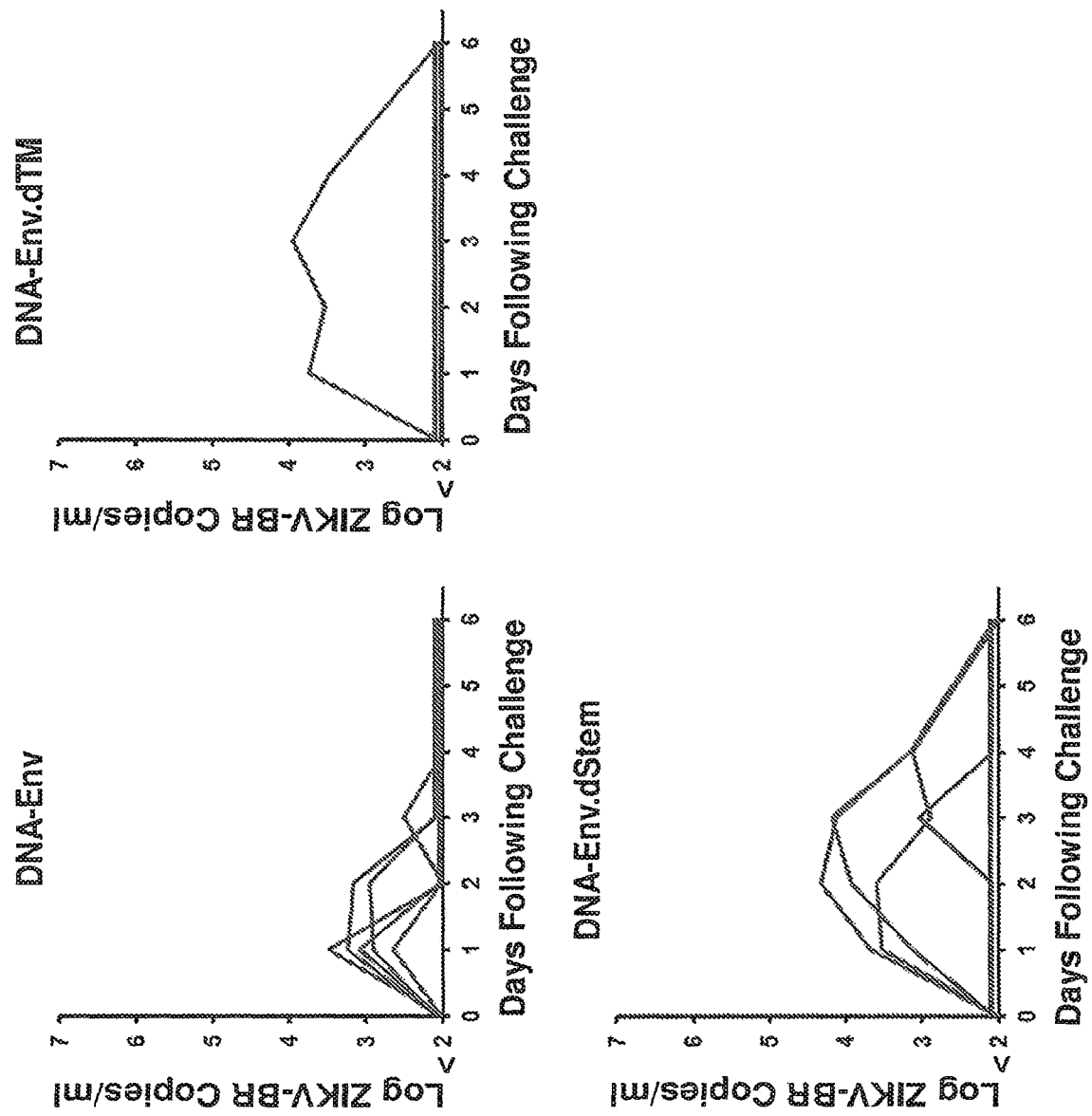
FIG. 7B are graphs comparing serum viral loads from C57BL/6 mice that were immunized with DNA-Env, DNA-Env.dTM, or DNA-ENV.dStem and subsequently challenged by ZIKV infection. C57BL/6 mice (N=5/group) received a single immunization of 50 μg vaccine by the i.m. route. Mice were then challenged four weeks after immunization by intravenous administration of $10^5$ VP ($10^2$ PFU) of ZIKV-BR.

The prM-Env DNA vaccine also provided complete protection against ZIKV-BR challenge in SJL mice (FIGS. 5A-5B) and against both ZIKV-BR and ZIKV-PR challenge in C57BL/6 mice (FIGS. 6-7B). ZIKV-BR replicated efficiently in SJL mice, consistent with a prior study (Cugola et al., Nature 2016), although at slightly lower levels (mean peak viral load 4.70 log copies/ml; range 3.50-5.92 log copies/ml; N=5) than in Balb/c mice (FIG. 4A). In contrast, both ZIKV-BR and ZIKV-PR replicated poorly in C57BL/6 mice (FIG. 6), also consistent with prior reports, potentially as a result of robust IFN-α mediated innate immune restriction in this strain of mice (Miner et al., Cell 165(5):1081-91, 2016; Cugola et al., Nature 2016; Rossi et al., Am. J. Trop. Med. Hyg. 94(6):1362-9, 2016; Hombach et al., Vaccine 23(45):5205-11, 2005).

Protective Efficacy of Antibodies Produced from DNA-prM-Env Immunization

Figure 8C:
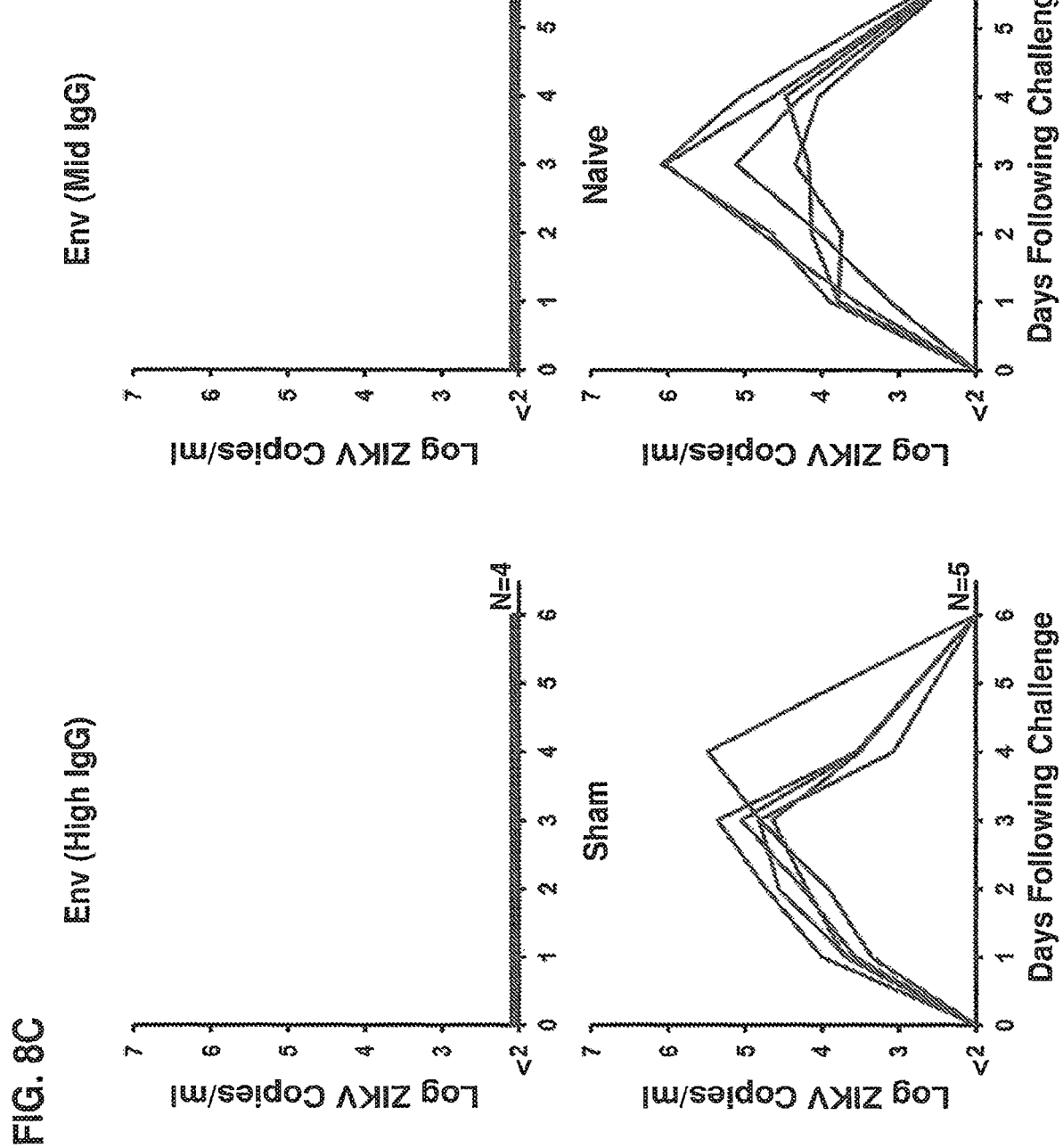
FIG. 8C are graphs comparing serum viral loads from mice that received adoptive transfer of serum containing high or mid titers of Env-specific IgG (FIG. 8A) that were challenged by intravenous administration of $10^5$ VP ($10^2$ PFU) of ZIKV-BR.
Figure 8D:
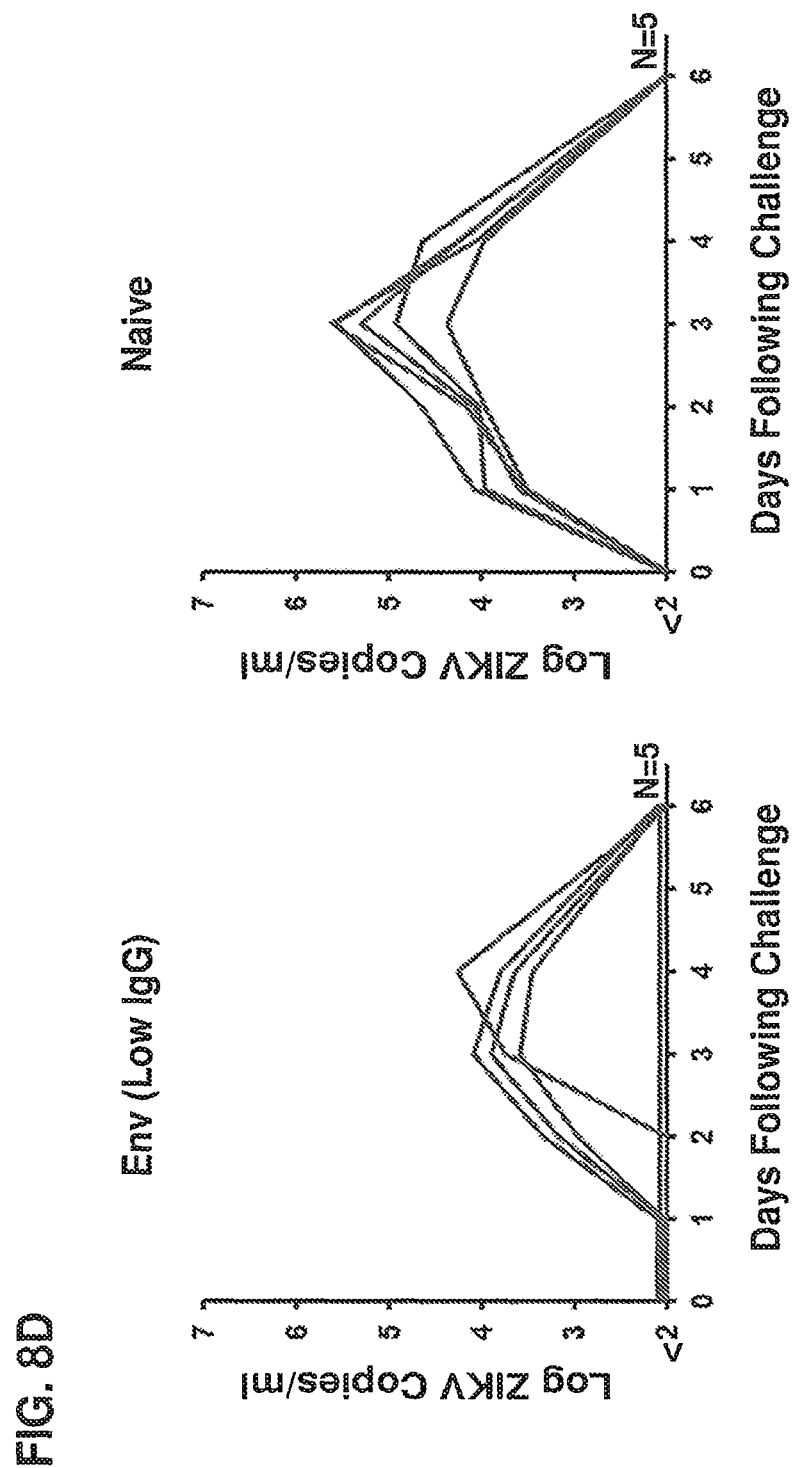
FIG. 8D are graphs comparing serum viral loads from mice that received adoptive transfer of serum containing low titers of Env-specific IgG (FIG. 8A) that were challenged by intravenous administration of 10 VP ($10^2$ PFU) of ZIKV-BR.

To investigate the immunologic mechanism of protection against ZIKV-BR challenge, serum was collected from prM-Env DNA vaccinated mice or naïve mice, and polyclonal IgG was purified using protein G purification kits (Thermo Fisher Scientific, MA, USA). Varying amounts of purified IgG was infused by the intravenous (i.v.) route into naïve recipient mice prior to ZIKV challenge. Passive infusion of varying quantities of purified IgG (e.g., 100 uL at varying titers between 25-2025) by the i.v. route resulted in median Env-specific log serum antibody titers of 2.82 (high), 2.35 (mid), and 1.87 (low) in recipient mice following adoptive transfer (FIG. 8A). All recipient mice with log serum titers of 2.35 or higher were protected against ZIKV-BR challenge (FIG. 8B-8C), demonstrating that protection can be mediated by vaccine-elicited IgG alone and confirming that the magnitude of Env-specific antibody titers correlates with protective efficacy (P<0.0001, FIG. 8B). In contrast, only 1 of 5 recipient mice that received low levels of Env-specific antibodies were protected, although they still exhibited reduced viral loads compared with sham controls (FIG. 8D). These data define a minimum threshold of Env-specific antibody titers that can be used to provide protection against a ZIKV infection.

Figure 8E:
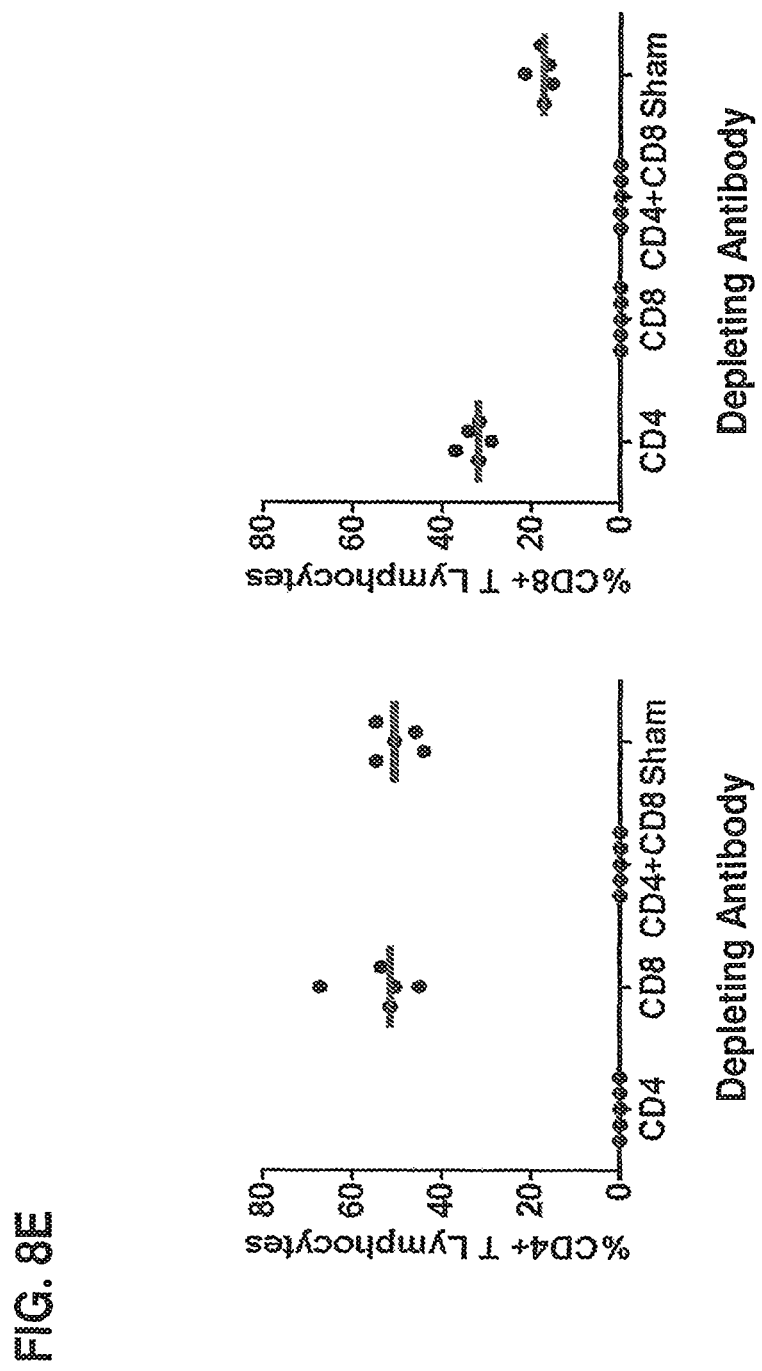
FIG. 8E are graphs showing CD4+ and CD8+ T lymphocyte depletion following anti-CD4 and/or anti-CD8 mAb treatment of DNA-prM-Env vaccinated Balb/c mice. Bars reflect medians values P-values reflect t-tests.

Depletion of T Lymphocytes We next depleted $CD4^+$ and/or $CD8^+$ T lymphocytes (>99.9% efficiency) in prM-Env vaccinated mice on day −2 and day −1 prior to challenge (FIG. 8D). Anti-CD4 (GK1.5) and/or anti-CD8 (2.43) (Bio X Cell, NH, USA) mAbs were administered at doses of 500 µg/mouse to prM-Env DNA vaccinated mice by the intraperitoneal (i.p.) route on day −2 and day −1 prior to ZIKV challenge. Antibody depletions were >99.9% efficient as determined by flow cytometry. Depletion of these T lymphocyte subsets did not detectably abrogate the protective efficacy of the prM-Env DNA vaccine against ZIKV-BR challenge (FIG. 8E). These data indicate that Env-specific T lymphocyte responses were not required for protection in this model, although these findings do not exclude the possibility that ZIKV-specific cellular immune responses may be beneficial in other settings.

Conclusion

Figure 4E:
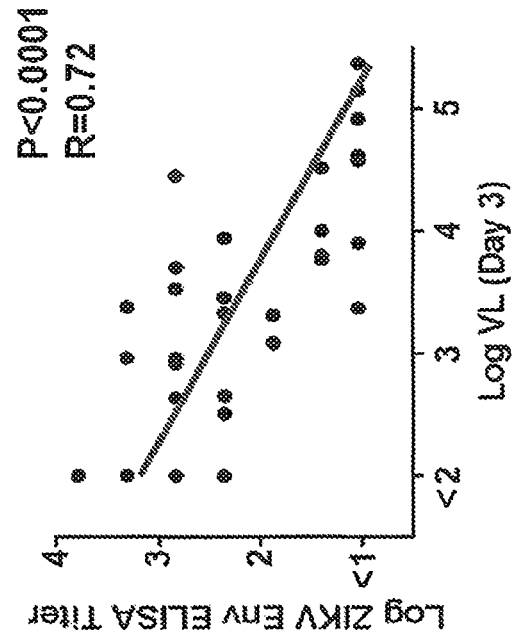
FIG. 4E is a graph comparing the relationship between day three viral loads and Env-specific antibody titers. Bars reflect medians. P-values reflect t-tests and Spearman rank-correlation tests.
Figure 4D:
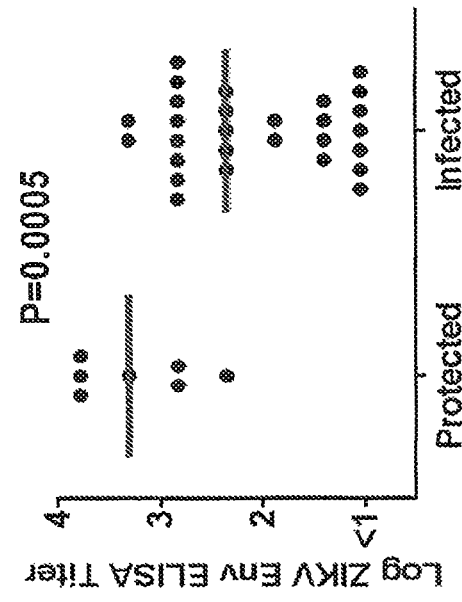
FIG. 4D is a graph examining the correlation between Env-specific antibody titers and protective efficacy. Bars reflect median values. P-values reflect t-tests and Spearman rank-correlation tests.
Figure 8F:
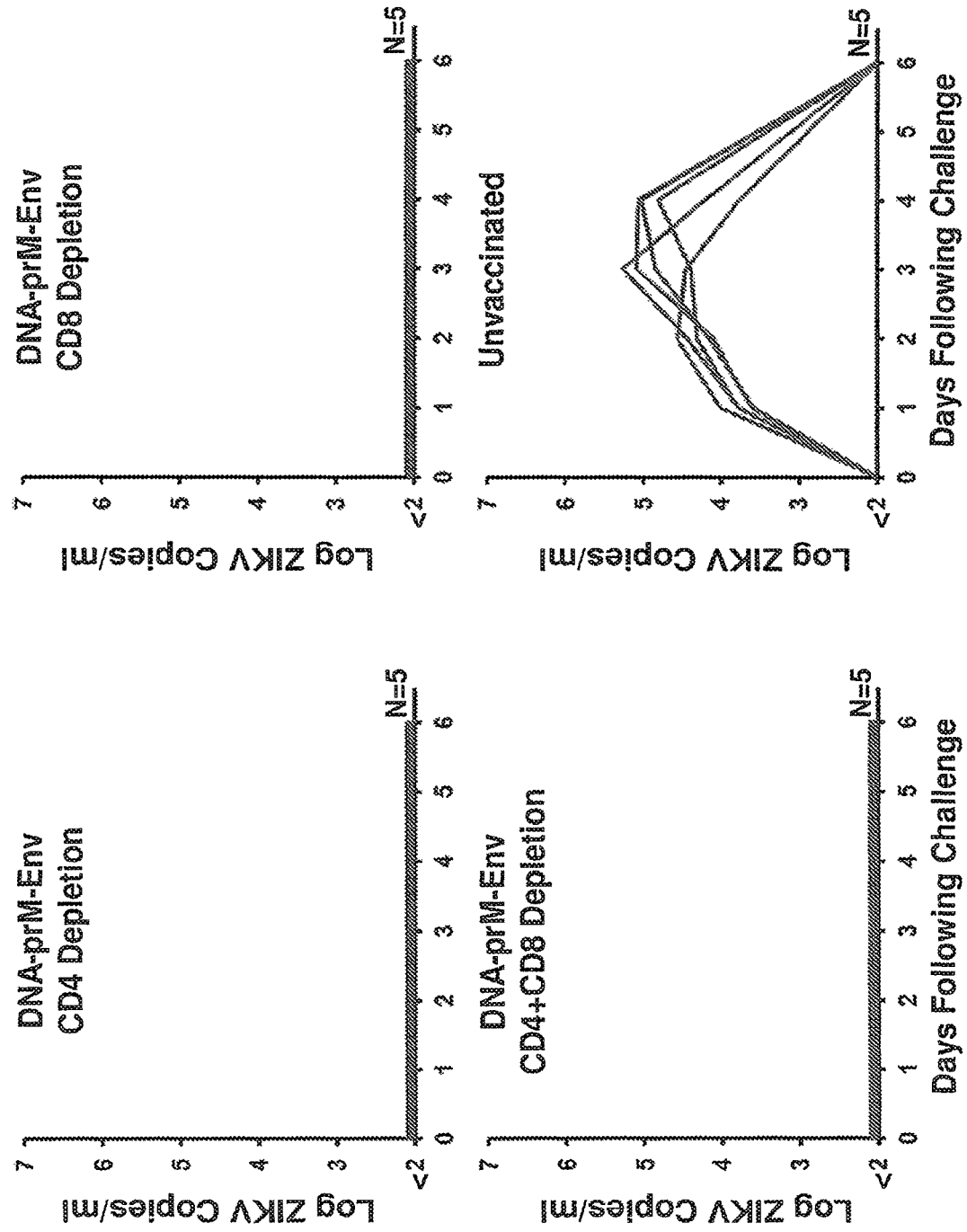
FIG. 8F are graphs comparing serum viral loads from DNA-prM-Env vaccinated mice that were depleted of CD4+ and/or CD8+ T lymphocytes and were challenged by intravenous administration of 10 VP ($10^2$ PFU) of ZIKV-BR.

The data presented here demonstrates that a single immunization with a DNA vaccine provided complete protection against parenteral ZIKV challenges in mice. The prM-Env DNA vaccine afforded protection in three strains of mice, and against ZIKV isolates from both Brazil and Puerto Rico, suggesting the generalizability of these observations. Moreover, the vaccine immunogens were designed to be heterologous sequences compared with the challenge viruses (FIG. 2). Protective efficacy was mediated by vaccine-elicited Env-specific antibodies, as evidenced by (i) statistical analyses of immune correlates of protection (FIGS. 4D-4E), (ii) adoptive transfer studies with purified IgG from vaccinated mice (FIG. 8A-8C), and (iii) T lymphocyte depletion studies in vaccinated mice (FIG. 8E-8F). The adoptive transfer studies also defined a threshold of Env-specific antibody titers that can achieve protection against ZIKV challenge in this model.

The robust protection observed in the present studies and the clear immune correlate of protection confirm the applicability of ZIKV vaccine development for use in humans. Moreover, the ZIKV-BR challenge isolate used in the present study has been shown in wildtype SJL mice to recapitulate certain key clinical findings of ZIKV infection in humans, including fetal microcephaly and intrauterine growth retardation. In addition, ZIKV-BR induced comparable magnitude and duration of viremia in Balb/c and SJL mice in our studies as compared with humans, suggesting the potential relevance of this model. It is notable that ZIKV-BR replicated efficiently in Balb/c and SJL mice (FIG. 4A, FIG. 5), but replicated poorly in C57BL/6 mice (FIG. 6), and suggests important strain-specific differences in terms of ZIKV infectivity.

The explosive epidemiology of the current ZIKV outbreak and the devastating clinical consequences for fetuses in pregnant women who become infected confirm the need for a ZIKV vaccine, such as those described herein. Our data demonstrate that complete protection against ZIKV challenge was reliably and robustly achieved with DNA vaccines and purified inactivated virus vaccines in susceptible mice. The compositions described herein offer safety advantages over live attenuated and replicating flavivirus vaccines, particularly for pregnant women. Moreover, the magnitude of Env-specific antibody titers that provide complete protection against ZIKV challenge in mice can be expected in humans as well, using DNA vaccines.

Example 2. Administration of a DNA Vaccine to a Human Subject

Compositions of the invention may be administered to human subjects, pre- or post-exposure to a ZIKV, according to the methods of the invention. The human subject may be one identified as being at high risk for infection, such as an individual who has or will be traveling to a region where ZIKV infection is prevalent.

For example, a pregnant woman or a women of childbearing age identified as having a risk of ZIKV infection may be administered a DNA vaccine containing a nucleic acid molecule encoding a ZIKV nucleic acid of the invention (e.g., prM-Env ("DNA-prM-Env," SEQ ID NO: 1)), e.g., in an adenoviral vector at a dose of between 10 µg and 10 mg. The patient is then monitored for presentation of symptoms of ZIKV infection or the resolution of symptoms. If necessary, a second dose or additional doses of the DNA vaccine can be administered.

Example 3. Administration of an Immunogenic ZIKV Polypeptide to a Human Subject A human subject identified as having a risk of ZIKV infection may be administered a ZIKV immunogen of the invention (e.g., prM-Env polypeptide (SEQ ID NO: 2)) or a nucleic acid molecule encoding a ZIKV polypeptide (e.g., SEQ ID NO: 1), e.g., in an adenoviral vector at a dose of between 10 µg and 10 mg. The patient is then monitored for presentation of symptoms of ZIKV infection or the resolution of symptoms. If necessary, a second dose of the DNA vaccine can be administered.

Example 4. Administration of Anti-ZIKV Antibodies to a Human Subject at Risk of ZIKV Infection A human subject identified as having a risk of ZIKV infection (e.g., due to travel to a region where ZIKV infection is prevalent, or the subject being a pregnant woman or a woman of childbearing age) may be administered an anti-ZIKV antibody that binds to an epitope within the prM-Env (SEQ ID NO: 2) polypeptide (e.g., the antibody may have been generated against the prM-Env polypeptide of SEQ ID NO: 2) at a dose of between 1-1.000 mg as a prophylactic therapy. The subject may be administered the anti-ZIKV antibody as a prophylactic therapy prior to or post-exposure to a ZIKV. The patient can then be monitored for presentation of symptoms of ZIKV infection or the resolution of symptoms. If necessary, a second dose or additional doses of the anti-ZIKV antibody can be administered.

Example 5. Administration of Anti-ZIKV Antibodies to a Human Subject Presenting Symptoms of ZIKV Infection A human subject identified as presenting symptoms of ZIKV may be administered an anti-ZIKV antibody that binds to an epitope within the prM-Env (SEQ ID NO: 2) polypeptide (e.g., the antibody may have been generated against the prM-Env polypeptide of SEQ ID NO: 2) at a dose of between 1-1,000 mg. The subject (e.g., a male or female subject, such as a pregnant woman or a woman of childbearing age) may have recently traveled to a region where ZIKV infection is prevalent. After diagnosis of ZIKV infection by a medical practitioner, the subject can be administered a dose of the anti-ZIKV antibody. The patient can then be monitored for resolution of symptoms. If necessary, a second dose or additional doses of the anti-ZIKV antibody can be administered.

Example 6. Development and Characterization of ZIKV Adenovirus Vector-Based Vaccines Design of ZIKV Adenovirus Vaccines Adenovirus vaccines were generated by incorporating a nucleic acid molecule of FIG. 3A into Ad5, RhAd52, and Ad26. Specifically, the nucleic acid molecule prM-Env (SEQ ID NO: 1) was incorporated into adenovirus vectors Ad5, RhAd52, and Ad26 to generate the Ad5-prM-Env vaccine ("Ad5-prM-Env"), RhAd52-prM-Env vaccine ("RhAd52-prM-Env"), and Ad26-prM-Env vaccine ("Ad26-prM-Env"), respectively.

Figure 9:
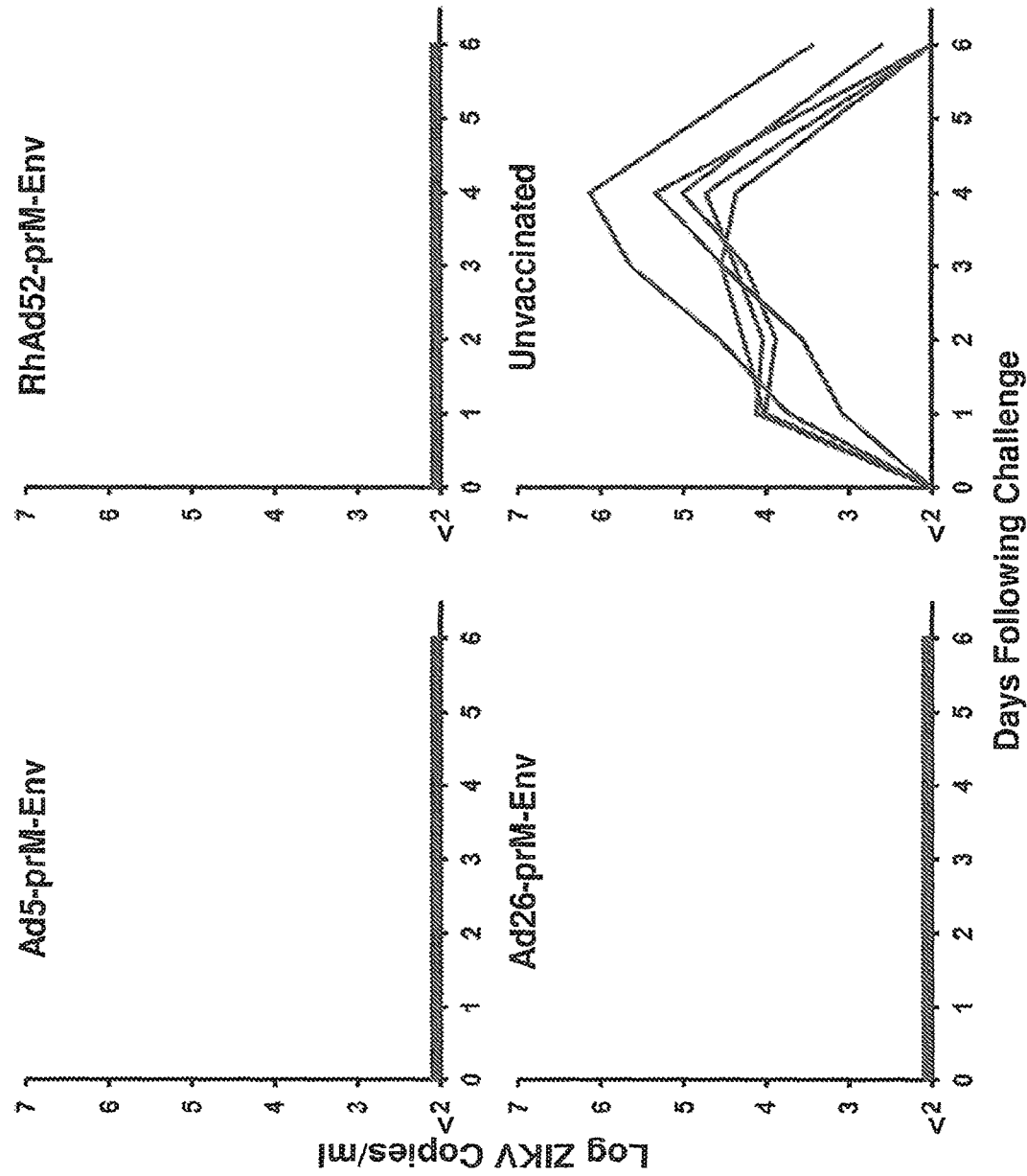
FIG. 9 are graphs comparing serum viral loads from Balb/c mice (N=5 mice/group) that were immunized with the Ad5-prM-Env vaccine ("Ad5-prM-Env;" containing SEQ ID NO: 1), RhAd52-prM-Env vaccine ("RhAd52-prM-Env," containing SEQ ID NO: 1), or Ad26-prM-Env vaccine ("Ad26-prM-Env," containing SEQ ID NO: 1), or unvaccinated, and subsequently challenged by ZIKV infection. Balb/c mice received a single immunization of $10^9$ VP by the i.m. route. Mice were then challenged four weeks after immunization by intravenous administration of ZIKV-BR.

In Vivo Assessment of the Protective Efficacy of ZIKV Adenovirus Vector-Based Vaccines Against ZIKV Challenge To assess the protective efficacy of these adenovirus vector-based vaccines against ZIKV challenge, vaccinated or sham vaccinated (i.e., unvaccinated) control Balb/c mice were challenged at week four post immunization by the intramuscular (i.m.) route with $10^5$ viral particles (VP) [$10^2$ plaque-forming units (PFU)] of ZIKV-BR. Viral loads following ZIKV challenge were determined by RT-PCR (Larocca et al. *Science*. 353(6304):1129-1132, 2016), as generally described herein. Sham vaccinated mice inoculated with ZIKV-BR developed approximately 6 days of detectable viremia following challenge (FIG. 9). In contrast, a single immunization with the Ad5-prM-Env vaccine, RhAd52-prM-Env vaccine, or Ad26-prM-Env vaccine provided complete protection against ZIKV-BR challenge with no detectable viremia at any timepoint (FIG. 9).

Figure 10A:
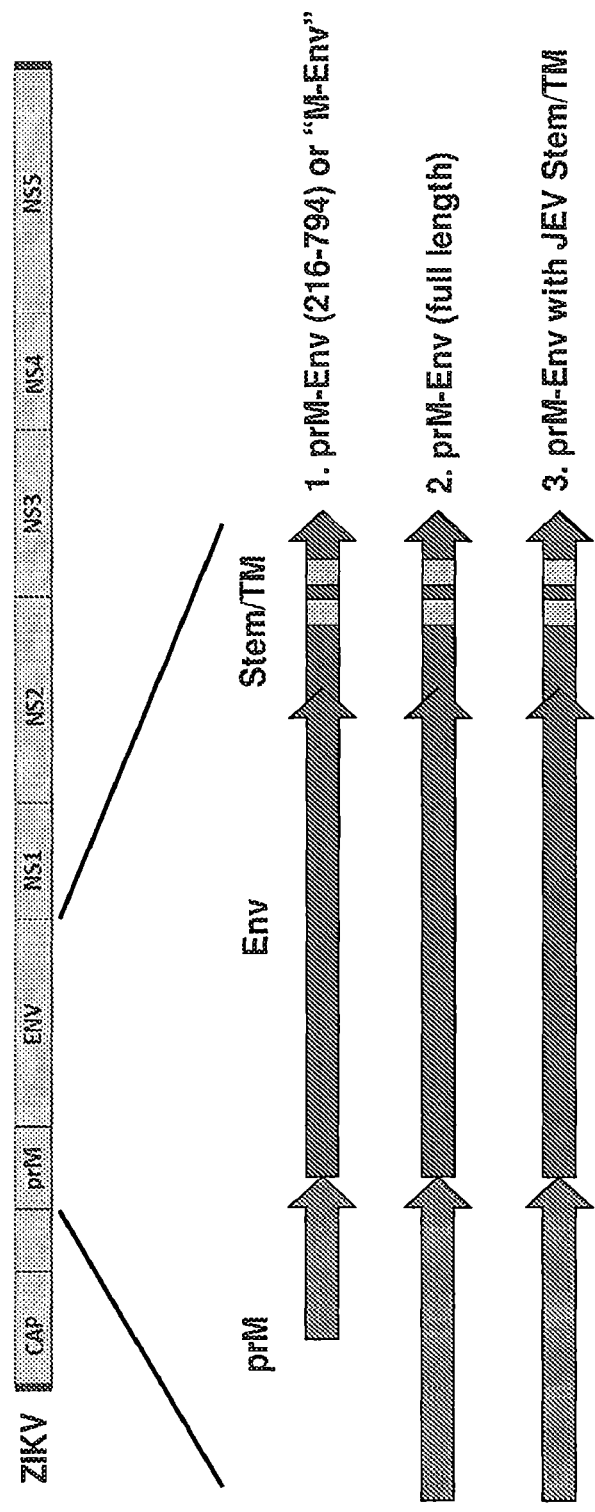
FIG. 10A is a schematic diagram showing the design of ZIKV prM-Env DNA immunogens. The DNA immunogens encode a truncated (referred to throughout as either "prM-Env," "prM-Env encoding amino acids 216-794 (216-794) of prM-Env," or "M-Env"; SEQ ID NO: 1) or a full-length pre-membrane and envelope region ("prM-Env (full-length);" SEQ ID NO:24), and a mutant having a full-length pre-membrane and envelope region with the ZIKV prM signal region of Japanese encephalitis virus (JEV), wherein the final 98 amino acids comprising the stem and transmembrane regions have been exchanged with corresponding JEV sequences ("prM-Env with JEV Stem/TM;" SEQ ID NO:28).

Example 7. Optimization of ZIKV prM-Env Immunogens and ZIKV prM-Env DNA Vaccines Following the methodology described in Example 1, additional DNA vaccines were generated by incorporating a nucleic acid molecule of FIG. 10A into the mammalian expression vector pcDNA3.1+(Invitrogen, CA, USA). Specifically, the nucleic acid molecules prM-Env (full length) (SEQ ID NO: 24), prM-Env with JEV Stem/TM (SEQ ID NO: 26), were incorporated into the mammalian expression vector pcDNA3.1+ (Invitrogen, CA, USA) to generate the prM-Env vaccine ("DNA-prM-Env (M-Env)"), prM-Env (full-length) vaccine ("DNA-prM-Env (full-length)"), and prM-Env with JEV Stem/TM vaccine ("DNA-prM-Env (JEV Stem)"), respectively. Transgene expression was verified in 293T cells by Western blot (FIG. 10B) according to the methods described in Example 1.

Figures 10B, 10C:
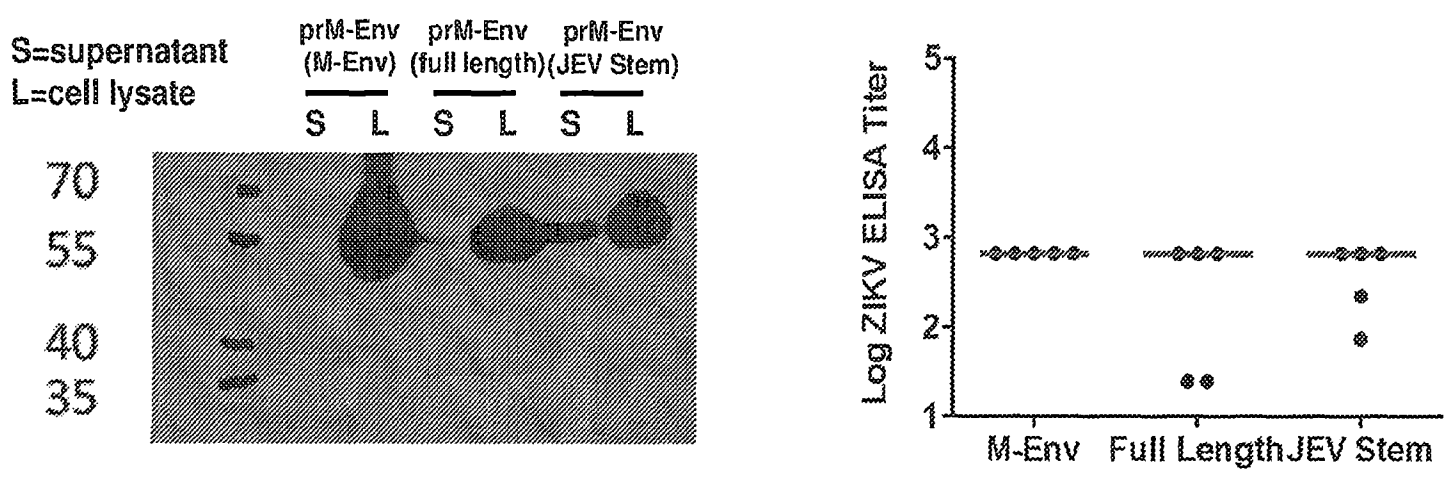
Figure 11:
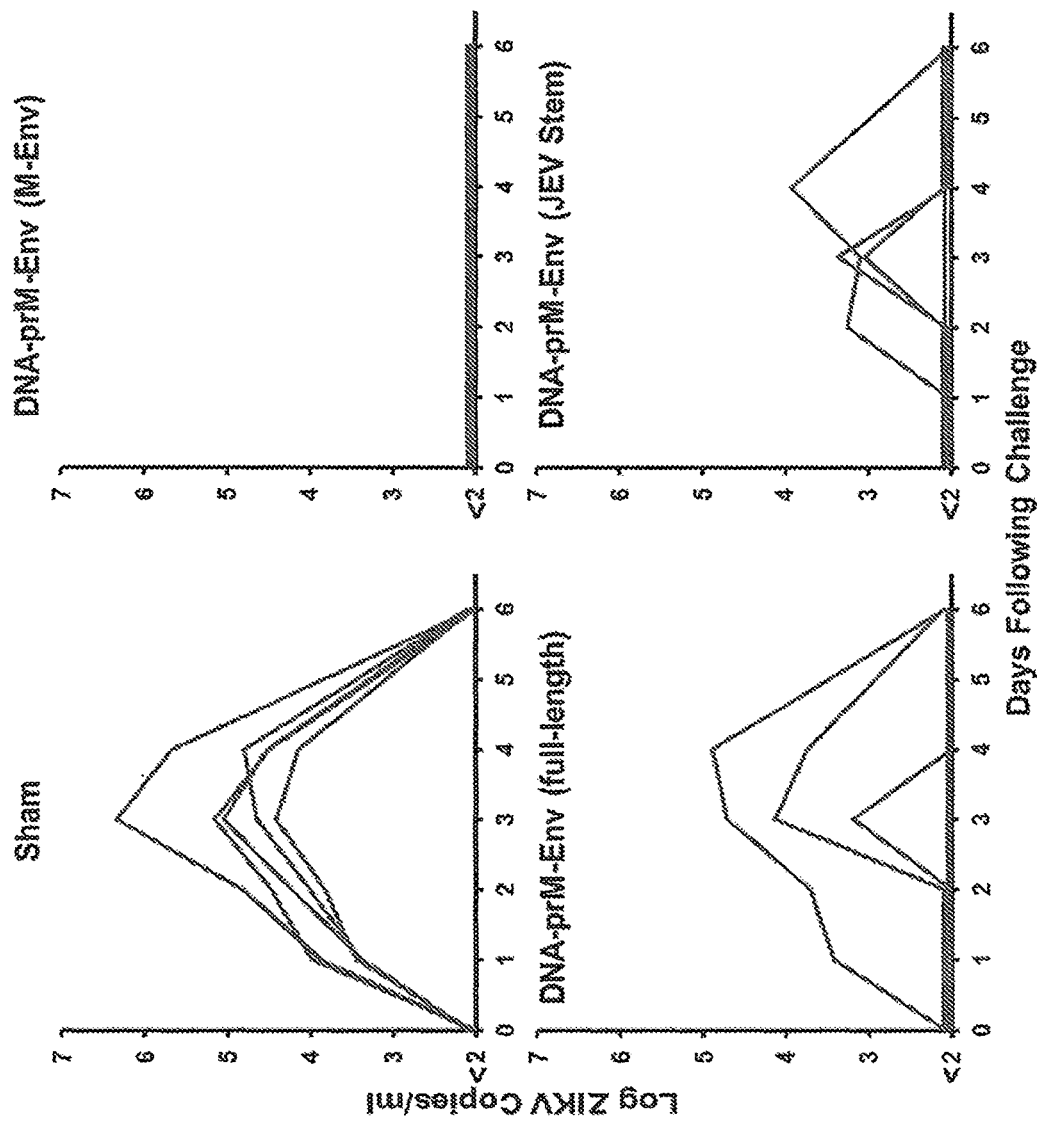
FIG. 11 are graphs comparing serum viral loads from Balb/c mice that were immunized with either DNA vaccines DNA-prM-Env (M-Env), DNA-prM-Env (full length), DNA-prM-Env (JEV Stem), or sham control, and subsequently challenged by ZIKV-BR infection. Balb/c mice received a single immunization of 50 μg vaccine by the i.m. route. Mice were then challenged four weeks after immunization by intravenous administration of ZIKV-BR.

Immunogenicity of the DNA vaccines prM-Env or "M-Env" ("DNA-prM-Env (M-Env)," comprising SEQ ID NO: 1), prM-Env (full-length) ("DNA-prM-Env (full-length)," comprising SEQ ID No: 24), and prM-Env with JEV Stem/TM vaccine ("DNA-prM-Env (JEV Stem)," comprising SEQ ID No: 26) was compared using the methods described in Example 1. The prM-Env or "M-Env" vaccine, prM-Env (full-length) vaccine, and prM-Env with JEV Stem/TM vaccine were found elicited approximately equivalent median Env-specific antibody titers (FIG. 10C). To assess the protective efficacy of the DNA vaccines prM-Env or "M-Env", prM-Env (full-length), and prM-Env with JEV Stem/TM against ZIKV challenge, vaccinated or sham vaccinated control Balb/c mice (N=5 mice/group) were challenged at week four post immunization by the intravenous (i.v.) route with $10^5$ viral particles (VP) [$10^2$ plaque-forming units (PFU)] of ZIKV-BR. Viral loads following ZIKV challenge were determined according to the methods described in Example 1. Sham vaccinated mice inoculated with ZIKV-BR developed approximately 6 days of detectable viremia following challenge (FIG. 11). In contrast, a single immunization of the prM-Env or "M-Env" vaccine provided complete protection against ZIKV-BR challenge with no detectable viremia at any timepoint (FIG. 11). In comparison, a single immunization of the prM-Env (full-length) vaccine or the prM-Env with JEV Stem/TM vaccine did not provide complete protection against ZIKV-BR challenge (FIG. 11).

These data suggest that the prM-Env or "M-Env" vaccine, comprising SEQ ID NO: 1, provides increased antigen expression, immunogenicity, and improved protective efficacy in mice over the prM-Env (full-length) vaccine and the prM-Env with JEV Stem/TM vaccine. Additionally, the addition of the JEV stem was found to impair protective efficacy.

Figure 12:
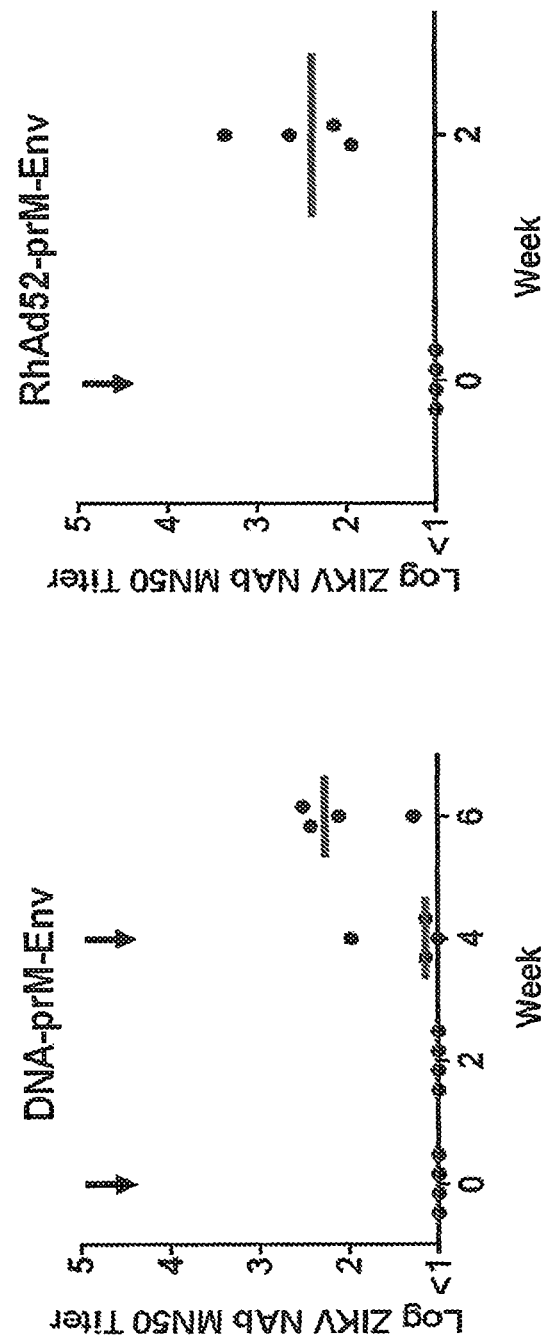
FIG. 12 are graphs comparing the ability of the DNA vaccine DNA-prM-Env (M-Env) or adenovirus vector-based vaccine RhAd52-prM-Env, each containing SEQ ID NO: 1, to induce a humoral response in rhesus monkeys. Rhesus monkeys (N=4/group) received immunization with 5 mg DNA-prM-Env (M-Env) by the i.m. route at week zero and week 4, a single immunization with $10^{10}$ VP of RhAd52-prM-Env at week zero, or a sham control. Monkeys were then challenged four weeks after immunization by intravenous administration of ZIKV-BR and assessed for cellular immune responses using IFN-γ ELISPOT assays to prM, Env, Cap, and NS1 at week 6 for the DNA vaccine or at week 2 for the RhAd52-prM-Env vaccine. Bars reflect the median values.
Figure 13:
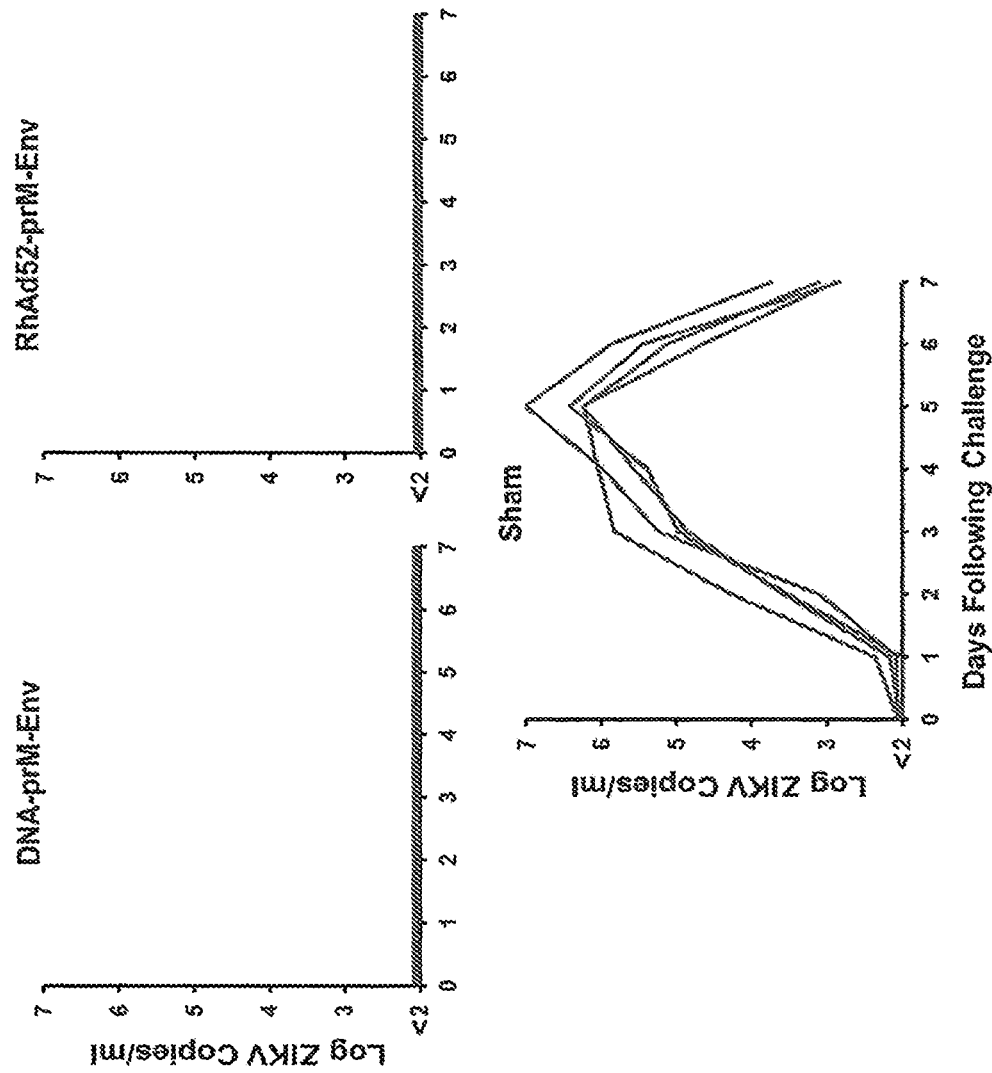
FIG. 13 are graphs comparing serum viral loads from rhesus monkeys (N=4/group) that were immunized with either DNA vaccine DNA-prM-Env (M-Env), adenovirus vector-based vaccine RhAd52-prM-Env, or sham control, and subsequently challenged by ZIKV-BR infection.

Example 8. Evaluation of ZIKV DNA and Adenovirus Vector-Based Vaccines in Rhesus Monkeys To assess the immunogenicity of the DNA vaccine prM-Env or "M-Env" ("DNA-prM-Env (M-Env)," comprising SEQ ID NO: 1) and the adenovirus vector-based vaccine RhAd52-prM-Env ("RhAd52-prM-Env," comprising SEQ ID No: 1) groups of rhesus monkeys (N=4/group) received immunization with 5 mg of DNA vaccine by the intramuscular (i.m.) route at week zero and week four, or a single immunization with $10^{10}$ virus particles (VP) of RhAd52-prM-Env vaccine at week zero. Cellular immune responses were measured using IFN-γ ELISPOT assays to prM, Env, Cap, and NS1 at week 6 for the DNA vaccine or at week 2 for the RhAd52-prM-Env vaccine. The DNA-prM-Env vaccine induced ZIKV-specific neutralizing antibody titers in all animals after the week 4 boost immunization, although only minimal 50% microneutralization (MN50) titers were detected after the initial priming immunization (FIG. 12). In contrast, the RhAd52-prM-Env vaccine induced ZIKV-specific neutralizing antibody responses in all animals at week 2 after the initial priming immunization (FIG. 12). The DNA-prM-Env vaccine also induced detectable Env-specific IFN-γ ELISPOT responses after the week 4 boost immunization, and the RhAd52-prM-Env vaccine induced Env-specific cellular immune responses after the initial week 0 priming immunization (FIG. 12). Monkeys were challenged 4 weeks after the final vaccination, and both the DNA and RhAd52 vaccines provided complete protection against subcutaneous challenge with $10^6$ VP ($10^3$ PFU) of ZIKV-BR as measured by plasma viral loads compared to the sham control (FIG. 13).

Figure 14:
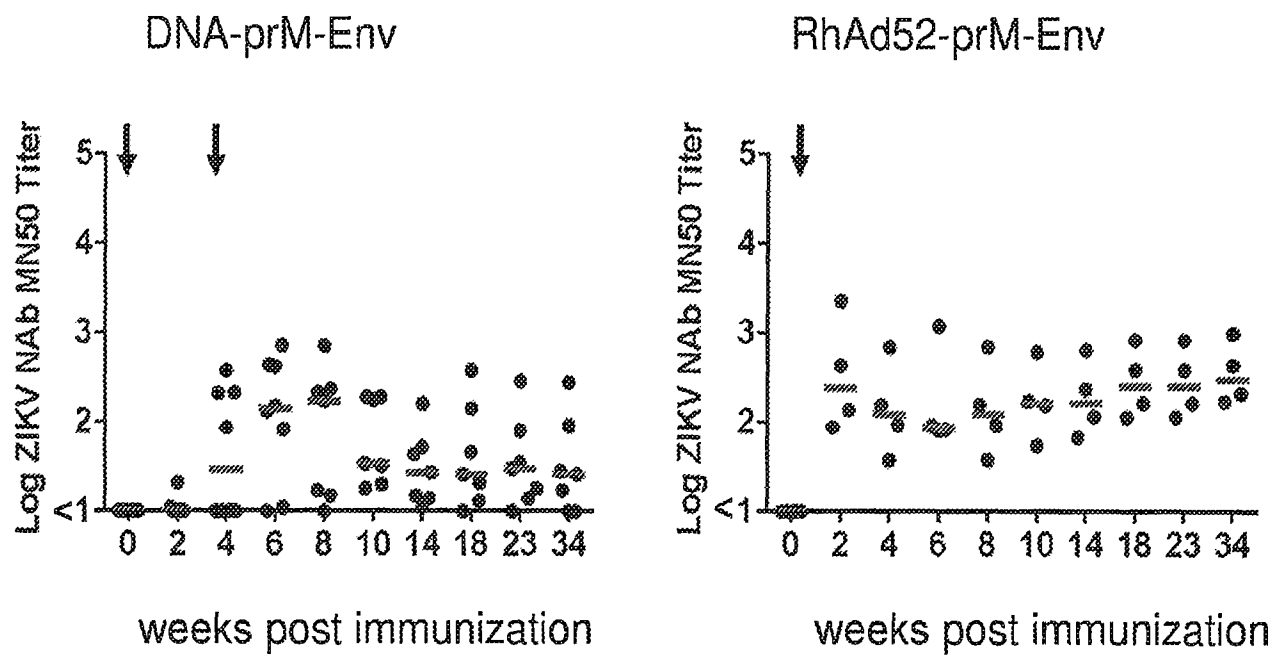
Figure 15:
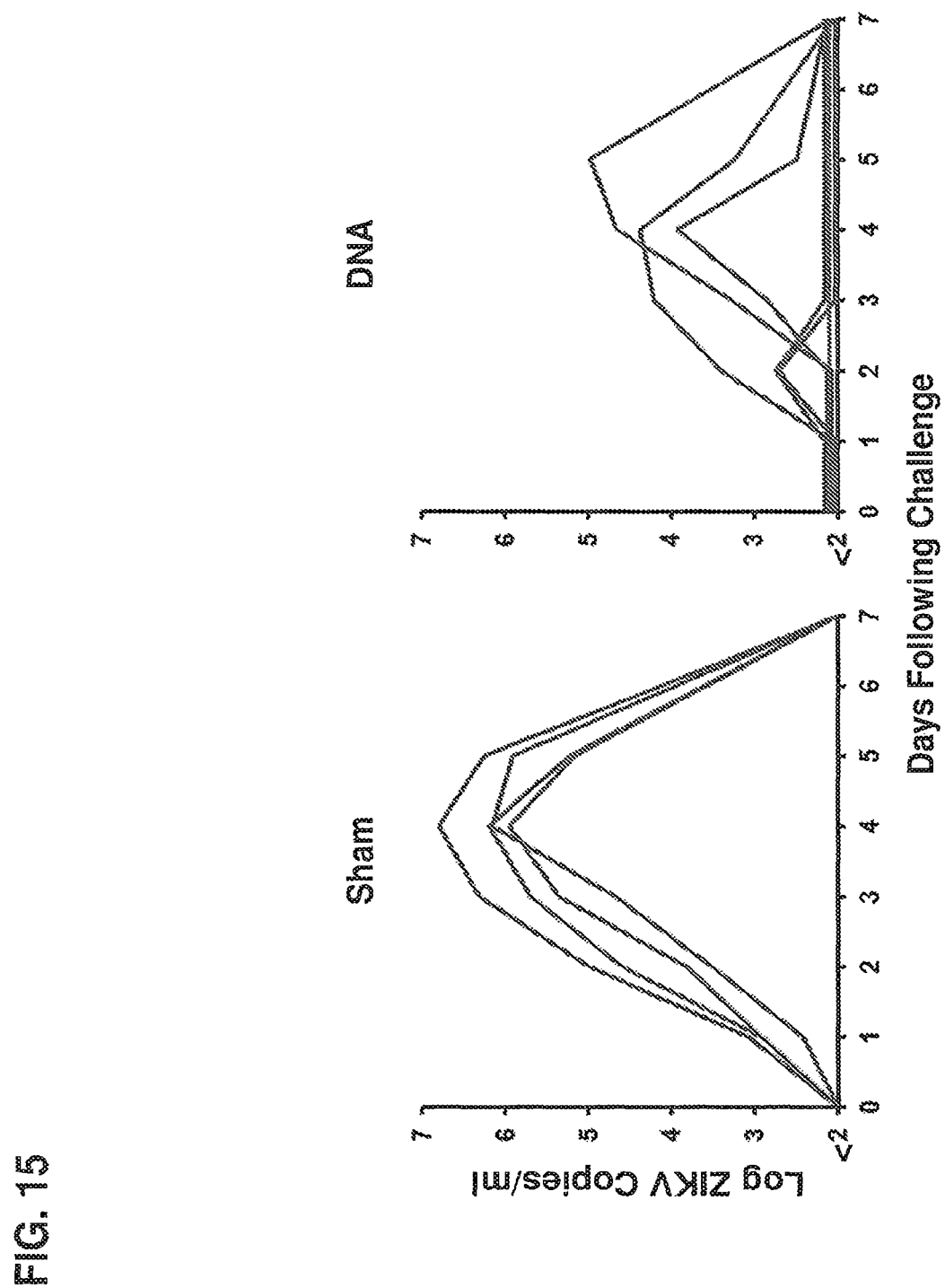
FIG. 15 is a graph comparing serum viral loads from rhesus monkeys (N=4/group) that were immunized with either DNA vaccine DNA-prM-Env (M-Env) or sham control and subsequently challenged by ZIKV-BR infection one year post immunization.
Figure 16:
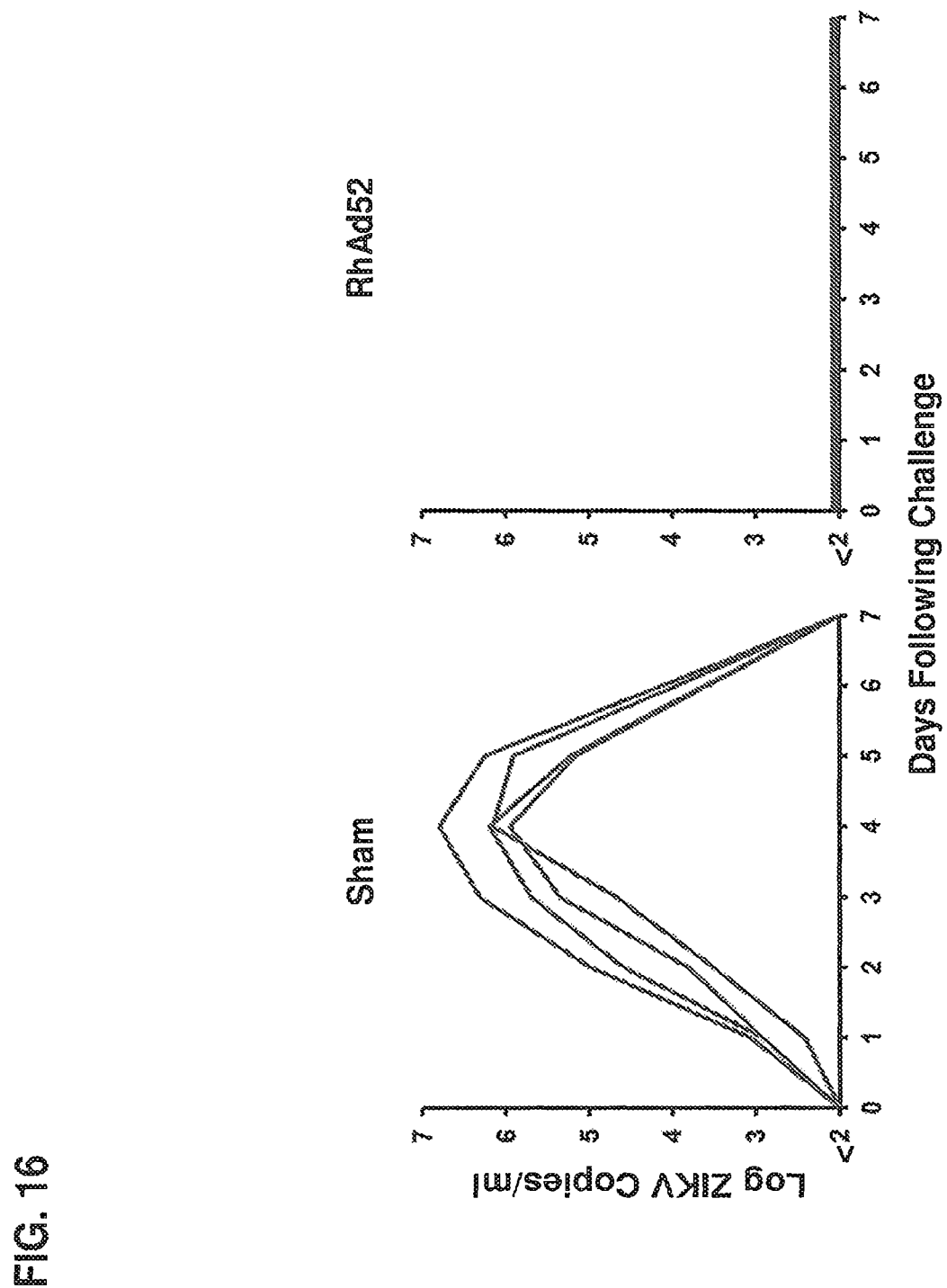
FIG. 16 are graphs comparing serum viral loads from rhesus monkeys (N=4/group) that were immunized with either adenovirus vector-based vaccine RhAd52-prM-Env or sham control and subsequently challenged by ZIKV-BR one year post immunization.

Additionally, the durability of the protective efficacy of immunization with DNA-prM-Env or RhAd52-prM-Env, as described above, was assessed one year after immunization. One year post immunization monkeys were challenged with $10^8$ VP ($10^3$ PFU) of ZIKV-BR, generally as described herein. Detectable Env-specific antibody responses were observed 2, 4, 6, 8, 10, 14, 18, 23, and 34 weeks post immunization (FIG. 14). Viral loads following ZIKV challenge at one year were determined by RT-PCR (Larocca et al., Science. 353(6304):1129-1132, 2016) (FIGS. 15 and 16). Monkeys administered the DNA-prM-Env vaccine were found to have reduced protection against ZIKV challenge 1 year post immunization (FIG. 15). In contrast, monkeys administered the RhAd52-prM-Env vaccine had complete protection against ZIKV challenge 1 year post immunization.

Figure 17:
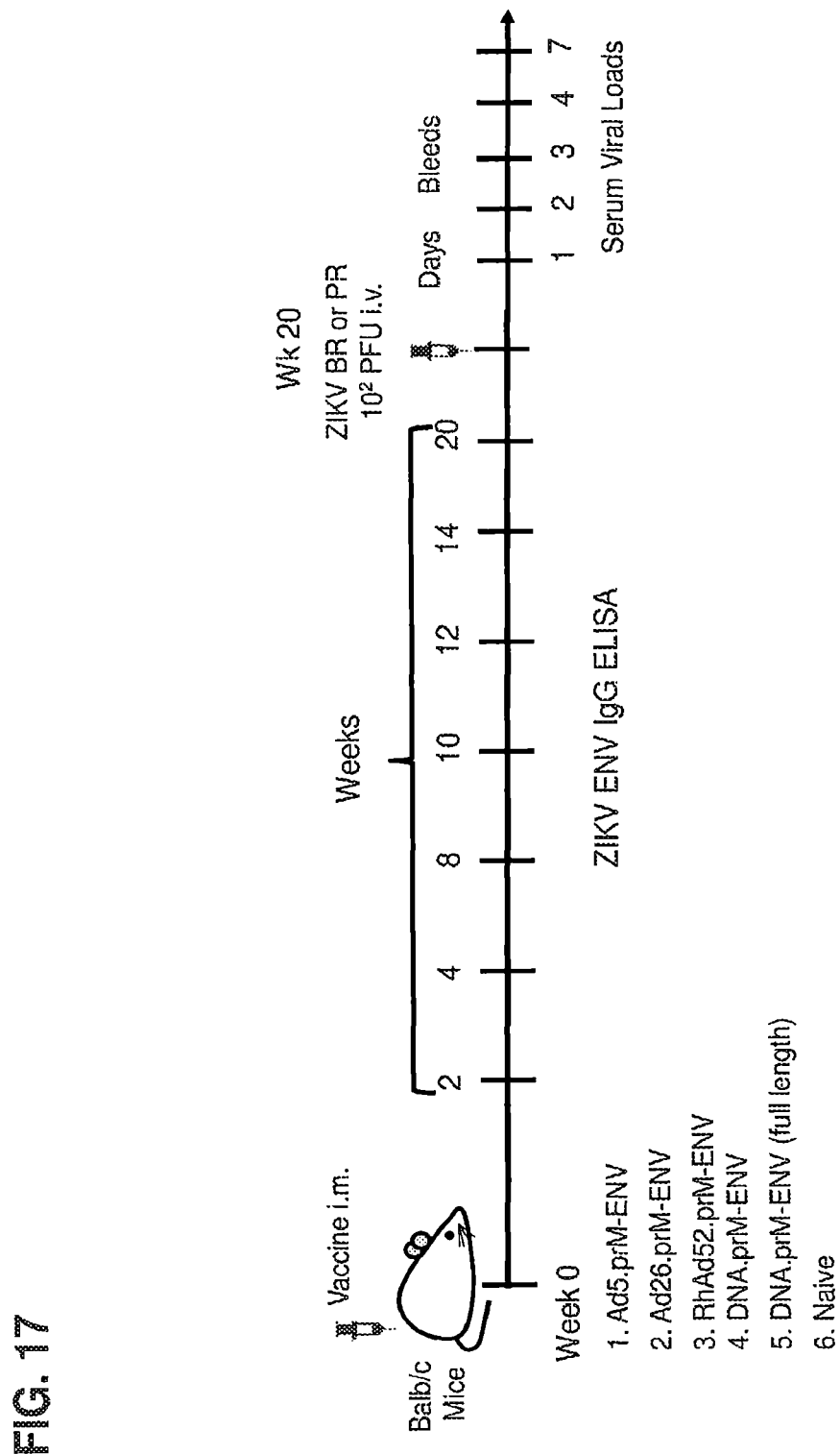
FIG. 17 is a schematic diagram showing the study design to assess durability of the protective efficacy of the ZIKV DNA and adenovirus vector-based vaccines of the invention in Balb/c mice.
Figure 18:
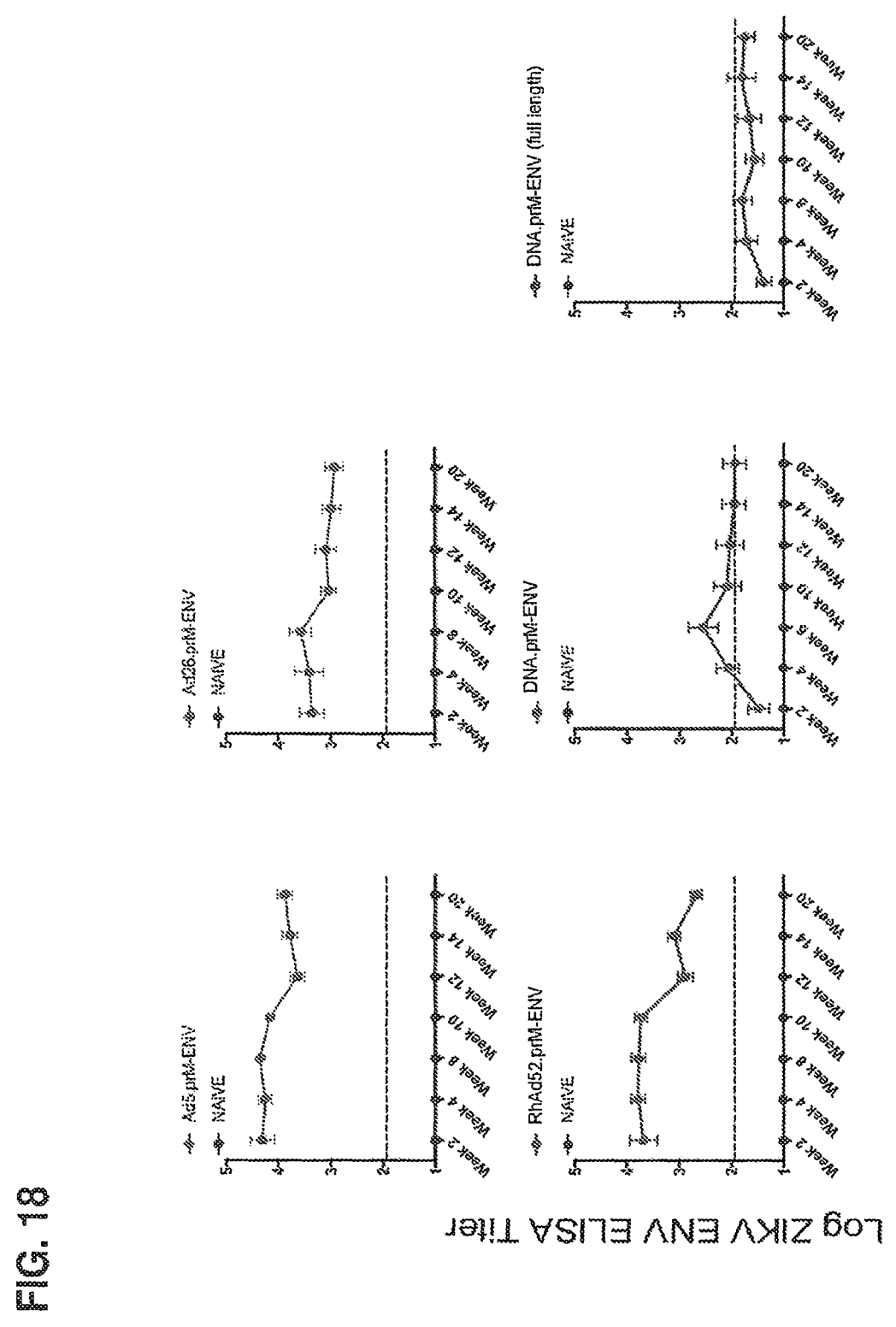
Figure 19:
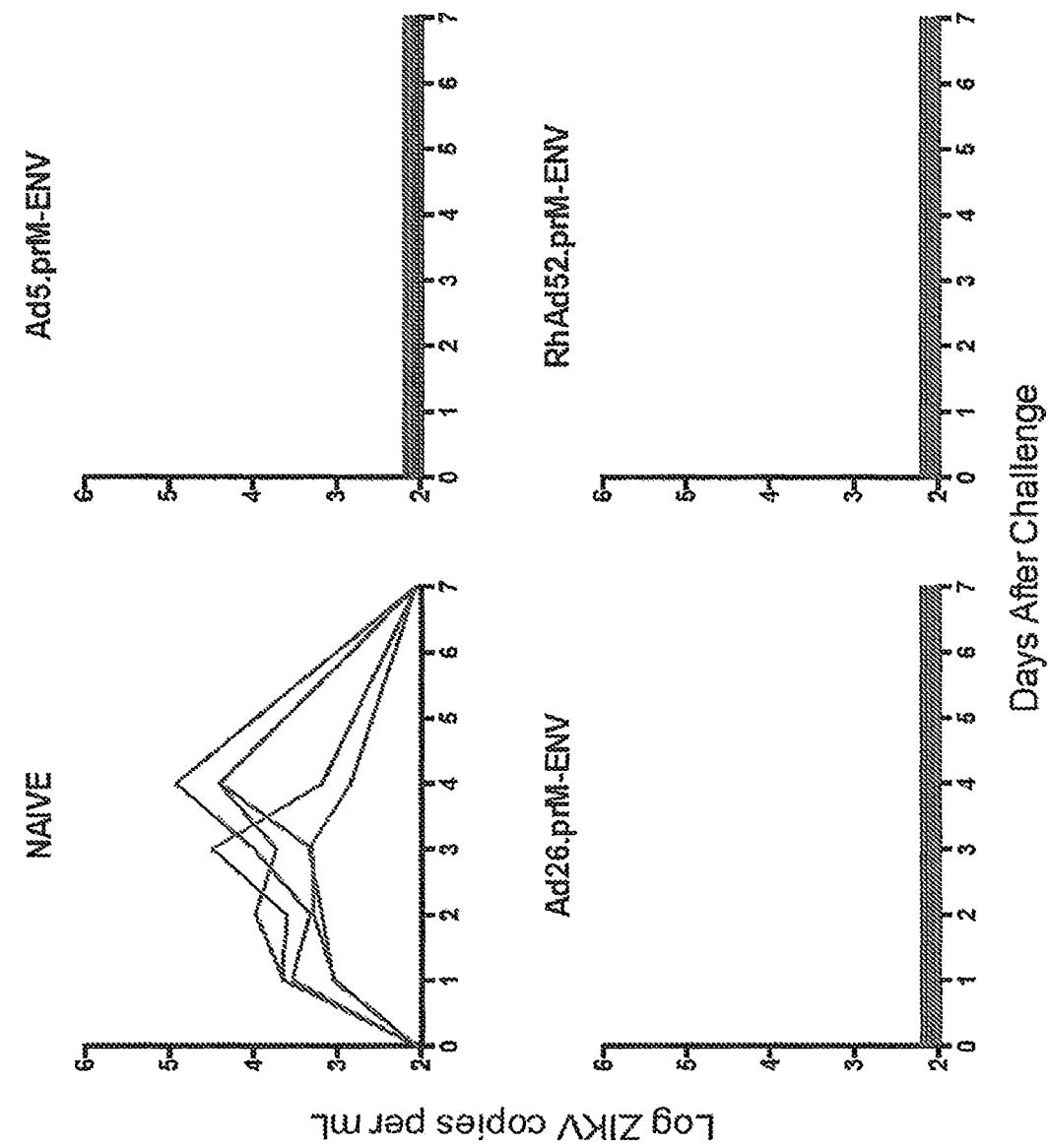
FIG. 19 are graphs comparing serum viral loads from Balb/c mice that were immunized with adenovirus vector-based vaccines Ad5-prM-ENV, ad26-prM-ENV, or RhAd52-prM-ENV and subsequently challenged by ZIKV-BR.
Figure 20:
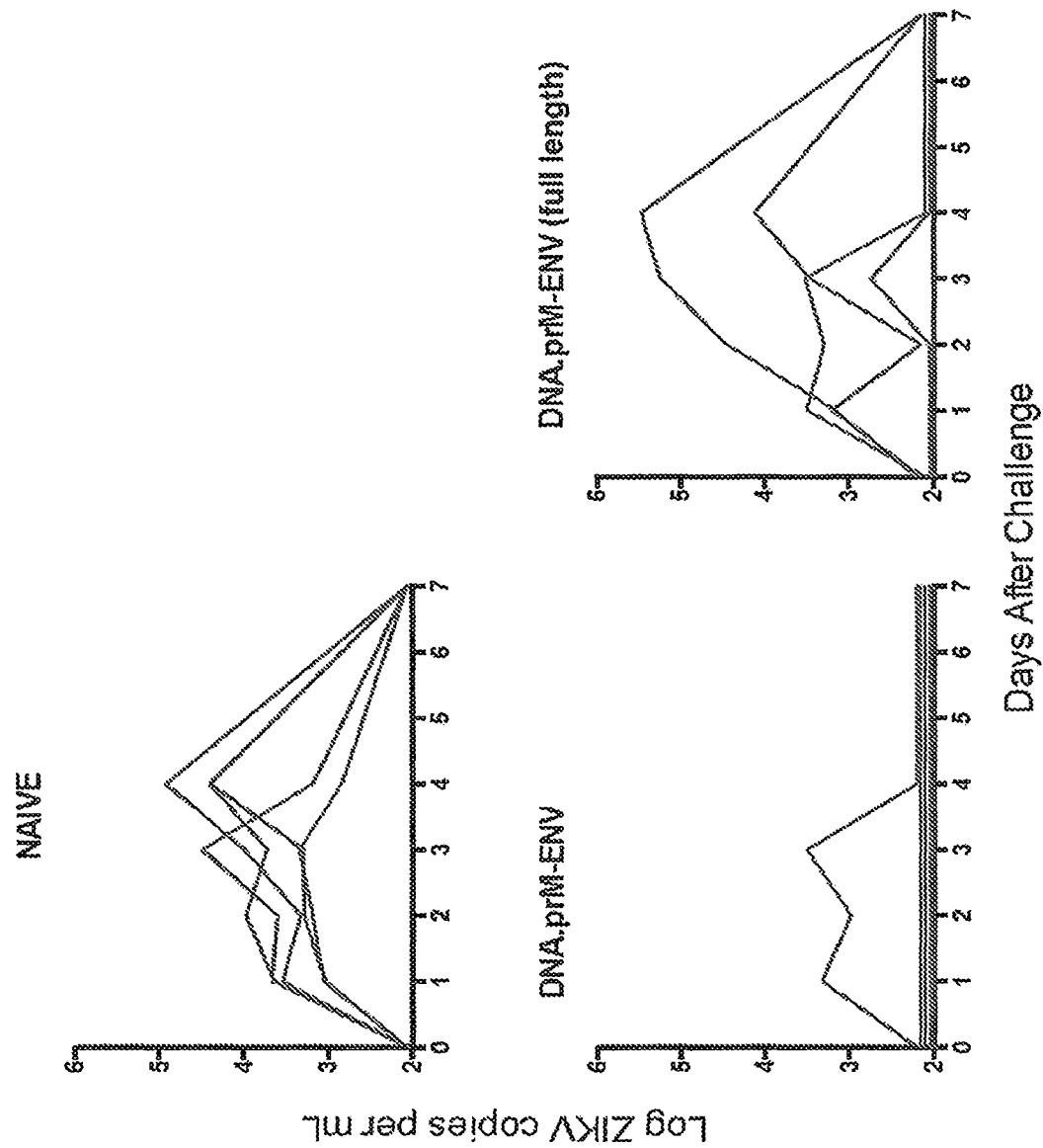
FIG. 20 are graphs comparing serum viral loads from Balb/c mice that were immunized with DNA vaccine DNA-prM-ENV (containing SEQ ID NO: 1), and DNA-prM-ENV (full-length) (containing SEQ ID NO: 24), and subsequently challenged by ZIKV-BR.

Example 9: Evaluating the Durability of the Protective Effect of ZIKV DNA and Adenovirus Vector-Based Vaccines in Balb/c Mice To access the durability of the protective efficacy of the ZIKV DNA and adenovirus vector-based vaccines of the invention vaccinated or naive control Balb/c mice were challenged at week 20 post immunization by the intramuscular (i.m.) route with $10^2$ plaque-forming units (PFU) of ZIKV-BR (FIG. 17). Env-specific antibody responses were evaluated at week two, week four, week eight, week ten, week twelve, week fourteen, and week twenty post immunization by ELISA (FIG. 18). Viral loads following ZIKV challenge were determined by RT-PCR (Larocca et al., Science. 353(6304):1129-1132, 2016) (FIGS. 19 and 20). The Ad5-prM-Env, Ad26-prM-Env, and RhAd52-prm-Env were found to provide complete protection from ZIKV challenge as compared to the sham control (FIG. 19). In contrast, the DNA vaccines DNA-prM-ENV and DNA-prM-ENV (full-length) did not offer complete protection from ZIKV challenge (FIG. 20), however animals administered the DNA-prM-ENV offered better protection than the DNA-prM-ENV (full-length). These data show that DNA vaccines provided less robust protection against ZIKV challenge compared to the adenovirus vector-based vaccines. Additionally, these data show that the prM-Env or "M-Env"

immunogen is superior to the prM-Env (full-length) immunogen in eliciting an effective immune response in a treated subject.

Generally, an adenovirus vector-based vaccine containing the prM-Env immunogen (SEQ ID NO: 1) was found to offer robust protection to both mice and monkeys, when administered as a single shot vaccine. Adenovirus vector-based vaccine containing the prM-Env Immunogen (SEQ ID NO: 1) were also found to be more potent than DNA vaccines containing the prM-Env immunogen (SEQ ID NO: 1) in both mice and monkeys.

Figure 21:
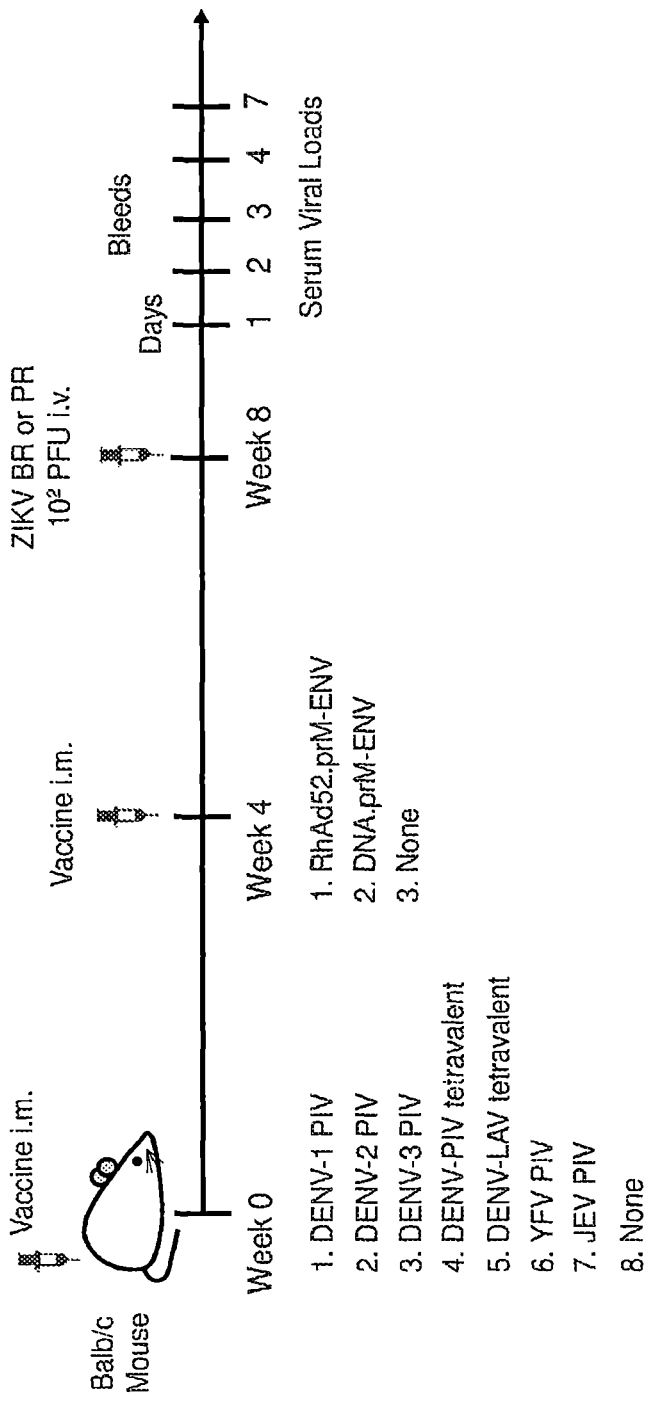
FIG. 21 is a schematic diagram showing the study design to assess durability of the protective efficacy of the ZIKV DNA and adenovirus vector-based vaccines comprising SEQ ID NO: 1 in Balb/c mice having baseline Flavivirus immunity.
Figure 22:
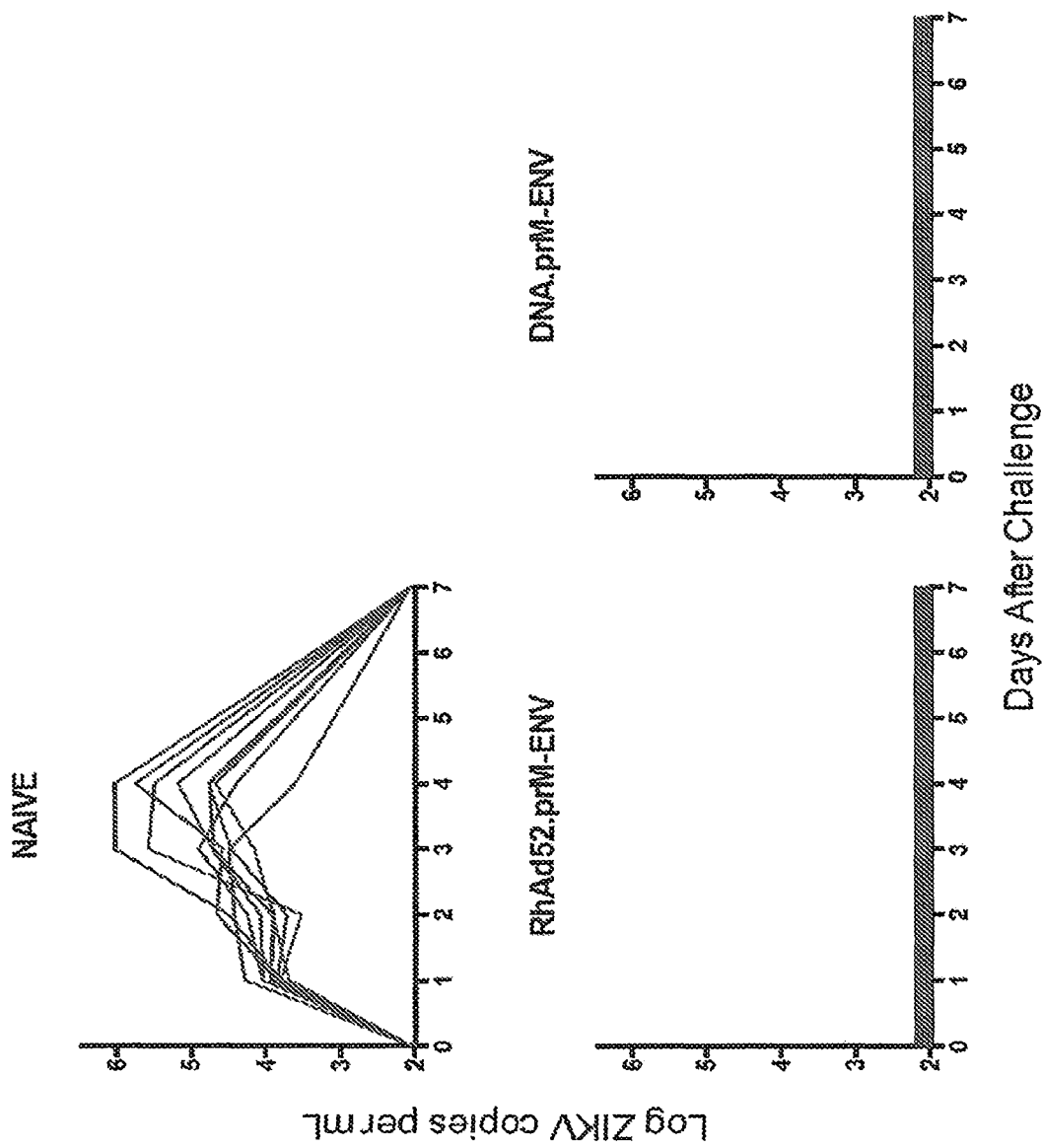
FIG. 22 are graphs comparing serum viral loads from Balb/c mice having no baseline Flavivirus immunity that were immunized with DNA vaccine DNA-prM-ENV (containing SEQ ID NO: 1), and RhAd52-prM-ENV (containing SEQ ID NO: 1), or were naïve, and subsequently challenged by ZIKV-BR.
Figure 23:
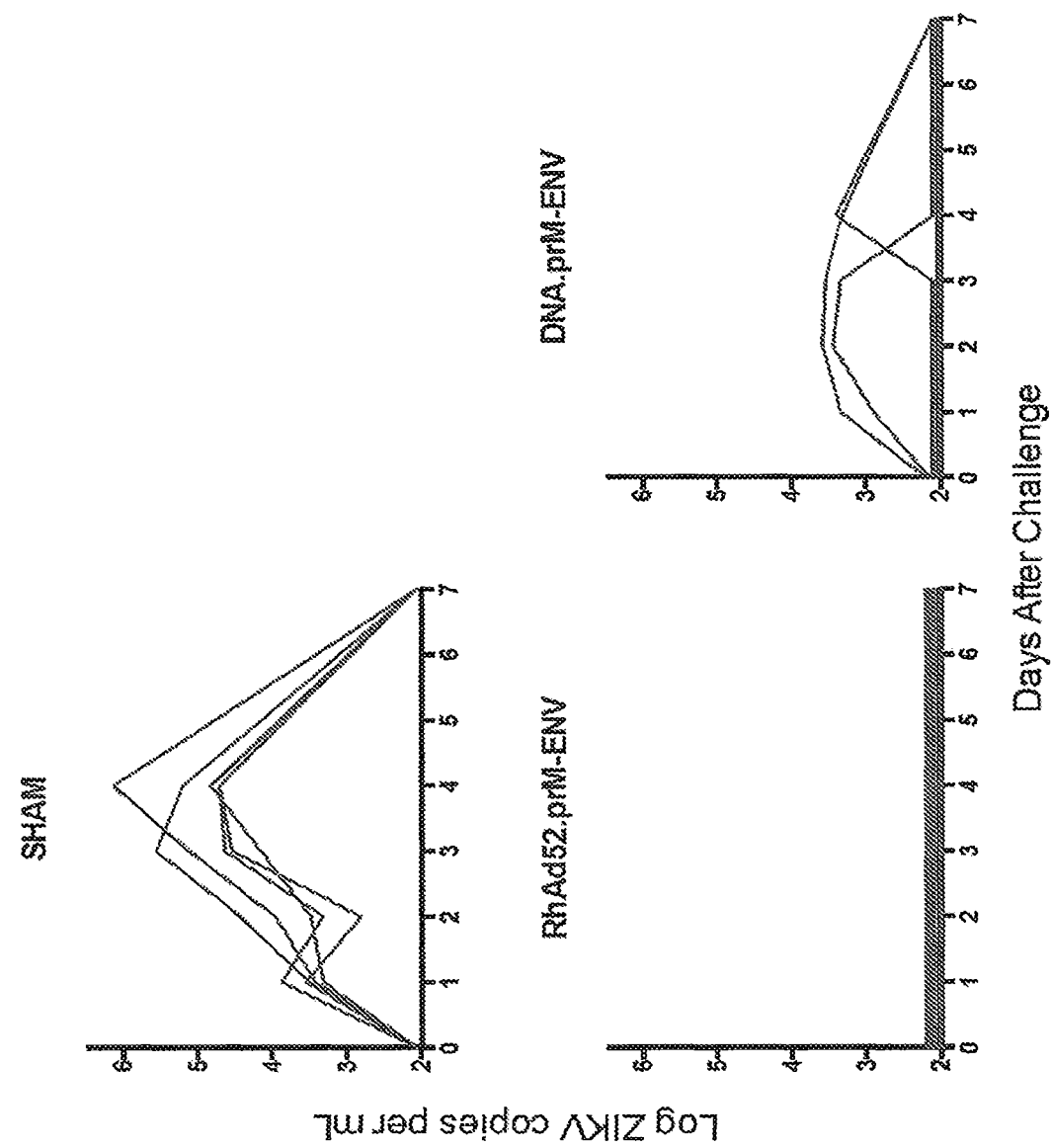
FIG. 23 are graphs comparing serum viral loads from Balb/c mice having DENV-1 immunity that were immunized with DNA vaccine DNA-prM-ENV (containing SEQ ID NO: 1), and RhAd52-prM-ENV, (containing SEQ ID NO: 1), or sham control, and subsequently challenged by ZIKV-BR.
Figure 24:
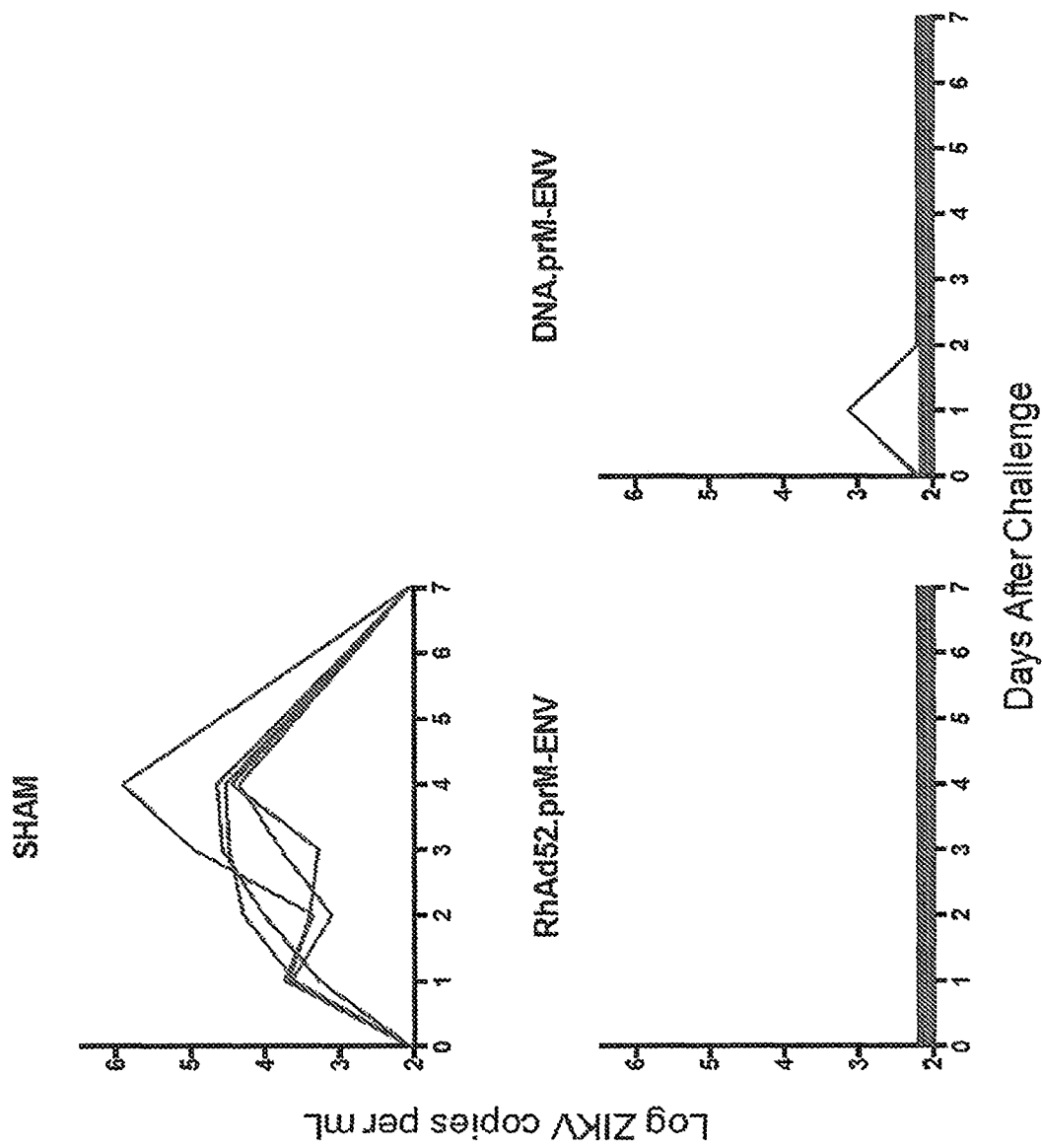
FIG. 24 are graphs comparing serum viral loads from Balb/c mice having DENV-2 immunity that were immunized with DNA vaccine DNA-prM-ENV (containing SEQ ID NO: 1), and RhAd52-prM-ENV, (containing SEQ ID NO: 1), or sham control, and subsequently challenged by ZIKV-BR.
Figure 25:
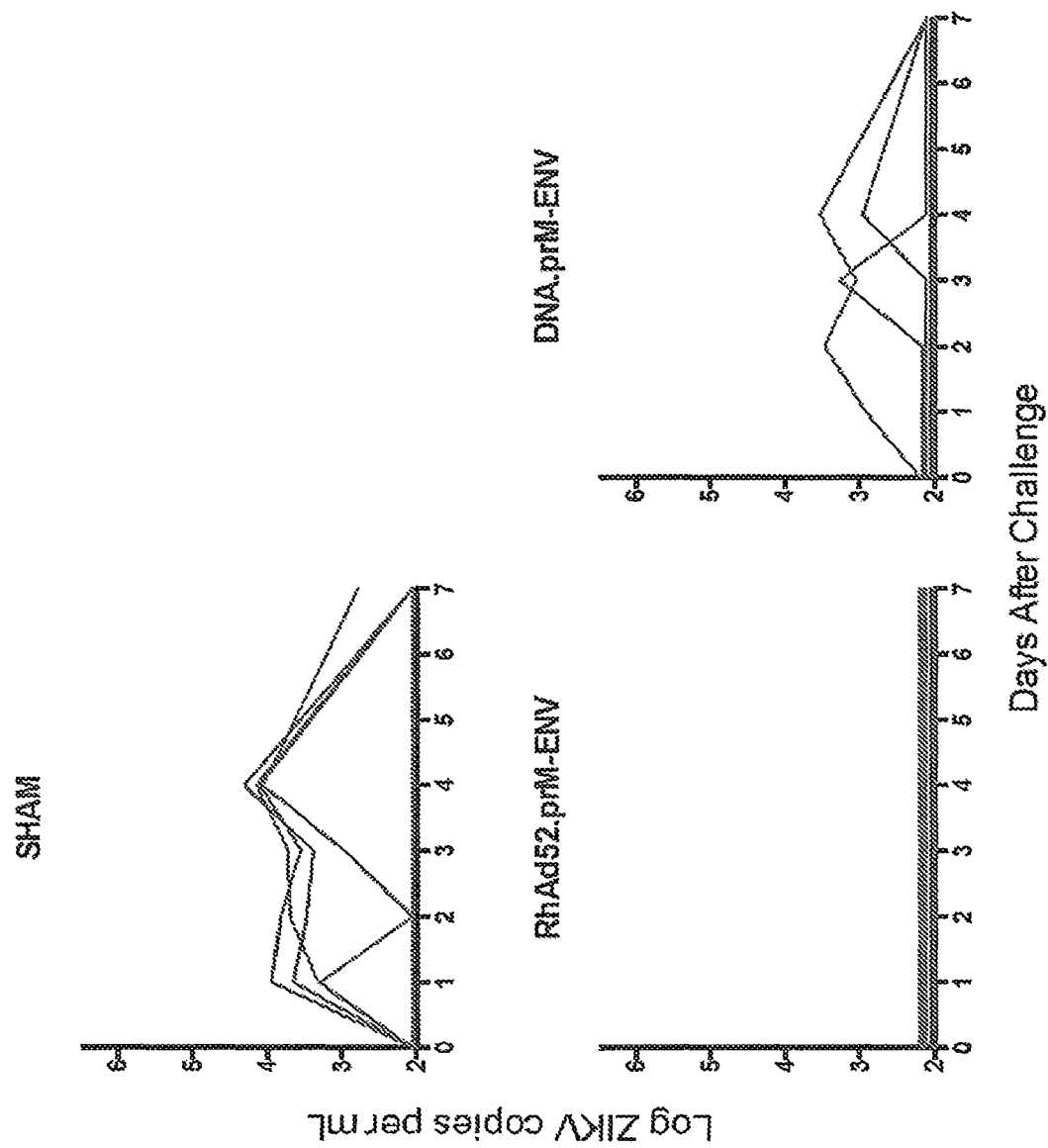
FIG. 25 are graphs comparing serum viral loads from Balb/c mice having DENV-3 immunity that were immunized with DNA vaccine DNA-prM-ENV (containing SEQ ID NO: 1), and RhAd52-prM-ENV, (containing SEQ ID NO: 1), or sham control, and subsequently challenged by ZIKV-BR.
Figure 26:
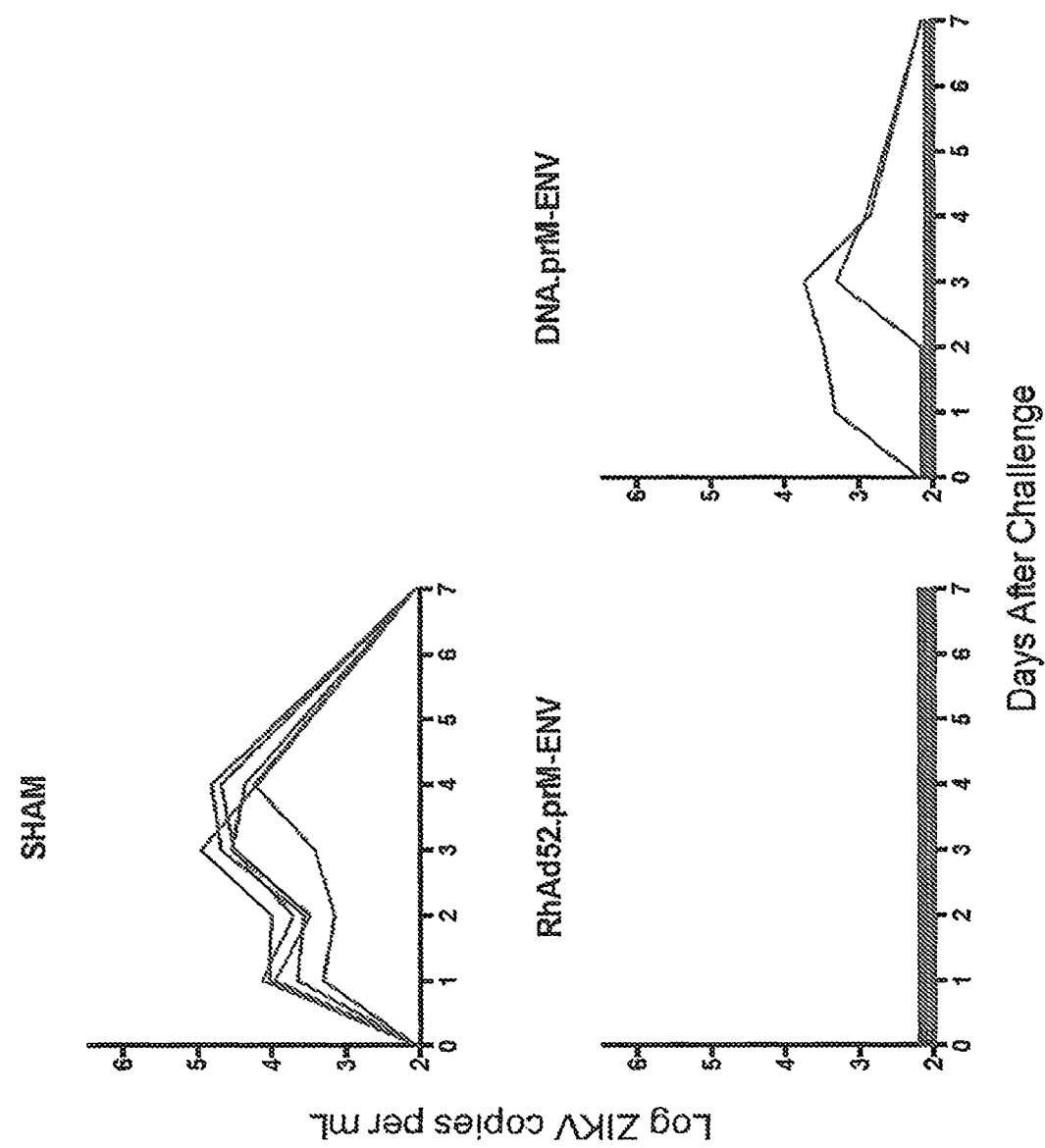
FIG. 26 are graphs comparing serum viral loads from Balb/c mice having YFV immunity that were immunized with DNA vaccine DNA-prM-ENV (containing SEQ ID NO: 1), and RhAd52-prM-ENV, (containing SEQ ID NO: 1), or sham control, and subsequently challenged by ZIKV-BR.
Figure 27:
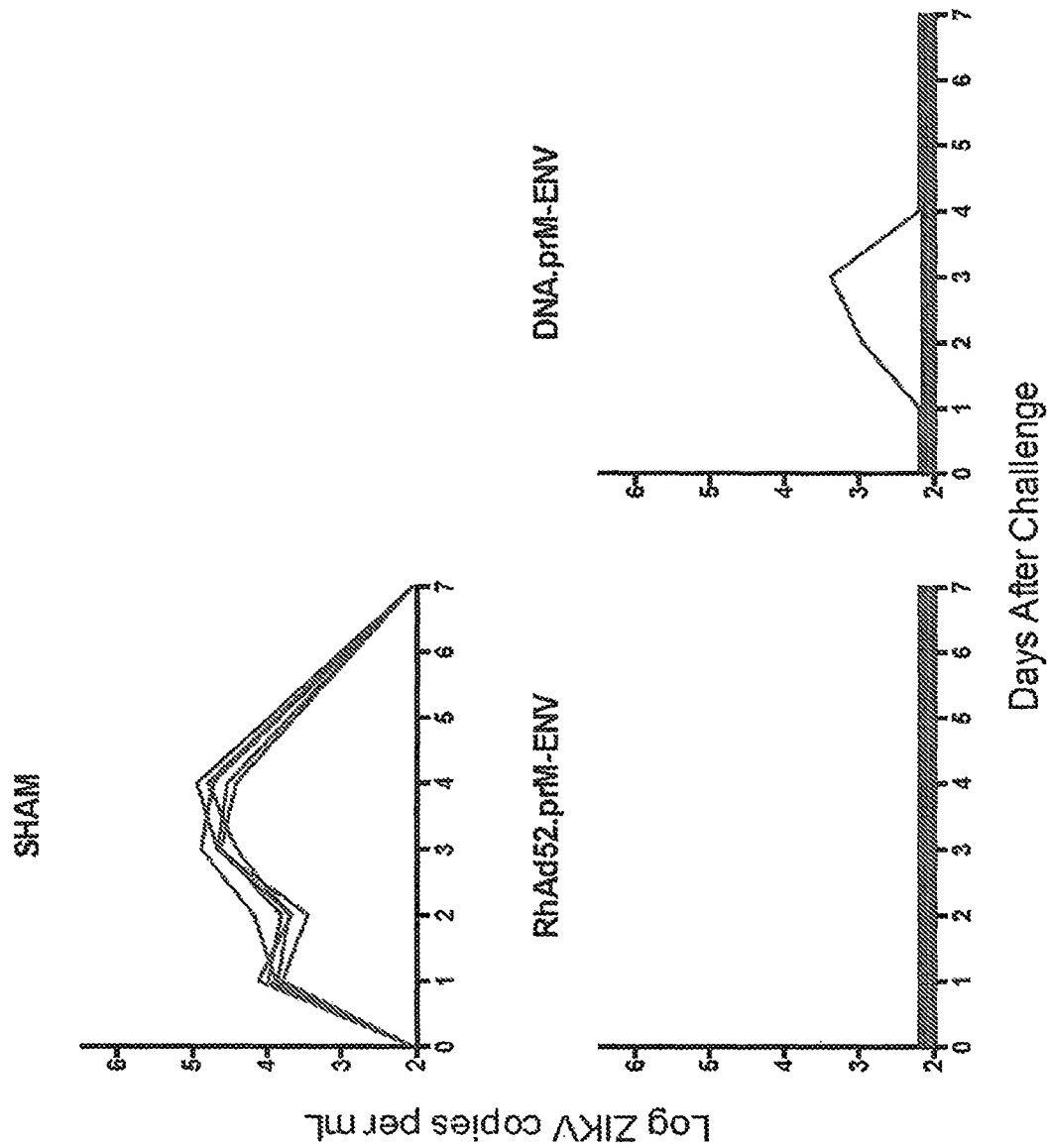
FIG. 27 are graphs comparing serum viral loads from Balb/c mice having JEV immunity that were immunized with DNA vaccine DNA-prM-ENV (containing SEQ ID NO: 1), and RhAd52-prM-ENV, (containing SEQ ID NO: 1), or sham control, and subsequently challenged by ZIKV-BR.
Figure 28:
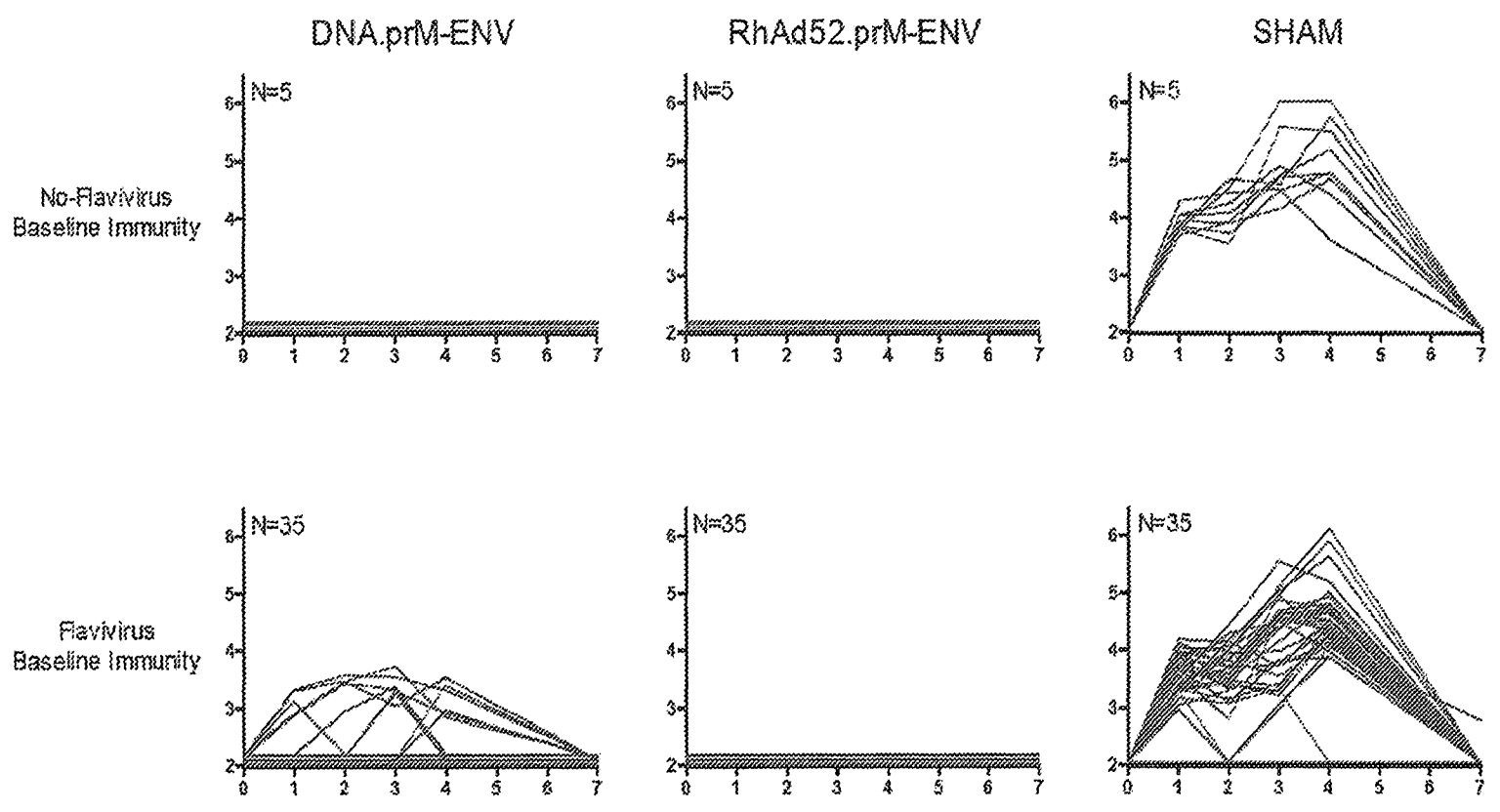

Example 10: Evaluating the Protective Effect of ZIKV DNA and Adenovirus Vector-Based Vaccines in Balb/c Mice Having a Baseline Flavivirus Immunity The protective efficacy of the ZIKV DNA and adenovirus vector-based vaccines of the invention was evaluated in Balb/c mice having a baseline immunity to a Flavivirus or naive controls (FIG. 21). Immunization against a Flavivirus occurred at week zero, and with a ZIKV DNA or adenovirus vector-based vaccine of the invention at week 4. Flavivirus vaccines were provided by WRAIR and were GMP grade. Mice were challenged at week 8 post immunization by the intravenous (i.v.) route with $10^2$ plaque-forming units (PFU) of ZIKV-BR. Viral loads following ZIKV challenge were determined by RT-PCR (Larocca et al., *Science.* 353(6304): 1129-1132, 2016) (FIGS. 22-28). The RhAd52-prm-Env and DNA-prM-ENV were found to provide complete protection in animals having no baseline Flavivirus immunity to ZIKV challenge (FIG. 22). The RhAd52-prm-Env was found to provide complete protection in animals having baseline DENV-1 (FIG. 23), DENV-2 (FIG. 24), DENV-3 (FIG. 25). YFV (FIG. 26). JEV (FIG. 27), and Flavivirus (FIG. 28) immunity compared to sham control and DNA-prM-ENV treated mice. The DNA-prM-ENV vaccine was found to provide incomplete protection in animals having baseline DENV-1 (FIG. 23), DENV-2 (FIG. 24), DENV-3 (FIG. 25), YFV (FIG. 26), JEV (FIG. 27), and Flavivirus (FIG. 28) immunity. These data show that vaccination with a DNA or adenovirus vector-based vaccine of the invention provides benefit to a subject having a Flavivirus immunity, however immunization with an adenovirus vector-based vaccine offers more robust protection.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

The invention claimed is:

1. An isolated nucleic acid molecule comprising:
   (i) a nucleotide sequence having at least 85% sequence identity to the sequence of any one of SEQ ID NOs: 1, 3, 5, 7, 9, and 11, or a complementary sequence thereof; and/or
   (ii) a nucleotide sequence that encodes a polypeptide having at least 85% sequence identity to the amino acid sequence of any one of SEQ ID NOs: 2, 4, 6, 8, 10, and 12.

2. An isolated polypeptide comprising an amino acid sequence having at least 85% sequence identity to the sequence of any one of SEQ ID NOs: 2, 4, 6, 8, 10, or 12.

3. A vector comprising one or more of the nucleic acid molecules of claim 1.

4. The vector of claim 3, wherein the vector is a mammalian, bacterial, or viral derived expression vector.

5. The vector of claim 4, wherein the vector is:
   (i) a viral vector derived from a virus selected from the group consisting of a retrovirus, adenovirus, adeno-associated virus, parvovirus, coronavirus, negative strand RNA viruses, orthomyxovirus, rhabdovirus, paramyxovirus, positive strand RNA viruses, picornavirus, alphavirus, double stranded DNA viruses, herpesvirus, Epstein-Barr virus, cytomegalovirus, fowlpox, and canarypox;
   (ii) an adenoviral vector derived from an adenovirus selected from the group consisting of Ad2, Ad5, Ad11, Ad12, Ad24, Ad26, Ad34, Ad35, Ad40, Ad48, Ad49, Ad50, Ad52, and Pan9; or
   (iii) an adenoviral vector derived from a human, chimpanzee, or rhesus adenovirus.

6. A composition comprising the nucleic acid molecule of claim 1, a polypeptide encoded by the nucleic acid molecule, or a vector comprising the nucleic acid molecule, wherein, optionally, the composition further comprises:
   (i) a pharmaceutically acceptable carrier, excipient, or diluent; and/or
   (ii) an adjuvant or an immunostimulatory agent.

7. An immunogenic composition comprising the composition of claim 6, wherein said immunogenic composition:
   (i) is capable of treating or reducing the risk of a ZIKV infection in a subject in need thereof; and/or
   (ii) elicits production of neutralizing anti-ZIKV antisera after administration to said subject.

8. An isolated antibody or an antigen-binding fragment thereof that specifically binds to the polypeptide of claim 2.

9. The antibody of claim 8, wherein the antibody or antigen-binding fragment thereof is generated by immunizing a mammal with the nucleic acid molecule of claim 1, a polypeptide encoded by the nucleic acid molecule, a vector comprising the nucleic acid molecule, a composition comprising the nucleic acid molecule, polypeptide, or vector, and/or an immunogenic composition comprising the composition.

10. A method of producing anti-ZIKV antibodies, comprising administering to a subject an amount of at least one of the nucleic acid molecule of claim 1, a polypeptide encoded by the nucleic acid molecule, a vector comprising the nucleic acid molecule, a composition comprising the nucleic acid molecule, polypeptide or vector, and/or an immunogenic composition comprising the composition, wherein the amount is sufficient to elicit production of neutralizing anti-ZIKV antisera after administration to said subject.

11. An isolated anti-ZIKV antibody produced by the method of claim 10, wherein the isolated anti-ZIKV antibody binds to an epitope within any one of SEQ ID NOs: 2, 4, 6, 8, 10, or 12.

12. A method of treating or reducing the risk of a ZIKV infection in a subject in need thereof and/or reducing a ZIKV-mediated activity in a subject infected with a ZIKV, wherein said ZIKV-mediated activity is viral titer, viral spread, infection, or cell fusion, the method comprising administering to the subject a therapeutically effective amount of at least one of the nucleic acid molecule of claim 1, a polypeptide encoded by the nucleic acid molecule, a vector comprising the nucleic acid molecule, a composition comprising the nucleic acid molecule, polypeptide or vector, an immunogenic composition comprising the composition, an antibody specifically binding to the polypeptide, and/or a neutralizing anti-ZIKV antisera produced by administering to a subject the nucleic acid molecule, polypeptide, vector, composition, or immunogenic composition.

13. The method of claim 12, wherein:
   (i) the therapeutically effective amount of the nucleic acid molecule, the polypeptide, the vector, the composition, the immunogenic composition, the antibody, and/or the neutralizing anti-ZIKV antisera is sufficient to produce a log serum anti-Env antibody titer greater than 2 in the subject, as measured by an ELISA assay;

(ii) the therapeutically effective amount is between 15 μg and 300 μg of the nucleic acid molecule, the polypeptide, the vector, the composition, the immunogenic composition, the antibody, and/or the neutralizing anti-ZIKV antisera;

(iii) the ZIKV titer is decreased after administration of the nucleic acid molecule, the polypeptide, the vector, the composition, the immunogenic composition, the antibody, and/or the neutralizing anti-ZIKV antisera; and/or (iv) the ZIKV is undetectable after administration of the nucleic acid molecule, the polypeptide, the vector, the composition, the immunogenic composition, the antibody, and/or the neutralizing anti-ZIKV antisera.

14. The method of claim 12, wherein said administering occurs:

(i) prior to exposure to a ZIKV;

(ii) at least 1 hour prior to exposure to said ZIKV;

(iii) post-exposure to the ZIKV; or (iv) at least 15 minutes post-exposure to said ZIKV.

15. The method of claim 12, wherein:

(i) the nucleic acid molecule, the polypeptide, the vector, the composition, the immunogenic composition, the antibody, and/or the neutralizing anti-ZIKV antisera is administered to said subject in at least one dose, in at least two doses, as a prime, as a boost, or as a prime-boost; and/or (ii) the nucleic acid molecule, the polypeptide, the vector, the composition, the immunogenic composition, the antibody, and/or the neutralizing anti-ZIKV antisera is administered to said subject intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivelly, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, by gavage, in creams, or in lipid compositions.

16. The method of claim 12, wherein:

(i) the subject is a mammal;

(ii) the subject is a human;

(iii) the method promotes an immune response in said subject; and/or (iv) the method promotes a humoral immune response in said subject.

17. A method of manufacturing an immunogenic composition for treating or reducing the risk of a ZIKV infection in a subject in need thereof, said method comprising the steps of:

(a) forming the immunogenic composition by admixing at least one of the nucleic acid molecule of claim 1, a polypeptide encoded by the nucleic acid molecule, a vector comprising the nucleic acid molecule, a composition comprising the nucleic acid molecule, polypeptide or vector, an antibody specifically binding to the polypeptide, and/or a neutralizing anti-ZIKV antisera produced by administering to a subject the nucleic acid molecule, the polypeptide, the vector, or the composition with a pharmaceutically acceptable carrier, excipient, or diluent; and (b) placing the immunogenic composition in a container.

18. A kit comprising:

(a) a first container comprising at least one of the nucleic acid molecule of claim 1, a polypeptide encoded by the nucleic acid molecule, a vector comprising the nucleic acid molecule, a composition comprising the nucleic acid molecule, polypeptide or vector, an immunogenic composition comprising the composition, an antibody specifically binding to the polypeptide, and/or a neutralizing anti-ZIKV antisera produced by administering to a subject the nucleic acid molecule, the polypeptide, the vector, the composition or the immunogenic composition;

(b) instructions for use thereof; and optionally (c) a second container comprising a pharmaceutically acceptable carrier, excipient, or diluent.

19. The kit of claim 18, wherein:

(i) the first container further comprises a pharmaceutically acceptable carrier, excipient, or diluent; and/or (ii) the kit optionally includes an adjuvant and/or an immunostimulatory agent.

20. A composition comprising the polypeptide of claim 2.

21. A composition comprising the vector of claim 3.

22. An immunogenic composition comprising the composition of claim 20.

23. An immunogenic composition comprising the composition of claim 21.

24. The isolated antibody or antigen-binding fragment thereof of claim 8, wherein the isolated antibody or antigen-binding fragment thereof is an isolated humanized antibody or an antigen-binding fragment thereof, an isolated IgG antibody or an antigen-binding fragment thereof, or a bis-Fab, Fv, Fab, Fab'-SH, $F(ab')_2$, a diabody, a linear antibody, or a scFV.

25. The method of claim 12, wherein:

(i) the ZIKV is a ZIKV strain from an Asian or African lineage; or (ii) the ZIKV is a ZIKV strain from Brazil or Puerto Rico, wherein optionally the ZIKV is Brazil-ZKV2015 or PRVABC59.

26. The method of claim 12, wherein the antibody is an isolated humanized antibody or an antigen-binding fragment thereof, an isolated IgG antibody or an antigen-binding fragment thereof, or a bis-Fab, Fv, Fab, Fab'-SH, $F(ab')_2$, a diabody, a linear antibody, or a scFV.

27. The method of claim 17, wherein the antibody is an isolated humanized antibody or an antigen-binding fragment thereof, an isolated IgG antibody or an antigen-binding fragment thereof, or a bis-Fab, Fv, Fab, Fab'-SH, $F(ab')_2$, a diabody, a linear antibody, or a scFV.

28. The kit of claim 18, wherein the antibody is an isolated humanized antibody or an antigen-binding fragment thereof, an isolated IgG antibody or an antigen-binding fragment thereof, or a bis-Fab, Fv, Fab, Fab'-SH, $F(ab')_2$, a diabody, a linear antibody, or a scFV.

* * * * *